US009074005B2

(12) United States Patent
Poovaiah et al.

(10) Patent No.: US 9,074,005 B2
(45) Date of Patent: Jul. 7, 2015

(54) COMPOSITIONS AND METHODS FOR MODULATING PLANT DISEASE RESISTANCE AND IMMUNITY

(75) Inventors: Bachettira W. Poovaiah, Pullman, WA (US); Liqun Du, Pullman, WA (US)

(73) Assignee: Washington State University, Pullman, WA (US)

( * ) Notice: Subject to any disclaimer, the term of this patent is extended or adjusted under 35 U.S.C. 154(b) by 150 days.

(21) Appl. No.: 12/651,951

(22) Filed: Jan. 4, 2010

(65) Prior Publication Data
US 2010/0223690 A1   Sep. 2, 2010

Related U.S. Application Data

(60) Provisional application No. 61/142,323, filed on Jan. 2, 2009.

(51) Int. Cl.
*C07K 14/415* (2006.01)
*C12N 15/82* (2006.01)

(52) U.S. Cl.
CPC .......... *C07K 14/415* (2013.01); *C12N 15/8281* (2013.01)

(58) Field of Classification Search
USPC ......................................................... 800/279
See application file for complete search history.

(56) References Cited

U.S. PATENT DOCUMENTS

| | | | |
|---|---|---|---|
| 4,959,314 A | 9/1990 | Mark et al. | |
| 5,268,526 A | 12/1993 | Hershey et al. | |
| 5,510,471 A | 4/1996 | Lebrun et al. | |
| 5,571,706 A | 11/1996 | Baker et al. | |
| 5,589,615 A | 12/1996 | De Clercq et al. | |
| 5,597,945 A | 1/1997 | Jaynes et al. | |
| 5,677,175 A | 10/1997 | Hodges et al. | |
| 5,750,386 A | 5/1998 | Conkling et al. | |
| 5,750,871 A | 5/1998 | Moloney et al. | |
| 5,789,156 A | 8/1998 | Bujard et al. | |
| 5,814,618 A | 9/1998 | Bujard et al. | |
| 7,196,245 B2 * | 3/2007 | Jiang et al. | 800/278 |

OTHER PUBLICATIONS

Yang et al. A calmodulin-binding/CGCG box DNA-binding protein family involved in multiple signaling pathways in plants (2002) JBC 277: 45049-45058.*
Alonso et al. Genome-wide insetional mutagenesis of *Arabidopsis thaliana* (2003) Science 301: 653-657.*
Guo et al. Protein tolerance to random amino acid change (2004) PNAS. 101: 9205-9210.*
The *Arabidopsis* Information Resource Stock Center, www.arabidopsis.org, stock No. SALK_064889 (2007).*
*Ex parte Kubin*, No. 2007-0819 (B.P.A.I. May 31, 2007) ("Board Decision"), pp. 1 through 18 (in particular, pp. 10, 14 and 15).
Ainley, et al., "Regulatable Endogenous Production of Cytokinins up to 'Toxic' Levels in Transgenic Plants and Plant Tissue," *Plant Molecular Biology*, vol. 22, No. 1, pp. 13-23, 1993.
Ali, et al., "Death Don't Have No Mercy and Neither Does Calcium: *Arabidopsis* Cyclic Nucleotide Gated Channel2 and Innate Immunity," *The Plant Cell*, vol. 19, pp. 1081-1095, Mar. 2007.
Alonso, et al., "Genome-Wide Insertional Mutagenesis of *Arabidopsis thaliana*," *Science*, vol. 301, pp. 653-657, Aug. 1, 2003.
Alvarez, et al., "Reactive Oxygen Intermediates Mediate a Systemic Signal Network in the Establishment of Plant Immunity," *Cell*, vol. 92, pp. 773-784, Mar. 20, 1998.
An, et al., "Organ-Specific and Developmental Regulation of the Nopaline Synthase Promoter in Transgenic Tobacco Plants," *Plant Physiology*, vol. 88, pp. 547-552, 1988.
Benfey, et al., "The Cauliflower Mosaic Virus 35S Promoter: Combinatorial Regulation of Transcription in Plants," *Science*, vol. 250, pp. 959-966, Nov. 16, 1990.
Bieri, et al., "RAR1 Positively Controls Steady State Levels of Barley MLA Resistance Proteins and Enables Sufficient MLA6 Accumulation for Effective Resistance," *The Plant Cell*, vol. 16, pp. 3480-3495, Dec. 2004.
Bouché, et al., "A Novel Family of Calmodulin-Binding Transcription Activators in Multicellular Organisms," *The Journal of Biological Chemistry*, vol. 277, No. 24, pp. 21851-21861, Jun. 14, 2002.
Brisson, et al., "Section VIII, Chapter 27: Plant Virus Vectors: Cauliflower Mosaic Virus," In: *Methods for Plant Molecular Biology*, Arthur Weissbach and Herbert Weissbach, Editors, San Diego: Academic Press, pp. 437-446, 1988.
Bustos, et al., "Regulation of β-Glucuronidase Expression in Transgenic Tobacco Plants by an A/T-Rich, *cis*-Acting Sequence Found Upstream of a French Bean β-Phaseolin Gene," *The Plant Cell*, vol. 1, pp. 839-853, Sep. 1989.
Callis, et al, "Heat Inducible Expression of a Chimeric Maize hsp70CAT Gene in Maize Protoplasts," *Plant Physiology*, vol. 88, pp. 965-968, 1988.

(Continued)

*Primary Examiner* — Medina A Ibrahim
(74) *Attorney, Agent, or Firm* — Barry L. Davidson; Davis Wright Tremaine LLP

(57) ABSTRACT

Provided are methods for enhancing plant cell disease resistance, comprising (1) generating a homozygous gene modification of AtSR1 (or AtSR1 ortholog or homolog) in a plant or plant cell characterized by sialic acid-mediated systemic acquired resistance (SA-mediated SAR), wherein said gene modification reduces or eliminates the calmodulin-binding activity of the respective AtSR1 or AtSR1 ortholog or homolog; or (2) expression of a recombinant or mutant AtSR1 sequence (or AtSR1 gene ortholog or homolog sequence) encoding a modified AtSR1, or AtSR1 ortholog or homolog protein, in a plant or plant cell, wherein said protein modification reduces or eliminates the calmodulin-binding activity of the respective AtSR1 or AtSR1 ortholog or homolog protein. Plants and/or plant cells comprising said modified AtSR1, or AtSR1 ortholog or homolog proteins, and/or said expression means (e.g., recombinant expression vector or expressible recombinant and/or mutant sequences), along with nucleic acids encoding said modified proteins are provided.

21 Claims, 13 Drawing Sheets

(56) References Cited

OTHER PUBLICATIONS

Carpenter, et al., "Preferential Expression of an α-Tubulin Gene of *Arabidopsis* in Pollen," *The Plant Cell*, vol. 4, pp. 557-571, May 1992.

Chen, et al., "Sensitization of Defense Responses and Activation of Programmed Cell Death by a Pathogen-Induced Receptor-Like Protein Kinase in *Arabidopsis*," *Plant Molecular Biology*, vol. 53, pp. 61-74, 2003.

Choi, et al., "ABFs, a Family of ABA-Responsive Element Binding Factors," *The Journal of Biological Chemistry*, vol. 275, No. 3, pp. 1723-1730, Jan. 21, 2000.

Choi, et al., "Isolation of a Calmodulin-Binding Transcription Factor from Rice (*Oryza sativa* L.)," *Journal of Biological Chemistry*, vol. 280, No. 49, pp. 40820-40831, Dec. 9, 2005.

Clarke, et al., "Roles of Salicylic Acid, Jasmonic Acid, and Ethylene in *cpr*-Induced Resistance in *Arabidopsis*," *The Plant Cell*, vol. 12, pp. 2175-2190, Nov. 2000.

Cleland, et al., "The Development of Stable Protein Formulations: A Close Look at Protein Aggregation, Deamidation, and Oxidation," *Critical Reviews in Therapeutic Drug Carrier Systems*, vol. 10, No. 4, pp. 307-377, 1993.

Clough, et al., "The *Arabidopsis dnd1*"Defense, No Death" Gene Encodes a Mutated Cyclic Nucleotide-Gated *Ion Channel*," *Proceedings of the National Academy of Sciences of the United States of America*, vol. 97, No. 16, pp. 9323-9328, Aug. 1, 2000.

Cunningham, et al., "High-Resolution Epitope Mapping of hGH-Receptor Interactions by Alanine-Scanning Mutagenesis," *Science, New Series*, vol. 244, No. 4908, pp. 1081-1085, Jun. 2, 1989.

Dekeyser, et al., "Transient Gene Expression in Intact and Organized Rice Tissues," *The Plant Cell*, vol. 2, pp. 591-602, Jul. 1990.

Denis, et al., "Carrier-Mediated Uptake of Glyphosate in Broad Bean (*Vicia faba*) Via a Phospate Transporter," *Physiologia Plantarum*, vol. 87, pp. 569-575, 1993.

De Vos, et al., "Human Growth Hormone and Extracellular Domain of Its Receptor: Crystal Structure of the Complex," *Science*, vol. 255, pp. 306-312, Jan. 17, 1992.

Du, et al., "Identification of Genes Encoding Receptor-Like Protein Kinases as Possible Targets of Pathogen- and Salicylic Acid-Induced WRKY DNA-Binding Proteins in *Arabidopsis*," *The Plant Journal*, vol. 24, No. 6, pp. 837-847, 2000.

Du, et al., "A Novel Family of $Ca^{2+}$/Calmodulin-Binding Proteins Involved in Transcriptional Regulation: Interaction with fsh/Ring3 Class Transcription Activators," *Plant Molecular Biology*, vol. 54, pp. 549-569, 2004.

Du, et al., "$Ca^{2+}$/Calmodulin is Critical for Brassinosteroid Biosynthesis and Plant Growth," *Nature*, vol. 437, pp. 741-745, Sep. 29, 2005.

Durrant, et al., "Systemic Acquired Resistance," *Annual Review of Phytopathology*, vol. 42, pp. 185-209, 2004.

Fromm, et al., "An Octopine Synthase Enhancer Element Directs Tissue-Specific Expression and Binds ASF-1, a Factor from Tobacco Nuclear Extracts," *The Plant Cell*, vol. 1, pp. 977-984, Oct. 1989.

Gatz, C., "Chemical Control of Gene Expression," *Annual Reviews Plant Physiology Plant Molecular Biology*, vol. 48, pp. 89-108, 1997.

Gatz, et al., "Regulation of a Modified CaMV 35S Promoter by the Tn*10*-encoded Tet Repressor in Transgenic Tobacco," *Molecular and General Genetics*, vol. 227, pp. 229-237, 1991.

Gelvin, et al., "*vir* Genes Influence Conjugal Transfer of the Ti Plasmid of *Agrobacterium tumefaciens*," *Journal of Bacteriology*, vol. 172, No. 3, pp. 1600-1608, Mar. 1990.

Gilmartin, et al., "Characterization of a Gene Encoding a DNA Binding Protein," *The Plant Cell*, vol. 4, pp. 839-849, Aug. 1992.

Gleason, et al., "Nodulation Independent of Rhizobia Induced by a Calcium-Activated Kinase Lacking Autoinhibition," *Nature*, vol. 441, pp. 1149-1152, Jun. 29, 2006.

Guo, et al., "Identification of a Plant Nitric Oxide Synthase Gene Involved in Hormonal Signaling," *Science*, vol. 302, pp. 100-103, Oct. 3, 2003.

Han, et al., "The Fly CAMTA Transcription Factor Potentiates Deactivation of Rhodopsin, a G Protein-Coupled Light Receptor," *Cell*, vol. 127, pp. 847-858, Nov. 17, 2006.

Heil, et al., "Fitness Costs of Induced Resistance: Emerging Experimental Support for a Slippery Concept," *TRENDS in Plant Science*, vol. 7, No. 2, pp. 61-67, Feb. 2002.

Hernandez, et al., "The Basic Helix-Loop-Helix Domain of Maize R Links Transcriptional Regulation and Histone Modifications by Recruitment of an EMSY-Related Factor," *Proceedings of the National Academy of Sciences of the United States of America*, vol. 104, No. 43, pp. 17222-17227, Oct. 23, 2007.

Holt, et al., "Antagonistic Control of Disease Resistance Protein Stability in the Plant Immune System," *Science*, vol. 309, pp. 929-932, Aug. 5, 2005.

Kim, et al., "Calmodulin Interacts with MLO Protein to Regulate Defence Against Mildew in Barley," *Nature*, vol. 416, pp. 447-450, Mar. 28, 2002.

Kuhlemeier, et al., "The Pea *rbc*S-3A Promoter Mediates Light Responsiveness but not Organ Specificity," *The Plant Cell*, vol. 1, pp. 471-478, Apr. 1989.

Lecourieux, et al., "Calcium in Plant Defence-Signalling Pathways," *New Phytologist*, vol. 171, pp. 249-269, 2006.

Lorrain, et al., "Lesion Mimic Mutants: Keys for Deciphering Cell Death and Defense Pathways in Plants?," *TRENDS in Plant Science*, vol. 8, No. 6, pp. 263-271, Jun. 2003.

MacKey, et al., "*Arabidopsis* RIN4 Is a Target of the Type III Virulence Effector AvrRpt2 and Modulates RPS2-Mediated Resistance," *Cell*, vol. 112, pp. 379-389, Feb. 7, 2003.

Marcotte, et al., "Abscisic Acid-Responsive Sequences from the Em Gene of Wheat," *The Plant Cell*, vol. 1, pp. 969-976, Oct. 1989.

Mauch, et al., "Manipulation of Salicylate Content in *Arabidopsis thaliana* by the Expression of an Engineered Bacterial Salicylate Synthase," *The Plant Journal*, vol. 25, No. 1, pp. 67-77, 2001.

McNellis, et al., "Glucocorticoid-Inducible Expression of a Bacterial Avirulence Gene in Transgenic *Arabidopsis* Induces Hypersensitive Cell Death," *The Plant Journal*, vol. 14, No. 2, pp. 247-257, 1998.

Nawrath, et al., "EDS5, an Essential Component of Salicylic Acid-Dependent Signaling for Disease Resistance in *Arabidopsis*, Is a Member of the MATE Transporter Family," *The Plant Cell*, vol. 14, pp. 275-286, Jan. 2002.

Nimchuk, et al., "Recognition and Response in the Plant Immune System," *Annual Review of Genetics*, vol. 37, pp. 579-609, 2003.

Odell, et al., "Identification of DNA Sequences Required for Activity of the Cauliflower Mosaic Virus 35S Promoter," *Nature*, vol. 313, pp. 810-812, Feb. 28, 1985.

Opperman, et al., "Root-Knot Nematode-Directed Expression of a Plant Root-Specific Gene," *Science*, vol. 263, pp. 221-223, Jan. 14, 1994.

Paszkowski, et al., "Section VIII, Chapter 28: Direct Gene Transfer to Plants," In: *Methods for Plant Molecular Biology*, Arthur Weissbach and Herbert Weissbach, Editors, San Diego: Academic Press, pp. 447-463, 1988.

Petersen, et al., "*Arabidopsis* Map Kinase 4 Negatively Regulates Systemic Acquired Resistance," *Cell*, vol. 103, pp. 1111-1120, Dec. 22, 2000.

Pinckard, et al., "Factors Influencing the Immune Response, I. Effects of the Physical State of the Antigen and of Lymphoreticular Cell Proliferation on the Response to Intravenous Injection of Bovine Serum Albumin in Rabbits," *Clinical & Experimental Immunology*, vol. 2, pp. 331-341, 1967.

Reddy, et al., "A Calmodulin Binding Protein from *Arabidopsis* is Induced by Ethylene and Contains a DNA-Binding Motif," *Biochemical and Biophysical Research Communications*, vol. 279, No. 3, pp. 762-769, 2000.

Robbins, et al., "Antibodies to Covalent Aggregates of Insulin in Blood of Insulin-Using Diabetic Patients," *Diabetes*, vol. 36, pp. 838-841, Jul. 1987.

Rogers, et al., "Improved Vectors for Plant Transformation: Expression Cassette Vectors and New Selectable Markers," *Methods in Enzymology*, vol. 153, pp. 253-277, 1987.

Rogers, et al., "Section VIII, Chapter 26: Gene Transfer in Plants: Production of Transformed Plants Using Ti Plasmid Vectors," In:

(56) References Cited

OTHER PUBLICATIONS

*Methods for Plant Molecular Biology,* Arthur Weissbach and Herbert Weissbach, Editors, San Diego: Academic Press, pp. 423-436, 1988.
Rosahl, et al., "Expression of a Tuber-Specific Storage Protein in Transgenic Tobacco Plants: Demonstration of an Esterase Activity," *The European Molecular Biology Organization Journal,* vol. 6, No. 5, pp. 1155-1159, 1987.
Ryals, et al., "Systemic Acquired Resistance," *The Plant Cell,* vol. 8, pp. 1809-1819, Oct. 1996.
Schäffner, et al., "Maize rbcS Promoter Activity Depends on Sequence Elements Not Found in Dicot rbcS Promoters," *The Plant Cell,* vol. 3, pp. 997-1012, Sep. 1991.
Schena, et al., "A Steroid-Inducible Gene Expression System for Plant Cells," *Proceedings of the National Academy of Sciences of the United States of America,* vol. 88, pp. 10421-10425, Dec. 1991.
Schernthaner, et al., "Endosperm-Specific Activity of a Zein Gene Promoter in Transgenic Tobacco Plants," *The European Molecular Biology Organization Journal,* vol. 7, No. 5, pp. 1249-1255, 1988.
Shen, et al., "Nuclear Activity of MLA Immune Receptors Links Isolate-Specific and Basal Disease-Resistance Responses," *Science,* vol. 315, pp. 1098-1103, Feb. 23, 2007.
Siebertz, et al., "cis-Analysis of the Wound-Inducible Promoter *wun1* in Transgenic Tobacco Plants and Histochemical Localization of Its Expression," *The Plant Cell,* vol. 1, pp. 961-968, Oct. 1989.
Smith, et al., "Comparison of Biosequences," *Advances in Applied Mathematics,* vol. 2, pp. 482-489, 1981.
Smith, et al., "Human Interleukin 4 The Solution Structure of a Four-helix Bundle Protein," *Journal of Molecular Biology,* vol. 224, No. 4, pp. 899-904, 1992.
Song, et al., "The Transcriptional Coactivator CAMTA2 Stimulates Cardiac Growth by Opposing Class II Histone Deacetylases," *Cell,* vol. 125, pp. 453-466, May 5, 2006.
Stockhaus, et al., "The Promoter of the Gene Encoding the $C_4$ Form of Phosphoenolpyruvate Carboxylase Directs Mesophyll-Specific Expression in Transgenic $C_4$ *Flaveria* spp," *The Plant Cell,* vol. 9, pp. 479-489, Apr. 1997.
Takahashi, et al., "Generalized Lymphoproliferative Disease in Mice, Caused by a Point Mutation in the Fas Ligand," *Cell,* vol. 76, pp. 969-976, Mar. 25, 1994.
Terada, et al., "Expression of CaMV35S-GUS Gene in Transgenic Rice Plants," *Molecular and General Genetics,* vol. 220, No. 3, pp. 389-392, 1990.
Thordal-Christensen, et al., "Subcellular Localization of $H_2O_2$ in Plants. $H_2O_2$ Accumulation in Papillae and Hypersensitive Response During the Barley-Powdery Mildew Interaction," *The Plant Journal,* vol. 11, No. 6, pp. 1187-1194, 1997.
Timmermans, et al., "The pFF Plasmids: Cassettes Utilising CaMV Sequences for Expression of Foreign Genes in Plants," *Journal of Biotechnology,* vol. 14, pp. 333-344, 1990.
Uknes, et al., "Acquired Resistance in *Arabidopsis,*" *The Plant Cell,* vol. 4, pp. 645-656, Jun. 1992.
Van Ostade, et al., "Human TNF Mutants with Selective Activity on the p55 Receptor," *Nature,* vol. 361, pp. 266-269, Jan. 21, 1993.
Ward, et al., "Coordinate Gene Activity in Response to Agents That Induce Systemic Acquired Resistance," *The Plant Cell,* vol. 3, pp. 1085-1094, Oct. 1991.
Wiermer, et al., "Plant Immunity: The EDS1 Regulatory Node," *Current Opinion in Plant Biology,* vol. 8, pp. 383-389, 2005.
Wildermuth, et al., "Isochorismate Synthase is Required to Synthesize Salicylic Acid for Plant Defence," *Nature,* vol. 414, pp. 562-565, Nov. 29, 2001.
Xing, et al., "Effects of Mutations and Constitutive Overexpression of *EDS1* and *PAD4* on Plant Resistance to Different Types of Microbial Pathogens," *Plant Science,* vol. 171, pp. 251-262, 2006.
Yamamoto, et al., "Characterization of *cis*-Acting Sequences Regulating Root-Specific Gene Expression in Tobacco," *The Plant Cell,* vol. 3, pp. 371-382, Apr. 1991.
Yang, et al., "An Early Ethylene Up-Regulated Gene Encoding a Calmodulin-Binding Protein Involved in Plant Senescence and Death," *The Journal of Biological Chemistry,* vol. 275, No. 49, pp. 38467-38473, Dec. 8, 2000.
Yang, et al., "A Calmodulin-Binding/CGCG Box DNA-Binding Protein Family Involved in Multiple Signaling Pathways in Plants," *The Journal of Biological Chemistry,* vol. 277, No. 47, pp. 45049-45058, Nov. 22, 2002.
Yang, et al., "A Haplotype-Specific Resistance Gene Regulated by *BONZAI1* Mediates Temperature-Dependent Growth Control in *Arabidopsis,*" *The Plant Cell,* vol. 16, pp. 1060-1071, Apr. 2004.
Yoo, et al., "*Arabidopsis* Mesophyll Protoplasts: A Versatile Cell System for Transient Gene Expression Analysis," *Nature Protocols,* vol. 2, No. 7, pp. 1565-1572, 2007.
Yu, et al., "Gene-for-Gene Disease Resistance without the Hypersensitive Response in *Arabidopsis dnd1* Mutant," *Proceedings of the National Academy of Sciences of the United States of America,* vol. 95, pp. 7819-7824, Jun. 1998.
Zegzouti, et al., "Ethylene-Regulated Gene Expression in Tomato Fruit: Characterization of Novel Ethylene-Responsive and Ripening-Related Genes Isolated by Differential Display," *The Plant Journal,* vol. 18, No. 6, pp. 589-600, 1999.

* cited by examiner

Fig. 13

COMPOSITIONS AND METHODS FOR MODULATING PLANT DISEASE RESISTANCE AND IMMUNITY

CROSS-REFERENCE TO RELATED APPLICATIONS

This application claims the benefit of priority to U.S. Provisional Patent Application Ser. No. 61/142,323, filed 2 Jan. 2009 and entitled COMPOSITIONS AND METHODS FOR MODULATING PLANT DISEASE RESISTANCE AND IMMUNITY, which is incorporated by reference herein in its entirety.

ACKNOWLEDGEMENT OF FEDERAL FUNDING

Particular aspects of the present invention were, at least in part, supported by grants 2008-01034 from the United States Department of Agriculture, IOS-0642146 from the National Science Foundation, and the Washington State University Agricultural Research Center and the United States Government therefore has certain rights in the invention.

FIELD OF THE INVENTION

Aspects of the invention relate generally to plants and to disease resistance in plants, and in particular aspects to modified proteins (e.g., variant, mutants, muteins, fusions) (e.g., of AtSR1, and/or of an AtSR1 ortholog or homolog,), and nucleic acids encoding same, that have substantial utility to increase disease resistance in plants (e.g., in *Arabidopsis thaliana* and/or other plants). Certain aspects relate to plants and plant cells comprising said modified proteins, and methods for making same.

SEQUENCE LISTING

A Sequence Listing comprising SEQ ID NOS:1-74 is incorporated by reference herein in its entirety as part of this application.

BACKGROUND

Intracellular calcium transients during plant-pathogen interactions are necessary early events leading to local and systemic acquired resistance (SAR)[1]. Salicylic acid (SA), a critical messenger, is also required for both these responses[2, 3].

AtSRs/CAMTAs belong to a class of $Ca^{2+}$/CaM-binding transcription factors (TFs) [4-7]. In animals, AtSR/CaMTA homologs are involved in diverse functions[8, 9]. Although AtSRs are implicated in plant responses to stresses[6], the specific function of AtSRs remains unknown.

SUMMARY OF EXEMPLARY EMBODIMENTS

Provided are methods for enhancing plant cell disease resistance, comprising (1) generating a homozygous gene modification of AtSR1 (or AtSR1 ortholog or homolog) in a plant or plant cell characterized by salicylic acid-mediated systemic acquired resistance (SA-mediated SAR), wherein said gene modification reduces or eliminates the calmodulin-binding activity of the respective AtSR1 or AtSR1 ortholog or homolog; or (2) expression of a recombinant or mutant AtSR1 sequence (or AtSR1 gene ortholog or homolog sequence) encoding a modified AtSR1, or AtSR1 ortholog or homolog protein, in a plant or plant cell, wherein said protein modification reduces or eliminates the calmodulin-binding activity of the respective AtSR1 or AtSR1 ortholog or homolog protein. Plants and/or plant cells comprising said modified AtSR1, or AtSR1 ortholog or homolog proteins, and/or said expression means (e.g., recombinant expression vector or expressible recombinant and/or mutant sequences), along with nucleic acids encoding said modified proteins are provided.

Particular aspects provide a method for enhancing disease resistance in a plant or plant cell, comprising generating a homozygous gene modification of AtSR1, or of an AtSR1 ortholog or homolog, in a plant or plant cell, the plant or plant call characterized by salicylic acid-mediated systemic acquired resistance (SA-mediated SAR), wherein said gene modification reduces or eliminates the calmodulin-binding activity of the respective AtSR1 or AtSR1 ortholog or homolog, and wherein enhancing disease resistance in a plant or plant cell is afforded.

Additional aspects provide a method for enhancing disease resistance in a plant or plant cell, comprising recombinant expression of (or expression of a recombinant or mutant of) an AtSR1 sequence or AtSR1 gene ortholog or homolog sequence encoding a modified AtSR1 or AtSR1 ortholog or homolog protein, respectively, in a plant or plant cell, the plant or plant cell characterized by salicylic acid-mediated systemic acquired resistance (SA-mediated SAR), wherein said protein modification reduces or eliminates the calmodulin-binding activity of the respective AtSR1 or AtSR1 ortholog or homolog protein, and wherein enhancing disease resistance in a plant or plant cell is afforded. In certain aspects, expression (e.g., recombinant expression) comprises inducible expression (inducible recombinant expression).

In particular aspects of the above methods, the AtSR1 gene or AtSR1 gene ortholog or homolog is at least one encoding a protein selected from the group consisting of SEQ ID NOS:2, 8, 10, 12, 14, 16, 21, 23, 25, 27, 29, 31, 33, 35, sequences having at least 60%, 65%, 70%, 75%, 80%, 85%, 90%, 95%, 96%, 97%, 98% or 99% sequence identity thereto, and biologically active variants thereof. In certain embodiments, the AtSR1 gene modification provides for expression of at least one AtSR1 mutant selected from the group consisting of SEQ ID NOS:4 and 6. In particular embodiments, the modified AtSR1 or modified AtSR1 ortholog or homolog comprises at least one of insertions, deletions, substitutions, inversion, point mutations and null mutations.

In certain aspects of the above methods, the AtSR1 gene or AtSR1 gene ortholog or homolog is at least one selected from the group consisting of SEQ ID NOS:1, 7, 9, 11, 13, 15, 17, 18, 19, 20, 22, 24, 26, 28, 30, 32, 34, and sequences having at least 60%, 65%, 70%, 75%, 80%, 85%, 90%, 95%, 96%, 97%, 98% or 99% sequence identity thereto. In certain aspects, the plant characterized by salicylic acid-mediated systemic acquired resistance (SA-mediated SAR), comprises a monocot or dicot (e.g, cruciferous dicot). In certain aspects, the cruciferous dicot comprises at least one selected from the group consisting of *B. carinata* (Abyssinian Mustard or Cabbage, *B. elongata* (Elongated Mustard), *B. fruticulosa* (Mediterranean Cabbage), *B. juncea* (Indian Mustard, Brown and leaf mustards, Sarepta Mustard), *B. napous* (Rapeseed, Canola, Rutabaga, Nabicol), *B. narinosa* (Broadbeaked Mustard), *B. nigra* (Black Mustard), *B. oleracea* (Kale, Cabbage, Broccoli, Cauliflower, Kai-lan, Brussels sprouts), *B. perviridis* (Tender Green, Mustard Spinach), *B. rapa* (Chinese cabbage, Turnip, Rapini, Komatsuna), *B. rupestris* (Brown Mustard), *B. septiceps* (Seventop Turnip), and *B. tournefortii* (Asian Mustard).

In particular embodiments, the monocot comprises at least one of barley, sorghum, and rice.

Additional aspects provide a plant or plant cell, comprising a homozygous gene modification of AtSR1 or of an AtSR1 ortholog or homolog, said plant or plant cell characterized by salicylic acid-mediated systemic acquired resistance (SA-mediated SAR), said modification reducing or eliminating the calmodulin-binding activity of the respective AtSR1 or AtSR1 ortholog or homolog, and wherein an enhanced disease resistant plant or plant cell is afforded.

Yet further aspects provide a plant or plant cell, comprising a recombinant expression vector or expressible recombinant or mutant sequence suitable for expression of an AtSR1 gene or AtSR1 gene ortholog or homolog sequence encoding a modified AtSR1 or AtSR1 ortholog or homolog protein, respectively, in a plant or plant cell, the plant or plant call characterized by salicylic acid-mediated systemic acquired resistance (SA-mediated SAR), wherein said protein modification reduces or eliminates the calmodulin-binding activity of the respective AtSR1 or AtSR1 ortholog protein, and wherein an enhanced disease resistant plant or plant cell is afforded. In certain aspects, expression (.e.g., recombinant expression) comprises inducible expression (inducible recombinant expression).

In certain plant and/or plant cell embodiments, the AtSR1 gene or AtSR1 gene ortholog or homolog is at least one encoding a protein selected from the group consisting of SEQ ID NOS:2, 8, 10, 12, 14, 16, 21, 23, 25, 27, 29, 31, 33, 35, sequences having at least 60%, 65%, 70%, 75%, 80%, 85%, 90%, 95%, 96%, 97%, 98% or 99% sequence identity thereto, and biologically active variants thereof. In particular aspectgs, the AtSR1 gene modification provides for expression of at least one AtSR1 mutant selected from the group consisting of SEQ ID NOS:4 and 6. In certain aspects, the modified AtSR1 or modified AtSR1 ortholog or homolog comprises at least one of insertions, deletions, substitutions, inversion, point mutations and null mutations. In particular embodiments, the AtSR1 gene or AtSR1 gene ortholog or homolog is at least one selected from the group consisting of SEQ ID NOS:1, 7, 9, 11, 13, 15, 17, 18, 19, 20, 22, 24, 26, 28, 30, 32, 34, and sequences having at least 60%, 65%, 70%, 75%, 80%, 85%, 90%, 95%, 96%, 97%, 98% or 99% sequence identity thereto.

In certain embodiments of the above plants or plant cells, the plant or plant cell is one selected from the group consisting of Acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf grass, turnip, a vine, watermelon, wheat, yams, and zucchini. Preferably, the plant is more disease resistant relative to wild type. In certain aspects, the plant or plant cell is that of a monocot or dicot (e.g., cruciferous dicot). In particular embodiments, the cruciferous dicot comprises at least one selected from the group consisting of B. carinata (Abyssinian Mustard or Cabbage, B. elongata (Elongated Mustard), B. fruticulosa (Mediterranean Cabbage), B. juncea (Indian Mustard, Brown and leaf mustards, Sarepta Mustard), B. napous (Rapeseed, Canola, Rutabaga, Nabicol), B. narinosa (Broadbeaked Mustard), B. nigra (Black Mustard), B. oleracea (Kale, Cabbage, Broccoli, Cauliflower, Kai-Ian, Brussels sprouts), B. perviridis (Tender Green, Mustard Spinach), B. rapa (Chinese cabbage, Turnip, Rapini, Komatsuna), B. rupestris (Brown Mustard), B. septiceps (Seventop Turnip), and B. toumefortii (Asian Mustard).

In certain aspects, the monocot comprises at least one of barley, sorghum, and rice.

Yet further aspects provide an isolated nucleic acid comprising a modification of a AtSR1 gene or of an AtSR1 gene ortholog or homolog, said modification reducing or eliminating the respective calmodulin-binding activity (e.g., comprising at least one of a deletion, substitution, insertion, inversion and point mutation). In certain embodiments, the nucleic acid is selected from the group consisting of SEQ ID NOS:4 and 6.

Additional aspects provide a recombinant expression vector or virus, comprising, and suitable for expression of a nucleic acid comprising a modification of a AtSR1 gene or of an AtSR1 gene ortholog or homolog, said modification reducing or eliminating the calmodulin-binding activity of the respective encoded proteins.

BRIEF DESCRIPTION OF THE DRAWINGS

FIG. 13, shows an alignment of the plant protein calmodulin binding domains of superfamily c106741; accession numbers: gi 75335803; gi 75152791; gi 75152791; gi 75162033; gi 75152791; gi 75152789; gi 75203290; gi 75174046; gi 75328303; and gi 75152791 (SEQ ID NOS:59-68, respectively).

DETAILED DESCRIPTION OF EXEMPLARY EMBODIMENTS

Figures 1A, 1B, 1C, 1D, 1E, 1F, 1G, 1H, 1I:
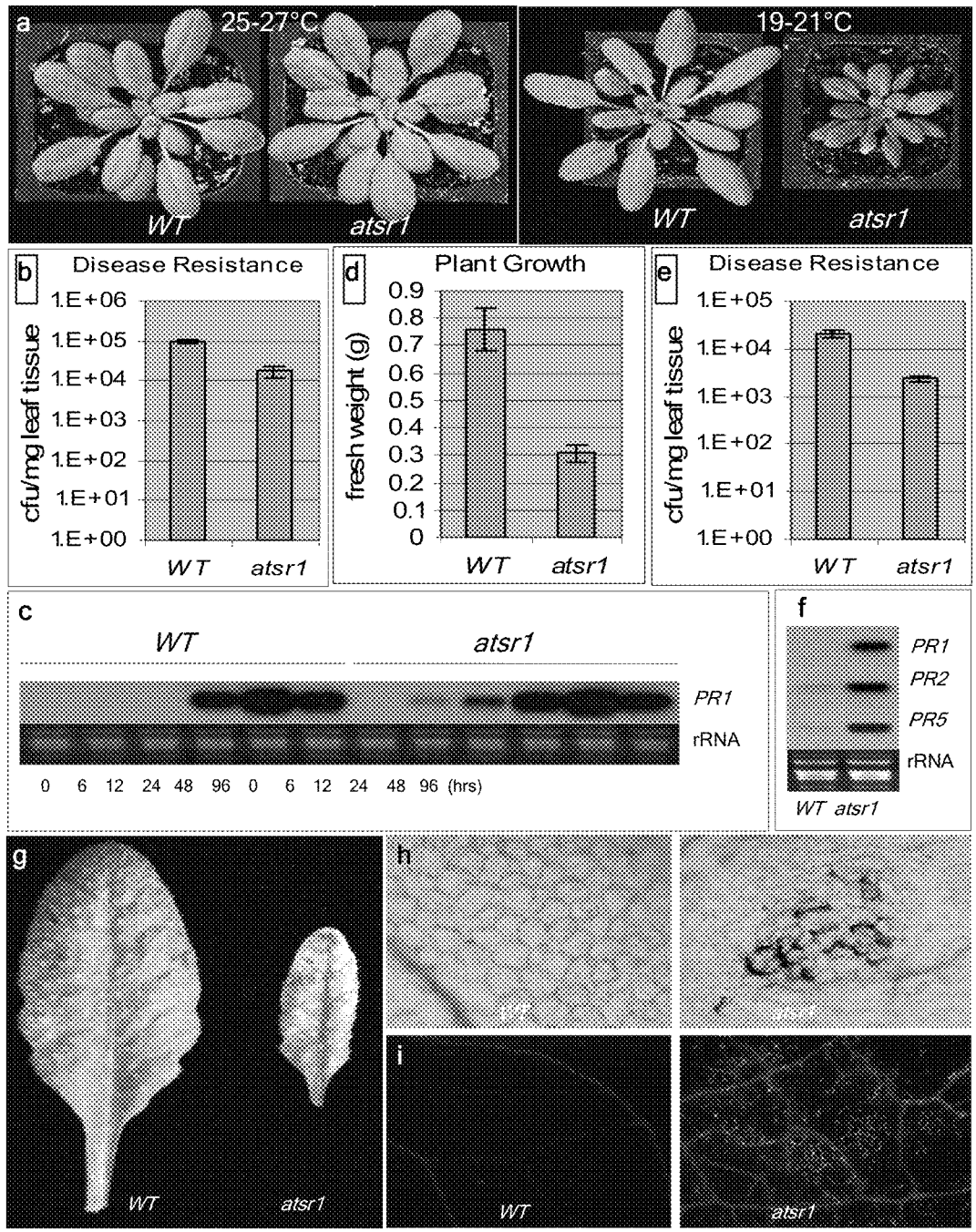
FIG. 1 demonstrates, according to particular exemplary embodiments, that the atsr1-1 mutant shows sensitized defense responses when compared to wildtype.

Provided are methods for enhancing plant cell disease resistance, comprising (1) generating a homozygous gene modification of AtSR1 (or AtSR1 ortholog or homolog) in a plant or plant cell characterized by salicylic acid-mediated systemic acquired resistance (SA-mediated SAR), wherein said gene modification reduces or eliminates the calmodulin-binding activity of the respective AtSR1 or AtSR1 ortholog or homolog; or (2) expression of a recombinant or mutant AtSR1 sequence (or AtSR1 gene ortholog or homolog sequence) encoding a modified AtSR1, or AtSR1 ortholog or homolog protein, in a plant or plant cell, wherein said protein modification reduces or eliminates the calmodulin-binding activity of the respective AtSR1 or AtSR1 ortholog or homolog protein. Plants and/or plant cells comprising said modified AtSR1, or AtSR1 ortholog or homolog proteins, and/or said expression means (e.g., recombinant expression vector or expressible recombinant and/or mutant sequences), along with nucleic acids encoding said modified proteins are provided.

In particular surprising exemplary aspects, the present applicants have found that a homozygous null mutant of atsr1 in *Arabidopsis* enhanced disease resistance.

In additional particular aspects a novel mechanism connecting $Ca^{2+}$ signal to salicylic acid-mediated immune response through calmodulin, AtSR1/CAMTA3, a $Ca^{2+}$/calmodulin-binding transcription factor, and EDS1, an established regulator of salicylic acid level. In further aspects, constitutive disease resistance and elevated levels of salicylic acid in loss-of-function alleles of AtSR1/CAMTA3 indicate that AtSR1 is a negative regulator of plant immunity. In additional particular aspects, Applicants confirmed by epistasis analyses with mutants of compromised salicylic acid accumulation and disease resistance. Additional aspects of the invention include that AtSR1 interacts with the promoter of EDS1 and represses its expression. Furthermore, $Ca^{2+}$/calmodulin-binding to AtSR1 is required for suppression of plant defense, indicating a direct role for $Ca^{2+}$/calmodulin in regulating the function of AtSR1. In particular aspects these results revealed a novel regulatory mechanism linking $Ca^2+$ signaling to salicylic acid level.

Definitions:

The term "generation" and/or "introduction", as used herein in particular embodiments with respect to gene modification, refer to the introduction of mutations using techniques including, but not limited to chemical mutagenesis, transposon mediated (e.g., by T-DNA), transfection, transformation, targeted replacement, UV-mediated mutagenesis, ionized radiation-mediated mutagenesis, PCR-mediated mutagenesis, directed mutagenesis, site-directed mutagenesis, and insertional mutagenesis.

Figure 13:
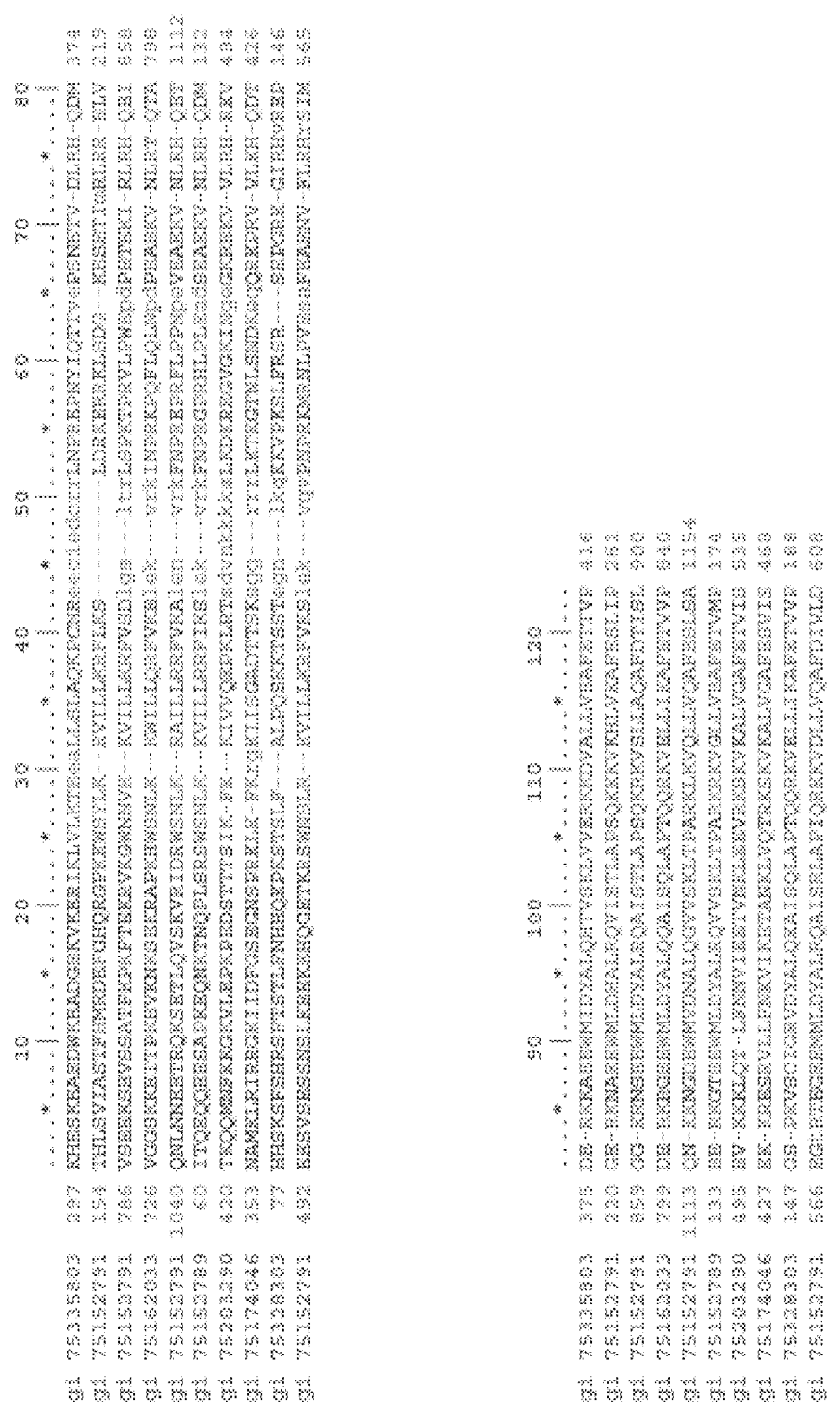

The phrase "homozygous gene modification of AtSR1 or of an ortholog thereof" as used herein refers to any modification of AtSR1 or of an orthology or homolog thereof including, but not limited to insertions, deletions, substitutions, frame shift and resulting in mutations including null mutations, DNA binding mutations, calmodulin-binding mutations, destablizing mutations. Plant protein calmodulin binding domains are exemplified by those of the superfamily c106741; accession numbers: gi 75335803; gi 75152791; gi 75152791; gi 75162033; gi 75152791; gi 75152789; gi 75203290; gi 75174046; gi 75328303; and gi 75152791 (SEQ ID NOS:59-68, respectively) (see FIG. 13). According to particular aspects, any modification of AtSR1 or of an ortholog or homolog thereof including, but not limited to insertions, deletions, substitutions, frame shift and resulting in calmodulin-binding mutations (e.g., decreasing or eliminating binding affinity), in both heterozygous or homozygous embodiments, are encompassed by the present invention. Plant calmodulin domains are readily identified in view, for example, of the superfamily c106741 and the conserved amino acid residue positions (e.g., see the alignment of FIG. 13), and modifications/mutants thereof, particularly at these conserved positions, can be readily assayed for modulation of calmodulin binding activity and modulation of disease resistance enhancing function, all as disclosed and taught herein.

The term "AtSR1 gene", or "ortholog thereof" as used herein in particular embodiments, refers not only to the *Arabidopsis thaliana* AtSR1 gene (accession numbers AtSR1=At2g22300, AtSR2=At5g09410, AtSR3=At3g16940, AtSR4=At5g64220, AtSR5=At1g67310, and AtSR6=At4g16150), but also to the orthologous genes in other plants, and including but not limited to the orthologous genes in other dicots, and particularly in other cruciferous dicots. In particular embodiments, examples of plants containing AtSR1 related gene sequences include but are not limited to Acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, castor-bean, cauliflower, celery, cherry, chicory, cilantro, citrus, clementines, clover, coconut, coffee, corn, cotton, cucumber, Douglas fir, eggplant, endive, escarole, eucalyptus, fennel, figs, garlic, gourd, grape, grapefruit, honey dew, jicama, kiwi-fruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf grass, turnip, a vine, watermelon, wheat, yams, and zucchini. Examples of AtSR1 related gene sequences in monocots include but are not limited to barley (gene bank accession number AV835190), sorghum (gene bank accession number BE341351), and rice OsCBT, gene bank accession numbers AU174776 and AF499741 (Choi et al., Journal of Biological Chemistry, 280, 40820-40831, incorporated herein by reference in its entirety)). Examples of AtSR1 related gene sequences in dicots include but are not limited to tobacco (NtER1, gene bank accession number: AF253511), parsley (gene bank accession number X79447), cotton (gene bank accession number AY181251), potato (gene bank accession number BE341351), and tomato (LeER66, gene bank accession number: AF096260 (Zeuzouti et al., Plant, 18, 589-600, 1999; incorporated herein by reference in its entirety)). Examples of AtSR1 related gene sequences in cruciferous dicots include but are not limited to rape seed (CAMTA, gene bank accession number AF491304). In particular aspects, the "AtSR1 gene", or "ortholog thereof comprises at least one sequence selected from SEQ ID NOS:1, 3, 5, 7, 9, 11, 13, 15, 17, 18, 19, 20, 22, 24, 26, 28, 30, 32, and 34, sequences having at least 60%, 65%, 70%, 75%, 80%, 85%, 90%, 95%, 96%, 97%, 98% or 99% sequence identity thereto, and biologically active variants thereof.

List of economically important cruciferous species: *B. carinata* (Abyssinian Mustard or Cabbage (important for biodiesel production), *B. elongata* (Elongated Mustard), *B. fruticulosa* (Mediterranean Cabbage), *B. juncea* (Indian Mustard, Brown and leaf mustards, Sarepta Mustard), *B. napous* (Rapeseed, Canola, Rutabaga, Nabicol), *B. narinosa* (Broad-beaked Mustard), *B. nigra* (Black Mustard), *B. oleracea* (Kale, Cabbage, Broccoli, Cauliflower, Kai-Ian, Brussels sprouts), *B. perviridis* (Tender Green, Mustard Spinach), *B. rapa* (Chinese cabbage, Turnip, Rapini, Komatsuna), *B. rupestris* (Brown Mustard), *B. septiceps* (Seventop Turnip), *B. toumefortii* (Asian Mustard).

The phrase "plant characterized by salicylic acid-mediated systemic acquired resistance (SA-mediated SAR)" as used herein in particular embodiments refers to any plant which elicits a salicylic acid-mediated resistance response that occurs following an earlier localized exposure to a pathogen. This resistance response occurs in the whole plant (systemically). SAR is analogous to the innate immune system found in animals, and there is evidence that SAR in plants and innate immunity in animals may be evolutionarily conserved. SAR is important mechanism by which plants resist and tolerate disease, and recover from a diseased state. Interestingly, a wide range of pathogens can elicit SAR. Many different types of genes, including pathogenesis-related genes (PR) are activated during the systemic acquired response. Additionally, the activation of SAR requires the accumulation of endogenous salicylic acid (SA). The pathogen-induced SA signal activates a molecular signal transduction pathway that is identified by a gene called NIM1, NPR1 or SAI1 (three names for the same gene) in the model genetic system *Arabidopsis thaliana*. SAR, for example, has been observed in a wide range of flowering plants, including dicotyledon and monocotyledon species. Plants that are representative members of SA-mediated SAR in monocots: maize and wheat; and in dicots: tobacco, tomato, pepper, leguminous bean, soybean, cotton, peanut, spinach, apple, and pear.

The phrase "reducing or eliminating the respective AtSR1 calmodulin-binding activity" as used herein in particular embodiments refers to altering (decreasing and/or eliminating) the calmodulin binding property of AtSR1 by mutatgensis, including but not limited to: insertions, deletions, substitutions, and frame shifts of AtSR1 or orthologs thereof.

"Functional variants" as used herein refers to at least one protein selected from the group consisting of SEQ ID NOS:1, 3, 5, 7, 9, 11, 13, 15, 17, 18, 19, 20, 22, 24, 26, 28, 30, 32, and 34, sequences having at least 60%, 65%, 70%, 75%, 80%, 85%, 90%, 95%, 96%, 97%, 98% or 99% sequence identity thereto, and biologically active variants thereof, where functional or biologically active variants are those proteins that display one or more of the biological activities of at least one protein selected from the group consisting of SEQ ID NOS: 2, 4, 6, 8, 10, 12, 14, 16, 21, 23, 25, 27, 29, 31, 33, and 35, sequences having at least 60%, 65%, 70%, 75%, 80%, 85%, 90%, 95%, 96%, 97%, 98% or 99% sequence identity thereto, including but not limited to the activities disclosed herein (e.g., in mutations of increasing SA-mediated SAR, or the increase in immune response in plants. As used herein, a biological activity refers to a function of a polypeptide including but not limited to complexation (e.g., with other transcription factors, proteins, calmodulin binding, etc), dimerization, multimerization, receptor-associated kinase activity, receptor-associated protease activity, phosphorylation, dephosphorylation, autophosphorylation, ability to form complexes with other molecules, ligand binding, catalytic or enzymatic activity, activation including auto-activation and activation of other polypeptides, inhibition or modulation of another molecule's function, stimulation or inhibition of signal transduction and/or cellular responses and SA-mediated SAR. A biological activity can be assessed by assays described herein and by any suitable assays known to those of skill in the art, including, but not limited to in vitro assays, including cell-based assays, in vivo assays, including assays in plant models and for disease resistance.

Variants of at least one protein selected from the group consisting of SEQ ID NOS: 2, 4, 6, 8, 10, 12, 14, 16, 21, 23, 25, 27, 29, 31, 33, and 35, sequences having at least 60%, 65%, 70%, 75%, 80%, 85%, 90%, 95%, 96%, 97%, 98% or 99% sequence identity thereto have utility for aspects of the present invention. Variants can be naturally or non-naturally occurring. Naturally occurring variants (e.g., polymorphisms) are found in cruciferous dicots or other species and comprise amino acid sequences which are substantially identical to the amino acid sequences disclosed herein. Species homologs of the protein can be obtained using subgenomic polynucleotides of the invention, as described below, to make suitable probes or primers for screening cDNA expression libraries from other species, such as tobacco, tomato, yeast, or bacteria, identifying cDNAs which encode homologs of the protein, and expressing the cDNAs as is known in the art.

Non-naturally occurring variants which retain substantially the same biological activities as naturally occurring protein variants. Preferably, naturally or non-naturally occurring variants have amino acid sequences which are at least 60%, 65%, 70%, 75%, 80%, 85%, 90%, 95%, 96%, 97%, 98% or 99% identical to the amino acid sequenced disclosed herein. More preferably, the molecules are at least 98% or 99% identical. Percent identity is determined using any method known in the art. A non-limiting example is the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* 2:482-489, 1981.

As used herein, "amino acid residue" refers to an amino acid formed upon chemical digestion (hydrolysis) of a polypeptide at its peptide linkages. The amino acid residues described herein are generally in the "L" isomeric form. Residues in the "D" isomeric form can be substituted for any L-amino acid residue, as long as the desired functional property is retained by the polypeptide. NH2 refers to the free amino group present at the amino terminus of a polypeptide. COOH refers to the free carboxy group present at the carboxyl terminus of a polypeptide. In keeping with standard polypeptide nomenclature described in J. Biol. Chem., 243: 3552-59 (1969) and adopted at 37 C.F.R. §§ 1.821-1.822, abbreviations for amino acid residues are shown in Table 2:

TABLE 1

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Praline |
| K | Lys | Lysine |
| H | His | Histidine |
| Q | Gln | Glutamine |
| E | Glu | glutamic acid |
| Z | Glx | Glu and/or Gln |
| W | Trp | Tryptophan |
| R | Arg | Arginine |
| D | Asp | aspartic acid |
| N | Asn | Asparagines |
| B | Asx | Asn and/or Asp |
| C | Cys | Cysteine |
| X | Xaa | Unknown or other |

It should be noted that all amino acid residue sequences represented herein by a formula have a left to right orientation in the conventional direction of amino-terminus to carboxyl-terminus. In addition, the phrase "amino acid residue" is defined to include the amino acids listed in the Table of Correspondence and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues or to an amino-terminal group such as NH$_2$ or to a carboxyl-terminal group such as COOH.

Guidance in determining which amino acid residues can be substituted, inserted, or deleted without abolishing biological or immunological activity can be found using computer programs well known in the art, such as DNASTAR software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting variant.

Variants of the at least one protein selected from the group consisting of SEQ ID NOS: 2, 4, 6, 8, 10, 12, 14, 16, 21, 23, 25, 27, 29, 31, 33, and 35, sequences having at least 60%, 65%, 70%, 75%, 80%, 85%, 90%, 95%, 96%, 97%, 98% or 99% sequence identity thereto disclosed herein include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

A subset of mutants, called muteins, is a group of polypeptides in which neutral amino acids, such as serines, are substituted for cysteine residues which do not participate in disulfide bonds. These mutants may be stable over a broader temperature range than native secreted proteins (see, e.g., Mark et al., U.S. Pat. No. 4,959,314).

Preferably, amino acid changes in the variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting secreted protein or polypeptide variant. Properties and functions of the variants are of the same type as a protein comprising the amino acid sequence encoded by the nucleotide sequence shown in SEQ ID NOS: 2, 4, 6, 8, 10, 12, 14, 16, 21, 23, 25, 27, 29, 31, 33, and 35, and sequences having at least 60%, 65%, 70%, 75%, 80%, 85%, 90%, 95%, 96%, 97%, 98% or 99% sequence identity thereto, although the properties and functions of variants can differ in degree.

Variants of at least one protein selected from the group consisting of SEQ ID NOS: 2, 4, 6, 8, 10, 12, 14, 16, 21, 23, 25, 27, 29, 31, 33, and 35, sequences having at least 60%, 65%, 70%, 75%, 80%, 85%, 90%, 95%, 96%, 97%, 98% or 99% sequence identity thereto include glycosylated forms, aggregative conjugates with other molecules, and covalent conjugates with unrelated chemical moieties (e.g., pegylated molecules). The variants also include allelic variants, species variants, and muteins. Truncations or deletions of regions which do not affect functional activity of the proteins are also variants. Covalent variants can be prepared by linking functionalities to groups which are found in the amino acid chain or at the N- or C-terminal residue, as is known in the art.

It will be recognized in the art that some amino acid sequences of the polypeptides of the invention can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. The replacement of amino acids can also change the selectivity of binding to cell surface receptors (Ostade et al., Nature 361:266-268, 1993). Thus, the polypeptides of the present invention may include one or more amino acid substitutions, deletions or additions, either from natural mutations or human manipulation.

Of particular interest are substitutions of charged amino acids with another charged amino acid and with neutral or negatively charged amino acids. The latter results in proteins with reduced positive charge to improve the characteristics of the disclosed protein. The prevention of aggregation is highly desirable. Aggregation of proteins not only results in a loss of activity but can also be problematic when preparing pharmaceutical formulations, because they can be immunogenic (see, e.g., Pinckard et al., *Clin. Exp. Immunol.* 2:331-340 (1967); Robbins et al., *Diabetes* 36:838-845 (1987); and Cleland et al., *Crit. Rev. Therapeutic Drug Carrier Systems* 10:307-377 (1993)).

Amino acids in polypeptides of the present invention that are essential for function can be identified by methods known in the art, such as site-directed mutagenesis or alanine-scanning mutagenesis (Cunningham and Wells, *Science* 244: 1081-1085 (1989)). The latter procedure introduces single alanine mutations at every residue in the molecule. The resulting mutant molecules are then tested for biological activity such as binding to a natural or synthetic binding partner. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given polypeptide will not be more than 50, 40, 30, 25, 20, 15, 10, 5 or 3.

In addition, pegylation of the inventive polypeptides and/or muteins is expected to provide such improved properties as increased half-life, solubility, and protease resistance. Pegylation is well known in the art.

Fusion Proteins:

Fusion proteins comprising proteins or polypeptide fragments of at least one protein selected from the group consisting of SEQ ID NOS: 2, 4, 6, 8, 10, 12, 14, 16, 21, 23, 25, 27, 29, 31, 33, and 35 sequences having at least 60%, 65%, 70%, 75%, 80%, 85%, 90%, 95%, 96%, 97%, 98% or 99% sequence identity thereto can also be constructed. Fusion proteins are useful for generating antibodies against amino acid sequences and for use in various targeting and assay systems. For example, fusion proteins can be used to identify proteins which interact with a polypeptide of the invention or which interfere with its biological function. Physical methods, such as protein affinity chromatography, or library-based assays for protein-protein interactions, such as the yeast two-hybrid or phage display systems, can also be used for this purpose. Such methods are well known in the art and can also be used as drug screens. Fusion proteins comprising a signal sequence can be used.

A fusion protein comprises two protein segments fused together by means of a peptide bond. Amino acid sequences for use in fusion proteins of the invention can be utilize the amino acid sequence shown in SEQ ID NOS: 2, 4, 6, 8, 10, 12, 14, 16, 21, 23, 25, 27, 29, 31, 33, and 35 and sequences having at least 60%, 65%, 70%, 75%, 80%, 85%, 90%, 95%, 96%, 97%, 98% or 99% sequence identity thereto, or can be prepared from biologically active variants such as those described above. The first protein segment can include of a full-length polypeptide selected from the group consisting of SEQ ID NOS: 2, 4, 6, 8, 10, 12, 14, 16, 21, 23, 25, 27, 29, 31, 33, and 35, sequences having at least 60%, 65%, 70%, 75%, 80%, 85%, 90%, 95%, 96%, 97%, 98% or 99% sequence identity thereto.

Other first protein segments can consist of biologically active portions of SEQ ID NOS: 2, 4, 6, 8, 10, 12, 14, 16, 21, 23, 25, 27, 29, 31, 33, and 35, sequences having at least 60%, 65%, 70%, 75%, 80%, 85%, 90%, 95%, 96%, 97%, 98% or 99% sequence identity thereto.

The second protein segment can be a full-length protein or a polypeptide fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions.

These fusions can be made, for example, by covalently linking two protein DNA segments or by standard procedures in the art of molecular biology. Recombinant DNA methods can be used to prepare fusion proteins, for example, by making a construct which comprises a coding region for the protein sequence of SEQ ID NOS: 2, 4, 6, 8, 10, 12, 14, 16, 21, 23, 25, 27, 29, 31, 33, and 35 sequences having at least 60%, 65%, 70%, 75%, 80%, 85%, 90%, 95%, 96%, 97%, 98% or 99% sequence identity thereto in proper reading frame with a nucleotide encoding the second protein segment and expressing the construct in a host cell, as is known in the art. Many kits for constructing fusion proteins are available from companies that supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Plant Vectors:

A vector is, in particular aspects, a nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art. Examples of plant expression systems (vectors) include but are not limited to: PTGS-MAR expression system. p4OCS Δ 35SIGN, pCaMVCN pEmuGN, and vectors derived from the tumor inducing (Ti) plasmid of *Agrobacterium tumefaciens* described by Rogers et al., Meth. Enzymol., 153:253-277, 1987).

Vector Construction:

A number of recombinant vectors suitable for stable transfection of plant cells or for the establishment of transgenic plants have been described including those described in Weissbach and Weissbach, (1989), and Gelvin et al., (1990). Typically, plant transformation vectors include one or more cloned plant genes (or cs) under the transcriptional control of 5' and 3' regulatory sequences, together with a dominant selectable marker. Such plant transformation vectors typically also contain a promoter regulatory region (e.g., a regulatory region controlling inducible or constitutive, environmentally or developmentally regulated, or cell- or tissue-specific expression), a transcription initiation start site, a ribosome binding site, an RNA processing signal, a transcription termination site, and/or a polyadenylation signal. As described above, the first genetic element according to the present invention may be a native R gene, in which case the gene is already present in the plant genome to be transformed. In cases where the first genetic element is a heterologous gene, it may be introduced into the plant tissue using a transformation vector, but will typically be used with its own regulatory sequences.

The second genetic element is generally constructed using regulatory sequences that produce expression levels that are higher than expression levels produced by the regulatory sequences of the corresponding gene. Such regulatory sequences may provide constitutive expression (i.e., expression regardless of triggering stimulus) or expression that is inducible (i.e., expression in response to a triggering stimulus) or expression that is tissue-specific (i.e., expression that is restricted to, or enhanced in, certain tissues of the plant).

Examples of constitutive plant promoters that may be useful for expressing the second genetic element include: the cauliflower mosaic virus (CaMV) 35S promoter, which confers constitutive, high-level expression in most plant tissues (see, e.g., Odel et al., 1985, Dekeyser et al., 1990, Terada and Shimamoto, 1990; Benfey and Chua, 1990); the nopaline synthase promoter (An et al., 1988); and the octopine synthase promoter (Fromm et al., 1989).

A variety of plant gene promoters that are regulated in response to environmental, hormonal, chemical, and/or developmental signals, also can be used for expression of the cDNA in plant cells, including promoters regulated by (a) heat (Callis et al, 1988; Ainley, et al. 1993; Gilmartin et al. 1992); (b) light (e.g., the pea rbcS-3A promoter, Kuhlemeier et al., 1989, and the maize rbcS promoter, Schaffner and Sheen, 1991); (c) hormones and other signaling molecules, such as abscisic acid (Marcotte et al., 1989), methyl jasmonate or salicylic acid (see also Gatz et al., 1997); and (d) wounding (e.g., wunl, Siebertz et al., 1989).

Chemical-regulated promoters can be used to modulate the expression of a nucleic acid construct of the invention in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible and tetracycline-repressible promoters (see, for example, Gatz et al. (1991) Mol. Gen. Genet. 227: 229-237, and U.S. Pat. Nos. 5,814,618 and 5,789,156), herein incorporated by reference.

Alternatively, tissue specific (root, leaf, flower, and seed for example) promoters (Carpenter et al. 1992, Denis et al. 1993, Opperman et al. 1993, Yamamoto et al. (1991) Plant Cell 3:371-82, Stockhause et al. 1997; Roshal et al., 1987; Schernthaner et al., 1988; and Bustos et al., 1989) can be fused to the coding sequence to obtained particular expression in respective organs.

Plant transformation vectors may also include RNA processing signals, for example, introns, which may be positioned upstream or downstream of the ORF sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase (NOS) 3' terminator regions.

Finally, as noted above, plant transformation vectors may also include dominant selectable marker genes to allow for the ready selection of transformants. Such genes include those encoding antibiotic resistance genes (e.g., resistance to hygromycin, kanamycin, bleomycin, G418, streptomycin or spectinomycin) and herbicide resistance genes (e.g., phosphinothricin acetyltransferase).

Transformation and Regeneration Techniques:

Transformation and regeneration of both monocotyledonous and dicotyledonous plant cells is now routine, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumefaciens* (AT) mediated transformation.

Successful examples of the modification of plant characteristics by transformation with cloned nucleic acid sequences are replete in the technical and scientific literature. Selected examples, which serve to illustrate the knowledge in this field of technology include, but are not limited to, U.S. Pat. No. 5,571,706 ("Plant Virus Resistance Gene and Methods"); U.S. Pat. No 5,677,175 ("Plant Pathogen Induced Proteins"); U.S. Pat. No. 5,510,471 ("Chimeric Gene for the Transformation of Plants"); U.S. Pat. No. 5,750,386 ("Pathogen-Resistant Transgenic Plants"); U.S. Pat. No. 5,597,945 ("Plants Genetically Enhanced for Disease Resistance"); U.S. Pat. No. 5,589,615 ("Process for the Production of Transgenic Plants with Increased Nutritional Value Via the Expression of Modified 2S Storage Albumins"); U.S. Pat. No. 5,750,871 ("Transformation and Foreign Gene Expression in *Brassica* Species"); U.S. Pat. No. 5,268,526 ("Overexpression of Phytochrome in Transgenic Plants").

Selection of Transformed Plants:

Following transformation and regeneration of plants with the transformation vector, transformed plants are usually selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

After transformed plants are selected and grown to maturity, they can be assayed using the methods described below to assess whether a constitutive SAR phenotype is expressed.

Assessment of Systemic Acquired Resistance (SAR) Response:

The SAR response can be distinguished from other disease resistance responses both functionally and at the molecular level. Functionally, the SAR provides enhanced resistance against a broad spectrum of pathogens. At the molecular level, the SAR response is associated with the expression of a number of SAR-specific proteins.

SAR proteins are proteins that are closely associated with the maintenance of a resistance response; many of these proteins belong to the class of pathogenesis-related (PR) proteins. PR proteins were originally identified in tobacco as novel proteins that accumulate after TMV infection (Ryals et al., 1996). In tobacco, SAR proteins fall into about nine families: acidic forms of PR-1 (PR-1a, PR-1b and PR-1c); beta-1,3-glucanase (PR-2a, PR-2b and PR-2c); class II chitinases (PR-3a and PR-3b, also termed PR-Q); hevein-like protein (PR-4a and PR-4b); thaumatin-like protein (PR-5a and PR-5b); acidic and basic isoforms class III chitinase; an extracellular beta-1,3-glucanase (PR-Q'); and the basic isoform of PR-1 (Ward et al., 1991). In *Arabidopsis*, the SAR marker proteins are PR-1, PR-2 and PR-5 (Uknes et al., 1992). The genes encoding these SAR markers have been cloned and characterized and used extensively to evaluate the onset of SAR (see Ward et al., 1991, and Uknes et al., 1992). The relative expression of the various SAR proteins vary between species. For example, acidic PR-1 is weakly expressed in the SAR response in cucumber, but is the predominant SAR protein in tobacco and *Arabidopsis*. Conserved homologs of SAR proteins, including PR-1, have been identified in monocotyledenous species, including maize and barley.

The PR-1 proteins are highly conserved and so represent a good molecular marker for detecting SAR. A constitutive SAR response may thus be detected by growing plants in the absence of pathogen, and then assaying for the expression of PR-1 RNA or protein. Plants carrying the R gene that are either exposed or not exposed to the pathogen may be used as positive and negative controls, respectively. Because PR-1 proteins are highly conserved, antibodies that raised against the tobacco PR-1 proteins, including the PR-1c protein, also recognize PR-1 proteins from other plant species (see Takahashi et al., 1994). Therefore, anti-PR-1 antibodies may conveniently be used across a range of plant species to detect SAR proteins.

At the functional level, the SAR response provides enhanced resistance to a wide range of pathogens. While the individual assays for detecting such resistance will vary depending on the particular pathogen, the general observation of enhanced resistance against a number of pathogens (compared to a control R plant) in the absence of a prior triggering infection is indicative of a constitutive SAR response.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened. While the invention does not depend of any particular reduction in the severity of disease symptoms, the methods and plants of the invention will generally reduce the disease symptoms resulting from a pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

EXAMPLE 1

Methods and Materials

Identification of *Arabidopsis* Knockout Mutants and Generation of Double Mutants

*Arabidopsis* homozygous knockout plants were isolated from plants germinated from the Salk T-DNA insertion collection using PCR analysis[31]. The effects of the T-DNA insert on the interrupted genes were confirmed by Northern blot analysis or RT-PCR. The primers used for analysis of mutants are listed in supplementary Table 1.

*Arabidopsis* AtSR1 homozygous knockout line atsr1-1 (Salk_001152) was crossed with ics1/sid2 (Salk_088254), pad4 (Salk_089936), eds5 (Salk_091541). Double mutants were selected from the F2 population by PCR analysis.

Pseudomonas syringae Infection, Time Course Induction and Disease Resistance Assay

*Pseudomonas syringae* pv. tomato DC3000 culture and inoculation was performed as previously described[32, 33]. Briefly, leaves of 4- to 5-week-old plants grown at 25-27° C. with 12 hr photoperiod were infiltrated with Pst. DC3000 at $OD_{600}$=0.001 in 10 mM $MgCl_2$ for time course induction and disease resistance test. Leaves of 5-week-old plants grown at 19-21° C. with 12 hr photoperiod were infiltrated with Pst. DC3000 at $OD_{600}$=0.0001 in 10 mM $MgCl_2$ for disease resistance assay. Each disease resistant result is the average of 4 replicates, the results are presented mean±s.d.

Detection of $H_2O_2$ and Autofluorescence

In situ $H_2O_2$-detection was performed essentially as described earlier[34]. Leaves from WT and mutant plants were vacuum-infiltrated with 1 mg/ml, 3,3'-diaminobenzidine (DAB) (Sigma). The infiltrated leaves were incubated in the DAB solution for 6 hours under high humidity conditions. Leaves were fixed and cleared of chlorophyll with several changes of a 1:3:1 mixture of lactic acid:ethanol:glycerol and mounted in Tris/glycerol and examined under a dissecting scope for reddish-brown precipitate. Autofluorescence compounds were detected with a fluorescence microscope with a 488 nm excitation and 510 emission filter[35].

Measurement of SA through HPLC

SA quantification was performed as previously described[36] with minor modification. Briefly, leaf tissue was collected from 5-week-old plants. For each sample, 150-200 mg tissue was ground in liquid nitrogen, and extracted with 90% methanol. After the extraction was dried, 500 I of 5% trichloracetic acid was added to the residue. The free SA was extracted from the aqueous phase with ethylacetate-cyclopentane (1:1), and the organic phase was dried under nitrogen. The conjugated SA in the aqueous phase was hydrolyzed at 100° C. in HCl solution with pH 1 for 30 minutes. The released free SA was extracted with organic mixture and dried as described above.

The dried extract was dissolved in 100 µl HPLC mobile phase, and 10 µl was injected into the HPLC column(SPHERISORD™ ODS-2, 4.6×150 mm, 5 µm, Waters), and chromatographic separation was performed at 40° C. with a flow rate of 1.0 ml/min. SA was detected by a fluorescence detector.

Wild-Type and Mutated Versions of AtSR1 cDNA and −1.5 kb EDS1 Promoter

Full-length AtSR1 cDNA was isolated from an *Arabidopsis* ZAP Express® (Stratagene) by library screening. The full-length AtSR1 cDNA was cut from the pBK-CMV vector with BamH I and Xba I and cloned into a modified pBluescript II KS+ vector without a Sac I site for DNA manipulation. The 3' region starting from the SacI site in AtSR1 cDNA to the end of the coding sequence covering the CaM-binding domain was re-synthesized with PCR to generate site-directed and deletion mutants[32] (FIG. 5b) and also to remove the stop codon and add an Xba I site for the purpose of fusing to the Flag Tag, these fragments were used to replace the original 3' region of AtSR1 cDNA clone to produce wild-type and mutated versions of AtSR1 cDNA.

The -1.5 kb EDS1 promoter region (EDS1P) was amplified from genomic DNA using EDS1 P-F (GCAAGCTTA-GAGCTTTTAAGAATATTATGCACAAGAGAGAG; SEQ ID NO:37) and EDS1 P-R (GCGGATCCTGATCTATATC-TATTCTCTTTTCTTTAGTGGA CTTTCTT; SEQ ID NO:38) primers. Site-directed mutagenesis was used to change its ACGCGT(-746-741) to ACCCGT(eds1p mutant)[32].

Preparation of Expression Constructs

Bacterial expression constructs for recombinant AtSR1 and AtSR6 proteins: the 3' region of AtSR1 containing the CaMBD or the 5' region, AtSR1 or AtSR6 covering the CG-1 DNA binding domain were re-synthesized with PCR and EcoR I and Xho I sites were added to the 5' and 3' end of these fragments, and cloned into pET32A between its EcoR I and Xho I sites. The coding region of ABF1 was amplified by PCR, BamH I and Xho I sites were added to 5' and 3' end of the fragments and were cloned into pET32a.

Plant expression constructs: The plant expression vector pDL28F is a derivative of pCambia1300 (AF234296) containing an extra cassette of "35S promoter-MCS-Flag-35S PolyA" modified from pFF19[37]. Wild-type and mutated versions of AtSR1 full-length c without a stop codon were cloned into pDL28F between its BamH I and Xba I sites and fused to its Flag tag. NahG (M60055) was also cloned into pDL28F but not fitted into the reading frame of Flag tag. The –1.5 kb EDS1 promoter and its mutated version were digested with HindIII and BamHI and used to replace the 35S promoter in pDL28F. The coding region of luciferase (ABL09838) was amplified by PCR using Luc-F (GCGGATCCATGGAA-GACGCCAAAAACATAAAGAAAGG; SEQ ID NO: 39) Luc-F; and Luc-R (GCGTCGACTTACAATTTG-GACTTTCCGCCCTTCTTGG; SEQ ID NO: 40) primers, and cloned into the pDL28F/EDS1P to produce EDS1P::Luc (pDL326) or into pDL28F/eds1p to produce eds1p::Luc (pDL327) constructs. Flower dipping approach was used to deliver plant expression constructs for stable transformation.

Recombinant Protein Purification, EMSA, and [35]S-CaM Binding Assay

The *E. coli* strain BL21(DE3)/pLysS carrying the above pET32a derived plasmids for expression of recombinant proteins of the wild-type and mutated versions of AtSR1, AtSR6 or ABF1 were induced with 0.5 mM IPTG for 3 hours. 6×His tagged recombinant proteins were purified using Ni-NTA agarose affinity beads (Qiagen) as described by the manufacturer. Recombinant AtSR1 or AtSR6 covering CG-1 domain, or ABF1 was used for EMSA[32] to detect its interaction with WT or mutated EDS1 promoter fragments. Recombinant AtSR1 containing CaMBD was used for CaM overlay assay[38].

ChIP Analysis

Thirty million leaf mesophyll protoplasts from 4-week old WT *Arabidopsis* plants were transfected with 60 µg of YFP control or AtSR1-YFP with the PEG-mediated transformation method[39]. Protoplasts were incubated at 25° C. under dark for 16 hours before ChIP assay[40]. The harvested cells were resuspended in W5 medium containing 1% formaldehyde and cross-linked for 20 minutes. The protoplasts were lysed and was sheared on ice with sonication. The pre-cleared lysate was incubated with 60 µl anti-GFP Agarose beads (D153-8, MBL) for 12 hours at 4° C. Beads were washed five times, resuspended in elution buffer and incubated at 65° C. for 12 hours. After purification, the was amplified with PCR using EDSUE-F (TGGCTTTTCGTAGAAATTTCCC; SEQ ID NO:51) and EDSUE-R (GGAACCGGTTC-GATTTCTCTC; SEQ ID NO:52) primers.

Eds1: Luciferase Transient Expression Assays

One million protoplasts from 4 to 5-week old WT and atsr1-1 plants grown at 20° C. were transfected in four replicates with 5 µg GUS plasmid (as internal control) and 5 µg pDL326 or pDL327 plasmids with the PEG-mediated transfection method[39]. After 16 to 17 hours incubation at 20° C., the protoplasts were harvested and luciferase assays were performed using a luciferase assay kit (Promega). To account for variation in transfection efficiencies, GUS assays were performed with each treatment using standard Methyl Umbelliferyl Glucoronide substrate. The data presented are the average of LUC/GUS ratios of four replications±SD.

EXAMPLE 2

The atsr1-1 Mutant was Shown to Have Sensitized Defense Responses when Compared to Wildtype In these experiments, two loss-of-function mutants (atsr1-1 and atsr1-2) isolated were isolated (FIGS. 5 panel a, 6 panel a, 6 panel e). At 25-27° C. (12-hr or other photoperiods), no noticeable difference between the wild-type (WT) and atsr1 mutants was observed (FIG. 1 panel a). 32-day (left) and 35-day (right) old plants grown at indicated temperature.

Supplementary table 1:
list of primers for characterizing *Arabidopsis* mutants

| Gene | mutant line | L primer | R primer |
| --- | --- | --- | --- |
| AtSR1 | Salk_001152 | GAACTACTGAACATTTTCTAGAAGTTACTCAC (SEQ ID NO: 41) | TGTTTGGGCAAACAGAAGTTC (SEQ ID NO: 42) |
|  | Salk_064889 | TTCAGCCCAGTTCATGAATTAG (SEQ ID NO: 43) | CCATCCATGTCCCTCCTAGA (SEQ ID NO: 44) |
| PAD4 | Salk_089936 | TCATTCCGCGTCTTTTGTATC (SEQ ID NO: 45) | CAAAGATCTCCTCTGGGGATC (SEQ ID NO: 46) |
| EDS5 | Salk_091541 | ATGGGAACTCACGTTTTAGCC (SEQ ID NO: 47) | TCTCCACCGTGTATGGACTC (SEQ ID NO: 48) |
| ICS1 | Salk_088254 | ACTTATTTTCTGGCCCACAAAAC (SEQ ID NO: 49) | CACTTTACGAATTTCTGCAATGG (SEQ ID NO: 50) |

However, atsr1-1 showed elevated resistance to virulent *Pseudomonas syringae* pv. tomato DC3000 (Pst DC3000) (FIG. 1 panel b), as well as avirulent Pst (AvrRpt2) (data not shown). Pst. DC3000 ($OD_{600}$ 0.001) was infiltrated into rosette leaves (4 weeks, 25-27° C.), and the cfu of 3 days post inoculation (dpi) was presented. Since elevated resistance to pathogens is usually correlated with induced expression of PR genes[10], applicants analyzed the expression of PR1 in WT and atsr1-1 plants inoculated with Pst DC3000. In WT PR1 expression did not start until 24 hours after inoculation, whereas in atsr1-1 its expression started 6 hours after inoculation. However, the maximum expression of PR1 remained similar between WT and atsr1 (FIG. 1 panel c). Rosette leaves (4 week old, 25-27° C.) were infiltrated with Pst DC3000 ($OD_{600}$ 0.001), samples were taken at indicated time for Northern blot. The elevated disease resistance and sensitized PR1 expression in atsr1-1 indicate that it is a repressor of plant immunity.

At 19-21° C. (12-hr photoperiod), atsr1-1 showed reduced growth in terms of fresh rosette weight (5 weeks, 19-21° C.). (FIGS. 1 panel a, 1 panel d, 6 panel d). The expression of systemic acquired resistance-associated marker genes[10], PR1, PR2, and PR5, was constitutively activated under lower temperature in atsr1-1 plants (FIG. 1 panel f). Total RNA samples were prepared from rosette leaves grown at 19-21° C.; identical blots were hybridized to indicated probes. Predictably, the disease resistance of atsr1-1 was also enhanced as compared to plants grown under higher temperature (FIGS. 1 panel b, 1 panel e). Pst. DC3000 ($OD_{600}$ 0.0001) was infiltrated into rosette leaves (19-21° C.), and the cfu of 3 dpi was presented. The atsr1 plants displayed chlorosis and autonomous lesions when compared to wildtype of same age (FIGS. 1 panel g, 6 panel b, 6 panel d). Plants undergoing HR produce ROS and autofluorescent compounds[11, 12]. Staining for $H_2O_2$ with 3,3'-diaaminobenzidine (DAB) revealed numerous brown patches on atsr1-1 leaves, which were comparable to similar age WT plants infected with incompatible Pst (AvrRpt2) (FIGS. 1 panel h, 7). atsr1-1 leaves also showed extensive autofluorescence (FIG. 1 panel i). Autofluorescence image of WT (left) and atsr1-1(right). All plants were grown under 12 hr photoperiod, all data are expressed as mean±s.d (n=4), and Ethidium bromide stained rRNA was used as loading control for all Northern blot (rRNA). These results indicate that atsr1 plants grown at a lower temperature exhibit hallmarks of constitutive defense responses commonly found in lesion-mimicking mutants[11] or WT plants inoculated with avirulent bacterial pathogens[12]. The temperature-dependent autoimmunity further suggests that AtSR1 represses R-protein-mediated defense activation. Recent reports show that the stability of active R proteins is regulated by co-chaperone RAR1 in plants in a temperature-dependent manner with lower temperatures favoring the accumulation of R proteins[13, 14]. Conceivably, lower temperatures could favor the accumulation of some R proteins in *Arabidopsis*, but AtSR1 represses the mis-activation of defense whereas its absence in atsr1 does not. The expression of AtSR1 cDNA in atsr1 restored all mutant phenotypes (FIG. 8), confirming that the atsr1 phenotypes are caused by loss of AtSR1.

EXAMPLE 3

The Pleiotropic Phenotype of atsr1-1 was Shown to be Dependent on Salicylic Acid (SA)

Figures 2A, 2B, 2C, 2D, 2E, 2F:
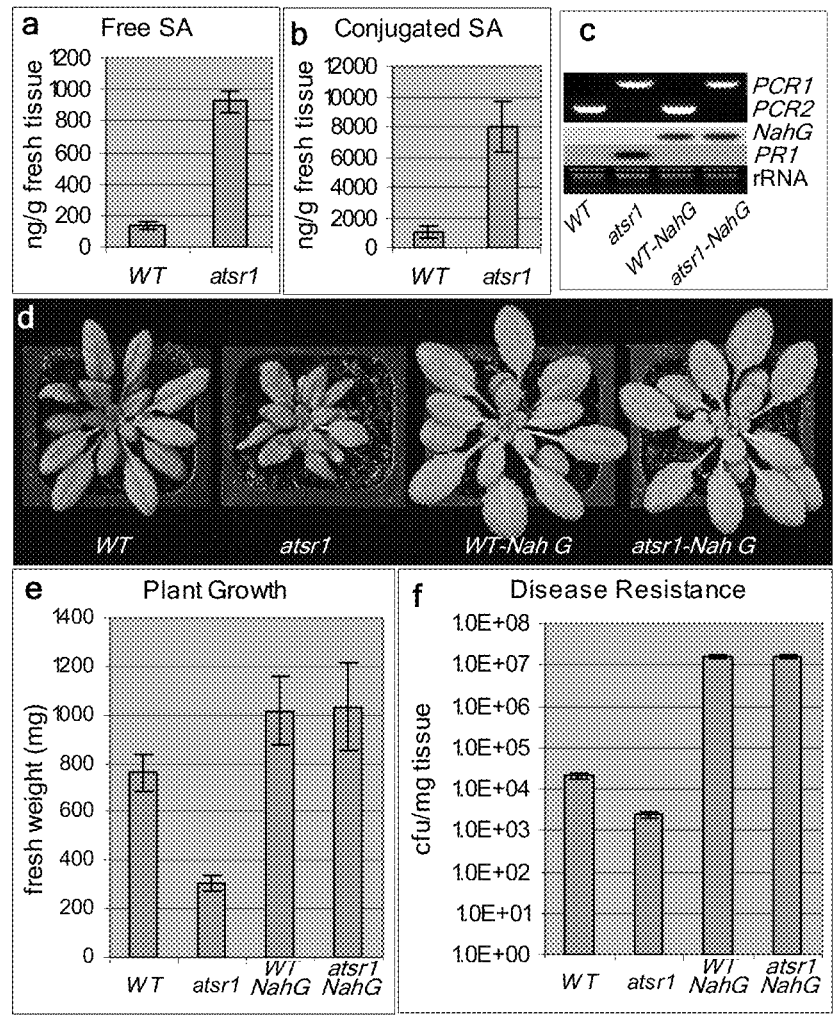
FIG. 2 shows, according to particular exemplary embodiments, that the pleiotropic phenotype of atsr1-1 is dependent on salicylic acid (SA).
Figure 9:
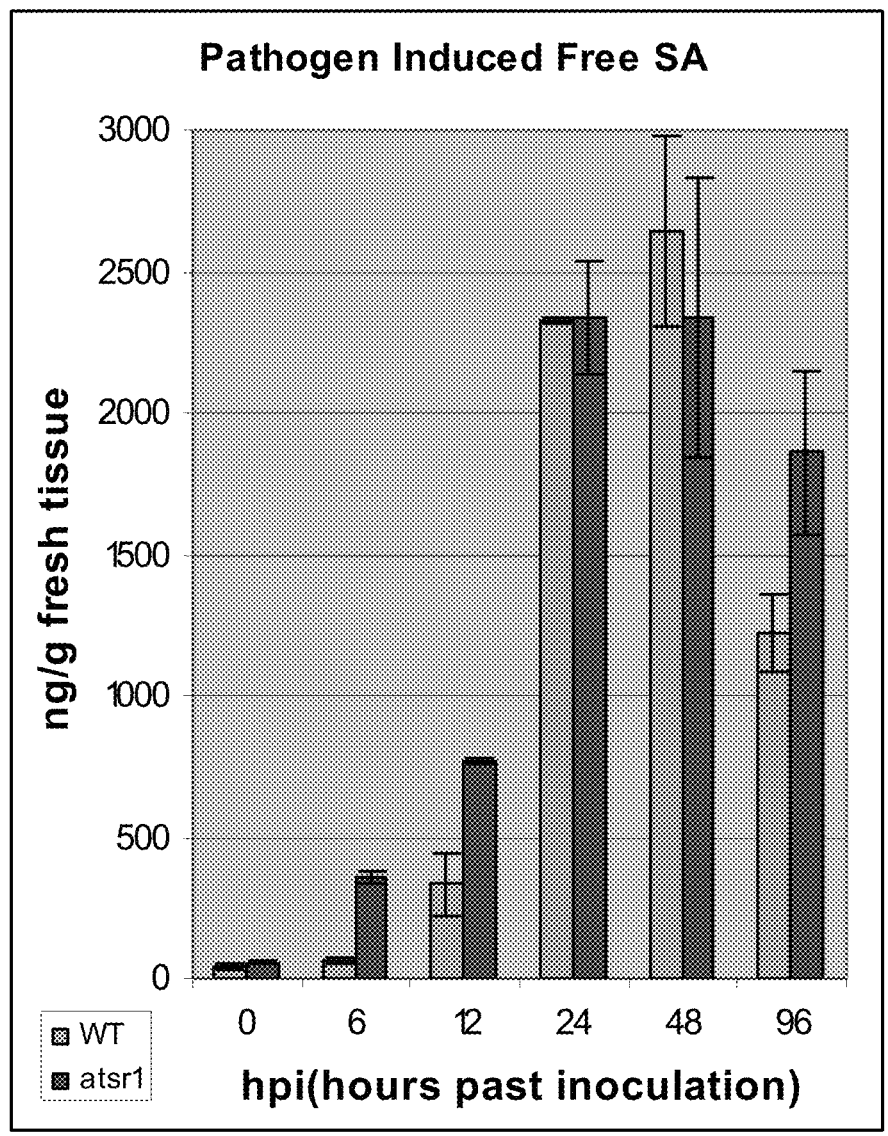
FIG. 9 shows, according to particular exemplary embodiments, pathogen induced SA accumulation in WT and atsr1-1(atsr1) grown at 25-27° C.

Since atsr1s resemble mutants with increased SA level[11, 15], Applicants quantified SA in the mutant and WT plants grown at 19-21° C. for five days. Free and conjugated SA levels were increased ~7- and ~8-fold, respectively, in the atsr1-1 (FIGS. 2 panel a, 2 panel b). In uninfected plants grown at 25-27° C., SA levels in atsr1 and WT were similar. However, the SA level increased faster in atsr1 than in WT when inoculated with Pst. DC3000 (FIG. 9). Previous studies have shown that elevating SA alone is enough to cause an enhanced immune response and reduced growth[2, 16]. Expressing the SA-degrading enzyme NahG suppressed both disease resistance and retarded growth in some disease resistant mutants (acd6, bon1 and ssi1) with elevated SA levels[15, 17], but only disease resistance in other mutants (mpk4 and dnd1)[18, 19]. To determine if the reduced growth and enhanced disease resistance of atsr1 are caused by elevated SA level or other mechanism(s), Applicants eliminated SA by expressing NahG in WT and atsr1-1. WT and atsr1-1 plants expressing NahG, appeared to be similar but both were bigger than the WT (FIGS. 2 panel c, 2 panel d, 2 panel e). Furthermore, constitutively activated PR1 expression was blocked in atsr1-1 NahG as shown in Northern blots with rRNA used as loading control (FIG. 2 panel c); both atsr1-1 NahG and WT NahG plants were more sensitive to Pst DC3000 than WT (FIG. 2 panel f). Pst. DC3000 ($OD_{600}$ 0.0001) was infiltrated into rosette leaves, and the cfu of 3 dpi was presented. All plants were grown at 19-21° C. with 12 hr photoperiod for 5 weeks, and all data are expressed as mean±s.d (n=4). These results indicate that the elevated SA level is the major cause of atsr1-1 phenotypes.

Figures 10A, 10B, 10C, 10D, 10E:
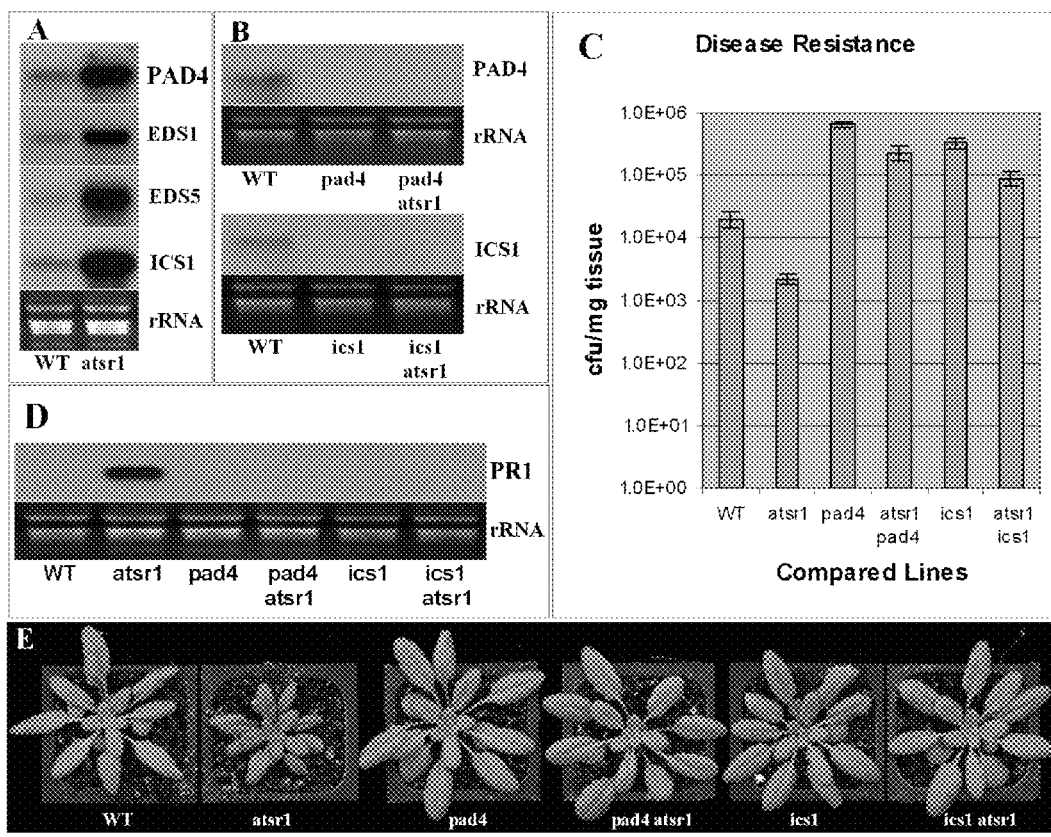
FIG. 10 shows, according to particular exemplary embodiments, epistasis analysis of AtSR1 and key SA signaling components.

Consistent with elevated SA levels, the expression of ICS1, PAD4, EDS1 and EDS5, important positive regulators of SA biosynthesis, are highly induced in atsr1-1 (FIG. 10 panel a). ICS1, PAD4, EDS1 and EDS5 are arranged in a sequential order of PAD4/EDS1, EDS5, and ICS1[2, 20, 21]. The expression of EDS1, PAD4 and EDS5 is induced by SA[2] and ICS1 is induced in the constitutively resistant mutant[22]. Therefore, the elevated expression of these genes in atsr1 could either be the direct result of a failure in AtSR1 regulation, or merely the consequence of constitutively activated immunity and elevated SA. Epistasis analysis between atsr1 and these regulators could lead us closer to the AtSR1-regulated step. Since there are two closely linked functional EDS1 genes in Columbia ecotype[17], it was not used for epistasis analysis. The pad4 and ics1, atsr1-pad4 and atsr1-ics1 double mutants were more sensitive to Pst DC3000 than the WT (FIG. 10 panel c). Furthermore, in the double mutants constitutive expression of PR1 and the dwarf phenotype of atsr1-1 is restored to WT level (FIGS. 10 panel d, 10 panel e). The eds5 mutation also blocked the atsr1 phenotypes (data not shown). These results suggest that AtSR1 functions at a step no later than PAD4 in the SA activation cascade.

EXAMPLE 4

AtSR1 was Shown to be Involved in Transcriptional Regulation of EDS1

Figures 3A, 3B, 3C, 3D, 3E:
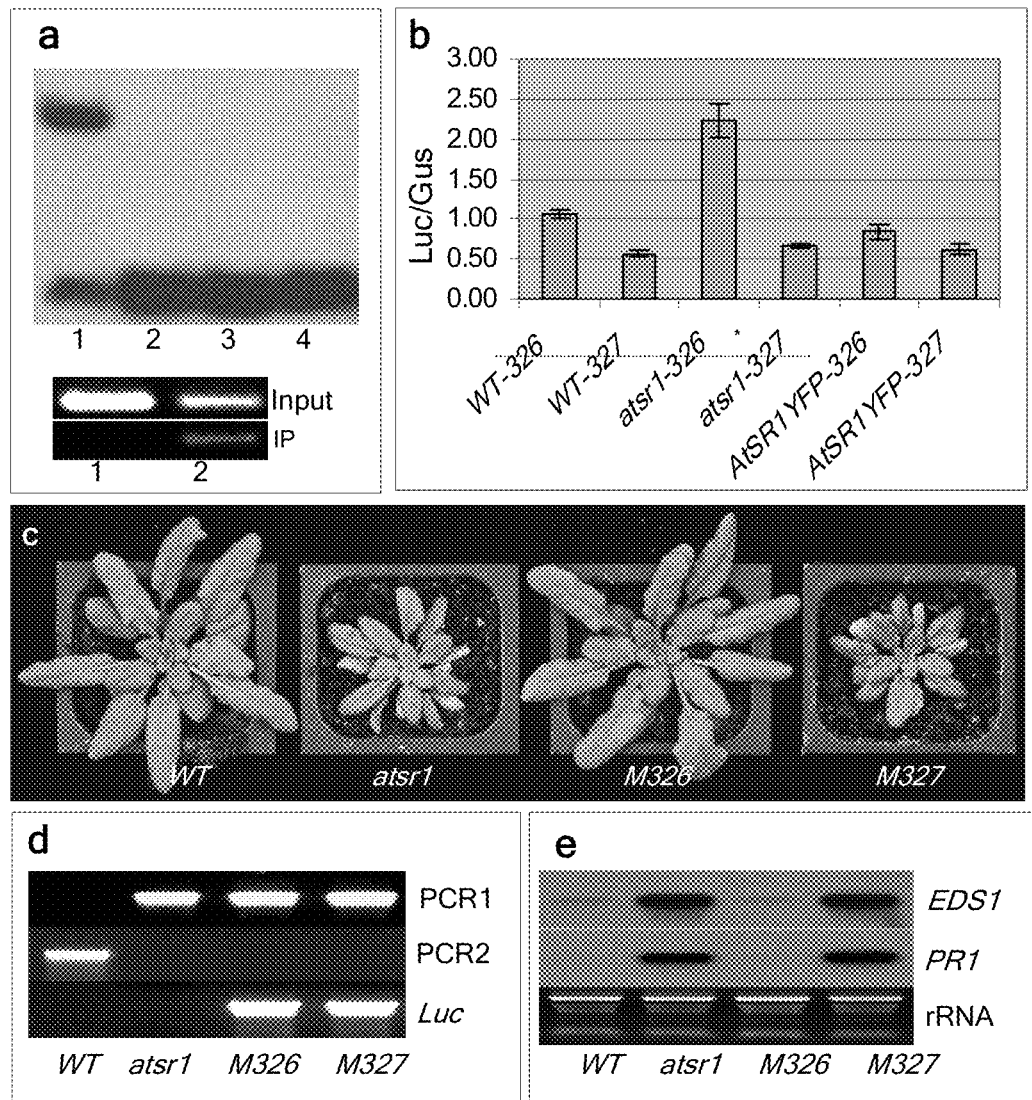
FIG. 3 shows, according to particular exemplary embodiments, that AtSR1 is involved in transcriptional regulation of EDS1.
Figures 11A, 11B, 11C:
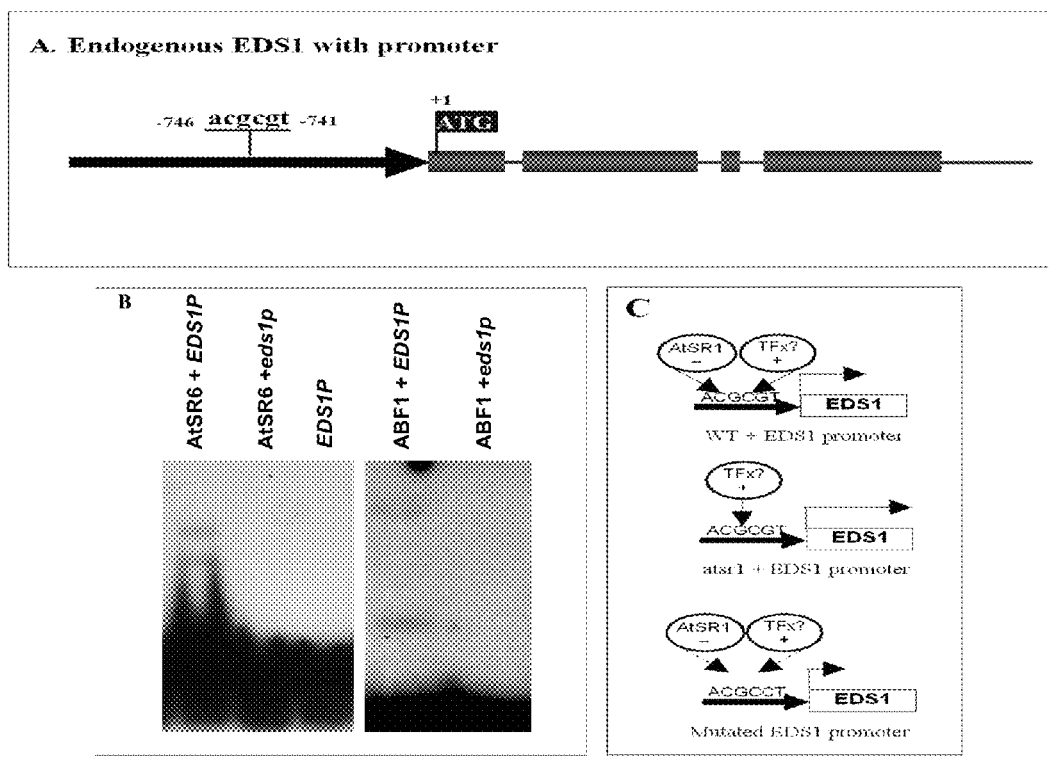
FIG. 11 shows, according to particular exemplary embodiments, schematic illustration of EDS1 structure and interaction of transcription factors with EDS1 promoter.

AtSR1 and its homologs bind to the conserved CGCG box and regulate the expression of target genes[6, 8]. Analysis of ICS1, PAD4, EDS1 and EDS5 promoters revealed a typical CGCG box (ACGCGT) only in the EDS1 promoter (-746 to -741, FIG. 11 panel a), indicating a direct regulation of EDS1 by AtSR1. We showed that the AtSR1 DNA-binding domain (1-153 aa) binds the EDS1 promoter fragment (-762 to -731) in an ACGCGT-dependent (FIG. 3 panel a), and $Ca^{2+}$/CaM-independent manner (data not shown). ChIP assay further confirmed that a full-length AtSR1-YFP interacts with EDS1 promoter in vivo (FIG. 3 panel a). To study the functional significance of AtSR1 binding to the EDS1 promoter, the -1.5 kb promoter of EDS1(EDS1P) was cloned and the ACGCGT element was mutated to ACCCGT (eds1p mutant) to abolish its interaction with AtSR1. Both EDS1P and eds1p were fused to luciferase (Luc) and expressed in protoplasts of WT, atsr1-1 and atsr1-1 expressing 35S::AtSR1YFP. The EDS1P::Luc (pDL326) activity was about 2-fold higher in atsr1-1 than in WT (FIG. 3 panel b), indicating that AtSR1 negatively regulates EDS1. Predictably, EDS1 promoter activity in atsr1-1 protoplasts overexpressing AtSR1 is reduced to a level slightly lower than that in WT (FIG. 3 panel b). This, together with a recent report that elevated expression of EDS1 alone is adequate to constitutively activate immunity[23], indicate that the derepression of EDS1 in atsr1 could have caused the constitutive immunity. Logically, eds1p does not bind AtSR1 and should result in elevated activity even in WT if AtSR1 is the only trans-acting factor binding to the mutated region. Surprisingly, the activity of eds1p::Luc (pDL327) decreased to a similar level and is significantly lower than that of the EDS1P in all three cases (FIG. 3 panel b). These results suggest that the ACCCGT mutation may have interfered with the binding of other trans-acting factor(s) to the CGCG box or a recognition core overlapping it, which is essential for the basal and/or induced transcription of EDS1. Our data indicate that these kinds of TFs do exist in *Arabidopsis* (FIG. 11 panel b). According to particular aspects, a model presented in FIG. 11 panel c, illustrates the regulation of EDS1 promoter.

Figures 12A, 12B, 12C:
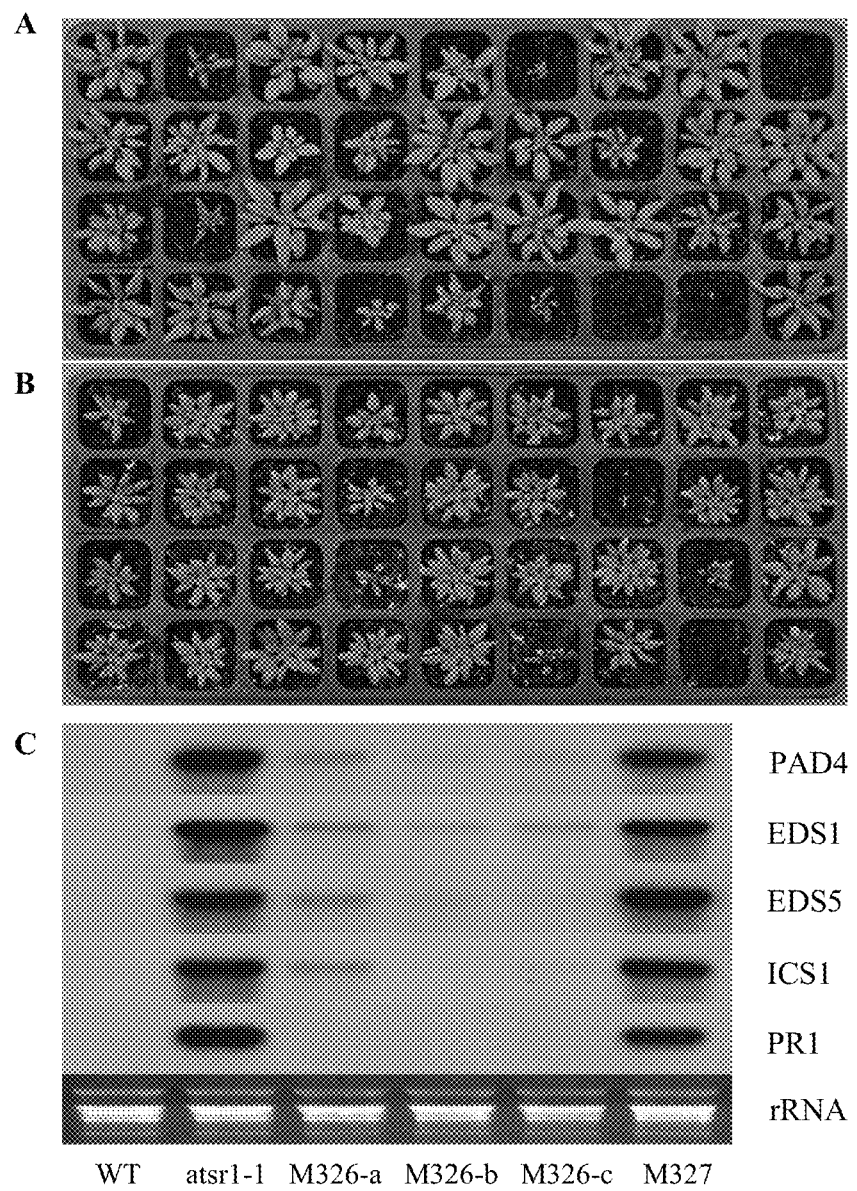
FIG. 12 shows, according to particular exemplary embodiments, plants carrying EDS1 promoter in atsr1-1 background.

The activity of EDS1::Luc is ~2-fold higher in atsr1 (FIG. 3 panel b), noticeably less than the 4- to 5-fold difference revealed by Northern analysis (FIG. 10 panel a). Besides the diluted feed-back induction of EDS1 by SA or other messengers by protoplast maintaining buffer, the introduction of extra copy(ies) of EDS1 promoter into atsr1 may have reduced the induction of EDS1P::Luc as well as endogenous EDS1, since the elevated expression of EDS1 in atsr1 is driven by unidentified positive TF(s) (see model, FIG. 11 panel c). To test this, we generated stable WT and atsr1 transformants carrying pDL326 or pDL327. All WT plants (grown for 39-days) carrying pDL326 or pDL327 grew like WT (data not shown); all the atsr1-1 plants carrying pDL327 (M327) grew like atsr1-1 (FIGS. 3 panel c, 12 panel b). Interestingly, most of the atsr1-1 plants carrying pDL326 (M326) showed varying degrees of phenotypic rescue (FIG. 12 panel a). Nearly 10% of them grew like WT during their entire life cycle (FIGS. 3 panel c; 12 panel a) and lacked AtSR1 (FIG. 3 panel d). Remarkably, the expression of endogenous EDS1 in these lines was restored to WT level (FIGS. 3 panel e, 12 panel c), indicating that the phenotypic restoration is due to the quenched EDS1 expression. Consistently, constitutive PR1 expression was also abolished in rescued M326 lines (FIGS. 3 panel e, 12 panel c). Segregation analysis of T2 progeny of M326 lines indicated that the phenotypic rescue is mostly correlated with particular insertion events rather than dosage effect of insertion (data not shown). It appears that insertion of EDS1 promoter at some particular positions in the atsr1 genome competes for the ACGCGT-binding positive regulator(s) and quenches the endogenous EDS1 expression, although the precise mechanism remains to be resolved. Failure of eds1p::Luc to rescue the atsr1 phenotype (FIGS. 3 panel c, 3 panel e, 12 panel b) further supports this notion.

EXAMPLE 5

Figures 4A, 4B, 4C, 4D, 4E, 4F, 4G:
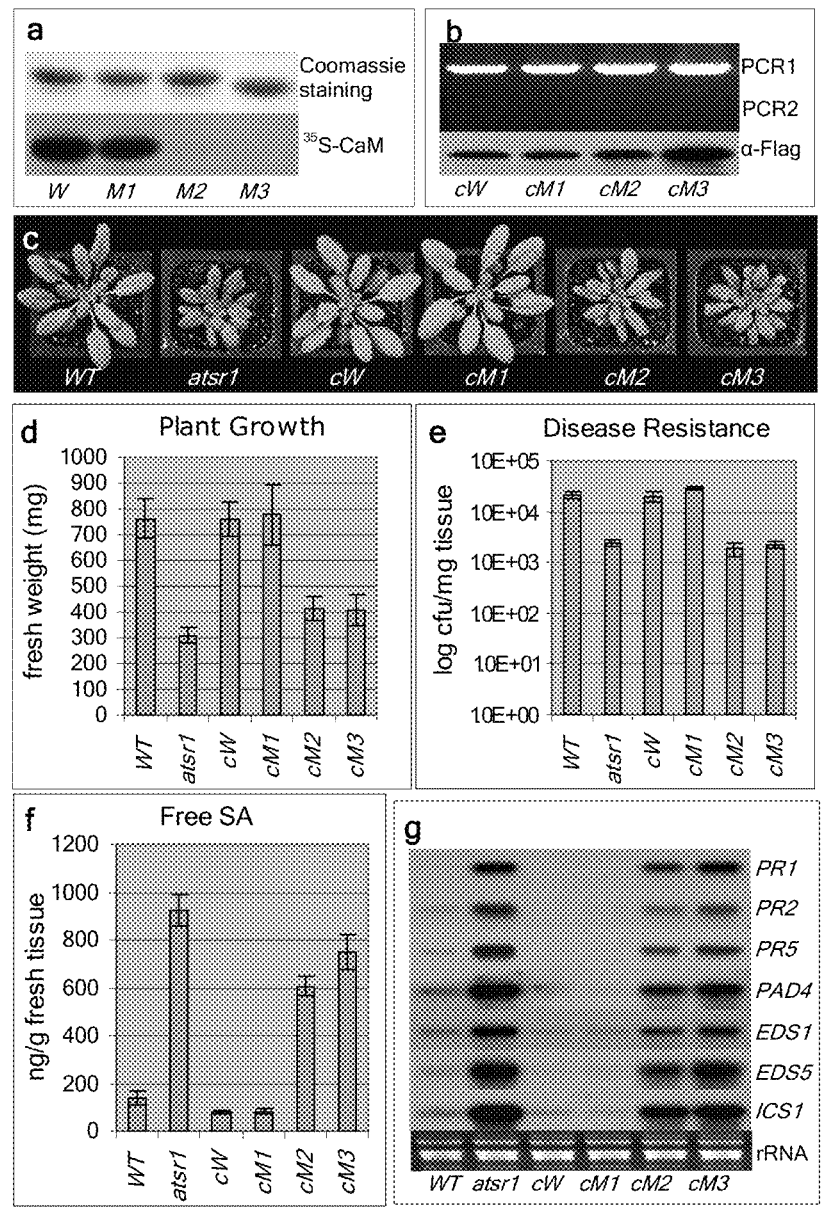
FIG. 4 shows, according to particular exemplary embodiments, that the repression of immune response by AtSR1 is regulated by $Ca^{2+}$/CaM.
Figures 5A, 5B:
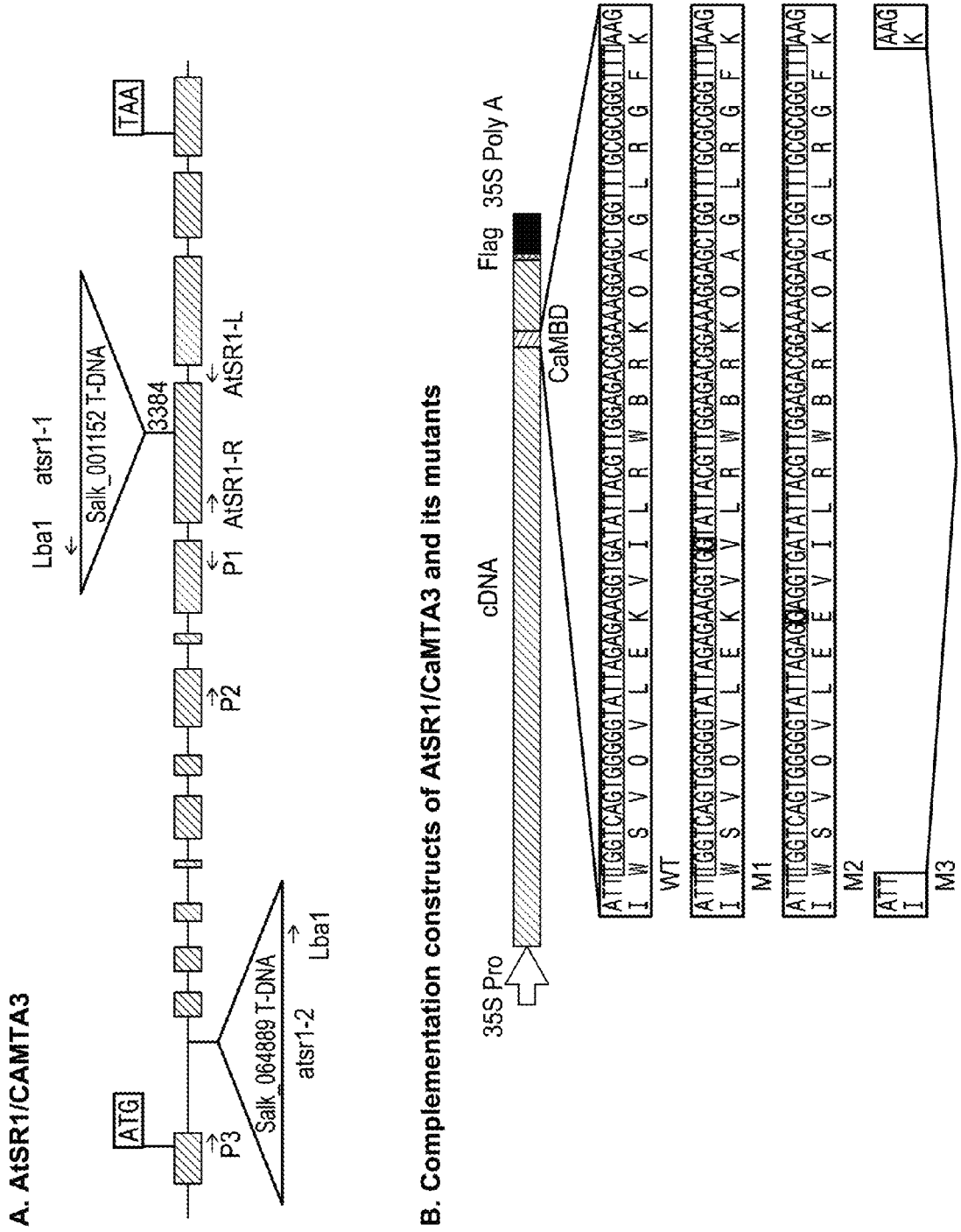
FIG. 5 shows, according to particular exemplary embodiments, a schematic illustration of AtSR1/CaMTA3 and its complementation constructs. The first mutation I909V (M1) nucleotide and amino acid sequences (SEQ ID NOS:71 and 72, respectively) does not disrupt the conserved secondary structure of the AtSR1 CaMBD. The second mutation K907E (M2) nucleotide and amino acid sequences (SEQ ID NOS:73 and 74, respectively) drastically alters the surface static charge of its CaM-binding helix. The third mutation (M3) Δ900-922 nucleotide and amino acid sequences is a deletion of the whole CaMBD from aa 900 to 922 of AtSR1.

The Repression of Immune Response by AtSR1 was Shown to be Regulated by $Ca^{2+}$/CaM Functional tests of mutations in null mutant background[24,25] provide an effective strategy to study regulation of AtSR1 function by $Ca^{2+}$/CaM. Three mutations (M1=I909V; M2=K907E; M3=Δ900-922) in the CaMBD of AtSR1[5-7] were generated (FIG. 5b). WT AtSR1 and M1 bound CaM, whereas M2 and M3 did not (FIG. 4a). Purified recombinant proteins of wild-type (W), and three mutated versions I909V (M1), K907E (M2) and Δ900-922 (M3) of AtSR1 were bound to $^{35}S$ labeled calmodulin ($^{35}S$-CaM), Coomassie stained proteins were used as a loading control (Coomassie Staining). WT and mutated atsr1s were fused to Flag-tag (FIG. 5b), and expressed in atsr1-1. Most of the T1 plants (>30) complemented with 35S::AtSR1$_{I909V}$ (cM1) exhibited rescued phenotype. None of the >30 individual T1 plants complemented with either 35S::AtSR1$_{K907E}$ (cM2) or 35S::AtSR1$_{\Delta900-922}$ (cM3) were restored to the WT growth level. For accurate comparison of all the complemented lines, T2 plants with verified genotype and similar transgene expression (FIG. 4b) were compared for their phenotypes. Molecular characterization demonstrating the genotypes of the atsr1-1 plants complemented with wild-type (cW) and three mutants (cM1, cM2, cM3) of AtSR1 cDNA. PCR1, PCR2: α-FLAG: Western blot detected with anti-Flag M2 monoclonal antibody. 20 µg of total protein was loaded per lane. The atsr1-1 complemented with 35S::AtSR1 (cW) or cM1 plants were restored to WT in their morphology (FIG. 4c), growth in fresh rosette weight (FIG. 4d) and disease resistance (FIG. 4e; Pst. DC3000 (OD$_{600}$ 0.0001) was infiltrated into the tested plants, and the cfu was measured 3 days after infiltration). The level of SA in cW and cM1 plants was ~60% of WT (FIG. 4f), and expression of PR and SA signaling genes in cW and cM1 plants were also slightly lower than in WT (FIG. 4g). However, cM2 and cM3 plants resembled the atsr1-1 plants with chlorosis (FIG. 4c) and slightly increased growth (FIG. 4d). The level of SA in cM2 and cM3 plants was slightly lower than that in atsr1-1 plants, but still drastically higher than that in WT (FIG. 4f). The level of disease resistance of cM2 and cM3 plants was similar to that of atsr1-1 (FIG. 4e). Expression of PR and SA signaling genes in cM2 and cM3 plants was also slightly lower than in atsr1 but significantly higher than in WT (FIG. 4g). The fact that atsr1 mutants that lost their CaM-binding activity are compromised in their function indicates that $Ca^{2+}$/CaM-binding is required for AtSR1 to suppress plant immunity.

EXAMPLE 6

Schematic Illustration of AtSR1/CaMTA3 and its Complementation Constructs

Specifically, FIG. 5 panel A shows the endogenous AtSR1, T-DNA insert in "Salk_001152 (atsr1-1)" and "Salk_064489 (atsr1-2)" lines, and also the orientation of the primers used for checking the T-DNA insert, knockout status, and RT-PCR, AtSR1-L: GAACTACTGAACATTTTCTA-GAAGTTACTCAC; SEQ ID NO:53, AtSR1-R: TGTTT GGGCAAACAGAAGTTC; SEQ ID NO:54, "LBa1" sequence was previously described[1], "P1": CCATCCAT-GTCCCTCCTAGA; SEQ ID NO:55, "P2": TCCATTGAT-TCCCA AACCTG; SEQ ID NO:56, "P3": TTCAGC-CCAGTTCATGAATTAG; SEQ ID NO: 57.

In FIG. 5 panel B the complementation constructs of AtSR1/CaMTA3 and its mutants are shown. The CaMBD is enlarged, nucleotide and amino acid sequences of wild-type CaMBD (SEQ ID NOS:69 and 70, respectively) are in grey, the mutated positions are underlined, deleted parts are joined with a bent line. The first mutation I909V (M1) nucleotide and amino acid sequences (SEQ ID NOS:71 and 72. respectively) does not disrupt the conserved secondary structure of the AtSR1 CaMBD. The second mutation K907E (M2) nucleotide and amino acid sequences (SEQ ID NOS:73 and 74, respectively) drastically alters the surface static charge of its CaM-binding helix. The third mutation (M3) Δ900-922 is a deletion of the whole CaMBD from aa 900 to 922 of AtSR1.

EXAMPLE 7

Figures 6A, 6B, 6C, 6D, 6E:
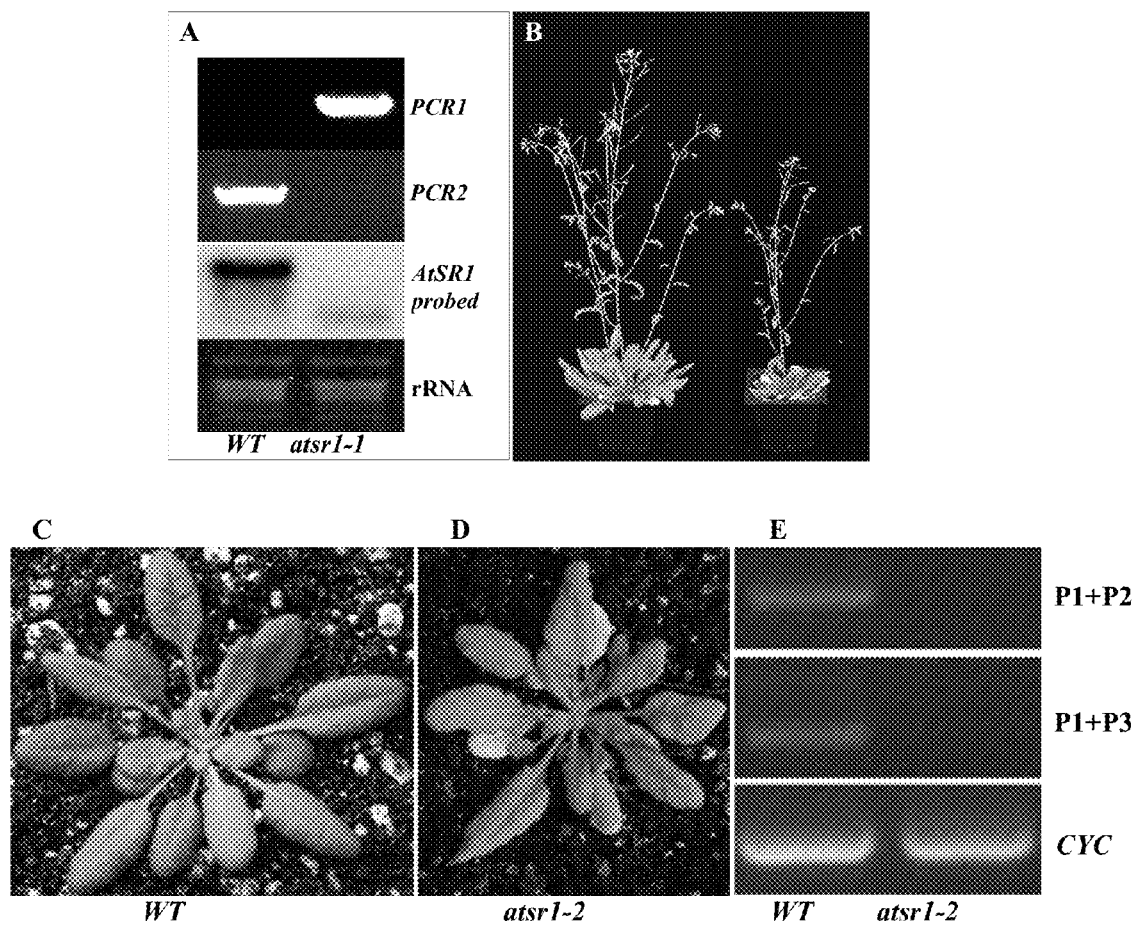
FIG. 6 shows, according to particular exemplary embodiments, a phenotypic and genotypic comparison of wild-type and atsr1 mutants.

A Phenotypic and Genotypic Comparison of Wild-Type and atsr1 Mutants was Conducted Molecular characterization demonstrating the genotype of WT and atsr1-1 is shown in FIG. 6 panel A. PCR1: DNA amplified with AtSR1 specific primer AtSR1-R and T-DNA specific primer Lba1; PCR2: DNA amplified with AtSR1 specific primer AtSR1-L and AtSR1-R (see FIG. S1*a* for primer sequences). AtSR1 probed: Northern blot shows the expression of AtSR1 gene in both WT and atsr1-1 knockout mutant, EtBR stained rRNA was used as loading control (rRNA). FIG. 6 panel B shows the phenotypic comparison between 7-week-old WT and atsr1-1 mutant plants grown at 19-21° C. with 12 hr photoperiod. FIG. 6 panel C and D shows the phenotypic comparison between five-week-old WT (C) and atsr1-2 mutant (D) plants grown at 19-21° C. with a 12-hr photoperiod. In FIG. 6 panel E the genotype of atsr1-2 was confirmed by RT PCR with AtSR1-specific primers (see Table 1). AtSR1 transcript was shown to be absent in the atsr1-2 mutant by RT-PCR using two pairs of primers: one on either side of the insertion and one downstream of the insertion (FIG. 5*a*). Expression of cyclophilin (At4g38740) was used as loading control.

EXAMPLE 8

Figure 7A:
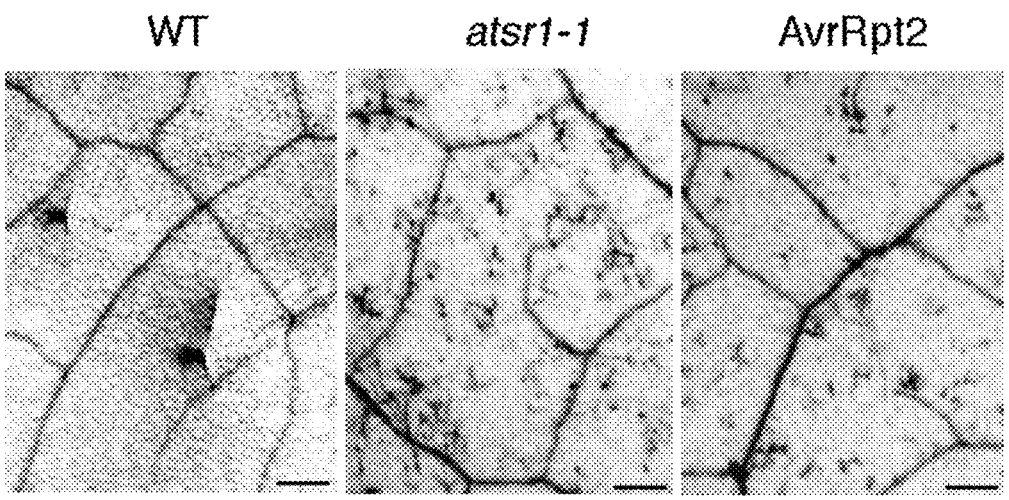
FIG. 7 shows, according to particular exemplary embodiments, staining of similar age leaves from uninfected WT, atsr1-1 and WT inoculated with *Pseudomonas syringae* pv tomato.
Figure 7B:
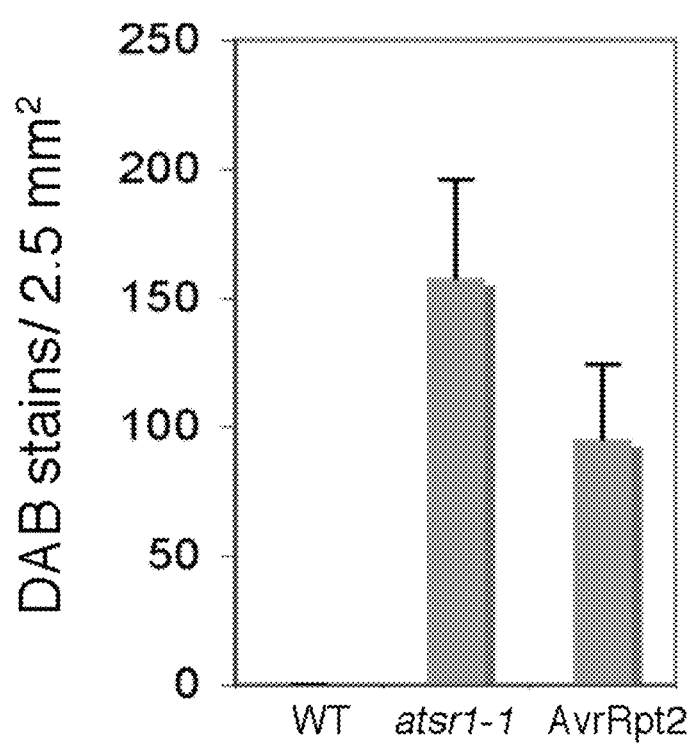

Similar Age Leaves from Uninfected WT, atsr1-1 and WT Inoculated with *Pseudomonas Syringae* pv Tomato Were Stained FIG. 7 panel A compares similar age leaves from uninfected WT, atsr1-1 and WT staining with 3,3'-diaminobenzidine (DAB). The plants were inoculated with a $10^5$ CFU $mL^{-1}$ suspension of *Pseudomonas syringae* pv tomato carrying AvrRpt2 and then stained with DAB, which reveals accumulation of $H_2O_2$ in atsr1 and WT inoculated with Pst AvrRpt2. Panel B is a graphical representation of the quantification of DAB stains per 2.5 mm². Each bar is the average of at least four leaves. Error bars represent standard deviation (SD).

EXAMPLE 9

Figures 8A, 8B, 8C, 8D, 8E:
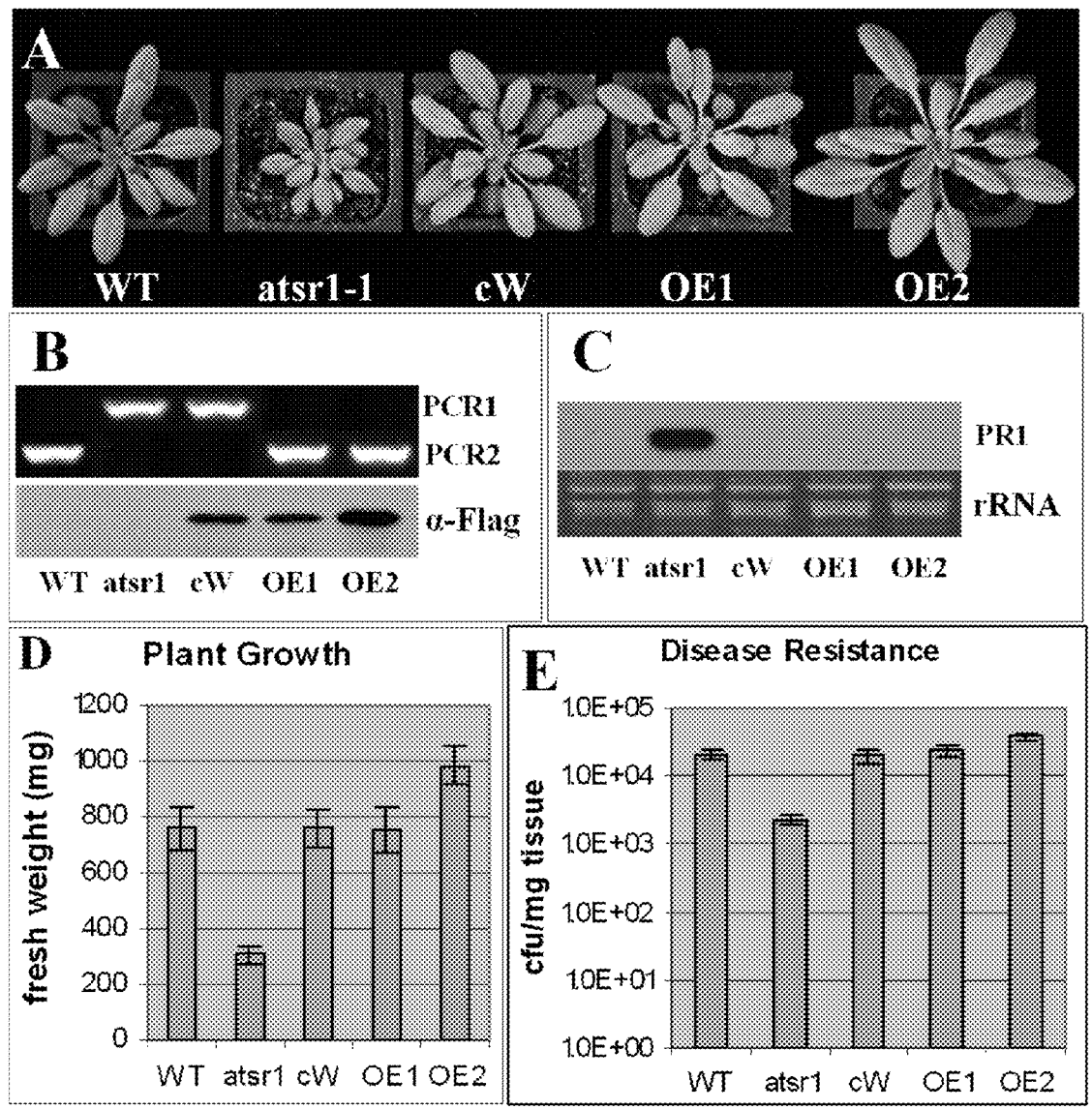
FIG. 8 shows, according to particular exemplary embodiments, the functional complementation and overexpression of AtSR1 in *Arabidopsis*.

Functional Complementation and Overexpression of AtSR1 in *Arabidopsis* was Demonstrated FIG. 8 panel A compares 5-week-old plants of wild-type (WT), atsr1-1 mutant (atsr1-1), atsr1-1 complemented with wild-type AtSR1 gene (cW), and two overexpression (OE) lines of AtSR1 gene with different transgene expression levels (OE1 and OE2). All the plants used in these experiments were grown at 19-21° C. with 12 hr photoperiod. FIG. 8 panel B is the molecular characterization demonstrating the genotype of the plant lines listed in "A". PCR1, PCR2: see "legend of FIG. 52A". atsr1-1 is marked as atsr1 in all panels hereafter. α-FLAG: 20 μg of total protein from each sample was used in the Western blot detected with anti-Flag M2 monoclonal antibody (Sigma). FIG. 8 panel C shows the PR1 expression in plant lines as listed in "A". FIG. 8 panel D compares the Growth, in terms of fresh weight measured at five weeks, between plant lines are the same as listed in "A". FIG. 8 panel E compares Disease Resistance between the plant lines as listed in "A". Pst. DC3000 (0.0001 OD600) was infiltrated into the rosette leaves, and the cfu was measured 3 days after infiltration. Data are expressed as mean±s.d (n=4, *p<0.045 by T-test).

EXAMPLE 10

Pathogen Induced SA Accumulation in WT and atsr1-1(atsr1) Grown at 25-27° C. was Demonstrated Leaves of 5-week-old plants grown at 25-27° C. with 12 hr photoperiod were infiltrated with Pst. DC3000 at $OD_{600}$=0.001. Infected leaves were collected at the indicated times after inoculation and used for free SA quantification. Each result is expressed as mean±s.d.(n=4).

EXAMPLE 11

Epistatis Analysis of AtSR1 and Key SA Signaling Components was Conducted

FIG. 10 panel A shows the expression of key SA signaling and synthetic genes in wild-type (WT) and atsr1-1 (atsr1, hereafter). Identical blots were hybridized to PAD4, EDS1, EDS5 and ICS1 probes, EB stained rRNA was used as loading control (rRNA). FIG. 10 panel B shows Northern blots showing loss-of-function mutation in pad4 and ics1 knockout backgrounds. RNA samples were prepared from 5-week-old plants. Genotypes are marked beneath and probes to the right of the panel. EB stained rRNA was used as loading control (rRNA). FIG. 10 panel C demonstrates the impact of SA signaling and synthesis mutants on disease resistance of atsr1. Pst. DC3000 ($OD_{600}$ 0.0001) was infiltrated into the leaves of 5-week-old plants grown at 19-21° C., and the cfu was measured 3 days after infiltration. The results of 4 replicates were averaged. Genotypes are marked beneath the panel and the same as in panel B. FIG. 10 panel D compares PR1 expression in different plant genotypic backgrounds. RNA samples were prepared from 5-week-old plants grown at 19-21° C., and the RNA blot was hybridized to PR1 probe. EB stained rRNA was used as loading control (rRNA). Genotypes are marked beneath the panel and the same as in panel B. FIG. 10 panel shows a comparison of plant growth between different plant genotypes. 5-week-old plants grown at 19-21° C. Genotypes are marked beneath the panel and the same as in panel B.

EXAMPLE 12

Schematic Illustration of EDS1 Structure and Interaction of Transcription Factors with EDS1 Promoter In FIG. 11 panel A, the EDS1 promoter structure is shown. Position of starter codon ATG and position of CGCG box is illustrated. FIG. 11 panel B is a gel shift assay showing a putative transcription factor binding box (ACGCGT) and mutant thereof. There are other TFs in the *Arabidopsis* genome which might bind to an ACGCGT motif in the EDS1 promoter. Possible candidates include other AtSR homologs, ABFs (ABRE binding factor) which recognize ACGCGT-like motif[2]. AtSR6 and ABF1 were selected for testing. EDS1 promoter fragment (EDS1P, GTA AAA GTC GAA TGT G ACGCGTCT TGC CGA AC; SEQ ID NO:58) or a mutated version with its ACGCGT changed to ACCCGT (eds1p mutant) was labeled as probe, recombinant AtSR6 contains a CG-1-binding domain, ABF1 (ABRE binding factor 1) is a full-length recombinant protein. FIG. 11 panel C demonstrates the regulatory model of EDS1 promoter. Negative regulator (−), AtSR1, competes for the CGCG box with unidentified TF(s), a positive regulator (+), required for the normal function of EDS1 promoter. In WT, because of the balanced action of AtSR1 and the unknown TF, EDS1 is slightly expressed (upper C panel). In the absence of AtSR1, the repression of AtSR1 is removed, and EDS1 expression is activated (middle C panel). When the CGCG box was mutated, the promoter lost its response to positive, as well as negative regulation because the critical unknown TF could no longer bind to EDS1 promoter (lower C panel).

EXAMPLE 13

Plants Carrying EDS1 Promoter in atsr1-1 Background Were Constructed

FIG. 12 panel A shows 6-week-old atsr1-1 plants carrying EDS1P::Luc construct (pDL326). FIG. 12 panel B shows 6-week-old atsr1-1 plants carrying eds1p::Luc construct (pDL327). FIG. 12 panel C demonstrates the Northern analysis of independent rescued M326 lines probed with PAD4, EDS1 EDS5, ICS1 or PR1. EtBR stained rRNA was used as a control.

EXAMPLE 14

AtSR1 and its Homologs, Including Calmodulin-Binding Mutants Thereof as Disclosed Herein, Bind to the Conserved CGCG Box and Regulate the Expression of Target Genes[6, 8]

Previously, applicants showed that AtSR1 binds to ACGCGG, CCGCGT, ACGCGT, CCGCGG, ACGCGC, GCGCGT, CCGCGC, and GCGCGG[6]. Each binding site shares the consensus sequence CGCG[6]. Mutations of any one of GCGC abolishes binding[6]. Applicants have also shown that AtSR1 binds to the promoter regions of the genes for ethylene-insensitive 3 (EIN3), calmodulin 2 (CaM2), and phytase (phyA)[6]. Briefly, EIN3 is involved in ethylene signaling; phyA is involved in light perception; and CaM2 is a calmodulin.

According to certain preferred embodiments, AtSR1 is responsible for repressing transcription from the enhanced disease susceptibility (EDS) 1 promoter and potentially other promoters. EDS1 and its interacting partner, phytoalexin deficient 4 (PAD4), isochorismate synthase (ICS1), and EDS5 constitute a regulatory core for pathogenic resistance and are important positive regulators of salicylic acid biosynthesis[6, 20] (Wiermer, et al., Current Opinion in Plant Biology, incorporated herein by reference in its entirety).

According to certain preferred embodiments, calmodulin-binding mutants of AtSR-1 are capable of binding to even though deficient in binding calmodulin. These calmodulin-binding AtSR-1 mutants include, but are not limited to, proteins listed as SEQ ID NOS 4 and 6. According to particular aspects, these calmodulin-binding AtSR-1 mutants bind to their binding sites and interfere with endogenous AtSR-1 binding. In certain preferred embodiments, these calmodulin-binding AtSR-1 mutants bind to the conserved CGCG box. According to particular aspects, these calmodulin-binding AtSR-1 mutants bind to the ACGCGT binding region of the EDS1 promoter from *Arabidopsis thaliana*. In certain preferred embodiments, the EDS1 promoter includes, but is not limited to, EDS1, ICS1, PAD4, EIN3, CaM2, phyA, and EDS5 promoter regions. According to further preferred embodiments, a plant expression vector containing the coding sequence for a calmodulin-binding AtSR-1 mutant (SEQ ID 3 and/or 5) is introduced into wildtype plant and/or plant cells. In certain preferred aspects, the calmodulin-binding AtSR-1 mutant expression is controlled by a constitutive promoter. In other preferred aspects, the calmodulin-binding AtSR-1 mutant expression is controlled by an inducible promoter. In further preferred aspects, the calmodulin-binding AtSR-1 mutant expression is controlled by its own promoter. In other preferred aspects, the calmodulin-binding AtSR-1 mutant expression is controlled by a tissue specific promoter, or other suitable promoters as described herein or recognized in the art.

It should be understood that the Examples and embodiments described herein are for illustrative purposes only and that various modifications or changes in light thereof will be suggested to persons skilled in the art and are encompassed within the spirit and purview of this application.

References cited and incorporated by reference herein for their teachings as referred to herein:

1. Lecourieux, D., Ranjeva, R. & Pugin, A. Calcium in plant defence-signalling pathways. *New Phytol* 171, 249-269 (2006).
2. Durrant, W. E. & Dong, X. Systemic acquired resistance. *Annual Review of Phytopathology* 42, 185-209 (2004).
3. Nimchuk, Z., Eulgem, T., Holt, B. F., 3rd & Dangl, J. L. Recognition and response in the plant immune system. *Annual review of genetics* 37, 579-609 (2003).
4. Yang, T. & Poovaiah, B. W. An early ethylene up-regulated gene encoding a calmodulin-binding protein involved in plant senescence and death. *J Biol Chem* 275, 38467-38473 (2000).
5. Reddy, A. S., Reddy, V. S. & Golovkin, M. A calmodulin binding protein from *Arabidopsis* is induced by ethylene and contains a DNA-binding motif. *Biochem Biophys Res Commun* 279, 762-769 (2000).
6. Yang, T. & Poovaiah, B. W. A calmodulin-binding/CGCG box DNA-binding protein family involved in multiple signaling pathways in plants. *J Biol Chem* 277, 45049-45058 (2002).
7. Bouche, N., Scharlat, A., Snedden, W., Bouchez, D. & Fromm, H. A novel family of calmodulin-binding transcription activators in multicellular organisms. *J Biol Chem* 277, 21851-21861 (2002).
8. Han, J. et al. The Fly CAMTA Transcription Factor Potentiates Deactivation of Rhodopsin, a G Protein-Coupled Light Receptor. *Cell* 127, 847-858 (2006).
9. Song, K. et al. The Transcriptional Coactivator CAMTA2 Stimulates Cardiac Growth by Opposing Class II Histone Deacetylases. *Cell* 1125, 453-466 (2006).
10. Ryals, J. A. et al. Systemic Acquired Resistance. *Plant Cell* 8, 1809-1819 (1996).
11. Lorrain, S., Vailleau, F., Balague, C. & Roby, D. Lesion mimic mutants: keys for deciphering cell death and defense pathways in plants? *Trends Plant Sci* 8, 263-271 (2003).
12. Alvarez, M. E. et al. Reactive oxygen intermediates mediate a systemic signal network in the establishment of plant immunity. *Cell* 92, 773-784 (1998).
13. Bieri, S. et al. RAR1 positively controls steady state levels of barley MLA resistance proteins and enables sufficient MLA6 accumulation for effective resistance. *Plant Cell* 16, 3480-3495 (2004).
14. Holt, B. F., 3rd, Belkhadir, Y. & Dangl, J. L. Antagonistic control of disease resistance protein stability in the plant immune system. *Science* 309, 929-932 (2005).

15. Heil, M. & Baldwin, I. T. Fitness costs of induced resistance: emerging experimental support for a slippery concept. *Trends Plant Sci* 7, 61-67 (2002).
16. Mauch, F. et al. Manipulation of salicylate content in *Arabidopsis thaliana* by the expression of an engineered bacterial salicylate synthase. *The Plant Journal* 25, 67-77 (2001).
17. Yang, S. & Hua, J. A haplotype-specific Resistance gene regulated by BONZAI1 mediates temperature-dependent growth control in *Arabidopsis*. *Plant Cell* 16, 1060-1071 (2004).
18. Clough, S. J. et al. The *Arabidopsis* dnd1 "defense, no death" gene encodes a mutated cyclic nucleotide-gated ion channel. *Proc Natl Acad Sci USA* 97, 9323-9328 (2000).
19. Petersen, M. et al. *Arabidopsis* map kinase 4 negatively regulates systemic acquired resistance. *ell* 103, 1111-1120 (2000).
20. Wiermer, M., Feys, B. J. & Parker, J. E. Plant immunity: the EDS1 regulatory node. *Curr Opin Plant Biol* 8, 383-389 (2005).
21. Nawrath, C., Heck, S., Parinthawong, N. & Metraux, J. P. EDS5, an essential component of salicylic acid-dependent signaling for disease resistance in *Arabidopsis*, is a member of the MATE transporter family. *Plant Cell* 14, 275-286 (2002).
22. Wildermuth, M. C., Dewdney, J., Wu, G. & Ausubel, F. M. Isochorismate synthase is required to synthesize salicylic acid for plant defence. *Nature* 414, 562-565 (2001).
23. Xing, D. & Chen, Z. Effects of mutations and constitutive overexpression of EDS1 and PAD4 on plant resistance to different types of microbial pathogens. *Plant Science* 171, 251-262 (2006).
24. Du, L. & Poovaiah, B. W. Ca2+/calmodulin is critical for brassinosteroid biosynthesis and plant growth. *Nature* 437, 741-745 (2005).
25. Gleason, C. et al. Nodulation independent of rhizobia induced by a calcium-activated kinase lacking autoinhibition. *Nature* 441, 1149-1152 (2006).
26. Guo, F.-Q., Okamoto, M. & Crawford, N. M. Identification of a Plant Nitric Oxide Synthase Gene Involved in Hormonal Signaling. *Science* 302, 100-103 (2003).
27. Ali, R. et al. Death don't have no mercy and neither does calcium: *Arabidopsis* cyclic nucleotide gated channel2 and innate immunity. *Plant Cell* 19, 1081-1095 (2007).
28. Mackey, D., Belkhadir, Y., Alonso, J. M., Ecker, J. R. & Dangl, J. L. *Arabidopsis* RIN4 is a target of the type III virulence effector AvrRpt2 and modulates RPS2-mediated resistance. *Cell* 112, 379-389 (2003).
29. Kim, M. C. et al. Calmodulin interacts with MLO protein to regulate defence against mildew in barley. *Nature* 416, 447-451 (2002).
30. Shen, Q. H. et al. Nuclear activity of MLA immune receptors links isolate-specific and basal disease-resistance responses. *Science* 315, 1098-1103 (2007).
31. Alonso, J. M. et al. Genome-Wide Insertional Mutagenesis of *Arabidopsis thaliana*. *Science* 301, 653-657 (2003).
32. Du, L. & Chen, Z. Identification of genes encoding receptor-like protein kinases as possible targets of pathogen- and salicylic acid-induced WRKY DNA-binding proteins in *Arabidopsis*. *Plant J* 24, 837-847 (2000).
33. Chen, K., Du, L. & Chen, Z. Sensitization of defense responses and activation of programmed cell death by a pathogen-induced receptor-like protein kinase in *Arabidopsis*. *Plant Molecular Biology* 53, 61-74 (2003)
34. Thordal-Christensen, H., Zhang, Z., Wei, Y. & Collinge, D. B. Subcellular localization of $H_2O_2$ in plants. $H_2O_2$ accumulation in papillae and hypersensitive response during the barley—powdery mildew interaction. *Plant J* 11, 1187-1194 (1997).
35. Yu, I. C., Parker, J. & Bent, A. F. Gene-for-gene disease resistance without the hypersensitive response in *Arabidopsis* dnd1 mutant. *Proc Natl Acad Sci USA* 95, 7819-7824 (1998).
36. Clarke, J. D., Volko, S. M., Ledford, H., Ausubel, F. M. & Dong, X. Roles of salicylic acid, jasmonic acid, and ethylene in cpr-induced resistance in *Arabidopsis*. *Plant Cell* 12, 2175-2190 (2000).
37. Timmermans, M. C., Maliga, P., Vieira, J. & Messing, J. The pFF plasmids: cassettes utilising CaMV sequences for expression of foreign genes in plants. *Journal of biotechnology* 14, 333-344 (1990).
38. Du, L. & Poovaiah, B. W. A Novel Family of $Ca^{2+}$/Calmodulin-Binding Proteins Involved in Transcriptional Regulation: Interaction with fsh/Ring3 Class Transcription Activators. *Plant Molecular Biology* 54, 549-569 (2004).
39. Yoo, S.-D., Cho, Y.-H. & Sheen, J. *Arabidopsis* mesophyll protoplasts: a versatile cell system for transient gene expression analysis. *Nat. Protocols* 2, 1565-1572 (2007).
40. Hernandez, J. M., Feller, A., Morohashi, K., Frame, K. & Grotewold, E. The basic helix loop helix domain of maize R links transcriptional regulation and histone modifications by recruitment of an EMSY-related factor. *Proceedings of the National Academy of Sciences* 104, 17222-17227 (2007).
41. Choi, H.-i., Hong, J.-h., Ha, J.-o., Kang, J.-y. & Kim, S. Y. ABFs, a Family of ABA-responsive Element Binding Factors. *Journal of Biological Chemistry* 275, 1723-1730 (2000).

The invention claimed is:

1. A method for enhancing disease resistance in a plant or plant cell, comprising generating a homozygous gene modification of AtSR1, or of an AtSR1 ortholog or homolog, in a plant or plant cell, the plant or plant cell characterized by salicylic acid-mediated systemic acquired resistance (SA-mediated SAR), wherein the AtSR1 gene or AtSR1 gene ortholog or homolog is at least one encoding a protein selected from the group consisting of SEQ ID NOS:2, 8, 10, 12, 14, 16, 25, 27, 29, 31, 33, and 35, and protein sequences having at least 97% sequence identity thereto having both a calmodulin-binding domain and an EDS1 promoter-binding domain, and wherein said gene modification reduces or eliminates the calmodulin-binding activity of the respective AtSR1 or AtSR1 ortholog or homolog, and wherein enhancing disease resistance in a plant or plant cell is conferred.

2. A method for enhancing disease resistance in a plant or plant cell, comprising expressing of a recombinant or mutant AtSR1 sequence or AtSR1 gene ortholog or homolog sequence encoding a modified AtSR1 or AtSR1 ortholog or homolog protein, respectively, in a plant or plant cell, the plant or plant cell characterized by salicylic acid-mediated systemic acquired resistance (SA-mediated SAR), wherein the AtSR1 gene or AtSR1 gene ortholog or homolog is at least one encoding a protein selected from the group consisting of SEQ ID NOS:2, 8, 10, 12, 14, 16, 25, 27, 29, 31, 33, and 35, and protein sequences having at least 97% sequence identity thereto having both a calmodulin-binding domain and an EDS1 promoter-binding domain, and wherein said protein modification reduces or eliminates the calmodulin-binding activity of the respective AtSR1 or AtSR1 ortholog or homolog protein, and wherein enhancing disease resistance in a plant or plant cell is conferred.

3. The method of claim 2, wherein expression comprises inducible recombinant expression.

4. The method of any one of claim 1 or 2, wherein the AtSR1 gene modification provides for expression of at least one AtSR1 mutant selected from the group consisting of SEQ ID NOS:4 and 6.

5. The method of any one of claim 1 or 2, wherein the modified AtSR1 or modified AtSR1 ortholog or homolog comprises at least one amino acid deletion.

6. The method of any one of claim 1 or 2, wherein the AtSR1 gene or AtSR1 gene ortholog or homolog is at least one selected from the group consisting of SEQ ID NOS:1, 7, 9, 11, 13, 15, 17, 18, 19, 24, 26, 28, 30, 32, and 34.

7. The method of any one of claim 1 or 2, wherein the plant or plant cell characterized by salicylic acid-mediated systemic acquired resistance (SA-mediated SAR), comprises a plant cell selected from the group consisting of a monocot and a dicot.

8. The method of claim 7, wherein the dicot comprises a cruciferous dicot.

9. The method of claim 8, wherein the cruciferous dicot comprises at least one selected from the group consisting of B. carinata (Abyssinian Mustard or Cabbage, B. elongata (Elongated Mustard), B. fruticulosa (Mediterranean Cabbage), B. juncea (Indian Mustard, Brown and leaf mustards, Sarepta Mustard), B. napous (Rapeseed, Canola, Rutabaga, Nabicol), B. narinosa (Broadbeaked Mustard), B. nigra (Black Mustard), B. oleracea (Kale, Cabbage, Broccoli, Cauliflower, Kai-lan, Brussels sprouts), B. perviridis (Tender Green, Mustard Spinach), B. rapa (Chinese cabbage, Turnip, Rapini, Komatsuna), B. rupestris (Brown Mustard), B. septiceps (Seventop Turnip), and B. tournefortii (Asian Mustard).

10. The method of claim 7, wherein the monocot comprises at least one of barley, sorghum, and rice.

11. A transgenic plant or transgenic plant cell, comprising a homozygous gene modification of AtSR1 or of an AtSR1 ortholog or homolog, said plant or plant cell characterized by salicylic acid-mediated systemic acquired resistance (SA-mediated SAR), said modification reducing or eliminating the calmodulin-binding activity of the respective AtSR1 or AtSR1 ortholog or homolog, wherein the AtSR1 gene or AtSR1 gene ortholog or homolog is at least one encoding a protein selected from the group consisting of SEQ ID NOS:2, 8, 10, 12, 14, 16, 25, 27, 29, 31, 33, and 35, and protein sequences having at least 97% sequence identity thereto having both a calmodulin-binding domain and an EDS1 promoter-binding domain, and wherein an enhanced disease resistant plant or plant cell is conferred.

12. A transgenic plant or transgenic plant cell, comprising a recombinant expression vector or expressible recombinant sequence or mutant sequence suitable for expression of an AtSR1 gene or AtSR1 gene ortholog or homolog sequence encoding a modified AtSR1 or AtSR1 ortholog or homolog protein, respectively, in a plant or plant cell, the plant or plant call characterized by salicylic acid-mediated systemic acquired resistance (SA-mediated SAR), wherein the AtSR1 gene or AtSR1 gene ortholog or homolog is at least one encoding a protein selected from the group consisting of SEQ ID NOS:2, 8, 10, 12, 14, 16, 25, 27, 29, 31, 33, and 35, and protein sequences having at least 97% sequence identity thereto having both a calmodulin-binding domain and an EDS1 promoter-binding domain, wherein said protein modification reduces or eliminates the calmodulin-binding activity of the respective AtSR1 or AtSR1 ortholog protein, and wherein an enhanced disease resistant plant or plant cell is conferred.

13. The plant or plant cell of any one of claim 11 or 12, wherein the plant or plant cell is one selected from the group consisting of Acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice,. rye, sorghum, Southern pine, soybean, spinach, squash, strawberry, sugarbeet, sugarcane, sunflower, sweet potato, sweetgum, tangerine, tea, tobacco, tomato, triticale, turf grass, turnip, a vine, watermelon, wheat, yams, and zucchini.

14. The plant or plant cell of any one of claim 11 or 12, wherein the plant or plant cell is more disease resistant relative to wild type.

15. The plant or plant cell of any one of claim 11 or 12, wherein the plant or plant cell comprises a plant cell selected from the group consisting of a monocot and dicot.

16. The plant or plant cell of claim 15, wherein the dicot plant comprises a cruciferous dicot plant cell.

17. The plant or plant cell of claim 16, wherein the cruciferous dicot is at least one selected from the group consisting of *B. carinata* (Abyssinian Mustard or Cabbage, *B. elongata* (Elongated Mustard), *B. fruticulosa* (Mediterranean Cabbage), *B. juncea* (Indian Mustard, Brown and leaf mustards, Sarepta Mustard), *B. napous* (Rapeseed, Canola, Rutabaga, Nabicol), *B. narinosa* (Broadbeaked Mustard), *B. nigra* (Black Mustard), *B. oleracea* (Kale, Cabbage, Broccoli, Cauliflower, Kai-lan, Brussels sprouts), *B. perviridis* (Tender Green, Mustard Spinach), *B. rapa* (Chinese cabbage, Turnip, Rapini, Komatsuna), *B. rupestris* (Brown Mustard), *B. septiceps* (Seventop Turnip), and *B. tournefortii* (Asian Mustard).

18. The plant or plant cell of claim 15, wherein the monocot is at least one of barley, sorghum, and rice.

19. The plant or plant cell of claim 12, wherein expression comprises inducible recombinant expression.

20. An isolated nucleic acid comprising a modification of a AtSR1 gene or of an AtSR1 gene ortholog or homolog, said AtSR1 gene ortholog or homolog having an EDS1 promoter-binding domain, and said modification reducing or eliminating the respective calmodulin-binding activity, wherein the nucleic acid encodes a protein is selected from the group consisting of SEQ ID NOS:4 and 6.

21. A recombinant plant expression vector or virus, comprising a promoter suitable for expression of a nucleic acid comprising a modification of a AtSR1 gene or of an AtSR1 gene ortholog or homolog, said AtSR1 gene ortholog or homolog having an EDS1 promoter-binding domain, and said modification reducing or eliminating the calmodulin-binding activity of the respective encoded proteins, wherein the nucleic acid encodes a protein selected from the group consisting of SEQ ID NOS:4 and 6.

* * * * *

SEQUENCE LISTING

<160> NUMBER OF SEQ ID NOS: 74

<210> SEQ ID NO 1
<211> LENGTH: 3252
<212> TYPE: DNA
<213> ORGANISM: Arabidopsis thaliana

<400> SEQUENCE: 1

```
atggcggaag caagacgatt cagcccagtt catgaattag atgttggaca aatactctca      60
gaagcacgac atcgatggct tcgtcctcct gaaatctgtg aaattttaca gaattaccaa     120
agatttcaaa tttctactga gccacctact acaccatcaa gtgggtctgt ttttatgttt     180
gatcgaaagg tgctcagata cttcaggaaa gacggtcaca attggaggaa gaaaaaagat     240
```

| | |
|---|---|
| ggaaagactg tgaaggaagc tcatgagagg ttgaaggcgg gaagcgttga tgttctacat | 300 |
| tgttactatg cgcatggaca ggacaatgaa aactttcaaa gacgcagtta ctggttgctt | 360 |
| caggaagaac tttcccacat agtttttgtt cactacctcg aagttaaggg tagtagagtt | 420 |
| tctacttctt ttaaccggat gcaaaggact gaagacgcgg ctcggtctcc tcaagaaact | 480 |
| ggggacgcct tgaccagtga acatgatggt tatgcttctt gcagcttcaa tcaaaatgat | 540 |
| catagcaatc attcacaaac tactgactca gcaagtgtca atggttttca ctctccagaa | 600 |
| cttgaagatg ctgaatcagc atacaatcag catggaagtt ccacagctta ctctcatcaa | 660 |
| gaacttcagc agcctgcaac aggaggaaac cttactggtt ttgatcctta ctatcaaatc | 720 |
| tctttgacgc ccagggatag ttatcaaaaa gagcttcgca caatccccgt aactgattct | 780 |
| tcaattatgg tagacaaaag caaaactatc aacagtcctg gagtaacaaa tgggttaaaa | 840 |
| aacagaaaat ccattgattc ccaaacctgg gaagagattc tgggaaattg tggttctgga | 900 |
| gttgaagcct tacctttgca gcctaacagt gagcatgaag tgctggacca atactcgaa | 960 |
| agctctttta caatgcaaga ttttgctagt ctacaagagt ccatggtcaa agccagaat | 1020 |
| caggagttaa attcaggact tacatctgat cgtaccgtgt ggttccaagg acaagatatg | 1080 |
| gagctaaatg ctataagcaa tctagcttcg aatgaaaaag ctccatatct atctacgatg | 1140 |
| aaacaacatc tgttacacgg tgcattgggc gaagaaggtc tgaaaaagat ggacagtttc | 1200 |
| aatcgctgga tgagcaaaga acttggagat gttggtgtta tagctgatgc aaacgagtcc | 1260 |
| tttactcaat caagttcaag aacctactgg gaagaagttg agagtgagga tgggtccaat | 1320 |
| ggtcacaact ctaggaggga catggatgga tatgttatga gtccttccct ctcaaaggaa | 1380 |
| cagctctttta gcatcaatga cttctctcca agctgggctt atgtgggttg tgaagtggtg | 1440 |
| gtttttgtca ctggaaaatt cttaaagact cgggaggaga ctgaaattgg cgagtggtct | 1500 |
| tgcatgtttg ggcaaacaga agttccagca gatgttatat ctaatggtat tctccaatgt | 1560 |
| gttgctccta tgcatgaggc tggaagagtt cccttttatg taacatgttc caacagattg | 1620 |
| gcatgcagtg aagtgcgtga attcgagtat aaggttgccg agtctcaagt ttttgataga | 1680 |
| gaagcagatg atgagtctac tattgacatt cttgaggcaa gatttgttaa actgttgtgc | 1740 |
| tcgaaatctg aaaatacaag ccctgttttct gggaatgaca gtgatttgtc acaattgagc | 1800 |
| gagaagatta gtttactact tttcgagaac gatgaccagt tggatcagat gctcatgaat | 1860 |
| gaaatctccc aagaaaatat gaaaacaac cttttgcagg aatttctgaa agaaagctta | 1920 |
| cactcatggc ttttacaaaa gatagcagaa ggtggaaaag gtccaagtgt tttggatgaa | 1980 |
| ggtggccaag gtgtattaca ttttgcagct tctcttggtt acaactgggc cttagaacca | 2040 |
| acaataatcg ctggtgtaag cgttgatttt cgcgatgtaa atggttggac cgcacttcat | 2100 |
| tgggcagctt tctttggcag ggagaggata attggttcac tcatagctct tggtgctgct | 2160 |
| cctgaaactt taactgaccc aaatccagat ttcccatcag gaagcacacc ttctgatcta | 2220 |
| gcctatgcta atggtcacaa aggaattgct ggttatctct cagaatatgc cttaagagct | 2280 |
| catgttttctt tgctcagtct aaatgataaa aatgccgaaa ctgttgagat ggctcctagc | 2340 |
| ccatccagct catcattgac agactcgttg acagctgtac gtaacgctac tcaggcagca | 2400 |
| gctcggattc atcaggtttt cagggctcag tcttttccaga agaagcaact aaaagaattt | 2460 |
| ggagataaaa agcttggaat gtcggaggag cgtgctcttt cgatgcttgc tcctaaaaca | 2520 |
| cacaaatcag gaagggcaca tagtgatgat tccgtgcaag ccgctgctat tcggattcag | 2580 |

-continued

```
aacaagttcc gaggttacaa gggaagaaaa gactatttga ttaccagaca aagaatcatc    2640
aaaatacagg ctcatgtgag aggttatcag tttaggaaaa actacagaaa gataatttgg    2700
tcagtggggg tattagagaa ggtgatatta cgttggagac ggaaaggagc tggtttgcgc    2760
gggtttaagt cagaagcact tgttgagaag atgcaagacg gaacagagaa agaagaagat    2820
gatgattttt tcaaacaagg aagaaagcaa acagaggata ggctacaaaa agctcttgca    2880
agagtgaaat ccatggttca atatcctgaa gctagagatc aataccgtag attgctaaat    2940
gttgtcaacg acatccaaga aagcaaggtt gaaaaagctc ttgaaaattc agaagcaact    3000
tgttttgatg atgatgatga tctgatagat attgaagcat tgttggaaga tgatgacaca    3060
ttgatgttgc ctatgtcctc atctttgtgg accagttaaa tcactctcaa gctttgttgt    3120
gatattgtgt cacagtatta ttgactcatt aaacttgtaa attcttgtgt aatcactctt    3180
ctcatatact gtaactgcat tcatgactct aatttaaatg atatatattt gaaacataaa    3240
tcaaacttat gt                                                        3252
```

<210> SEQ ID NO 2
<211> LENGTH: 1032
<212> TYPE: PRT
<213> ORGANISM: Arabidopsis thaliana

<400> SEQUENCE: 2

```
Met Ala Glu Ala Arg Arg Phe Ser Pro Val His Glu Leu Asp Val Gly
1               5                   10                  15

Gln Ile Leu Ser Glu Ala Arg His Arg Trp Leu Arg Pro Glu Ile
        20                  25                  30

Cys Glu Ile Leu Gln Asn Tyr Gln Arg Phe Gln Ile Ser Thr Glu Pro
    35                  40                  45

Pro Thr Thr Pro Ser Ser Gly Ser Val Phe Met Phe Asp Arg Lys Val
50                  55                  60

Leu Arg Tyr Phe Arg Lys Asp Gly His Asn Trp Arg Lys Lys Asp
65                  70                  75                  80

Gly Lys Thr Val Lys Glu Ala His Glu Arg Leu Lys Ala Gly Ser Val
                85                  90                  95

Asp Val Leu His Cys Tyr Tyr Ala His Gly Gln Asp Asn Glu Asn Phe
            100                 105                 110

Gln Arg Arg Ser Tyr Trp Leu Leu Gln Glu Glu Leu Ser His Ile Val
        115                 120                 125

Phe Val His Tyr Leu Glu Val Lys Gly Ser Arg Val Ser Thr Ser Phe
    130                 135                 140

Asn Arg Met Gln Arg Thr Glu Asp Ala Ala Arg Ser Pro Gln Glu Thr
145                 150                 155                 160

Gly Asp Ala Leu Thr Ser Glu His Asp Gly Tyr Ala Ser Cys Ser Phe
                165                 170                 175

Asn Gln Asn Asp His Ser Asn His Ser Gln Thr Thr Asp Ser Ala Ser
            180                 185                 190

Val Asn Gly Phe His Ser Pro Glu Leu Glu Asp Ala Glu Ser Ala Tyr
        195                 200                 205

Asn Gln His Gly Ser Ser Thr Ala Tyr Ser His Gln Glu Leu Gln Gln
    210                 215                 220

Pro Ala Thr Gly Gly Asn Leu Thr Gly Phe Asp Pro Tyr Tyr Gln Ile
225                 230                 235                 240

Ser Leu Thr Pro Arg Asp Ser Tyr Gln Lys Glu Leu Arg Thr Ile Pro
                245                 250                 255
```

```
Val Thr Asp Ser Ser Ile Met Val Asp Lys Ser Lys Thr Ile Asn Ser
            260                 265                 270

Pro Gly Val Thr Asn Gly Leu Lys Asn Arg Lys Ser Ile Asp Ser Gln
            275                 280                 285

Thr Trp Glu Glu Ile Leu Gly Asn Cys Gly Ser Gly Val Glu Ala Leu
290                 295                 300

Pro Leu Gln Pro Asn Ser Glu His Glu Val Leu Asp Gln Ile Leu Glu
305                 310                 315                 320

Ser Ser Phe Thr Met Gln Asp Phe Ala Ser Leu Gln Glu Ser Met Val
                325                 330                 335

Lys Ser Gln Asn Gln Glu Leu Asn Ser Gly Leu Thr Ser Asp Arg Thr
                340                 345                 350

Val Trp Phe Gln Gly Gln Asp Met Glu Leu Asn Ala Ile Ser Asn Leu
                355                 360                 365

Ala Ser Asn Glu Lys Ala Pro Tyr Leu Ser Thr Met Lys Gln His Leu
            370                 375                 380

Leu His Gly Ala Leu Gly Glu Gly Leu Lys Lys Met Asp Ser Phe
385                 390                 395                 400

Asn Arg Trp Met Ser Lys Glu Leu Gly Asp Val Gly Val Ile Ala Asp
                405                 410                 415

Ala Asn Glu Ser Phe Thr Gln Ser Ser Ser Arg Thr Tyr Trp Glu Glu
                420                 425                 430

Val Glu Ser Glu Asp Gly Ser Asn Gly His Asn Ser Arg Arg Asp Met
            435                 440                 445

Asp Gly Tyr Val Met Ser Pro Ser Leu Ser Lys Glu Gln Leu Phe Ser
            450                 455                 460

Ile Asn Asp Phe Ser Pro Ser Trp Ala Tyr Val Gly Cys Glu Val Val
465                 470                 475                 480

Val Phe Val Thr Gly Lys Phe Leu Lys Thr Arg Glu Glu Thr Glu Ile
                485                 490                 495

Gly Glu Trp Ser Cys Met Phe Gly Gln Thr Glu Val Pro Ala Asp Val
                500                 505                 510

Ile Ser Asn Gly Ile Leu Gln Cys Val Ala Pro Met His Glu Ala Gly
            515                 520                 525

Arg Val Pro Phe Tyr Val Thr Cys Ser Asn Arg Leu Ala Cys Ser Glu
            530                 535                 540

Val Arg Glu Phe Glu Tyr Lys Val Ala Glu Ser Gln Val Phe Asp Arg
545                 550                 555                 560

Glu Ala Asp Asp Glu Ser Thr Ile Asp Ile Leu Glu Ala Arg Phe Val
                565                 570                 575

Lys Leu Leu Cys Ser Lys Ser Glu Asn Thr Ser Pro Val Ser Gly Asn
            580                 585                 590

Asp Ser Asp Leu Ser Gln Leu Ser Glu Lys Ile Ser Leu Leu Leu Phe
            595                 600                 605

Glu Asn Asp Asp Gln Leu Asp Gln Met Leu Met Asn Glu Ile Ser Gln
            610                 615                 620

Glu Asn Met Lys Asn Asn Leu Leu Gln Glu Phe Leu Lys Glu Ser Leu
625                 630                 635                 640

His Ser Trp Leu Leu Gln Lys Ile Ala Glu Gly Lys Gly Pro Ser
                645                 650                 655

Val Leu Asp Glu Gly Gly Gln Gly Val Leu His Phe Ala Ala Ser Leu
            660                 665                 670
```

-continued

Gly Tyr Asn Trp Ala Leu Glu Pro Thr Ile Ile Ala Gly Val Ser Val
            675                 680                 685

Asp Phe Arg Asp Val Asn Gly Trp Thr Ala Leu His Trp Ala Ala Phe
    690                 695                 700

Phe Gly Arg Glu Arg Ile Ile Gly Ser Leu Ile Ala Leu Gly Ala Ala
705                 710                 715                 720

Pro Gly Thr Leu Thr Asp Pro Asn Pro Asp Phe Pro Ser Gly Ser Thr
                725                 730                 735

Pro Ser Asp Leu Ala Tyr Ala Asn Gly His Lys Gly Ile Ala Gly Tyr
            740                 745                 750

Leu Ser Glu Tyr Ala Leu Arg Ala His Val Ser Leu Leu Ser Leu Asn
        755                 760                 765

Asp Lys Asn Ala Glu Thr Val Glu Met Ala Pro Ser Pro Ser Ser Ser
    770                 775                 780

Ser Leu Thr Asp Ser Leu Thr Ala Val Arg Asn Ala Thr Gln Ala Ala
785                 790                 795                 800

Ala Arg Ile His Gln Val Phe Arg Ala Gln Ser Phe Gln Lys Lys Gln
                805                 810                 815

Leu Lys Glu Phe Gly Asp Lys Lys Leu Gly Met Ser Glu Glu Arg Ala
            820                 825                 830

Leu Ser Met Leu Ala Pro Lys Thr His Lys Ser Gly Arg Ala His Ser
        835                 840                 845

Asp Asp Ser Val Gln Ala Ala Ala Ile Arg Ile Gln Asn Lys Phe Arg
    850                 855                 860

Gly Tyr Lys Gly Arg Lys Asp Tyr Leu Ile Thr Arg Gln Arg Ile Ile
865                 870                 875                 880

Lys Ile Gln Ala His Val Arg Gly Tyr Gln Phe Arg Lys Asn Tyr Arg
                885                 890                 895

Lys Ile Ile Trp Ser Val Gly Val Leu Glu Lys Val Ile Leu Arg Trp
            900                 905                 910

Arg Arg Lys Gly Ala Gly Leu Arg Gly Phe Lys Ser Glu Ala Leu Val
        915                 920                 925

Glu Lys Met Gln Asp Gly Thr Glu Lys Glu Asp Asp Asp Phe Phe
    930                 935                 940

Lys Gln Gly Arg Lys Gln Thr Glu Asp Arg Leu Gln Lys Ala Leu Ala
945                 950                 955                 960

Arg Val Lys Ser Met Val Gln Tyr Pro Glu Ala Arg Asp Gln Tyr Arg
                965                 970                 975

Arg Leu Leu Asn Val Val Asn Asp Ile Gln Gly Ser Lys Val Glu Lys
            980                 985                 990

Ala Leu Glu Asn Ser Glu Ala Thr Cys Phe Asp Asp Asp Asp Leu
        995                 1000                1005

Ile Asp Ile Glu Ala Leu Leu Glu Asp Asp Thr Leu Met Leu
    1010                1015                1020

Pro Met Ser Ser Ser Leu Trp Thr Ser
    1025                1030

<210> SEQ ID NO 3
<211> LENGTH: 3252
<212> TYPE: DNA
<213> ORGANISM: Artificial Sequence
<220> FEATURE:
<223> OTHER INFORMATION: AtSR1 mutant 2 mRNA (LYS to GLU)

<400> SEQUENCE: 3

```
atggcggaag caagacgatt cagcccagtt catgaattag atgttggaca aatactctca        60
gaagcacgac atcgatggct tcgtcctcct gaaatctgtg aaattttaca gaattaccaa       120
agatttcaaa tttctactga gccacctact acaccatcaa gtgggtctgt ttttatgttt       180
gatcgaaagg tgctcagata cttcaggaaa gacggtcaca attggaggaa gaaaaaagat       240
ggaaagactg tgaaggaagc tcatgagagg ttgaaggcgg aagcgttga tgttctacat        300
tgttactatg cgcatggaca ggacaatgaa aactttcaaa gacgcagtta ctggttgctt       360
caggaagaac tttcccacat agttttttgtt cactacctcg aagttaaggg tagtagagtt     420
tctacttctt ttaaccggat gcaaggact gaagacgcgg ctcggtctcc tcaagaaact        480
ggggacgcct tgaccagtga acatgatggt tatgcttctt gcagcttcaa tcaaaatgat      540
catagcaatc attcacaaac tactgactca gcaagtgtca atggttttca ctctccagaa      600
cttgaagatg ctgaatcagc atacaatcag catggaagtt ccacagctta ctctcatcaa      660
gaacttcagc agcctgcaac aggaggaaac cttactggtt ttgatcctta ctatcaaatc     720
tctttgacgc ccagggatag ttatcaaaaa gagcttcgca caatcccgt aactgattct       780
tcaattatgg tagacaaaag caaaactatc aacagtcctg gagtaacaaa tgggttaaaa     840
aacagaaaat ccattgattc ccaaacctgg aagagattc tgggaaattg tggttctgga     900
gttgaagcct tacctttgca gcctaacagt gagcatgaag tgctggacca aatactcgaa      960
agctctttta caatgcaaga ttttgctagt ctacaagagt ccatggtcaa aagccagaat     1020
caggagttaa attcaggact acatctgat cgtaccgtgt ggttccaagg acaagatatg       1080
gagctaaatg ctataagcaa tctagcttcg aatgaaaaag ctccatatct atctacgatg     1140
aaacaacatc tgttacacgg tgcattgggc gaagaaggtc tgaaaaagat ggacagtttc     1200
aatcgctgga tgagcaaaga acttggagat gttggtgtta tagctgatgc aaacgagtcc     1260
tttactcaat caagttcaag aacctactgg gaagaagttg agagtgagga tgggtccaat     1320
ggtcacaact ctaggaggga catggatgga tatgttatga gtccttccct ctcaaaggaa    1380
cagctctttta gcatcaatga cttctctcca agctgggctt atgtgggttg tgaagtggtg     1440
gtttttgtca ctggaaaatt cttaaagact cgggaggaga ctgaaattgg cgagtggtct    1500
tgcatgtttg ggcaaacaga agttccagca gatgttatat ctaatggtat tctccaatgt    1560
gttgctccta tgcatgaggc tggaagagtt ccctttatg taacatgttc caacagattg     1620
gcatgcagtg aagtgcgtga attcgagtat aaggttgccg agtctcaagt ttttgataga    1680
gaagcagatg atgagtctac tattgacatt cttgaggcaa gatttgttaa actgttgtgc    1740
tcgaaatctg aaaatacaag ccctgttttct gggaatgaca gtgatttgtc acaattgagc    1800
gagaagatta gtttactact tttcgagaac gatgaccagt tggatcagat gctcatgaat    1860
gaaatctccc aagaaaatat gaaaaacaac cttttgcagg aatttctgaa agaaagctta    1920
cactcatggc tttacaaaa gatagcagaa ggtggaaaag gtccaagtgt tttggatgaa     1980
ggtggccaag gtgtattaca ttttgcagct tctcttggtt acaactgggc cttagaacca    2040
acaataatcg ctggtgtaag cgttgatttt cgcgatgtaa atggttggac cgcacttcat    2100
tgggcagctt ctttggcag ggagaggata attggttcac tcatagctct tggtgctgct     2160
cctggaactt taactgaccc aaatccagat ttcccatcag aagcacacc ttctgatcta     2220
gcctatgcta atggtcacaa aggaattgct ggttatctct cagaatatgc cttaagagct    2280
catgtttctt tgctcagtct aaatgataaa atgccgaaa ctgttgagat ggctcctagc    2340
ccatccagct catcattgac agactcgttg acagctgtac gtaacgctac tcaggcagca    2400
```

-continued

```
gctcggattc atcaggtttt cagggctcag tctttccaga agaagcaact aaaagaattt    2460
ggagataaaa agcttggaat gtcggaggag cgtgctcttt cgatgcttgc tcctaaaaca    2520
cacaaatcag gaagggcaca tagtgatgat ccgtgcaag ccgctgctat tcggattcag     2580
aacaagttcc gaggttacaa gggaagaaaa gactatttga ttaccagaca agaatcatc     2640 aaaatacagg ctcatgtgag aggttatcag tttaggaaaa actacagaaa gataatttgg    2700
tcagtggggg tattagagga ggtgatatta cgttggagac ggaaaggagc tggtttgcgc    2760
gggtttaagt cagaagcact tgttgagaag atgcaagacg gaacagagaa agaagaagat    2820
gatgattttt tcaaacaagg aagaaagcaa acagaggata ggctacaaaa agctcttgca    2880
agagtgaaat ccatggttca atatcctgaa gctagagatc aataccgtag attgctaaat    2940
gttgtcaacg acatccaaga aagcaaggtt gaaaaagctc ttgaaaattc agaagcaact    3000
tgttttgatg atgatgatga tctgatagat attgaagcat tgttggaaga tgatgacaca    3060
ttgatgttgc ctatgtcctc atctttgtgg accagttaaa tcactctcaa gctttgttgt    3120
gatattgtgt cacagtatta ttgactcatt aaacttgtaa attcttgtgt aatcactctt    3180
ctcatatact gtaactgcat tcatgactct aatttaaatg atatatattt gaaacataaa    3240
tcaaacttat gt                                                        3252
```

```
<210> SEQ ID NO 4
<211> LENGTH: 1032
<212> TYPE: PRT
<213> ORGANISM: Artificial Sequence
<220> FEATURE:
<223> OTHER INFORMATION: AtSR1 mutant 2 protein (LYS to GLU)

<400> SEQUENCE: 4
```

Met Ala Glu Ala Arg Arg Phe Ser Pro Val His Glu Leu Asp Val Gly
1               5                   10                  15

Gln Ile Leu Ser Glu Ala Arg His Arg Trp Leu Arg Pro Pro Glu Ile
            20                  25                  30

Cys Glu Ile Leu Gln Asn Tyr Gln Arg Phe Gln Ile Ser Thr Glu Pro
        35                  40                  45

Pro Thr Thr Pro Ser Ser Gly Ser Val Phe Met Phe Asp Arg Lys Val
    50                  55                  60

Leu Arg Tyr Phe Arg Lys Asp Gly His Asn Trp Arg Lys Lys Lys Asp
65                  70                  75                  80

Gly Lys Thr Val Lys Glu Ala His Glu Arg Leu Lys Ala Gly Ser Val
                85                  90                  95

Asp Val Leu His Cys Tyr Tyr Ala His Gly Gln Asp Asn Glu Asn Phe
            100                 105                 110

Gln Arg Arg Ser Tyr Trp Leu Leu Gln Glu Glu Leu Ser His Ile Val
        115                 120                 125

Phe Val His Tyr Leu Glu Val Lys Gly Ser Arg Val Ser Thr Ser Phe
    130                 135                 140

Asn Arg Met Gln Arg Thr Glu Asp Ala Ala Arg Ser Pro Gln Glu Thr
145                 150                 155                 160

Gly Asp Ala Leu Thr Ser Glu His Asp Gly Tyr Ala Ser Cys Ser Phe
                165                 170                 175

Asn Gln Asn Asp His Ser Asn His Ser Gln Thr Thr Asp Ser Ala Ser
            180                 185                 190

Val Asn Gly Phe His Ser Pro Glu Leu Glu Asp Ala Glu Ser Ala Tyr
        195                 200                 205

-continued

```
Asn Gln His Gly Ser Ser Thr Ala Tyr Ser His Gln Glu Leu Gln Gln
    210                 215                 220

Pro Ala Thr Gly Gly Asn Leu Thr Gly Phe Asp Pro Tyr Tyr Gln Ile
225                 230                 235                 240

Ser Leu Thr Pro Arg Asp Ser Tyr Gln Lys Glu Leu Arg Thr Ile Pro
                245                 250                 255

Val Thr Asp Ser Ser Ile Met Val Asp Lys Ser Lys Thr Ile Asn Ser
            260                 265                 270

Pro Gly Val Thr Asn Gly Leu Lys Asn Arg Lys Ser Ile Asp Ser Gln
        275                 280                 285

Thr Trp Glu Glu Ile Leu Gly Asn Cys Gly Ser Gly Val Glu Ala Leu
290                 295                 300

Pro Leu Gln Pro Asn Ser Glu His Glu Val Leu Asp Gln Ile Leu Glu
305                 310                 315                 320

Ser Ser Phe Thr Met Gln Asp Phe Ala Ser Leu Gln Glu Ser Met Val
                325                 330                 335

Lys Ser Gln Asn Gln Glu Leu Asn Ser Gly Leu Thr Ser Asp Arg Thr
            340                 345                 350

Val Trp Phe Gln Gly Gln Asp Met Glu Leu Asn Ala Ile Ser Asn Leu
        355                 360                 365

Ala Ser Asn Glu Lys Ala Pro Tyr Leu Ser Thr Met Lys Gln His Leu
370                 375                 380

Leu His Gly Ala Leu Gly Glu Gly Leu Lys Lys Met Asp Ser Phe
385                 390                 395                 400

Asn Arg Trp Met Ser Lys Glu Leu Gly Asp Val Gly Val Ile Ala Asp
                405                 410                 415

Ala Asn Glu Ser Phe Thr Gln Ser Ser Ser Arg Thr Tyr Trp Glu Glu
            420                 425                 430

Val Glu Ser Glu Asp Gly Ser Asn Gly His Asn Ser Arg Arg Asp Met
        435                 440                 445

Asp Gly Tyr Val Met Ser Pro Ser Leu Ser Lys Glu Gln Leu Phe Ser
450                 455                 460

Ile Asn Asp Phe Ser Pro Ser Trp Ala Tyr Val Gly Cys Glu Val Val
465                 470                 475                 480

Val Phe Val Thr Gly Lys Phe Leu Lys Thr Arg Glu Thr Glu Ile
                485                 490                 495

Gly Glu Trp Ser Cys Met Phe Gly Gln Thr Glu Val Pro Ala Asp Val
            500                 505                 510

Ile Ser Asn Gly Ile Leu Gln Cys Val Ala Pro Met His Glu Ala Gly
        515                 520                 525

Arg Val Pro Phe Tyr Val Thr Cys Ser Asn Arg Leu Ala Cys Ser Glu
530                 535                 540

Val Arg Glu Phe Glu Tyr Lys Val Ala Glu Ser Gln Val Phe Asp Arg
545                 550                 555                 560

Glu Ala Asp Asp Glu Ser Thr Ile Asp Ile Leu Glu Ala Arg Phe Val
                565                 570                 575

Lys Leu Leu Cys Ser Lys Ser Glu Asn Thr Ser Pro Val Ser Gly Asn
            580                 585                 590

Asp Ser Asp Leu Ser Gln Leu Ser Glu Lys Ile Ser Leu Leu Leu Phe
        595                 600                 605

Glu Asn Asp Asp Gln Leu Asp Gln Met Leu Met Asn Glu Ile Ser Gln
610                 615                 620
```

```
Glu Asn Met Lys Asn Asn Leu Leu Gln Glu Phe Leu Lys Glu Ser Leu
625                 630                 635                 640

His Ser Trp Leu Leu Gln Lys Ile Ala Glu Gly Gly Lys Gly Pro Ser
                645                 650                 655

Val Leu Asp Glu Gly Gly Gln Gly Val Leu His Phe Ala Ala Ser Leu
            660                 665                 670

Gly Tyr Asn Trp Ala Leu Glu Pro Thr Ile Ile Ala Gly Val Ser Val
        675                 680                 685

Asp Phe Arg Asp Val Asn Gly Trp Thr Ala Leu His Trp Ala Ala Phe
    690                 695                 700

Phe Gly Arg Glu Arg Ile Ile Gly Ser Leu Ile Ala Leu Gly Ala Ala
705                 710                 715                 720

Pro Gly Thr Leu Thr Asp Pro Asn Pro Asp Phe Pro Ser Gly Ser Thr
                725                 730                 735

Pro Ser Asp Leu Ala Tyr Ala Asn Gly His Lys Gly Ile Ala Gly Tyr
            740                 745                 750

Leu Ser Glu Tyr Ala Leu Arg Ala His Val Ser Leu Leu Ser Leu Asn
        755                 760                 765

Asp Lys Asn Ala Glu Thr Val Glu Met Ala Pro Ser Pro Ser Ser Ser
    770                 775                 780

Ser Leu Thr Asp Ser Leu Thr Ala Val Arg Asn Ala Thr Gln Ala Ala
785                 790                 795                 800

Ala Arg Ile His Gln Val Phe Arg Ala Gln Ser Phe Gln Lys Lys Gln
                805                 810                 815

Leu Lys Glu Phe Gly Asp Lys Lys Leu Gly Met Ser Glu Glu Arg Ala
            820                 825                 830

Leu Ser Met Leu Ala Pro Lys Thr His Lys Ser Gly Arg Ala His Ser
        835                 840                 845

Asp Asp Ser Val Gln Ala Ala Ala Ile Arg Ile Gln Asn Lys Phe Arg
    850                 855                 860

Gly Tyr Lys Gly Arg Lys Asp Tyr Leu Ile Thr Arg Gln Arg Ile Ile
865                 870                 875                 880

Lys Ile Gln Ala His Val Arg Gly Tyr Gln Phe Arg Lys Asn Tyr Arg
                885                 890                 895

Lys Ile Ile Trp Ser Val Gly Val Leu Glu Glu Val Ile Leu Arg Trp
            900                 905                 910

Arg Arg Lys Gly Ala Gly Leu Arg Gly Phe Lys Ser Glu Ala Leu Val
        915                 920                 925

Glu Lys Met Gln Asp Gly Thr Glu Lys Glu Asp Asp Asp Phe Phe
930                 935                 940

Lys Gln Gly Arg Lys Gln Thr Glu Asp Arg Leu Gln Lys Ala Leu Ala
945                 950                 955                 960

Arg Val Lys Ser Met Val Gln Tyr Pro Glu Ala Arg Asp Gln Tyr Arg
                965                 970                 975

Arg Leu Leu Asn Val Val Asn Asp Ile Gln Glu Ser Lys Val Glu Lys
            980                 985                 990

Ala Leu Glu Asn Ser Glu Ala Thr Cys Phe Asp Asp Asp Asp Leu
        995                 1000                1005

Ile Asp Ile Glu Ala Leu Leu Glu Asp Asp Thr Leu Met Leu
    1010                1015                1020

Pro Met Ser Ser Ser Leu Trp Thr Ser
    1025                1030
```

<210> SEQ ID NO 5
<211> LENGTH: 3183
<212> TYPE: DNA
<213> ORGANISM: Artificial Sequence
<220> FEATURE:
<223> OTHER INFORMATION: AtSR1 mutant 3 (deletion)

<400> SEQUENCE: 5

```
atggcggaag caagacgatt cagcccagtt catgaattag atgttggaca aatactctca      60
gaagcacgac atcgatggct tcgtcctcct gaaatctgtg aaattttaca gaattaccaa     120
agatttcaaa tttctactga gccacctact acaccatcaa gtgggtctgt ttttatgttt     180
gatcgaaagg tgctcagata cttcaggaaa gacggtcaca attggaggaa gaaaaaagat     240
ggaaagactg tgaaggaagc tcatgagagg ttgaaggcgg aagcgttga tgttctacat      300
tgttactatg cgcatggaca ggacaatgaa aactttcaaa gacgcagtta ctggttgctt     360
caggaagaac tttcccacat agttttgtt cactacctcg aagttaaggg tagtagagtt      420
tctacttctt ttaaccggat gcaaaggact gaagacgcgg ctcggtctcc tcaagaaact     480
ggggacgcct tgaccagtga acatgatggt tatgcttctt gcagcttcaa tcaaaatgat     540
catagcaatc attcacaaac tactgactca gcaagtgtca atggttttca ctctccagaa     600
cttgaagatg ctgaatcagc atacaatcag catggaagtt ccacagctta ctctcatcaa     660
gaacttcagc agcctgcaac aggaggaaac cttactggtt ttgatcctta ctatcaaatc     720
tctttgacgc cagggatag ttatcaaaaa gagcttcgca caatccccgt aactgattct      780
tcaattatgg tagacaaaag caaaactatc aacagtcctg gagtaacaaa tgggttaaaa     840
aacagaaaat ccattgattc ccaaacctgg gaagagattc tgggaaattg tggttctgga     900
gttgaagcct tacctttgca gcctaacagt gagcatgaag tgctggacca aatactcgaa     960
agctctttta caatgcaaga ttttgctagt ctacaagagt ccatggtcaa aagccagaat    1020
caggagttaa attcaggact acatctgat cgtaccgtgt ggttccaagg acaagatatg     1080
gagctaaatg ctataagcaa tctagcttcg aatgaaaaag ctccatatct atctacgatg    1140
aaacaacatc tgttacacgg tgcattgggc gaagaaggtc tgaaaaagat ggacagtttc    1200
aatcgctgga tgagcaaaga acttggagat gttggtgtta tagctgatgc aaacgagtcc    1260
tttactcaat caagttcaag aacctactgg gaagaagttg agagtgagga tgggtccaat    1320
ggtcacaact ctaggaggga catggatgga tatgttatga gtccttccct ctcaaaggaa    1380
cagctctttta gcatcaatga cttctctcca agctgggctt atgtggggttg tgaagtggtg    1440
gttttttgtca ctggaaaatt cttaaagact cgggaggaga ctgaaattgg cgagtggtct    1500
tgcatgtttg ggcaaacaga agttccagca gatgttatat ctaatggtat tctccaatgt    1560
gttgctccta tgcatgaggc tggaagagtt cccttttatg taacatgttc caacagattg    1620
gcatgcagtg aagtgcgtga attcgagtat aaggttgccg agtctcaagt ttttgataga    1680
gaagcagatg atgagtctac tattgacatt cttgaggcaa gatttgttaa actgttgtgc    1740
tcgaaatctg aaaatacaag ccctgttcct gggaatgaca gtgatttgtc acaattgagc    1800
gagaagatta gttactact ttcgagaac gatgaccagt tggatcagat gctcatgaat      1860
gaaatctccc aagaaaatat gaaaaacaac cttttgcagg aatttctgaa agaaagctta    1920
cactcatggc ttttacaaaa gatagcagaa ggtggaaaag gtccaagtgt tttggatgaa    1980
ggtggccaag gtgtattaca ttttgcagct tctcttggtt acaactgggc cttagaacca    2040
acaataatcg ctggtgtaag cgttgatttt cgcgatgtaa atggttggac cgcacttcat    2100
```

```
tgggcagctt tctttggcag ggagaggata attggttcac tcatagctct tggtgctgct    2160
cctggaactt taactgaccc aaatccagat ttcccatcag gaagcacacc ttctgatcta    2220
gcctatgcta atggtcacaa aggaattgct ggttatctct cagaatatgc cttaagagct    2280
catgtttctt tgctcagtct aaatgataaa aatgccgaaa ctgttgagat ggctcctagc    2340
ccatccagct catcattgac agactcgttg acagctgtac gtaacgctac tcaggcagca    2400
gctcggattc atcaggtttt cagggctcag tctttccaga gaagcaact aaaagaattt     2460 ggagataaaa agcttggaat gtcggaggag cgtgctcttt cgatgcttgc tcctaaaaca    2520
cacaaatcag gaagggcaca tagtgatgat tccgtgcaag ccgctgctat tcggattcag    2580
aacaagttcc gaggttacaa gggaagaaaa gactatttga ttaccagaca agaatcatc     2640 aaaatacagg ctcatgtgag aggttatcag tttaggaaaa actacagaaa gataattaag    2700
tcagaagcac ttgttgagaa gatgcaagac ggaacagaga agaagaaga tgatgatttt     2760 ttcaaacaag gaagaaagca aacagaggat aggctacaaa aagctcttgc aagagtgaaa    2820
tccatggttc aatatcctga agctagagat caataccgta gattgctaaa tgttgtcaac    2880
gacatccaag aaagcaaggt tgaaaaagct cttgaaaatt cagaagcaac ttgttttgat    2940
gatgatgatg atctgataga tattgaagca ttgttggaag atgatgacac attgatgttg    3000
cctatgtcct catctttgtg gaccagttaa atcactctca gctttgttg tgatattgtg     3060 tcacagtatt attgactcat taaacttgta aattcttgtg taatcactct ctcatatac     3120 tgtaactgca ttcatgactc taatttaaat gatatatatt tgaaacataa atcaaactta    3180
tgt                                                                  3183
```

<210> SEQ ID NO 6
<211> LENGTH: 1009
<212> TYPE: PRT
<213> ORGANISM: Artificial Sequence
<220> FEATURE:
<223> OTHER INFORMATION: AtSR1 mutant 3 protein (deletion)

<400> SEQUENCE: 6

```
Met Ala Glu Ala Arg Arg Phe Ser Pro Val His Glu Leu Asp Val Gly
1               5                   10                  15

Gln Ile Leu Ser Glu Ala Arg His Arg Trp Leu Arg Pro Glu Ile
            20                  25                  30

Cys Glu Ile Leu Gln Asn Tyr Gln Arg Phe Gln Ile Ser Thr Glu Pro
        35                  40                  45

Pro Thr Thr Pro Ser Ser Gly Ser Val Phe Met Phe Asp Arg Lys Val
    50                  55                  60

Leu Arg Tyr Phe Arg Lys Asp Gly His Asn Trp Arg Lys Lys Asp
65                  70                  75                  80

Gly Lys Thr Val Lys Glu Ala His Glu Arg Leu Lys Ala Gly Ser Val
                85                  90                  95

Asp Val Leu His Cys Tyr Tyr Ala His Gly Gln Asp Asn Glu Asn Phe
            100                 105                 110

Gln Arg Arg Ser Tyr Trp Leu Leu Gln Glu Glu Leu Ser His Ile Val
        115                 120                 125

Phe Val His Tyr Leu Glu Val Lys Gly Ser Arg Val Ser Thr Ser Phe
    130                 135                 140

Asn Arg Met Gln Arg Thr Glu Asp Ala Ala Arg Ser Pro Gln Glu Thr
145                 150                 155                 160

Gly Asp Ala Leu Thr Ser Glu His Asp Gly Tyr Ala Ser Cys Ser Phe
```

```
                    165                 170                 175
Asn Gln Asn Asp His Ser Asn His Ser Gln Thr Thr Asp Ser Ala Ser
                180                 185                 190

Val Asn Gly Phe His Ser Pro Glu Leu Glu Asp Ala Glu Ser Ala Tyr
            195                 200                 205

Asn Gln His Gly Ser Ser Thr Ala Tyr Ser His Gln Glu Leu Gln Gln
        210                 215                 220

Pro Ala Thr Gly Gly Asn Leu Thr Gly Phe Asp Pro Tyr Tyr Gln Ile
225                 230                 235                 240

Ser Leu Thr Pro Arg Asp Ser Tyr Gln Lys Glu Leu Arg Thr Ile Pro
                245                 250                 255

Val Thr Asp Ser Ser Ile Met Val Asp Lys Ser Lys Thr Ile Asn Ser
                260                 265                 270

Pro Gly Val Thr Asn Gly Leu Lys Asn Arg Lys Ser Ile Asp Ser Gln
            275                 280                 285

Thr Trp Glu Glu Ile Leu Gly Asn Cys Gly Ser Gly Val Glu Ala Leu
        290                 295                 300

Pro Leu Gln Pro Asn Ser Glu His Glu Val Leu Asp Gln Ile Leu Glu
305                 310                 315                 320

Ser Ser Phe Thr Met Gln Asp Phe Ala Ser Leu Gln Glu Ser Met Val
                325                 330                 335

Lys Ser Gln Asn Gln Glu Leu Asn Ser Gly Leu Thr Ser Asp Arg Thr
            340                 345                 350

Val Trp Phe Gln Gly Gln Asp Met Glu Leu Asn Ala Ile Ser Asn Leu
        355                 360                 365

Ala Ser Asn Glu Lys Ala Pro Tyr Leu Ser Thr Met Lys Gln His Leu
        370                 375                 380

Leu His Gly Ala Leu Gly Glu Glu Gly Leu Lys Lys Met Asp Ser Phe
385                 390                 395                 400

Asn Arg Trp Met Ser Lys Glu Leu Gly Asp Val Gly Val Ile Ala Asp
                405                 410                 415

Ala Asn Glu Ser Phe Thr Gln Ser Ser Arg Thr Tyr Trp Glu Glu
            420                 425                 430

Val Glu Ser Glu Asp Gly Ser Asn Gly His Asn Ser Arg Arg Asp Met
        435                 440                 445

Asp Gly Tyr Val Met Ser Pro Ser Leu Ser Lys Glu Gln Leu Phe Ser
450                 455                 460

Ile Asn Asp Phe Ser Pro Ser Trp Ala Tyr Val Gly Cys Glu Val Val
465                 470                 475                 480

Val Phe Val Thr Gly Lys Phe Leu Lys Thr Arg Glu Glu Thr Glu Ile
                485                 490                 495

Gly Glu Trp Ser Cys Met Phe Gly Gln Thr Glu Val Pro Ala Asp Val
            500                 505                 510

Ile Ser Asn Gly Ile Leu Gln Cys Val Ala Pro Met His Glu Ala Gly
        515                 520                 525

Arg Val Pro Phe Tyr Val Thr Cys Ser Asn Arg Leu Ala Cys Ser Glu
        530                 535                 540

Val Arg Glu Phe Glu Tyr Lys Val Ala Glu Ser Gln Val Phe Asp Arg
545                 550                 555                 560

Glu Ala Asp Asp Glu Ser Thr Ile Asp Ile Leu Glu Ala Arg Phe Val
                565                 570                 575

Lys Leu Leu Cys Ser Lys Ser Glu Asn Thr Ser Pro Val Ser Gly Asn
            580                 585                 590
```

```
Asp Ser Asp Leu Ser Gln Leu Ser Glu Lys Ile Ser Leu Leu Leu Phe
            595                 600                 605

Glu Asn Asp Asp Gln Leu Asp Gln Met Leu Met Asn Glu Ile Ser Gln
610                 615                 620

Glu Asn Met Lys Asn Asn Leu Leu Gln Glu Phe Leu Lys Glu Ser Leu
625                 630                 635                 640

His Ser Trp Leu Leu Gln Lys Ile Ala Glu Gly Gly Lys Gly Pro Ser
            645                 650                 655

Val Leu Asp Glu Gly Gly Gln Gly Val Leu His Phe Ala Ala Ser Leu
            660                 665                 670

Gly Tyr Asn Trp Ala Leu Glu Pro Thr Ile Ile Ala Gly Val Ser Val
            675                 680                 685

Asp Phe Arg Asp Val Asn Gly Trp Thr Ala Leu His Trp Ala Ala Phe
            690                 695                 700

Phe Gly Arg Glu Arg Ile Ile Gly Ser Leu Ile Ala Leu Gly Ala Ala
705                 710                 715                 720

Pro Gly Thr Leu Thr Asp Pro Asn Pro Asp Phe Pro Ser Gly Ser Thr
            725                 730                 735

Pro Ser Asp Leu Ala Tyr Ala Asn Gly His Lys Gly Ile Ala Gly Tyr
            740                 745                 750

Leu Ser Glu Tyr Ala Leu Arg Ala His Val Ser Leu Leu Ser Leu Asn
            755                 760                 765

Asp Lys Asn Ala Glu Thr Val Glu Met Ala Pro Ser Pro Ser Ser Ser
770                 775                 780

Ser Leu Thr Asp Ser Leu Thr Ala Val Arg Asn Ala Thr Gln Ala Ala
785                 790                 795                 800

Ala Arg Ile His Gln Val Phe Arg Ala Gln Ser Phe Gln Lys Lys Gln
            805                 810                 815

Leu Lys Glu Phe Gly Asp Lys Lys Leu Gly Met Ser Glu Glu Arg Ala
            820                 825                 830

Leu Ser Met Leu Ala Pro Lys Thr His Lys Ser Gly Arg Ala His Ser
            835                 840                 845

Asp Asp Ser Val Gln Ala Ala Ile Arg Ile Gln Asn Lys Phe Arg
            850                 855                 860

Gly Tyr Lys Gly Arg Lys Asp Tyr Leu Ile Thr Arg Gln Arg Ile Ile
865                 870                 875                 880

Lys Ile Gln Ala His Val Arg Gly Tyr Gln Phe Arg Lys Asn Tyr Arg
            885                 890                 895

Lys Ile Ile Lys Ser Glu Ala Leu Val Glu Lys Met Gln Asp Gly Thr
            900                 905                 910

Glu Lys Glu Glu Asp Asp Phe Phe Lys Gln Gly Arg Lys Gln Thr
            915                 920                 925

Glu Asp Arg Leu Gln Lys Ala Leu Ala Arg Val Lys Ser Met Val Gln
            930                 935                 940

Tyr Pro Glu Ala Arg Asp Gln Tyr Arg Arg Leu Leu Asn Val Val Asn
945                 950                 955                 960

Asp Ile Gln Glu Ser Lys Val Glu Lys Ala Leu Glu Asn Ser Glu Ala
            965                 970                 975

Thr Cys Phe Asp Asp Asp Asp Leu Ile Asp Ile Glu Ala Leu Leu
            980                 985                 990

Glu Asp Asp Asp Thr Leu Met Leu Pro Met Ser Ser Ser Leu Trp Thr
            995                 1000                1005
```

Ser

<210> SEQ ID NO 7
<211> LENGTH: 2136
<212> TYPE: DNA
<213> ORGANISM: Nicotiana tabacum

<400> SEQUENCE: 7

| | | | | | |
|---|---|---|---|---|---|
| agaaccgatc | attcatcttt | aaaacaacct | tgttagatg | gcgtcttgag | agaaggttta | 60 |
| aagaagcttg | atagctttga | ccggtggatg | agtaaggaac | ttgaagatgt | aagtgagcca | 120 |
| catatgcaat | ccaattctag | ttcctattgg | gataatgtcg | gagatgacga | tggagttgat | 180 |
| aattccacaa | ttgcttcgca | agtgcagtta | gacacctaca | tgctaagtcc | ttcactctcc | 240 |
| caagatcagt | tctttagcat | tattgatttc | tcaccaagct | gggcatttgc | tgggtcagaa | 300 |
| attaaggttc | tcatcaccgg | gaagtttttg | aaatcccagc | cagaagtgga | gaagtgggca | 360 |
| tgcatgtttg | gtgagttgga | agttccagca | gaagtaatag | ctgatggtgt | tctacgctgc | 420 |
| catacaccta | atcaaaaggt | gggaagagtt | ccatttttata | taacatgttc | caataggttg | 480 |
| gcatgtagtg | aagtaagaga | atttgaattt | agggtcagtg | agagccaaga | tgttgatgtt | 540 |
| gcaaatagtt | gcagctccag | tgaaagtctt | cttcatatga | gattcggaaa | attattatct | 600 |
| ttggaatcca | ctgtttccct | aagttctccg | cctcgcagcg | aggatgatgt | ttccaatgtg | 660 |
| tgcagtaaaa | tcaattcatt | gctaaaagag | gatgacaatg | agtgggaaga | aatgttgaac | 720 |
| cttacttatg | agaacaactt | tatggcggag | aaggtaaaag | accagctcct | acaaaagctt | 780 |
| ctaaaagaga | agttacgtgt | ttggctcctc | caaaaggttg | ctgaaggcgg | gaaaggcccct | 840 |
| aacgtactgg | acgaaggtgg | tcaaggagtc | ctacattttg | cggcagctct | tggttatgac | 900 |
| tgggctatac | cacctactat | agctgcaggt | gtaagcgtca | atttccgaga | tgtgaatgga | 960 |
| tggactgcac | tccattgggc | agcatcttat | ggaagagagc | ggacagtggg | tttcctcatc | 1020 |
| atctccttag | gtgcagctcc | tggagcattg | acagatccta | ctcctaaaca | tccttcagga | 1080 |
| agaacacctg | ctgacttagc | ttctagcaat | ggacataaag | gaattgctgg | ttatttagca | 1140 |
| gagtcatcct | taagctccca | ccttcttct | ctcgagttga | aggaaatgaa | gcagggtgag | 1200 |
| actgtgcaac | cctttggaga | ggctgttcaa | acagtttctg | aacggtcagc | tacaccagct | 1260 |
| tgggatggtg | actggccaca | tggagtctca | ttgaaggatt | ctctagctgc | tgttcgtaat | 1320 |
| gcaactcaag | cagccgctcg | tattcaccaa | gtcttcaggg | tgcagtcgtt | ccagaggaag | 1380 |
| cagctaaaag | aacacggtgg | cagtgaattt | ggactatcag | atgagcatgc | tctctctctt | 1440 |
| cttgctttga | agacaaacaa | ggctggtcaa | catgatgagc | cggtacacac | tgctgcggtg | 1500 |
| cgtatacaaa | ataaatttcg | cagttggaag | ggaagaagag | actatcttct | aatccgccaa | 1560 |
| cgaattatta | aaattcaggc | tcatgtaaga | ggacaccagg | taaggaacaa | atacaaaaac | 1620 |
| ataatatggt | ctgtggggat | cttagagaag | gtaattttgc | gatggaggcg | gaaaggaagt | 1680 |
| ggattgcgtg | ggtttaaacc | agaagcaaca | cttactgaag | gaagcaacat | gcaagatcga | 1740 |
| ccagtgcagg | aggatgacta | tgatttttta | aagaaggca | gaaagcaaac | tgagcaaagg | 1800 |
| ttgcagaagg | ctctggcaag | ggtaaagtcg | atggttcaat | atcctgaggc | cagggatcaa | 1860 |
| tatcggaggc | tgctgaatgt | tgtgtccgac | atgaaggaca | ccacgactac | gagcgatggt | 1920 |
| gcaccaagca | actcggggga | agcagctgat | tcggtgacg | atttgatcga | tcttgatgat | 1980 |
| ctattggacg | acgacacttt | tatgtctacg | gcaccttgaa | ttctgtattg | ataatatacc | 2040 |
| atgtgtgaat | tagcatttgt | tacatggcta | ttagagttgt | aaataggctg | cactaactag | 2100 |

```
tttgtaaatc tgaaaccaga gtgacaaagg tattta                                    2136
```

<210> SEQ ID NO 8
<211> LENGTH: 672
<212> TYPE: PRT
<213> ORGANISM: Nicotiana tabacum

<400> SEQUENCE: 8

| Arg | Thr | Asp | His | Ser | Ser | Leu | Lys | Gln | Pro | Leu | Leu | Asp | Gly | Val | Leu |
|---|---|---|---|---|---|---|---|---|---|---|---|---|---|---|---|
| 1 | | | | 5 | | | | | 10 | | | | | 15 | |

| Arg | Glu | Gly | Leu | Lys | Lys | Leu | Asp | Ser | Phe | Asp | Arg | Trp | Met | Ser | Lys |
| | | | 20 | | | | | 25 | | | | | 30 | | |

| Glu | Leu | Glu | Asp | Val | Ser | Glu | Pro | His | Met | Gln | Ser | Asn | Ser | Ser | Ser |
| | | | 35 | | | | | 40 | | | | | 45 | | |

| Tyr | Trp | Asp | Asn | Val | Gly | Asp | Asp | Gly | Val | Asp | Asn | Ser | Thr | Ile |
| | 50 | | | | | 55 | | | | | 60 | | | | |

| Ala | Ser | Gln | Val | Gln | Leu | Asp | Thr | Tyr | Met | Leu | Ser | Pro | Ser | Leu | Ser |
| 65 | | | | | 70 | | | | | 75 | | | | | 80 |

| Gln | Asp | Gln | Phe | Phe | Ser | Ile | Ile | Asp | Phe | Ser | Pro | Ser | Trp | Ala | Phe |
| | | | | 85 | | | | | 90 | | | | | 95 | |

| Ala | Gly | Ser | Glu | Ile | Lys | Val | Leu | Ile | Thr | Gly | Lys | Phe | Leu | Lys | Ser |
| | | | 100 | | | | | 105 | | | | | 110 | | |

| Gln | Pro | Glu | Val | Glu | Lys | Trp | Ala | Cys | Met | Phe | Gly | Glu | Leu | Glu | Val |
| | | | 115 | | | | | 120 | | | | | 125 | | |

| Pro | Ala | Glu | Val | Ile | Ala | Asp | Gly | Val | Leu | Arg | Cys | His | Thr | Pro | Asn |
| | 130 | | | | | 135 | | | | | 140 | | | | |

| Gln | Lys | Val | Gly | Arg | Val | Pro | Phe | Tyr | Ile | Thr | Cys | Ser | Asn | Arg | Leu |
| 145 | | | | | 150 | | | | | 155 | | | | | 160 |

| Ala | Cys | Ser | Glu | Val | Arg | Glu | Phe | Glu | Phe | Arg | Val | Ser | Glu | Ser | Gln |
| | | | | 165 | | | | | 170 | | | | | 175 | |

| Asp | Val | Asp | Val | Ala | Asn | Ser | Cys | Ser | Ser | Ser | Glu | Ser | Leu | Leu | His |
| | | | 180 | | | | | 185 | | | | | 190 | | |

| Met | Arg | Phe | Gly | Lys | Leu | Leu | Ser | Leu | Glu | Ser | Thr | Val | Ser | Leu | Ser |
| | | | 195 | | | | | 200 | | | | | 205 | | |

| Ser | Pro | Pro | Arg | Ser | Glu | Asp | Asp | Val | Ser | Asn | Val | Cys | Ser | Lys | Ile |
| | 210 | | | | | 215 | | | | | 220 | | | | |

| Asn | Ser | Leu | Leu | Lys | Glu | Asp | Asp | Asn | Glu | Trp | Glu | Glu | Met | Leu | Asn |
| 225 | | | | | 230 | | | | | 235 | | | | | 240 |

| Leu | Thr | Tyr | Glu | Asn | Asn | Phe | Met | Ala | Glu | Lys | Val | Lys | Asp | Gln | Leu |
| | | | | 245 | | | | | 250 | | | | | 255 | |

| Leu | Gln | Lys | Leu | Leu | Lys | Glu | Lys | Leu | Arg | Val | Trp | Leu | Leu | Gln | Lys |
| | | | 260 | | | | | 265 | | | | | 270 | | |

| Val | Ala | Glu | Gly | Gly | Lys | Gly | Pro | Asn | Val | Leu | Asp | Glu | Gly | Gly | Gln |
| | | | 275 | | | | | 280 | | | | | 285 | | |

| Gly | Val | Leu | His | Phe | Ala | Ala | Ala | Leu | Gly | Tyr | Asp | Trp | Ala | Ile | Pro |
| | 290 | | | | | 295 | | | | | 300 | | | | |

| Pro | Thr | Ile | Ala | Ala | Gly | Val | Ser | Val | Asn | Phe | Arg | Asp | Val | Asn | Gly |
| 305 | | | | | 310 | | | | | 315 | | | | | 320 |

| Trp | Thr | Ala | Leu | His | Trp | Ala | Ser | Tyr | Gly | Arg | Glu | Arg | Thr | Val |
| | | | | 325 | | | | | 330 | | | | | 335 | |

| Gly | Phe | Leu | Ile | Ile | Ser | Leu | Gly | Ala | Ala | Pro | Gly | Ala | Leu | Thr | Asp |
| | | | 340 | | | | | 345 | | | | | 350 | | |

| Pro | Thr | Pro | Lys | His | Pro | Ser | Gly | Arg | Thr | Pro | Ala | Asp | Leu | Ala | Ser |
| | | | 355 | | | | | 360 | | | | | 365 | | |

Ser Asn Gly His Lys Gly Ile Ala Gly Tyr Leu Ala Glu Ser Ser Leu
    370                 375                 380

Ser Ser His Leu Ser Ser Leu Glu Leu Lys Glu Met Lys Gln Gly Glu
385                 390                 395                 400

Thr Val Gln Pro Phe Gly Glu Ala Val Gln Thr Val Ser Glu Arg Ser
                405                 410                 415

Ala Thr Pro Ala Trp Asp Gly Asp Trp Pro His Gly Val Ser Leu Lys
            420                 425                 430

Asp Ser Leu Ala Ala Val Arg Asn Ala Thr Gln Ala Ala Ala Arg Ile
        435                 440                 445

His Gln Val Phe Arg Val Gln Ser Phe Gln Arg Lys Gln Leu Lys Glu
    450                 455                 460

His Gly Gly Ser Glu Phe Gly Leu Ser Asp Glu His Ala Leu Ser Leu
465                 470                 475                 480

Leu Ala Leu Lys Thr Asn Lys Ala Gly Gln His Asp Glu Pro Val His
                485                 490                 495

Thr Ala Ala Val Arg Ile Gln Asn Lys Phe Arg Ser Trp Lys Gly Arg
            500                 505                 510

Arg Asp Tyr Leu Leu Ile Arg Gln Arg Ile Ile Lys Ile Gln Ala His
        515                 520                 525

Val Arg Gly His Gln Val Arg Asn Lys Tyr Lys Asn Ile Ile Trp Ser
    530                 535                 540

Val Gly Ile Leu Glu Lys Val Ile Leu Arg Trp Arg Arg Lys Gly Ser
545                 550                 555                 560

Gly Leu Arg Gly Phe Lys Pro Glu Ala Thr Leu Thr Glu Gly Ser Asn
                565                 570                 575

Met Gln Asp Arg Pro Val Gln Glu Asp Asp Tyr Asp Phe Leu Lys Glu
            580                 585                 590

Gly Arg Lys Gln Thr Glu Gln Arg Leu Gln Lys Ala Leu Ala Arg Val
        595                 600                 605

Lys Ser Met Val Gln Tyr Pro Glu Ala Arg Asp Gln Tyr Arg Arg Leu
    610                 615                 620

Leu Asn Val Val Ser Asp Met Lys Asp Thr Thr Thr Thr Ser Asp Gly
625                 630                 635                 640

Ala Pro Ser Asn Ser Gly Glu Ala Ala Asp Phe Gly Asp Leu Ile
                645                 650                 655

Asp Leu Asp Asp Leu Leu Asp Asp Thr Phe Met Ser Thr Ala Pro
            660                 665                 670

<210> SEQ ID NO 9
<211> LENGTH: 1867
<212> TYPE: DNA
<213> ORGANISM: Lycopersicon esculentum

<400> SEQUENCE: 9
gcacgaggtg gagaactgta gttgggcatg catgtttggt gagttggaag ttcccgcaga      60
agtaatagct gatggtgttc ttcgctgcca tactccggtt caaaaggctg aagagttcc     120 attctacata acatgctcca ataggttggc atgtagtgag gtgagagaat tgaatttcg     180 ggtcactgaa ggccaagatg ttgatgttgc aaatccaaat agttgcagct ccagtgaaag    240
tcttcttcat atgagaattcg gaaaattatt atctctggaa tcctttgttt cccaaacttc   300
tccacctatc agtgaggaca atgtttccta tatccagt aaaattaact cattgctaag      360
agacgatgac aatgagtgga aggaaatgtt gcaccttact aatgagaaca actttatggc    420

-continued

```
agagaaagta aaagaccagc tcctacaaaa gcttctaaaa gagaagttgc atgtttggct    480
ccttcaaaag gttgctgagg gtgggaaagg ccctaacata ctggatgaag gtggtcaagg    540
agttctacat tttgcagctg ctcttggtta tgactgggct gtaccaccta ctatagctgc    600
aggcgtaagc gtcaatttcc gagatgtgaa tggatggact gcactccatt gggcagcatc    660
atatggaaga gagcggacag tgggtttcct tatctcctta ggtgcagcta ctggagcatt    720
gacagatcct actcctaaac atccttcagg cagaacacct gctgatctag cttccagcaa    780
tggacataaa ggaattgctg ttacttagc agagtcttcc ttgagctccc accttttttc     840
tcttgagttg aaggaaaaga agcagggtga gaatgaacaa gcttttgggg aagctgttca    900
aacggtttct gaaaggactg ctacaccagc ttgggatggt gactggtcac atggagtctc    960
attgaaggat tctcttgcag ctgttcgtaa tgctactcaa gcagctgctc gtattcatca    1020
ggtcttcagg ttgcagtcat tccagaggaa gcagctaaaa gaatacggtg cagtgaatt    1080 tggactatca gatgagcgtg ctctctcact tctcgccatg aagacaaata gggctggaca    1140
gtatgatgag cctcacgctg ctgctgtccg tatacaaaat aaacttcgca gttggaaggg    1200
aagaagagat tttcttctaa tccgccaacg aattattaaa attcaggctc atgtgagagg    1260
acaccaggta aggaacaaat acaaaaacat aatatggtct gtggggatct tagagaaggt    1320
aattttgcga tggaggcgga aaggaagtgg attgcgtgga tttaaaccag aagcacctac    1380
tgaaggaagc aacatgcaag atcaaccagt gcaggaggat gactatgatt tcttaaaaga    1440
aggcagaaag caaactgaag aaaggttgca gaaggctctg gaaagggtaa agtcgatggt    1500
tcaatacccg gaggctaggg accagtatag gaggctgctg aatgttgtgt ccgacatgca    1560
agaacccaat agtactgcag ccagctacaa ctcagcggaa gcagttgatt tcaatgatga    1620
tttgatcgat cttggtgatt tattggatga tgatactttt atgcctacag caccttgagt    1680
tctgtgttaa taatatacca tttgtggatt agtatttgtt atacatggct gttagagttg    1740
ttgtatacat aggctgcact aactagtttg taaatgtgaa atcaaaaat ccattgtgca     1800 gattgacaag aatttgagat ttaaaggtag taagattatg gtatgtttga tgttttcttt    1860
tcgttgt                                                              1867
```

<210> SEQ ID NO 10
<211> LENGTH: 558
<212> TYPE: PRT
<213> ORGANISM: Lycopersicon esculentum

<400> SEQUENCE: 10

```
His Glu Val Glu Asn Cys Ser Trp Ala Cys Met Phe Gly Glu Leu Glu
1               5                   10                  15

Val Pro Ala Glu Val Ile Ala Asp Gly Val Leu Arg Cys His Thr Pro
            20                  25                  30

Val Gln Lys Ala Gly Arg Val Pro Phe Tyr Ile Thr Cys Ser Asn Arg
        35                  40                  45

Leu Ala Cys Ser Glu Val Arg Glu Phe Glu Phe Arg Val Thr Glu Gly
    50                  55                  60

Gln Asp Val Asp Val Ala Asn Pro Asn Ser Cys Ser Ser Ser Glu Ser
65                  70                  75                  80

Leu Leu His Met Arg Phe Gly Lys Leu Leu Ser Leu Glu Ser Phe Val
                85                  90                  95

Ser Gln Thr Ser Pro Pro Ile Ser Glu Asp Asn Val Ser Tyr Ile Ser
            100                 105                 110
```

```
Ser Lys Ile Asn Ser Leu Leu Arg Asp Asp Asn Glu Trp Lys Glu
        115                 120                 125
Met Leu His Leu Thr Asn Glu Asn Asn Phe Met Ala Glu Lys Val Lys
130                 135                 140
Asp Gln Leu Leu Gln Lys Leu Leu Lys Glu Lys Leu His Val Trp Leu
145                 150                 155                 160
Leu Gln Lys Val Ala Glu Gly Lys Gly Pro Asn Ile Leu Asp Glu
        165                 170                 175
Gly Gly Gln Gly Val Leu His Phe Ala Ala Ala Leu Gly Tyr Asp Trp
        180                 185                 190
Ala Val Pro Pro Thr Ile Ala Ala Gly Val Ser Val Asn Phe Arg Asp
        195                 200                 205
Val Asn Gly Trp Thr Ala Leu His Trp Ala Ala Ser Tyr Gly Arg Glu
        210                 215                 220
Arg Thr Val Gly Phe Leu Ile Ser Leu Gly Ala Ala Thr Gly Ala Leu
225                 230                 235                 240
Thr Asp Pro Thr Pro Lys His Pro Ser Gly Arg Thr Pro Ala Asp Leu
        245                 250                 255
Ala Ser Ser Asn Gly His Lys Gly Ile Ala Gly Tyr Leu Ala Glu Ser
        260                 265                 270
Ser Leu Ser Ser His Leu Phe Ser Leu Glu Leu Lys Glu Lys Lys Gln
        275                 280                 285
Gly Glu Asn Glu Gln Ala Phe Gly Glu Ala Val Gln Thr Val Ser Glu
        290                 295                 300
Arg Thr Ala Thr Pro Ala Trp Asp Gly Asp Trp Ser His Gly Val Ser
305                 310                 315                 320
Leu Lys Asp Ser Leu Ala Ala Val Arg Asn Ala Thr Gln Ala Ala Ala
        325                 330                 335
Arg Ile His Gln Val Phe Arg Leu Gln Ser Phe Gln Arg Lys Gln Leu
        340                 345                 350
Lys Glu Tyr Gly Gly Ser Glu Phe Gly Leu Ser Asp Glu Arg Ala Leu
        355                 360                 365
Ser Leu Leu Ala Met Lys Thr Asn Arg Ala Gly Gln Tyr Asp Glu Pro
        370                 375                 380
His Ala Ala Ala Val Arg Ile Gln Asn Lys Leu Arg Ser Trp Lys Gly
385                 390                 395                 400
Arg Arg Asp Phe Leu Leu Ile Arg Gln Arg Ile Ile Lys Ile Gln Ala
        405                 410                 415
His Val Arg Gly His Gln Val Arg Asn Lys Tyr Lys Asn Ile Ile Trp
        420                 425                 430
Ser Val Gly Ile Leu Glu Lys Val Ile Leu Arg Trp Arg Arg Lys Gly
        435                 440                 445
Ser Gly Leu Arg Gly Phe Lys Pro Glu Ala Pro Thr Glu Gly Ser Asn
        450                 455                 460
Met Gln Asp Gln Pro Val Gln Glu Asp Tyr Asp Phe Leu Lys Glu
465                 470                 475                 480
Gly Arg Lys Gln Thr Glu Glu Arg Leu Gln Lys Ala Leu Glu Arg Val
        485                 490                 495
Lys Ser Met Val Gln Tyr Pro Glu Ala Arg Asp Gln Tyr Arg Arg Leu
        500                 505                 510
Leu Asn Val Val Ser Asp Met Gln Glu Pro Asn Ser Thr Ala Ala Ser
        515                 520                 525
```

Tyr Asn Ser Ala Glu Ala Val Asp Phe Asn Asp Asp Leu Ile Asp Leu
                530                 535                 540

Gly Asp Leu Leu Asp Asp Asp Thr Phe Met Pro Thr Ala Pro
545                 550                 555

<210> SEQ ID NO 11
<211> LENGTH: 1480
<212> TYPE: DNA
<213> ORGANISM: Arabidopsis thaliana

<400> SEQUENCE: 11

| | | | | | |
|---|---|---|---|---|---|
| gttaaactgt | tgtgctcgaa | atctgaaaat | acaagccctg | tttctgggaa | tgacagtgat | 60 |
| ttgtcacaat | tgagcgagaa | gattagttta | ctacttttcg | agaacgatga | ccagttggat | 120 |
| cagatgctca | tgaatgaaat | ctcccaagaa | aatatgaaaa | acaaccttt | gcaggaattt | 180 |
| ctgaaagaaa | gcttacactc | atggctttta | caaaagatag | cagaaggtgg | aaaaggtcca | 240 |
| agtgttttgg | atgaaggtgg | ccaaggtgta | ttacattttg | cagcttctct | tggttacaac | 300 |
| tgggccttag | aaccaacaat | aatcgctggt | gtaagcgttg | attttcgcga | tgtaaatggt | 360 |
| tggaccgcac | ttcattgggc | agctttcttt | ggcagggaga | ggataattgg | ttcactcata | 420 |
| gctcttggtg | ctgctcctgg | aactttaact | gacccaaatc | cagatttccc | atcaggaagc | 480 |
| acaccttctg | atctagccta | tgctaatggt | cacaaggaa | ttgctggtta | tctctcagaa | 540 |
| tatgccttaa | gagctcatgt | ttctttgctc | agtctaaatg | ataaaaatgc | cgaaactgtt | 600 |
| gagatggctc | ctagcccatc | cagctcatca | ttgacagact | cgttgacagc | tgtacgtaac | 660 |
| gctactcagg | cagcagctcg | gattcatcag | gtttttcaggg | ctcagtcttt | ccagaagaag | 720 |
| caactaaaag | aatttggaga | taaaaagctt | ggaatgtcgg | aggagcgtgc | tctttcgatg | 780 |
| cttgctccta | aaacacacaa | atcaggaagg | gcacatagtg | atgattccgt | gcaagccgct | 840 |
| gctattcgga | ttcagaacaa | gttccgaggt | tacaagggaa | gaaaagacta | tttgattacc | 900 |
| agacaaagaa | tcatcaaaat | acaggctcat | gtgagaggtt | atcagtttag | gaaaaactac | 960 |
| agaaagataa | tttggtcagt | gggggtatta | gagaaggtga | tattacgttg | gagacggaaa | 1020 |
| ggagctggtt | tgcgcgggtt | taagtcgaaa | gcacttgttg | agaagatgca | agacggaaca | 1080 |
| gagaaagaag | aagatgatga | ttttttcaaa | caaggaagaa | agcaaacaga | ggataggcta | 1140 |
| caaaaagctc | ttgcaagagt | gaaatccatg | gttcaatatc | ctgaagctag | agatcaatac | 1200 |
| cgtagattgc | taaatgttgt | caacgacatc | caagaaagca | aggttgaaaa | agctcttgaa | 1260 |
| aattcagaag | caacttgttt | tgatgatgat | gatgatctga | tagatattga | agcattgttg | 1320 |
| gaagatgatg | acacattgat | gttgcctatg | tcctcatctt | tgtggaccag | ttaaatcact | 1380 |
| ctcaagcttt | gttgtgatat | tgtgtcacag | tattattgac | tcattaaact | tgtaaattct | 1440 |
| tgtgtaatca | ctcttctcat | atactgtaac | tgcattcatg | | | 1480 |

<210> SEQ ID NO 12
<211> LENGTH: 457
<212> TYPE: PRT
<213> ORGANISM: Arabidopsis thaliana

<400> SEQUENCE: 12

Val Lys Leu Leu Cys Ser Lys Ser Glu Asn Thr Ser Pro Val Ser Gly
1               5                   10                  15

Asn Asp Ser Asp Leu Ser Gln Leu Ser Glu Lys Ile Ser Leu Leu Leu
                20                  25                  30

Phe Glu Asn Asp Asp Gln Leu Asp Gln Met Leu Met Asn Glu Ile Ser

```
                35                  40                  45
Gln Glu Asn Met Lys Asn Asn Leu Leu Gln Glu Phe Leu Lys Glu Ser
         50                  55                  60
Leu His Ser Trp Leu Leu Gln Lys Ile Ala Glu Gly Gly Lys Gly Pro
 65                  70                  75                  80
Ser Val Leu Asp Glu Gly Gly Gln Gly Val Leu His Phe Ala Ala Ser
                 85                  90                  95
Leu Gly Tyr Asn Trp Ala Leu Glu Pro Thr Ile Ile Ala Gly Val Ser
                100                 105                 110
Val Asp Phe Arg Asp Val Asn Gly Trp Thr Ala Leu His Trp Ala Ala
            115                 120                 125
Phe Phe Gly Arg Glu Arg Ile Ile Gly Ser Leu Ile Ala Leu Gly Ala
130                 135                 140
Ala Pro Gly Thr Leu Thr Asp Pro Asn Pro Asp Phe Pro Ser Gly Ser
145                 150                 155                 160
Thr Pro Ser Asp Leu Ala Tyr Ala Asn Gly His Lys Gly Ile Ala Gly
                165                 170                 175
Tyr Leu Ser Glu Tyr Ala Leu Arg Ala His Val Ser Leu Leu Ser Leu
            180                 185                 190
Asn Asp Lys Asn Ala Glu Thr Val Glu Met Ala Pro Ser Pro Ser Ser
        195                 200                 205
Ser Ser Leu Thr Asp Ser Leu Thr Ala Val Arg Asn Ala Thr Gln Ala
210                 215                 220
Ala Ala Arg Ile His Gln Val Phe Arg Ala Gln Ser Phe Gln Lys Lys
225                 230                 235                 240
Gln Leu Lys Glu Phe Gly Asp Lys Lys Leu Gly Met Ser Glu Glu Arg
                245                 250                 255
Ala Leu Ser Met Leu Ala Pro Lys Thr His Lys Ser Gly Arg Ala His
            260                 265                 270
Ser Asp Asp Ser Val Gln Ala Ala Ala Ile Arg Ile Gln Asn Lys Phe
        275                 280                 285
Arg Gly Tyr Lys Gly Arg Lys Asp Tyr Leu Ile Thr Arg Gln Arg Ile
290                 295                 300
Ile Lys Ile Gln Ala His Val Arg Gly Tyr Gln Phe Arg Lys Asn Tyr
305                 310                 315                 320
Arg Lys Ile Ile Trp Ser Val Gly Val Leu Glu Lys Val Ile Leu Arg
                325                 330                 335
Trp Arg Arg Lys Gly Ala Gly Leu Arg Gly Phe Lys Ser Glu Ala Leu
            340                 345                 350
Val Glu Lys Met Gln Asp Gly Thr Glu Lys Glu Glu Asp Asp Asp Phe
        355                 360                 365
Phe Lys Gln Gly Arg Lys Gln Thr Glu Asp Arg Leu Gln Lys Ala Leu
    370                 375                 380
Ala Arg Val Lys Ser Met Val Gln Tyr Pro Glu Ala Arg Asp Gln Tyr
385                 390                 395                 400
Arg Arg Leu Leu Asn Val Val Asn Asp Ile Gln Glu Ser Lys Val Glu
                405                 410                 415
Lys Ala Leu Glu Asn Ser Glu Ala Thr Cys Phe Asp Asp Asp Asp
            420                 425                 430
Leu Ile Asp Ile Glu Ala Leu Leu Glu Asp Asp Thr Leu Met Leu
        435                 440                 445
Pro Met Ser Ser Ser Leu Trp Thr Ser
    450                 455
```

<210> SEQ ID NO 13
<211> LENGTH: 443
<212> TYPE: DNA
<213> ORGANISM: Petroselinum crispum

<400> SEQUENCE: 13

```
aatactcttg gaagctcaaa atcgatggct acgccagctg aaatatgtga aattcttaga      60
aattacaaca agtttcgtat ttctcctgag ccagcacata gacctccaaa tggttccact     120
tttctttttt gaccgtaaag ttttgaggta ttttagaaaa gatggacata attggaggaa     180
aaaaagggat ggaaagactg ttaaggaagc tcatgaaaga ctcaaggccg aagcgttga      240
tgttttgcac tgttactatg ctcatggaga agataatgaa aattttcaaa ggcgcagcta     300
ctggttgctt gaagaggagc tctccaacat agttcttgtc cactaccgtg aagtaaaggg     360
aaacaggaca cactacaatc gtacgagggg aactgaagga gctattccta actctgtaga     420
agaagaaagc atgcctaatt ctg                                             443
```

<210> SEQ ID NO 14
<211> LENGTH: 147
<212> TYPE: PRT
<213> ORGANISM: Petroselinum crispum

<400> SEQUENCE: 14

Ile Leu Leu Glu Ala Gln Asn Arg Trp Leu Arg Gln Leu Lys Tyr Val
1               5                   10                  15

Lys Phe Leu Glu Ile Thr Thr Ser Phe Val Phe Leu Leu Ser Gln His
            20                  25                  30

Ile Asp Leu Gln Met Val Pro Leu Phe Leu Phe Asp Arg Lys Val Leu
        35                  40                  45

Arg Tyr Phe Arg Lys Asp Gly His Asn Trp Arg Lys Arg Asp Gly
    50                  55                  60

Lys Thr Val Lys Glu Ala His Glu Arg Leu Lys Ala Gly Ser Val Asp
65                  70                  75                  80

Val Leu His Cys Tyr Tyr Ala His Gly Glu Asp Asn Glu Asn Phe Gln
                85                  90                  95

Arg Arg Ser Tyr Trp Leu Leu Glu Glu Glu Leu Ser Asn Ile Val Leu
            100                 105                 110

Val His Tyr Arg Glu Val Lys Gly Asn Arg Thr His Tyr Asn Arg Thr
        115                 120                 125

Arg Gly Thr Glu Gly Ala Ile Pro Asn Ser Val Glu Glu Ser Met
    130                 135                 140

Pro Asn Ser
145

<210> SEQ ID NO 15
<211> LENGTH: 3134
<212> TYPE: DNA
<213> ORGANISM: Oryza sativa

<400> SEQUENCE: 15

```
cagcggcgga ggcggaggcg gcggccatgg cgggagcggg cggatgggac ccgctcgtcg      60
gctccgagat ccacggtttc ctcacttacc cagacttgaa ctatgataag ctggtggcgg     120
aggcggcggc gcgtggttc cggcctaatg agatctacgc gatattggcg aaccacgcga      180
ggttcaagat ccacgcacaa ccggtcgaca agcccgtgag tggaactgtt gttctatatg     240
```

```
atcgtaaagt agtcaggaac ttccgtaagg atggccataa ttggaaaaaa aagaaggatg    300
gcaggacggt ccaagaagct catgaaaaat taaagattgg taacgaagaa agggttcatg    360
tctattatgc tcgaggtgaa aatgatccaa atttctttcg aagatgctac tggctacttg    420
acaaagattt ggagcgcata gttcttgtgc attatcggca aacagctgag gaaaatgcaa    480
tggttcttcc gaacccagaa cctgaagttg cagatgttcc tacagtgaat ttgatccatt    540
acacctttct tctgacctct gcagattcaa cctctggtca tactgagcta tctttgccag    600
aggaaattaa ttcacatggt ggcatatcag cttctagtga gactggcaat catgattcca    660
gcctggagga gttttgggct aatcttttag agtcatctat aaaaaacgac ccaaaagttg    720
ttacttctgc ctgcggtggt tcctttgtgt ccagtcagca gattaataat gggccgaaga    780
attctggaaa cattgtcaat accagtatgg caagtaatgc tatcccagca cttaatgtgg    840
tgtcagaaac ttatgctaca aatcatggcc tcaatcaagt aaatgcaaat cattttggag    900
ctctgaagca tcaaggagat cagactcaat ctcttttggc gtctgatgta gattctcaat    960
cagatcaatt tataagttct tcggtgaaat ctccaatgga tggtaacaca tctattccta   1020
atgaggtgcc tgctaggcaa acattcttg gattgtggaa ttacttggat gatgacagtc   1080
ctggtttagg agataatcca agttcagttc cacagagctt ctgtccagtg accaatgaaa   1140
gactattaga aatcaatgag atctccccag aatgggctta ctctacagat actaccaagg   1200
tcgtggtgat tgggaatttc tatgagcaat acaaccattt ggctgggtct gctatgtttg   1260
gtgtctttgg tgagcaatgt gttgccggag atattgttca aactggtgtt taccgtttca   1320
tggttggacc acatacacct ggaaaagtgg attttattt gactttggat gggaaaacgc   1380
caatcagtga gatttgcagt ttcacgtatc atgttatgca tggtagttcc ttggaggcta   1440
ggctgccgcc atctgaggat gattacaaaa ggacaaatct taagatgcag atgagactag   1500
ctcgcttgtt gtttgccaca aacaagaaaa agatagcacc aaagttgctt gtagaaggca   1560
ccaaagttgc caatctcatg tcagcattac cagagaagga atggatggat ttgtggaata   1620
ttcttagtga cccagaaggc acatatgttc ctgttactga aagcttgctt gaactagtgt   1680
tgcgaaatag gttgcaagag tggcttgttg aaatggtaat ggaaggtcat aagtctactg   1740
gtcgcgatga tctaggacaa ggagctatcc atctgtgttc tttcctaggt tatacttggg   1800
ctattcgatt gttttctttg tcggggttct ccttggattt ccgtgattct tctggttgga   1860
ctgctttaca ctgggctgca taccacggga gggaaaggat ggttgccact cttttatctg   1920
ctggagcaaa tccaagttta gttacagacc ctactcccga atcccctgct ggactcactg   1980
ctgctgatct tgcagcaaga caaggttacg atggcttggc agcatatctt gctgagaaag   2040
gattgactgc acatttgag gccatgtcac tgtccaagga tactgagcaa tcaccatcaa   2100
agactaggct aacaaaacta caaagcgaga gtttgagca ccttagtgaa caagaacttt   2160
gcttaaaaga atctctagca gcctatcgca atgctgctga tgctgccagt aatatccaag   2220
ctgcactcag ggagagaact cttaagcttc aaacaaaagc aattcaattg ctaatcctg   2280 agattgaagc atctgagata gttgctgctt tgaagattca acatgcattt cggaactaca   2340
acagaaagaa agcaatgaga gctgctgcac gaatacagag tcatttccgt acatggaaga   2400
tgaggaggaa cttcattaac atgcgaagac aagttatcag gatacaagct gcgtaccgag   2460
gtcatcaagt gagaaggcag taccgcaagg taatatggtc tgttggaatt gttgagaaag   2520
caattttgcg atggagaaag aagagaaaag cccttcgtgg gatcgcatct ggaatgccag   2580
tagttatgac tgtggatgcc gaagcagaac cagcaagtac tgcagaagaa gacttcttcc   2640
```

```
aggccggccg gcaacaagcc gaggacaggt tcaatagatc tgtggttcgc gttcaagccc    2700
tgttccgttc ttacaaggca caacaggagt accggaggat gaagattgct catgaggagg    2760
ccaagattga gttcagtgaa gggcagctag gagcagcatg caggagttga aatggttttt    2820
agggacagct agtttctcta attcttgtct tgtacattat tggaaatgat agaacaacct    2880
gcagtttgcc gacgctgtac attttaggac catctgaatg atctgataca gcttttgctg    2940
accccttatg gctgatgaat ttgatgttag ccctgtagta actgtggtgg tttgcgtttg    3000
gctggcttta agctggacat aaacagcgtg tgcttcaatg tacatgtaga tgcaatgcaa    3060
gtacatgtca tgttgtaaat gctaataaga ttagcaataa tcagcaaaaa aaaaaaaaa    3120 aaaaaaaaaa aaaa                                                      3134
```

<210> SEQ ID NO 16
<211> LENGTH: 927
<212> TYPE: PRT
<213> ORGANISM: Oryza sativa

<400> SEQUENCE: 16

```
Met Ala Gly Ala Gly Gly Trp Asp Pro Leu Val Gly Ser Glu Ile His
1               5                   10                  15

Gly Phe Leu Thr Tyr Pro Asp Leu Asn Tyr Asp Lys Leu Val Ala Glu
            20                  25                  30

Ala Ala Ala Arg Trp Phe Arg Pro Asn Glu Ile Tyr Ala Ile Leu Ala
        35                  40                  45

Asn His Ala Arg Phe Lys Ile His Ala Gln Pro Val Asp Lys Pro Val
    50                  55                  60

Ser Gly Thr Val Val Leu Tyr Asp Arg Lys Val Val Arg Asn Phe Arg
65                  70                  75                  80

Lys Asp Gly His Asn Trp Lys Lys Lys Asp Gly Arg Thr Val Gln
                85                  90                  95

Glu Ala His Glu Lys Leu Lys Ile Gly Asn Glu Arg Val His Val
            100                 105                 110

Tyr Tyr Ala Arg Gly Glu Asn Asp Pro Asn Phe Phe Arg Arg Cys Tyr
        115                 120                 125

Trp Leu Leu Asp Lys Asp Leu Glu Arg Ile Val Leu Val His Tyr Arg
    130                 135                 140

Gln Thr Ala Glu Glu Asn Ala Met Val Leu Pro Asn Pro Glu Pro Glu
145                 150                 155                 160

Val Ala Asp Val Pro Thr Val Asn Leu Ile His Tyr Thr Phe Leu Leu
                165                 170                 175

Thr Ser Ala Asp Ser Thr Ser Gly His Thr Glu Leu Ser Leu Pro Glu
            180                 185                 190

Glu Ile Asn Ser His Gly Gly Ile Ser Ala Ser Ser Glu Thr Gly Asn
        195                 200                 205

His Asp Ser Ser Leu Glu Glu Phe Trp Ala Asn Leu Leu Glu Ser Ser
    210                 215                 220

Ile Lys Asn Asp Pro Lys Val Val Thr Ser Ala Cys Gly Gly Ser Phe
225                 230                 235                 240

Val Ser Ser Gln Gln Ile Asn Asn Gly Pro Lys Asn Ser Gly Asn Ile
                245                 250                 255

Val Asn Thr Ser Met Ala Ser Asn Ala Ile Pro Ala Leu Asn Val Val
            260                 265                 270

Ser Glu Thr Tyr Ala Thr Asn His Gly Leu Asn Gln Val Asn Ala Asn
```

```
                275                 280                 285
His Phe Gly Ala Leu Lys His Gln Gly Asp Gln Thr Gln Ser Leu Leu
290                 295                 300

Ala Ser Asp Val Asp Ser Gln Ser Asp Gln Phe Ile Ser Ser Ser Val
305                 310                 315                 320

Lys Ser Pro Met Asp Gly Asn Thr Ser Ile Pro Asn Glu Val Pro Ala
                325                 330                 335

Arg Gln Asn Ile Leu Gly Leu Trp Asn Tyr Leu Asp Asp Ser Pro
                340                 345                 350

Gly Leu Gly Asp Asn Pro Ser Ser Val Pro Gln Ser Phe Cys Pro Val
                355                 360                 365

Thr Asn Glu Arg Leu Leu Glu Ile Asn Glu Ile Ser Pro Glu Trp Ala
370                 375                 380

Tyr Ser Thr Asp Thr Thr Lys Val Val Ile Gly Asn Phe Tyr Glu
385                 390                 395                 400

Gln Tyr Asn His Leu Ala Gly Ser Ala Met Phe Gly Val Phe Gly Glu
                405                 410                 415

Gln Cys Val Ala Gly Asp Ile Val Gln Thr Gly Val Tyr Arg Phe Met
                420                 425                 430

Val Gly Pro His Thr Pro Gly Lys Val Asp Phe Tyr Leu Thr Leu Asp
                435                 440                 445

Gly Lys Thr Pro Ile Ser Glu Ile Cys Ser Phe Thr Tyr His Val Met
450                 455                 460

His Gly Ser Ser Leu Glu Ala Arg Leu Pro Ser Glu Asp Asp Tyr
465                 470                 475                 480

Lys Arg Thr Asn Leu Lys Met Gln Met Arg Leu Ala Arg Leu Leu Phe
                485                 490                 495

Ala Thr Asn Lys Lys Ile Ala Pro Lys Leu Leu Val Glu Gly Thr
                500                 505                 510

Lys Val Ala Asn Leu Met Ser Ala Leu Pro Glu Lys Glu Trp Met Asp
                515                 520                 525

Leu Trp Asn Ile Leu Ser Asp Pro Glu Gly Thr Tyr Val Pro Val Thr
530                 535                 540

Glu Ser Leu Leu Glu Leu Val Leu Arg Asn Arg Leu Gln Glu Trp Leu
545                 550                 555                 560

Val Glu Met Val Met Glu Gly His Lys Ser Thr Gly Arg Asp Asp Leu
                565                 570                 575

Gly Gln Gly Ala Ile His Leu Cys Ser Phe Leu Gly Tyr Thr Trp Ala
                580                 585                 590

Ile Arg Leu Phe Ser Leu Ser Gly Phe Ser Leu Asp Phe Arg Asp Ser
                595                 600                 605

Ser Gly Trp Thr Ala Leu His Trp Ala Ala Tyr His Gly Arg Glu Arg
                610                 615                 620

Met Val Ala Thr Leu Leu Ser Ala Gly Ala Asn Pro Ser Leu Val Thr
625                 630                 635                 640

Asp Pro Thr Pro Glu Ser Pro Ala Gly Leu Thr Ala Ala Asp Leu Ala
                645                 650                 655

Ala Arg Gln Gly Tyr Asp Gly Leu Ala Ala Tyr Leu Ala Glu Lys Gly
                660                 665                 670

Leu Thr Ala His Phe Glu Ala Met Ser Leu Ser Lys Asp Thr Glu Gln
                675                 680                 685

Ser Pro Ser Lys Thr Arg Leu Thr Lys Leu Gln Ser Glu Lys Phe Glu
690                 695                 700
```

His Leu Ser Glu Gln Glu Leu Cys Leu Lys Glu Ser Leu Ala Ala Tyr
705                 710                 715                 720

Arg Asn Ala Ala Asp Ala Ala Ser Asn Ile Gln Ala Ala Leu Arg Glu
            725                 730                 735

Arg Thr Leu Lys Leu Gln Thr Lys Ala Ile Gln Leu Ala Asn Pro Glu
        740                 745                 750

Ile Glu Ala Ser Glu Ile Val Ala Ala Leu Lys Ile Gln His Ala Phe
    755                 760                 765

Arg Asn Tyr Asn Arg Lys Lys Ala Met Arg Ala Ala Arg Ile Gln
770                 775                 780

Ser His Phe Arg Thr Trp Lys Met Arg Arg Asn Phe Ile Asn Met Arg
785                 790                 795                 800

Arg Gln Val Ile Arg Ile Gln Ala Ala Tyr Arg Gly His Gln Val Arg
                805                 810                 815

Arg Gln Tyr Arg Lys Val Ile Trp Ser Val Gly Ile Val Glu Lys Ala
            820                 825                 830

Ile Leu Arg Trp Arg Lys Lys Arg Ala Leu Arg Gly Ile Ala Ser
        835                 840                 845

Gly Met Pro Val Val Met Thr Val Asp Ala Glu Ala Glu Pro Ala Ser
    850                 855                 860

Thr Ala Glu Glu Asp Phe Phe Gln Ala Gly Arg Gln Gln Ala Glu Asp
865                 870                 875                 880

Arg Phe Asn Arg Ser Val Val Arg Val Gln Ala Leu Phe Arg Ser Tyr
                885                 890                 895

Lys Ala Gln Gln Glu Tyr Arg Arg Met Lys Ile Ala His Glu Glu Ala
            900                 905                 910

Lys Ile Glu Phe Ser Glu Gly Gln Leu Gly Ala Ala Cys Arg Ser
        915                 920                 925

<210> SEQ ID NO 17
<211> LENGTH: 549
<212> TYPE: DNA
<213> ORGANISM: Solanum tuberosum

<400> SEQUENCE: 17
tgttgccctc gttttccccc tttttcttgc caaaatcttg aacttgtttt gaccaaatcc    60
agttttcttt gattaatcca aaactttttg attcttttaac caaccccag ttcaattttt   120 aagtggaagc tcaactagtg ttttagatcg gagctgggtt agttcttttt gtatggtttt   180
ggagctgggt tcatggcaga cagtaggcgt tatggtctga atgctcaatt agatattgag   240
cagatacttt tagaagcgca gcatcgatgg ctacgcccag ctgaaatttg tgaaattctt   300
aaaaattacc agaagtttcg aattgctcca gagcctccaa acaggcctcc aagtggttca   360
ttgttccttt tgatcggaa ggttttacgg tatttccgca agatggcca tagttggaga    420 aagaaaaaag atgaaagac tgtgaaagag gctcatgaga ggctcaaggc tggaagcatt    480
gatgtgttac actgctacta tgctcatgga gaagagaatg agaatttcca aagacgcagc   540
tattggatg                                                          549

<210> SEQ ID NO 18
<211> LENGTH: 844
<212> TYPE: DNA
<213> ORGANISM: Gossypium arboreum
<220> FEATURE:
<221> NAME/KEY: misc_feature
<222> LOCATION: (591)..(591)

<223> OTHER INFORMATION: n is a, c, g, or t

<400> SEQUENCE: 18

```
gttcaaatga caaggatcgt gggtgttttg aatttcttat agaaaattga agatggcgca      60
atcagggtat gatattaata atctgtttcg ggaagctcaa tctcggtggt tgaagccagt     120
tgaagtactg tttatactac aaaaccatga gaagtatcag cttgagcaag agcccctca      180
caagccaaca agtggctcat tgtttctttt caacaagagg gttcttcggt tctttcgtaa     240
agatggccat agttggcgta agaagaagga tggaagaact gtcggggaag cccacgaaag     300
gcttaaggtt ggtaatgttg aaaccttgaa ttgttactat gctcatggag agcagaaccc     360
cagttttcag agacgtagct actggatgct ggacccggca tacgagcata ttgttcttgt     420
tcattataga gagataaatg aggctaagcc ctgttctgca tccactgtgc actcaccatt     480
atccaattct gctagtactc caagtccaat ctcatatact tctcaaaatc ctggatttaa     540
ctctctatct agtgatgtac atgaatcata tcagaactta cctagtcctg ngtctgctga     600
agttagctct gatatagtca ttaagaacaa tggaatagat aatacagtag agtatcccag     660
tccagatgat cttcaggttg ttcaagcttt aaagagggct tgagagcagc taagtttgaa     720
tgaagacagc gtgaaagaaa tgagtcaatt ctactgcgtg gatggggata caaatgattt     780
ggagtttcag gaatatggaa aggagatccc aagcaggagc acaggcagat ctctgtatga     840
ccga                                                                  844
```

<210> SEQ ID NO 19
<211> LENGTH: 635
<212> TYPE: DNA
<213> ORGANISM: Hordeum vulgare

<400> SEQUENCE: 19

```
ggcacgaggg cctgcgcggc ctgaccatag accgaccggg aaagtggaag cagcagccgc      60
ggcggctatg gagggaacgg ccgggaggga gagggacccg ctcctacgct ccagagatcca    120
cggcttcatc acctacgcag acttgaactt cgagaagctg aaagcagagg ccgcgtcgcg     180
ctggttccgg ccgaatgaga tctacgcggt cctggcgaac cacgagaggt tcaaggtcca     240
tgcacagccc attgacaagc ccgtgagtgg tactattgtt ctatatgatc gtaaagttgt     300
ccggaacttt cggaaggatg gccataattg gaagaaaaag aaggatggca aaactgtcca     360
agaagcgcat gaaaaattaa agattggtaa tgaagagagg gttcatgtct attatgctcg     420
aggtgaggat aatccaaatt tctttagaag gtgctactgg ctacttgaca agaggctga      480
acggatagtt cttgtgcatt atcgtcaaac atctgaggaa aatgccatag tacatccaag     540
cacagaagcc gaagccgaag tgcctacaat gaatgtgatt cagcattata cctctcctcc     600
ggtttcagca aactcagcct cagttcatac cgaga                                635
```

<210> SEQ ID NO 20
<211> LENGTH: 6582
<212> TYPE: DNA
<213> ORGANISM: Homo sapiens

<400> SEQUENCE: 20

```
gacgctcctc ccggagagta gtgagacccc tggtgcgggg cgattggcgg cgggagcgat      60
gagtggcagc cgcacggccc aacgggagct gtgcgtgggc cgcggggcgg ggccagggcg     120
ggtgcgcggc ggcggcgggg tggctgggcc ggcggcggcg gcggtacgag gcgcgcgctc     180
ggggtcccgg tcgcgaggag gaggaggatg tggcgcgcgg aggggaaatg gctgccgaaa     240
```

```
acaagccgga agagcgtttc ccaaagtgta ttctgcggaa ctagcaccta ctgtgttctc    300
aacaccgtgc cacctataga agatgatcat gggaacagca atagtagtca tgtaaaaatc    360
tttttaccga aaaagctgct tgaatgtctg ccgaaatgtt caagtttacc aaaagagagg    420
caccgctgga acactaatga ggaaattgca gcttatttaa taacatttga gaaacacgaa    480
gaatggctaa ccacctcccc taagacaaga ccacagaatg gctcaatgat actctacaac    540
aggaagaaag tgaaatacag gaaagatggg tattgctgga aaaagaggaa agatgggaaa    600
acgaccagag aggaccacat gaaactcaag gtccagggag tggagtgctt gtacggctgc    660
tatgtccatt cctccatcat ccccaccttc caccggaggt gctactggct ccttcagaac    720
cccgacatcg tcctggtgca ctacctgaac gtgccggcca tcgaggactg cggcaagcct    780
tgcggcccca tcctctgctc catcaacacc gacaagaagg agtgggcgaa atggacgaaa    840
gaagagctca tcgggcagct gaaacccatg ttccatggca tcaagtggac ctgcagcaat    900
gggaacagca gctcaggctt ctcggtggaa cagctggtgc agcagatcct cgacagccac    960
cagaccaagc cccagccgcg gacccacaac tgcctctgca ccggcagcct gggagctggc   1020
ggcagcgtgc atcacaagtg taacagcgcc aaacaccgca tcatctcgcc caaggtggag   1080
ccacggacag gggggtacgg gagccactcg gaggtgcagc acaatgacgt gtcggagggc   1140
aagcacgagc acagccacag caaggggctcc agccgtgaga agaggaacgg caaggtggcc   1200
aagcccgtgc tcctgcacca gagcagcacc gaggtctcct ccaccaacca ggtggaagtc   1260
cccgacacca cccagagctc ccctgtgtcc atcagcagcg ggctcaacag cgacccggac   1320
atggtggaca gcccggtggt cacaggtgtg tccggtatgg cggtggcctc tgtgatgggg   1380
agcttgtccc agagcgccac ggtgttcatg tcagaggtca ccaatgaggc cgtgtacacc   1440
atgtccccca ccgctggccc caaccaccac ctcctctcac ctgacgcctc tcagggcctc   1500
gtcctggccg tgagctctga tggccacaag ttcgcctttc ccaccacggg cagctcagag   1560
agcctgtcca tgctgcccac caacgtgtcc gaagagctgg tcctctccac caccctcgac   1620
ggtggccgga agattccaga aaccaccatg aactttgacc ccgactgttt ccttaataac   1680
ccaaagcagg gccagacgta cggggtgga ggcctgaaag ccgagatggt cagctccaac   1740
atccggcact cgccacccgg ggagcggagc ttcagctta ccaccgtcct caccaaggag   1800
atcaagaccg aggacacctc cttcgagcag cagatggcca agaagcgta tcctcctcc   1860 gcggcggctg tggcagccag ctccctcacc ctgaccgccg gctccagcct cctgccgtcg   1920
ggcggcggcc tgagtcccag caccaccctg gagcagatgg acttcagcgc catcgactcc   1980
aacaaggact acacgtccag cttcagccag acgggccaca gccccacat ccaccagacc   2040 ccctcccga gcttcttcct gcaggacgcc agcaaacccc tccccgtcga gcagaacacc   2100
cacagcagcc tgagtgactc tgggggcacc ttcgtgatgc ccacggtgaa acggaggcc   2160 tcgtcccaaa ccagctcctg cagcggtcac gtggagacgc ggatcgagtc cacttcctcc   2220
ctccacctca tgcagttcca ggccaacttc caggccatga cggcagaagg ggaggtcacc   2280
atggagacct cgcaggcggc ggaagggag gaggtcctgc tcaagtctgg ggagctgcag   2340
gcttgcagct ctgagcacta cctgcagccg agaccaacg gggtaatccg aagcgccggc   2400
ggcgtcccca tcctcccggg caacgtggtg cagggactct accccgtggc ccagcccagc   2460
ctcggcaacg cctccaacat ggagctcagc ctggaccact ttgacatctc cttcagcaac   2520
cagttctccg acctgatcaa cgacttcatc tccgtggagg ggggcagcag caccatctat   2580
```

```
gggcaccagc tggtgtcggg ggacagcacg gcgctctcac agtcagagga cggggcgcgg    2640
gcccccttca cccaggcaga gatgtgcctc ccctgctgta gcccccagca gggtagcctg    2700
cagctgagca gctcggaggg cggggccagc accatggcct acatgcacgt cgccgaggtg    2760
gtctcggccg cctcggccca gggcacccta ggcatgctgc agcagagcgg acgggtgttc    2820
atggtgaccg actactcccc agagtggtct tacccagagg gaggagtgaa ggtcctcatc    2880
acaggcccgt ggcaagaagc cagcaataac tacagctgcc tgtttgacca gatctcagtg    2940
cctgcatccc tgattcagcc tggggtgctg cgctgctact gcccagccca tgacactggt    3000
cttgtgaccc tacaagttgc cttcaacaac cagatcatct ccaactcggt ggtgtttgag    3060
tacaaagccc gggctctgcc cacgctccct tcctcccagc acgactggct gtcgttggac    3120
gataaccagt tcaggatgtc catcctggaa cgactggagc agatggagag gaggatggcc    3180
gagatgacgg ggtcccagca gcacaaacag gcgagcggag gcggcagcag tggaggcggc    3240
agcgggagcg ggaatggagg gagccaggca cagtgtgctt ctgggactgg ggccttgggg    3300
agctgctttg agagccgtgt ggtcgtgtta tgcgagaaga tgatgagccg agcctgctgg    3360
gcgaagtcca agcacttgat ccactcaaag actttccgcg gaatgaccct actccacctg    3420
gccgctgccc agggctatgc caccctaatc cagaccctca tcaaatggcg tacaaagcac    3480
gcggatagca ttgacctgga actggaagtt gaccccttga atgtggacca cttctcctgt    3540
actcctctga tgtgggcgtg tgccctaggg cacttggaag ctgccgtcgt gctgtacaag    3600
tgggaccgtc gggccatctc gattcccgac tctctaggaa ggctgccttt gggaattgcc    3660
aggtcacggg gtcatgtgaa attagcagag tgtctggagc acctgcagag agatgagcag    3720
gctcagctgg gacagaaccc cagaatccac tgtcctgcaa gcgaagagcc cagcacagag    3780
agctggatgc cccagtggca cagcgaagcc atcagctctc cagaaatacc caagggagtc    3840
actgttattg caagcaccaa cccagagctg agaagacctc gttctgaacc ctctaattac    3900
tacagcagtg agagccacaa agattatccg gctcccaaaa agcataaatt gaaccctgag    3960
tacttccaga caaggcagga gaagctgctt cccactgcac tgagtctgga gagccaaat    4020 atcaggaagc aaaagcctag ttctaagcag tctgtccccg agacactcag ccccagtgaa    4080
ggagtgaggg acttcagccg ggaactctcc cctcccactc cagagactgc agcatttcaa    4140
gcctctggat ctcagcctgt aggaaagtgg aattccaaag atctttacat tggtgtgtct    4200
acagtacagg tgactggaaa tccgaagggg accagtgtag gaaggaggc agcaccttca    4260 caggtgcgtc cacgggaacc aatgagtgtc ctgatgatgg ctaacagaga ggtggtgaat    4320
acagagctgg ggtcctaccg tgatagtgca gaaaatgaag aatgcggcca gcccatggat    4380
gacatacagg tgaacatgat gaccttggca gaacacatta ttgaagccac acctgaccga    4440
atcaagcagg agaattttgt gcccatggag tcctcaggat tggaaagaac agaccctgcc    4500
accattagca gtacaatgag ctggctggcc agttatctag cggatgctga ctgccttccc    4560
agtgctgccc agatccgaag tgcatataac gagcctctaa ccccttcttc taataccagc    4620
ttgagccctg ttggctctcc cgtcagtgaa atcgctttcg agaaacctaa ccttccctcc    4680
gccgcggatt ggtcagaatt cctgagtgca tctaccagtg agaaggtaga gaatgagttt    4740
gctcagctca ctctgtctga tcatgaacag agagaactct atgaggctgc caggcttgtc    4800
cagacagctt tccggaaaata caagggccga cccttgcggg aacagcaaga agtagctgct    4860
gctgttattc agcgttgtta cagaaaatat aaacagtacg cactttataa aaagatgaca    4920
caggctgcca tccttatcca gagcaaattc cgaagttact atgaacaaaa aaaattccag    4980
```

-continued

```
cagagccgac gggctgctgt gctcatccaa aagtactacc gaagttataa gaaatgtggc    5040
aaaagacggc aggctcgccg gacggctgtg attgtacaac agaaactcag gagcagtttg    5100
ctaaccaaaa agcaggatca agctgctcga aaataatgat ggtttcttcg ccgctgtcgc    5160
cacagccccc tggtggacca taggctgtac aaaaggagtg aaagaattga aaaaggccaa    5220
ggaacttgaa gacatacagc agcatcccct tagcaatgtga cattgctttt cagactgttt    5280
tcatttctgt ttttagcaga gacatgcaac aacaacacac acgcacacac gcacacacac    5340
acacgtacac acacatacaa aatccctctg cagttttggg gagatcagct gcaggatttt    5400
aacaggaatg ttttggtcat tgcatttgca ctttcatgga caacttttaa tttgatcagc    5460
aagacatctt ggaactcaat cttctgttgg atcacgggaa atcaagacac ccaggaggaa    5520
ttgaaagagg cttcctcttc tcaggaagaa gccatttcct tctcatatag ggctgtattc    5580
aaacatcgtg tggaactgta caaatattta taccaaaaat atagataaga aaggtgggg    5640 ctatactagc aacaaaaaaa agaatgctgt tcctgcacct gccggttatt tccaagaagc    5700
tgaatctttg ggactgattc tcagtggagg gcttagatca tacaaaaatc tttattgggt    5760
ccgtgtgttc tcatttcctt cactgtttat ttttgtttgt ttgtttgttt gttttaatct    5820
ctacagcaca tttaatgcaa cttttgaaat ctgcaggttt ttaatgtctt gtggaaattt    5880 gcagagggc aggtgtgtgg taaacgggta atgcatggga aataatgaga agcagctcac    5940
agagtttaaa ctattttctt gtccccacca ccttccaaga acctgcgagg gtagtaatca    6000
tcttgtcccc tttttcatgt tcagcacttt aattttttg ccttactttc atgtgcaatg    6060
agaattactt aagaattggt aacgcatgta gcctttttta gtaaccttgg aagctgtagt    6120
aattctaagg aatcatgaac cttgcctgga catttgccac ctaaacgatc agtgtggtgc    6180
tgcgttctgg ccagtaaatt ccatgttttt ggctatatct catccaaact gagcagtttc    6240
tgtgtatata tagaaggtag aaatgaaaag tgagaaaata tttgaaaggg attatattaa    6300
ttgctaaata ttttattcac aaaggtcaat aacatggcaa gataaaatta tttgtatagt    6360
tttgtctgaa tgagcgagaa aaatgtggat gtactgtttg tatatattgt atatatttaaa    6420 acagagatat gtgcatgaaa tcaagaaaaa agaaatgaac aaaagcaaag cattagtggc    6480
tatggtctgt aaaatgaaac aaaaaaactt tatttcacta taagagtact ttattttaaa    6540
tgttctttag gagaacattt tgctaaagca tgactaaact gc                       6582
```

<210> SEQ ID NO 21
<211> LENGTH: 1734
<212> TYPE: PRT
<213> ORGANISM: Homo sapiens

<400> SEQUENCE: 21

```
Asp Pro Trp Cys Gly Ala Ile Gly Gly Gly Ser Asp Glu Trp Gln Pro
1               5                   10                  15

His Gly Pro Thr Gly Ala Val Arg Gly Pro Arg Gly Gly Ala Arg Ala
            20                  25                  30

Gly Ala Arg Arg Arg Gly Gly Trp Ala Gly Gly Gly Gly Thr
        35                  40                  45

Arg Arg Ala Leu Gly Val Pro Val Ala Arg Arg Arg Met Trp Arg
    50                  55                  60

Ala Glu Gly Lys Trp Leu Pro Lys Thr Ser Arg Lys Ser Val Ser Gln
65                  70                  75                  80

Ser Val Phe Cys Gly Thr Ser Thr Tyr Cys Val Leu Asn Thr Val Pro
```

```
                 85                  90                  95
Pro Ile Glu Asp Asp His Gly Asn Ser Asn Ser Ser His Val Lys Ile
            100                 105                 110

Phe Leu Pro Lys Lys Leu Leu Glu Cys Leu Pro Lys Cys Ser Ser Leu
            115                 120                 125

Pro Lys Glu Arg His Arg Trp Asn Thr Asn Glu Glu Ile Ala Ala Tyr
        130                 135                 140

Leu Ile Thr Phe Glu Lys His Glu Glu Trp Leu Thr Thr Ser Pro Lys
145                 150                 155                 160

Thr Arg Pro Gln Asn Gly Ser Met Ile Leu Tyr Asn Arg Lys Lys Val
                165                 170                 175

Lys Tyr Arg Lys Asp Gly Tyr Cys Trp Lys Arg Lys Asp Gly Lys
        180                 185                 190

Thr Thr Arg Glu Asp His Met Lys Leu Lys Val Gln Gly Val Glu Cys
            195                 200                 205

Leu Tyr Gly Cys Tyr Val His Ser Ser Ile Ile Pro Thr Phe His Arg
        210                 215                 220

Arg Cys Tyr Trp Leu Leu Gln Asn Pro Asp Ile Val Leu Val His Tyr
225                 230                 235                 240

Leu Asn Val Pro Ala Ile Glu Asp Cys Gly Lys Pro Cys Gly Pro Ile
                245                 250                 255

Leu Cys Ser Ile Asn Thr Asp Lys Lys Glu Trp Ala Lys Trp Thr Lys
            260                 265                 270

Glu Glu Leu Ile Gly Gln Leu Lys Pro Met Phe His Gly Ile Lys Trp
        275                 280                 285

Thr Cys Ser Asn Gly Asn Ser Ser Gly Phe Ser Val Glu Gln Leu
        290                 295                 300

Val Gln Gln Ile Leu Asp Ser His Gln Thr Lys Pro Gln Pro Arg Thr
305                 310                 315                 320

His Asn Cys Leu Cys Thr Gly Ser Leu Gly Ala Gly Gly Ser Val His
                325                 330                 335

His Lys Cys Asn Ser Ala Lys His Arg Ile Ile Ser Pro Lys Val Glu
            340                 345                 350

Pro Arg Thr Gly Gly Tyr Gly Ser His Ser Glu Val Gln His Asn Asp
        355                 360                 365

Val Ser Glu Gly Lys His Glu His Ser His Ser Lys Gly Ser Ser Arg
    370                 375                 380

Glu Lys Arg Asn Gly Lys Val Ala Lys Pro Val Leu Leu His Gln Ser
385                 390                 395                 400

Ser Thr Glu Val Ser Thr Asn Gln Val Glu Val Pro Asp Thr Thr
                405                 410                 415

Gln Ser Ser Pro Val Ser Ile Ser Ser Gly Leu Asn Ser Asp Pro Asp
        420                 425                 430

Met Val Asp Ser Pro Val Val Thr Gly Val Ser Gly Met Ala Val Ala
            435                 440                 445

Ser Val Met Gly Ser Leu Ser Gln Ser Ala Thr Val Phe Met Ser Glu
        450                 455                 460

Val Thr Asn Glu Ala Val Tyr Thr Met Ser Pro Thr Ala Gly Pro Asn
465                 470                 475                 480

His His Leu Leu Ser Pro Asp Ala Ser Gln Gly Leu Val Leu Ala Val
                485                 490                 495

Ser Ser Asp Gly His Lys Phe Ala Phe Pro Thr Thr Gly Ser Ser Glu
        500                 505                 510
```

```
Ser Leu Ser Met Leu Pro Thr Asn Val Ser Glu Leu Val Leu Ser
        515                 520                 525
Thr Thr Leu Asp Gly Gly Arg Lys Ile Pro Glu Thr Thr Met Asn Phe
530                 535                 540
Asp Pro Asp Cys Phe Leu Asn Asn Pro Lys Gln Gly Gln Thr Tyr Gly
545                 550                 555                 560
Gly Gly Gly Leu Lys Ala Glu Met Val Ser Ser Asn Ile Arg His Ser
                565                 570                 575
Pro Pro Gly Glu Arg Ser Phe Ser Phe Thr Thr Val Leu Thr Lys Glu
                580                 585                 590
Ile Lys Thr Glu Asp Thr Ser Phe Glu Gln Gln Met Ala Lys Glu Ala
                595                 600                 605
Tyr Ser Ser Ser Ala Ala Ala Val Ala Ala Ser Ser Leu Thr Leu Thr
                610                 615                 620
Ala Gly Ser Ser Leu Leu Pro Ser Gly Gly Gly Leu Ser Pro Ser Thr
625                 630                 635                 640
Thr Leu Glu Gln Met Asp Phe Ser Ala Ile Asp Ser Asn Lys Asp Tyr
                645                 650                 655
Thr Ser Ser Phe Ser Gln Thr Gly His Ser Pro His Ile His Gln Thr
                660                 665                 670
Pro Ser Pro Ser Phe Phe Leu Gln Asp Ala Ser Lys Pro Leu Pro Val
                675                 680                 685
Glu Gln Asn Thr His Ser Ser Leu Ser Asp Ser Gly Gly Thr Phe Val
                690                 695                 700
Met Pro Thr Val Lys Thr Glu Ala Ser Ser Gln Thr Ser Ser Cys Ser
705                 710                 715                 720
Gly His Val Glu Thr Arg Ile Glu Ser Thr Ser Ser Leu His Leu Met
                725                 730                 735
Gln Phe Gln Ala Asn Phe Gln Ala Met Thr Ala Glu Gly Glu Val Thr
                740                 745                 750
Met Glu Thr Ser Gln Ala Ala Glu Gly Ser Glu Val Leu Leu Lys Ser
                755                 760                 765
Gly Glu Leu Gln Ala Cys Ser Ser Glu His Tyr Leu Gln Pro Glu Thr
                770                 775                 780
Asn Gly Val Ile Arg Ser Ala Gly Gly Val Pro Ile Leu Pro Gly Asn
785                 790                 795                 800
Val Val Gln Gly Leu Tyr Pro Val Ala Gln Pro Ser Leu Gly Asn Ala
                805                 810                 815
Ser Asn Met Glu Leu Ser Leu Asp His Phe Asp Ile Ser Phe Ser Asn
                820                 825                 830
Gln Phe Ser Asp Leu Ile Asn Asp Phe Ile Ser Val Glu Gly Gly Ser
                835                 840                 845
Ser Thr Ile Tyr Gly His Gln Leu Val Ser Gly Asp Ser Thr Ala Leu
                850                 855                 860
Ser Gln Ser Glu Asp Gly Ala Arg Ala Pro Phe Thr Gln Ala Glu Met
865                 870                 875                 880
Cys Leu Pro Cys Cys Ser Pro Gln Gln Gly Ser Leu Gln Leu Ser Ser
                885                 890                 895
Ser Glu Gly Gly Ala Ser Thr Met Ala Tyr Met His Val Ala Glu Val
                900                 905                 910
Val Ser Ala Ala Ser Ala Gln Gly Thr Leu Gly Met Leu Gln Gln Ser
                915                 920                 925
```

```
Gly Arg Val Phe Met Val Thr Asp Tyr Ser Pro Glu Trp Ser Tyr Pro
930                 935                 940

Glu Gly Gly Val Lys Val Leu Ile Thr Gly Pro Trp Gln Glu Ala Ser
945                 950                 955                 960

Asn Asn Tyr Ser Cys Leu Phe Asp Gln Ile Ser Val Pro Ala Ser Leu
            965                 970                 975

Ile Gln Pro Gly Val Leu Arg Cys Tyr Cys Pro Ala His Asp Thr Gly
            980                 985                 990

Leu Val Thr Leu Gln Val Ala Phe Asn Asn Gln Ile Ile Ser Asn Ser
        995                 1000                1005

Val Val Phe Glu Tyr Lys Ala Arg Ala Leu Pro Thr Leu Pro Ser
    1010                1015                1020

Ser Gln His Asp Trp Leu Ser Leu Asp Asp Asn Gln Phe Arg Met
    1025                1030                1035

Ser Ile Leu Glu Arg Leu Glu Gln Met Glu Arg Met Ala Glu
    1040                1045                1050

Met Thr Gly Ser Gln Gln His Lys Gln Ala Ser Gly Gly Ser
    1055                1060                1065

Ser Gly Gly Gly Ser Gly Ser Gly Asn Gly Gly Ser Gln Ala Gln
    1070                1075                1080

Cys Ala Ser Gly Thr Gly Ala Leu Gly Ser Cys Phe Glu Ser Arg
    1085                1090                1095

Val Val Val Cys Glu Lys Met Met Ser Arg Ala Cys Trp Ala
    1100                1105                1110

Lys Ser Lys His Leu Ile His Ser Lys Thr Phe Arg Gly Met Thr
    1115                1120                1125

Leu Leu His Leu Ala Ala Ala Gln Gly Tyr Ala Thr Leu Ile Gln
    1130                1135                1140

Thr Leu Ile Lys Trp Arg Thr Lys His Ala Asp Ser Ile Asp Leu
    1145                1150                1155

Glu Leu Glu Val Asp Pro Leu Asn Val Asp His Phe Ser Cys Thr
    1160                1165                1170

Pro Leu Met Trp Ala Cys Ala Leu Gly His Leu Glu Ala Ala Val
    1175                1180                1185

Val Leu Tyr Lys Trp Asp Arg Arg Ala Ile Ser Ile Pro Asp Ser
    1190                1195                1200

Leu Gly Arg Leu Pro Leu Gly Ile Ala Arg Ser Arg Gly His Val
    1205                1210                1215

Lys Leu Ala Glu Cys Leu Glu His Leu Gln Arg Asp Glu Gln Ala
    1220                1225                1230

Gln Leu Gly Gln Asn Pro Arg Ile His Cys Pro Ala Ser Glu Glu
    1235                1240                1245

Pro Ser Thr Glu Ser Trp Met Ala Gln Trp His Ser Glu Ala Ile
    1250                1255                1260

Ser Ser Pro Glu Ile Pro Lys Gly Val Thr Val Ile Ala Ser Thr
    1265                1270                1275

Asn Pro Glu Leu Arg Arg Pro Arg Ser Glu Pro Ser Asn Tyr Tyr
    1280                1285                1290

Ser Ser Glu Ser His Lys Asp Tyr Pro Ala Pro Lys Lys His Lys
    1295                1300                1305

Leu Asn Pro Glu Tyr Phe Gln Thr Arg Gln Glu Lys Leu Leu Pro
    1310                1315                1320

Thr Ala Leu Ser Leu Glu Glu Pro Asn Ile Arg Lys Gln Ser Pro
```

```
                    1325                1330                1335

Ser  Ser  Lys  Gln  Ser  Val  Pro  Glu  Thr  Leu  Ser  Pro  Ser  Glu  Gly
     1340                1345                1350

Val  Arg  Asp  Phe  Ser  Arg  Glu  Leu  Ser  Pro  Pro  Thr  Pro  Glu  Thr
     1355                1360                1365

Ala  Ala  Phe  Gln  Ala  Ser  Gly  Ser  Gln  Pro  Val  Gly  Lys  Trp  Asn
     1370                1375                1380

Ser  Lys  Asp  Leu  Tyr  Ile  Gly  Val  Ser  Thr  Val  Gln  Val  Thr  Gly
     1385                1390                1395

Asn  Pro  Lys  Gly  Thr  Ser  Val  Gly  Lys  Glu  Ala  Ala  Pro  Ser  Gln
     1400                1405                1410

Val  Arg  Pro  Arg  Glu  Pro  Met  Ser  Val  Leu  Met  Met  Ala  Asn  Arg
     1415                1420                1425

Glu  Val  Val  Asn  Thr  Glu  Leu  Gly  Ser  Tyr  Arg  Asp  Ser  Ala  Glu
     1430                1435                1440

Asn  Glu  Glu  Cys  Gly  Gln  Pro  Met  Asp  Asp  Ile  Gln  Val  Asn  Met
     1445                1450                1455

Met  Thr  Leu  Ala  Glu  His  Ile  Ile  Glu  Ala  Thr  Pro  Asp  Arg  Ile
     1460                1465                1470

Lys  Gln  Glu  Asn  Phe  Val  Pro  Met  Glu  Ser  Ser  Gly  Leu  Glu  Arg
     1475                1480                1485

Thr  Asp  Pro  Ala  Thr  Ile  Ser  Ser  Thr  Met  Ser  Trp  Leu  Ala  Ser
     1490                1495                1500

Tyr  Leu  Ala  Asp  Ala  Asp  Cys  Leu  Pro  Ser  Ala  Ala  Gln  Ile  Arg
     1505                1510                1515

Ser  Ala  Tyr  Asn  Glu  Pro  Leu  Thr  Pro  Ser  Ser  Asn  Thr  Ser  Leu
     1520                1525                1530

Ser  Pro  Val  Gly  Ser  Pro  Val  Ser  Glu  Ile  Ala  Phe  Glu  Lys  Pro
     1535                1540                1545

Asn  Leu  Pro  Ser  Ala  Ala  Asp  Trp  Ser  Glu  Phe  Leu  Ser  Ala  Ser
     1550                1555                1560

Thr  Ser  Glu  Lys  Val  Glu  Asn  Glu  Phe  Ala  Gln  Leu  Thr  Leu  Ser
     1565                1570                1575

Asp  His  Glu  Gln  Arg  Glu  Leu  Tyr  Glu  Ala  Ala  Arg  Leu  Val  Gln
     1580                1585                1590

Thr  Ala  Phe  Arg  Lys  Tyr  Lys  Gly  Arg  Pro  Leu  Arg  Glu  Gln  Gln
     1595                1600                1605

Glu  Val  Ala  Ala  Ala  Val  Ile  Gln  Arg  Cys  Tyr  Arg  Lys  Tyr  Lys
     1610                1615                1620

Gln  Tyr  Ala  Leu  Tyr  Lys  Lys  Met  Thr  Gln  Ala  Ala  Ile  Leu  Ile
     1625                1630                1635

Gln  Ser  Lys  Phe  Arg  Ser  Tyr  Tyr  Glu  Gln  Lys  Lys  Phe  Gln  Gln
     1640                1645                1650

Ser  Arg  Arg  Ala  Ala  Val  Leu  Ile  Gln  Lys  Tyr  Tyr  Arg  Ser  Tyr
     1655                1660                1665

Lys  Lys  Cys  Gly  Lys  Arg  Arg  Gln  Ala  Arg  Arg  Thr  Ala  Val  Ile
     1670                1675                1680

Val  Gln  Gln  Lys  Leu  Arg  Ser  Ser  Leu  Leu  Thr  Lys  Lys  Gln  Asp
     1685                1690                1695

Gln  Ala  Ala  Arg  Lys  Ile  Met  Arg  Phe  Leu  Arg  Arg  Cys  Arg  His
     1700                1705                1710

Ser  Pro  Leu  Val  Asp  His  Arg  Leu  Tyr  Lys  Arg  Ser  Glu  Arg  Ile
     1715                1720                1725
```

Glu Lys  Gly Gln Gly Thr
    1730

<210> SEQ ID NO 22
<211> LENGTH: 4465
<212> TYPE: DNA
<213> ORGANISM: Homo sapiens

<400> SEQUENCE: 22

| | | | | | |
|---|---|---|---|---|---|
| gccgctgccg | ccgtcacccg | cgggaccccg | ggagcacaga | ctcccctcc | ccccggcccc | 60 |
| tcaggccggg | ggtgaccttg | cccctggag | ccctcaccat | gaataccaag | gacaccaccg | 120 |
| aggttgctga | aaacagccac | cacctgaaga | tctttctccc | caagaagctg | ctggagtgtc | 180 |
| ttcctcgctg | cccgctgctg | cctccagaga | ggctacggtg | gaatacaaat | gaggagattg | 240 |
| catcctacct | gatcaccttt | gagaagcatg | atgagtggct | gtcttgtgcc | ccaaagacaa | 300 |
| ggcctcagaa | tggctccatc | atcctctaca | atcgcaagaa | ggtgaaatat | cggaaggatg | 360 |
| gttacctctg | gaagaagcgg | aaggatggga | agaccacccg | agaggaccac | atgaagctga | 420 |
| aggtccaggg | catggagtgt | ctctatggct | gctacgttca | ctcttccatc | gtccccacat | 480 |
| tccatcggcg | ctgctactgg | ctgctccaga | accctgacat | cgtccttgtg | cactacctga | 540 |
| acgtcccagc | cctggaggac | tgtggaaagg | gctgcagccc | catcttttgt | tccatcagca | 600 |
| gcgaccgtcg | agagtggctg | aagtggtccc | gggaggagtt | gttgggacag | ctgaagccca | 660 |
| tgtttcatgg | catcaagtgg | agctgcggga | atggaacaga | agagttctct | gtagaacacc | 720 |
| tggtgcagca | gatttggac | acccacccaa | ccaagcctgc | tccccgaacc | cacgcctgtc | 780 |
| tctgcagtgg | ggggcttggt | tctgggagcc | ttacccacaa | atgcagcagc | acgaaacacc | 840 |
| gcatcatctc | tcccaaagtg | gagccccgag | ctttaaccct | gacctctatc | ccccaccctc | 900 |
| accccccaga | gcctcctcca | ctgatagccc | cacttccccc | agagctcccc | aaggcacaca | 960 |
| cctccccatc | ttcttcctct | tcttcctcct | catcaggttt | tgcagagccc | ctagaaatca | 1020 |
| gacctagccc | tcccacttct | cgaggggtt | cttcaagagg | aggcactgct | atcctcctcc | 1080 |
| tgacaggact | ggagcagcgg | gctggaggct | tgacgcccac | caggcacttg | gctccacagg | 1140 |
| ctgatcctag | gccttccatg | agtttggcag | tggttgtagg | cactgagcct | tctgccccac | 1200 |
| cagctcctcc | cagtcctgcc | tttgaccctg | atcgttttct | caacagcccc | cagaggggcc | 1260 |
| agacatatgg | aggggggcag | ggagtaagcc | cagacttccc | cgaggcagag | gccgctcata | 1320 |
| cccctgttc | tgccctagag | cctgctgctg | ccctggagcc | ccaggcagct | gctcggggtc | 1380 |
| ccccaccaca | gtcagtagca | ggtgggagaa | gaggaaactg | cttcttcatc | caagatgatg | 1440 |
| acagtgggga | ggagctcaag | ggtcacgggg | ctgccccacc | catacctcca | ccccctccct | 1500 |
| caccccccacc | ctcacctgcc | cccttggagc | cgtcaagcag | ggtaggaaga | ggagaggcct | 1560 |
| tgtttggagg | acctgttggg | gccagtgaac | tggagccctt | cagtctttca | tcattcccag | 1620 |
| accttatggg | agaactcatc | agtgacgaag | ctccaagcat | ccctgctccg | accccccagc | 1680 |
| tgtctcctgc | tcttagcacc | atcacagact | tctcccccaga | gtggtcctac | ccagagggtg | 1740 |
| gggtcaaggt | gctcatcaca | ggtccttgga | ccgaagccgc | cgagcattac | tcctgtgtct | 1800 |
| ttgatcacat | cgcagtgcca | gcctcacttg | tccagcctgg | tgtcttacgc | tgctactgtc | 1860 |
| ccgcccatga | ggtagggctg | gtgtctttgc | aggtggcagg | gcgggagggg | cccctttctg | 1920 |
| cttctgtgct | ctttgagtat | cgagcccgcc | gattcctgtc | tctgcctagt | actcaacttg | 1980 |
| actggctgtc | actggacgac | aaccagttcc | ggatgtccat | actagagcga | ctggagcaga | 2040 |

```
tggagaagcg gatggcagag atcgcagcag ctgggcaggt gccttgccag ggtcctgatg    2100
ctcctccagt tcaggatgaa ggccaggggc ctgggttcga agcacgggta gtggtcttgg    2160
tagaaagcat gatcccacgc tccacctgga agggtcctga acgtctggcc catggaagcc    2220
ccttccgggg catgagcctt ctgcacctgg ctgctgccca gggctatgcc cgcctcatcg    2280
agaccctgag ccagtggcgg agtgtggaga ctggaagctt ggacttagag caggaggttg    2340
acccgctcaa cgtggatcat ttctcttgca cccctctgat gtgggcttgt gccctgggac    2400
acctggaagc tgctgtgctc cttttccgtt ggaaccgaca ggcactgagc attcccgact    2460
ctctgggccg tctgccattg tctgtggctc attcccgggg tcatgtgcgc cttgcccgct    2520
gccttgagga actacagaga caggagcctt cggtggagcc cccatttgcc ctatcgccac    2580
cctcctccag cccagacact ggtctgagca gcgtctcctc gccctcggag ctgtcggatg    2640 gcacctttc cgtcacgtca gcctattcta gtgccccaga tggcagtccc cccctgcac    2700 ctctgccagc ctctgagatg actatggagg acatggcccc aggccagctt tcctctggtg    2760
tcccagaagc ccccctactc ctcatggact atgaggctac caaccccaag gggcccctct    2820
cctcccttcc tgccctccca ccagcttcag atgatgggc tgctccagag gacgctgaca    2880
gcccacaggc tgtggatgtg atcccggtgg acatgatctc actagccaag cagatcatcg    2940
aagccacacc ggagcggatt aaacgagagg acttcgtggg gctgcccgag gctggagcct    3000
caatgcggga gcggacaggg gctgtggggc tcagtgagac catgtcctgg ctggccagct    3060
acctggagaa tgtggaccat ttccccagct caaccctcc cagcgaactg cccttgagc    3120 gaggtcgcct ggctgtccct tcagcaccct cctgggcaga gtttctctct gcatccacca    3180
gtggcaagat ggaaagtgat tttgccctgc tgacactatc agatcacgag cagcgggaac    3240
tgtatgaggc tgcccgagtc atccagacgg ccttccgaaa gtacaagggc cggcggctga    3300
aggagcagca ggaggtagca gcagctgtaa tccagcgctg ttaccggaag tacaagcagc    3360
tgacctggat tgcacttaag tttgcactct ataagaagat gacccaggcg ccatcctga    3420 tccagagcaa gttccgaagc tactatgaac agaagcgatt tcagcagagc cgccgagcgg    3480
ctgtgctcat ccagcagcac taccgctcct accgccgcag gccggccct ccccaccgga    3540 cttcggccac cctgcctgcc cgcaacaaag gctcctttct caccaagaag caggaccagg    3600
cagcccggaa gatcatgaga ttcctgcggc gctgccgaca caggatgagg gaactgaagc    3660
agaaccagga gctggaaggg cttccccagc cgggactggc cacatgacct ggccaccgcc    3720
tttctcacca ccctgggggc gcctcgtgca gtcttaacag ggagagggct ttctggggca    3780
gggggagccc ctgtcggcag ctttcctgtt cacctttgtt ggagccctct gtaggcctcc    3840
tccctcctcc ccacgccttg ctcccacacc cctctcctcg tccctcctgg tcgtgccccg    3900
tctcttttgg tcctggctcc agaaaacccg cgccccacat acctgcatct tccgctgtga    3960
cctccggagc cctgcctgcc cctgctcccc agctcctcct gcctgcaccc gactcggccc    4020
cctcctgact tgccttattt atttgttcga cgcgtctctg aatgtatccg cctcggttcc    4080
caccactgcc ttcgctgcgc acgcccctcg tgtttcaggg ctgaccgtgt ccccacccga    4140
ctccgcatgt ttgcgtctgt ttcctccctc tctggccctg tcttacccca tcacccgact    4200
ctggccactg acctcagggc cgaaggggag gtggtgtacg taggaacgcg ttgcggagtc    4260
cgccccgtcc cccgagggga ggggtcttgt acatactgta acatacagag tatagtgaag    4320 aatctatttta aggcgccgcg gggagggctg cacggccggg cttgtggttc tctagcgcgg    4380
```

```
cggggggcctc ctgccggctc cacgggcact ttctacttgt gcatgggctt ggtttatacg    4440
aattgccatt aaacatcgct gcacc                                           4465
```

<210> SEQ ID NO 23
<211> LENGTH: 1234
<212> TYPE: PRT
<213> ORGANISM: Homo sapiens

<400> SEQUENCE: 23

```
Arg Cys Arg Arg His Pro Arg Asp Pro Gly Ser Thr Asp Ser Pro Ser
1               5                   10                  15

Pro Arg Pro Leu Arg Pro Gly Val Thr Leu Pro Pro Gly Ala Leu Thr
            20                  25                  30

Met Asn Thr Lys Asp Thr Thr Glu Val Ala Glu Asn Ser His His Leu
        35                  40                  45

Lys Ile Phe Leu Pro Lys Lys Leu Leu Glu Cys Leu Pro Arg Cys Pro
    50                  55                  60

Leu Leu Pro Pro Glu Arg Leu Arg Trp Asn Thr Asn Glu Glu Ile Ala
65                  70                  75                  80

Ser Tyr Leu Ile Thr Phe Glu Lys His Asp Glu Trp Leu Ser Cys Ala
                85                  90                  95

Pro Lys Thr Arg Pro Gln Asn Gly Ser Ile Ile Leu Tyr Asn Arg Lys
            100                 105                 110

Lys Val Lys Tyr Arg Lys Asp Gly Tyr Leu Trp Lys Lys Arg Lys Asp
        115                 120                 125

Gly Lys Thr Thr Arg Glu Asp His Met Lys Leu Lys Val Gln Gly Met
    130                 135                 140

Glu Cys Leu Tyr Gly Cys Tyr Val His Ser Ser Ile Val Pro Thr Phe
145                 150                 155                 160

His Arg Arg Cys Tyr Trp Leu Leu Gln Asn Pro Asp Ile Val Leu Val
                165                 170                 175

His Tyr Leu Asn Val Pro Ala Leu Glu Asp Cys Gly Lys Gly Cys Ser
            180                 185                 190

Pro Ile Phe Cys Ser Ile Ser Ser Asp Arg Arg Glu Trp Leu Lys Trp
        195                 200                 205

Ser Arg Glu Glu Leu Leu Gly Gln Leu Lys Pro Met Phe His Gly Ile
    210                 215                 220

Lys Trp Ser Cys Gly Asn Gly Thr Glu Glu Phe Ser Val Glu His Leu
225                 230                 235                 240

Val Gln Gln Ile Leu Asp Thr His Pro Thr Lys Pro Ala Pro Arg Thr
                245                 250                 255

His Ala Cys Leu Cys Ser Gly Leu Gly Ser Gly Ser Leu Thr His
            260                 265                 270

Lys Cys Ser Ser Thr Lys His Arg Ile Ile Ser Pro Lys Val Glu Pro
        275                 280                 285

Arg Ala Leu Thr Leu Thr Ser Ile Pro His Pro His Pro Pro Glu Pro
    290                 295                 300

Pro Pro Leu Ile Ala Pro Leu Pro Glu Leu Pro Lys Ala His Thr
305                 310                 315                 320

Ser Pro Ser Ser Ser Ser Ser Ser Ser Gly Phe Ala Glu Pro
                325                 330                 335

Leu Glu Ile Arg Pro Ser Pro Pro Thr Ser Arg Gly Gly Ser Ser Arg
            340                 345                 350

Gly Gly Thr Ala Ile Leu Leu Leu Thr Gly Leu Glu Gln Arg Ala Gly
```

```
              355                 360                 365
Gly Leu Thr Pro Thr Arg His Leu Ala Pro Gln Ala Asp Pro Arg Pro
        370                 375                 380

Ser Met Ser Leu Ala Val Val Gly Thr Glu Pro Ser Ala Pro Pro
385                 390                 395                 400

Ala Pro Pro Ser Pro Ala Phe Asp Pro Asp Arg Phe Leu Asn Ser Pro
                405                 410                 415

Gln Arg Gly Gln Thr Tyr Gly Gly Gln Gly Val Ser Pro Asp Phe
                420                 425                 430

Pro Glu Ala Glu Ala Ala His Thr Pro Cys Ser Ala Leu Glu Pro Ala
                435                 440                 445

Ala Ala Leu Glu Pro Gln Ala Ala Arg Gly Pro Pro Gln Ser
        450                 455                 460

Val Ala Gly Gly Arg Arg Gly Asn Cys Phe Phe Ile Gln Asp Asp
465                 470                 475                 480

Ser Gly Glu Glu Leu Lys Gly His Gly Ala Ala Pro Ile Pro Ser
                485                 490                 495

Pro Pro Pro Ser Pro Pro Ser Pro Ala Pro Leu Glu Pro Ser Ser
                500                 505                 510

Arg Val Gly Arg Gly Glu Ala Leu Phe Gly Pro Val Gly Ala Ser
                515                 520                 525

Glu Leu Glu Pro Phe Ser Leu Ser Ser Phe Pro Asp Leu Met Gly Glu
        530                 535                 540

Leu Ile Ser Asp Glu Ala Pro Ser Ile Pro Ala Pro Thr Pro Gln Leu
545                 550                 555                 560

Ser Pro Ala Leu Ser Thr Ile Thr Asp Phe Ser Pro Glu Trp Ser Tyr
                565                 570                 575

Pro Glu Gly Gly Val Lys Val Leu Ile Thr Gly Pro Trp Thr Glu Ala
                580                 585                 590

Ala Glu His Tyr Ser Cys Val Phe Asp His Ile Ala Val Pro Ala Ser
                595                 600                 605

Leu Val Gln Pro Gly Val Leu Arg Cys Tyr Cys Pro Ala His Glu Val
        610                 615                 620

Gly Leu Val Ser Leu Gln Val Ala Gly Arg Glu Gly Pro Leu Ser Ala
625                 630                 635                 640

Ser Val Leu Phe Glu Tyr Arg Ala Arg Arg Phe Leu Ser Leu Pro Ser
                645                 650                 655

Thr Gln Leu Asp Trp Leu Ser Leu Asp Asp Asn Gln Phe Arg Met Ser
                660                 665                 670

Ile Leu Glu Arg Leu Glu Gln Met Glu Lys Arg Met Ala Glu Ile Ala
        675                 680                 685

Ala Ala Gly Gln Val Pro Cys Gln Gly Pro Asp Ala Pro Pro Val Gln
        690                 695                 700

Asp Glu Gly Gln Gly Pro Gly Phe Glu Ala Arg Val Val Leu Val
705                 710                 715                 720

Glu Ser Met Ile Pro Arg Ser Thr Trp Lys Gly Pro Glu Arg Leu Ala
                725                 730                 735

His Gly Ser Pro Phe Arg Gly Met Ser Leu Leu His Leu Ala Ala Ala
                740                 745                 750

Gln Gly Tyr Ala Arg Leu Ile Glu Thr Leu Ser Gln Trp Arg Ser Val
                755                 760                 765

Glu Thr Gly Ser Leu Asp Leu Glu Gln Glu Val Asp Pro Leu Asn Val
        770                 775                 780
```

-continued

```
Asp His Phe Ser Cys Thr Pro Leu Met Trp Ala Cys Ala Leu Gly His
785                 790                 795                 800

Leu Glu Ala Ala Val Leu Leu Phe Arg Trp Asn Arg Gln Ala Leu Ser
                805                 810                 815

Ile Pro Asp Ser Leu Gly Arg Leu Pro Leu Ser Val Ala His Ser Arg
            820                 825                 830

Gly His Val Arg Leu Ala Arg Cys Leu Glu Glu Leu Gln Arg Gln Glu
        835                 840                 845

Pro Ser Val Glu Pro Pro Phe Ala Leu Ser Pro Pro Ser Ser Ser Pro
850                 855                 860

Asp Thr Gly Leu Ser Ser Val Ser Ser Pro Glu Leu Ser Asp Gly
865                 870                 875                 880

Thr Phe Ser Val Thr Ser Ala Tyr Ser Ala Pro Asp Gly Ser Pro
                885                 890                 895

Pro Pro Ala Pro Leu Pro Ala Ser Glu Met Thr Met Glu Asp Met Ala
            900                 905                 910

Pro Gly Gln Leu Ser Ser Gly Val Pro Glu Ala Pro Leu Leu Leu Met
        915                 920                 925

Asp Tyr Glu Ala Thr Asn Pro Lys Gly Pro Leu Ser Ser Leu Pro Ala
930                 935                 940

Leu Pro Pro Ala Ser Asp Asp Gly Ala Ala Pro Glu Asp Ala Asp Ser
945                 950                 955                 960

Pro Gln Ala Val Asp Val Ile Pro Val Asp Met Ile Ser Leu Ala Lys
                965                 970                 975

Gln Ile Ile Glu Ala Thr Pro Glu Arg Ile Lys Arg Glu Asp Phe Val
            980                 985                 990

Gly Leu Pro Glu Ala Gly Ala Ser Met Arg Glu Arg Thr Gly Ala Val
        995                 1000                1005

Gly Leu Ser Glu Thr Met Ser Trp Leu Ala Ser Tyr Leu Glu Asn
    1010                1015                1020

Val Asp His Phe Pro Ser Ser Thr Pro Pro Ser Glu Leu Pro Phe
    1025                1030                1035

Glu Arg Gly Arg Leu Ala Val Pro Ser Ala Pro Ser Trp Ala Glu
    1040                1045                1050

Phe Leu Ser Ala Ser Thr Ser Gly Lys Met Glu Ser Asp Phe Ala
    1055                1060                1065

Leu Leu Thr Leu Ser Asp His Glu Gln Arg Glu Leu Tyr Glu Ala
    1070                1075                1080

Ala Arg Val Ile Gln Thr Ala Phe Arg Lys Tyr Lys Gly Arg Arg
    1085                1090                1095

Leu Lys Glu Gln Gln Glu Val Ala Ala Ala Val Ile Gln Arg Cys
    1100                1105                1110

Tyr Arg Lys Tyr Lys Gln Leu Thr Trp Ile Ala Leu Lys Phe Ala
    1115                1120                1125

Leu Tyr Lys Lys Met Thr Gln Ala Ala Ile Leu Ile Gln Ser Lys
    1130                1135                1140

Phe Arg Ser Tyr Tyr Glu Gln Lys Arg Phe Gln Gln Ser Arg Arg
    1145                1150                1155

Ala Ala Val Leu Ile Gln Gln His Tyr Arg Ser Tyr Arg Arg Arg
    1160                1165                1170

Pro Gly Pro Pro His Arg Thr Ser Ala Thr Leu Pro Ala Arg Asn
    1175                1180                1185
```

-continued

```
Lys Gly Ser Phe Leu Thr Lys Lys Gln Asp Gln Ala Ala Arg Lys
    1190            1195                1200
Ile Met Arg Phe Leu Arg Arg Cys Arg His Arg Met Arg Glu Leu
1205                1210                1215
Lys Gln Asn Gln Glu Leu Glu Gly Leu Pro Gln Pro Gly Leu Ala
    1220                1225                1230
Thr
```

```
<210> SEQ ID NO 24
<211> LENGTH: 3108
<212> TYPE: DNA
<213> ORGANISM: Brassica napus
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (2123)..(2123)
<223> OTHER INFORMATION: n is a, c, g, or t
<220> FEATURE:
<221> NAME/KEY: misc_feature
<222> LOCATION: (2235)..(2235)
<223> OTHER INFORMATION: n is a, c, g, or t
<220> FEATURE:
<221> NAME/KEY: misc_feature
<222> LOCATION: (2706)..(2706)
<223> OTHER INFORMATION: n is a, c, g, or t

<400> SEQUENCE: 24
gctgcaggaa ttcccggatc ttttggattt attagccctc ctcgattaga tatggaacag      60
ttgttatcgg aagctcaaca caggtggctg aggcctgctg agatttgtga gatccttcgg     120
aactatcaca agtttcatat tgcaacagag tctcccactc gaccagccag tggttcgctc     180 tttcttttg acaggaaggt gcttacatac tttaggaaag acggacataa ctggaggaag      240
aagaaggatg ggaaaacgat taaagaagct catgagaagc tcaaggtagg aagcattgat     300
gtgctacatt gttactatgc acatggggaa ggctacgaga atttcagag acgatgctac       360 tggatgctcg aaatagagct gatgcatatt gtgttcgtgc actacttgga ggttaagggg     420
agccggacaa gtatagggat gaaagaaaac aattcaaatt ctctaagtgg cacagcttca     480
gtgaatattg attcagcagc aagccccacg agcagattgt catcgtattg tgaagatgct     540
gattccggtg atagtcatca atcaagctct gtcttgcgag catctcctga acctcaaact     600
ggaaatcgca atggttggac atcagctcct gggatgcgta ttgcttcaca ggttcttggg     660
aacagagtcg gagaaactga ttcccagaga tcatttgatg tccaggcttg ggatgccgtc     720
gagaatttag tgacaaggta tgatcaacct tgcaacaatt tgttggtgga agagcgtaca     780
aacaaatttg gaatgttacc agcagagcat ctcagaagtc ctcttcaaaa ccaactaaat     840
tggcagattc cngctcagga tgatctacca ttgccaaaat ggcctggtta tctggttcca     900
cattctggaa tgactgatga cactgatctg gcgttattcg ggcaaagtgc acaagacaat     960
tttgagtcat tttccagtct ccttgacatt gaacatctgc aatctgatgg gattcctcct    1020
tcagatatgg aaagtgaata tatacctgta aagaaatcct tgttgaggca cgaagatagt    1080
ttgaaaaagg tcgatagttt ttctcggtgg gctagtaaag agctaggcga gatggaggat    1140
ttgcagatgc agtcttcgcg tggagatatt gcatgggcct ctgttgattg tgaaactgca    1200
gcagctgggc tctcctttag cccttctctc tccgaggacc agcgtttcac catagttgat    1260
tattggccaa aatgcgcaca gactgacgct gatgttgagg tcttggttat tgggacgttt    1320
```

```
ctgcttaatc ctcaagaagt aactatatgc agctggtcat gcatgtttgg tgaagtggag    1380
gttcctgctg agattctagt ggacggtgtt ctttgctgcc atgctccacc gcatacagct    1440
ggccaagtgc cctttttacgt tacctgttca aacagatttg cttgcagtga attacgagaa    1500
tttgatttcc tttctggctc taccaaaaag atcgacgccg ctggtattta tggatactct    1560
acaaaagaag catcacttca gatgcggttt gaggagctgc ttgctcatag agctttcgtt    1620
caagaacacc aaatatttga agatgttgtg gagaaacgaa gaaagataag taagatcatg    1680
ttgctaaatg aggaaaaaga gaatctcttt ccagggatat atgagagaga ttcaaccaaa    1740
caagaaccaa agaacgggt tctcagaaaa cagtttgagg atgaactcta tatatggctc    1800
atccataaag tgaccgaaga gggtaaggga ccaaacatac tggatgaagg cggacagggt    1860
gttctacact tcgttgcagc acttgggtat gattgggcta tcaaaccgat tttagcagca    1920
ggagttaaca ttaacttccg tgatgcaaat gggtggtccg cccttcactg ggctgcgttt    1980
agtggcaggg aggaaactgt cgctgtgctt gtctctctag gtgctgatgc tgggcattg    2040 acggatccat ctccagagct tccattgggc aaaacagctg ctgatctggc ttacggaaag    2100
gaacacaggg ggatttcggg ttntcttgca gagtcatcct taaccagtta ccttgaaaag    2160
ctaacgatgg agtcaaagga aaacagccct gccaactctg gtggaccaaa agctgttcag    2220
acagtctatg agagnaccgc tgctcctatg agctatggtg acgtaccaga aacgctttcc    2280
ttgaaggatt cactcaccgc tgtccgtaat gcgacgcaag cagctgatcg tctccatcaa    2340
gtattcagga tgcaatcttt ccagcggaaa cagctgtctg gatttgatga cgatgatggt    2400
gacgagattg gtatctccaa cgagttagcg gtttctttg cagcttctaa agctaagaat    2460
ccaggacaga gtgaagtctt tgttcattct gctgttaccc acatccagaa aaaataccgt    2520
ggttggaaga gaggaaaga gtttctttta atccgacaaa gagtcgttaa gattcaggct    2580
catgtgagag gacatcaggt caggaaacaa tacaaaccaa tcgtttggtc agtgggattg    2640
ctcgagaaaa tcattttgcg ttggagacgc aaaggtactg gactaagagg gtttaaacgc    2700
aatgcngtcc ccaaaaccgt tgagccagaa ccacaatgcc ctatgattcc aaaggagggt    2760
gactatgatt ttctagaaaa gggaagaaaa caaacggagg aaaggctcca aaaggctctc    2820
acgcgggtta agtcgatggt tcaatacccct gaagcacgtg atcagtaccg tagactcctc    2880
accgttgtcg aaggcttccg tgaaaacgag gcttcatcaa gtttatctgt aaacaacaga    2940
gaggagccag tcaactgtga agatgacgat ttaattgaca ttgattctct tttgaacgat    3000
gacattttga tgtccacttc tcccttgaat gactcgtttg tgtattcatt ttcattcttt    3060
caactttcta acttttgca cctttcctct gtaaatatca taagttga             3108
```

<210> SEQ ID NO 25
<211> LENGTH: 1035
<212> TYPE: PRT
<213> ORGANISM: Brassica napus
<220> FEATURE:
<221> NAME/KEY: misc_feature
<222> LOCATION: (708)..(708)
<223> OTHER INFORMATION: Xaa can be any naturally occurring amino acid
<220> FEATURE:
<221> NAME/KEY: misc_feature
<222> LOCATION: (745)..(745)
<223> OTHER INFORMATION: Xaa can be any naturally occurring amino acid

<400> SEQUENCE: 25

```
Ala Ala Gly Ile Pro Gly Ser Phe Gly Phe Ile Ser Pro Pro Arg Leu
1               5                   10                  15
```

-continued

Asp Met Glu Gln Leu Leu Ser Glu Ala Gln His Arg Trp Leu Arg Pro
            20                  25                  30
Ala Glu Ile Cys Glu Ile Leu Arg Asn Tyr His Lys Phe His Ile Ala
            35                  40                  45
Thr Glu Ser Pro Thr Arg Pro Ala Ser Gly Ser Leu Phe Leu Phe Asp
        50                  55                  60
Arg Lys Val Leu Thr Tyr Phe Arg Lys Asp Gly His Asn Trp Arg Lys
65                  70                  75                  80
Lys Lys Asp Gly Lys Thr Ile Lys Glu Ala His Glu Lys Leu Lys Val
                85                  90                  95
Gly Ser Ile Asp Val Leu His Cys Tyr Tyr Ala His Gly Glu Gly Tyr
            100                 105                 110
Glu Asn Phe Gln Arg Arg Cys Tyr Trp Met Leu Glu Ile Glu Leu Met
            115                 120                 125
His Ile Val Phe Val His Tyr Leu Glu Val Lys Gly Ser Arg Thr Ser
        130                 135                 140
Ile Gly Met Lys Glu Asn Asn Ser Asn Ser Leu Ser Gly Thr Ala Ser
145                 150                 155                 160
Val Asn Ile Asp Ser Ala Ala Ser Pro Thr Ser Arg Leu Ser Ser Tyr
                165                 170                 175
Cys Glu Asp Ala Asp Ser Gly Asp Ser His Gln Ser Ser Ser Val Leu
            180                 185                 190
Arg Ala Ser Pro Glu Pro Gln Thr Gly Asn Arg Asn Gly Trp Thr Ser
        195                 200                 205
Ala Pro Gly Met Arg Ile Ala Ser Gln Val Leu Gly Asn Arg Val Gly
    210                 215                 220
Glu Thr Asp Ser Gln Arg Ser Phe Asp Val Gln Ala Trp Asp Ala Val
225                 230                 235                 240
Glu Asn Leu Val Thr Arg Tyr Asp Gln Pro Cys Asn Asn Leu Leu Val
                245                 250                 255
Glu Glu Arg Thr Asn Lys Phe Gly Met Leu Pro Ala Glu His Leu Arg
            260                 265                 270
Ser Pro Leu Gln Asn Gln Leu Asn Trp Gln Ile Pro Ala Gln Asp Asp
        275                 280                 285
Leu Pro Leu Pro Lys Trp Pro Gly Tyr Leu Val Pro His Ser Gly Met
    290                 295                 300
Thr Asp Asp Thr Asp Leu Ala Leu Phe Gly Gln Ser Ala Gln Asp Asn
305                 310                 315                 320
Phe Glu Ser Phe Ser Ser Leu Leu Asp Ile Glu His Leu Gln Ser Asp
                325                 330                 335
Gly Ile Pro Pro Ser Asp Met Glu Ser Glu Tyr Ile Pro Val Lys Lys
            340                 345                 350
Ser Leu Leu Arg His Glu Asp Ser Leu Lys Lys Val Asp Ser Phe Ser
        355                 360                 365
Arg Trp Ala Ser Lys Glu Leu Gly Glu Met Glu Asp Leu Gln Met Gln
    370                 375                 380
Ser Ser Arg Gly Asp Ile Ala Trp Ala Ser Val Asp Cys Glu Thr Ala
385                 390                 395                 400
Ala Ala Gly Leu Ser Phe Ser Pro Ser Leu Ser Glu Asp Gln Arg Phe
                405                 410                 415
Thr Ile Val Asp Tyr Trp Pro Lys Cys Ala Gln Thr Asp Ala Asp Val
            420                 425                 430
Glu Val Leu Val Ile Gly Thr Phe Leu Leu Asn Pro Gln Glu Val Thr

```
                435                 440                 445
Ile Cys Ser Trp Ser Cys Met Phe Gly Glu Val Glu Val Pro Ala Glu
450                 455                 460

Ile Leu Val Asp Gly Val Leu Cys Cys His Ala Pro Pro His Thr Ala
465                 470                 475                 480

Gly Gln Val Pro Phe Tyr Val Thr Cys Ser Asn Arg Phe Ala Cys Ser
                485                 490                 495

Glu Leu Arg Glu Phe Asp Phe Leu Ser Gly Thr Lys Lys Ile Asp
            500                 505                 510

Ala Ala Gly Ile Tyr Gly Tyr Ser Thr Lys Glu Ala Ser Leu Gln Met
        515                 520                 525

Arg Phe Glu Glu Leu Leu Ala His Arg Ala Phe Val Gln Glu His Gln
530                 535                 540

Ile Phe Glu Asp Val Val Glu Lys Arg Lys Ile Ser Lys Ile Met
545                 550                 555                 560

Leu Leu Asn Glu Glu Lys Glu Asn Leu Phe Pro Gly Ile Tyr Glu Arg
                565                 570                 575

Asp Ser Thr Lys Gln Glu Pro Lys Glu Arg Val Leu Arg Lys Gln Phe
            580                 585                 590

Glu Asp Glu Leu Tyr Ile Trp Leu Ile His Lys Val Thr Glu Glu Gly
        595                 600                 605

Lys Gly Pro Asn Ile Leu Asp Glu Gly Gly Gln Gly Val Leu His Phe
610                 615                 620

Val Ala Ala Leu Gly Tyr Asp Trp Ala Ile Lys Pro Ile Leu Ala Ala
625                 630                 635                 640

Gly Val Asn Ile Asn Phe Arg Asp Ala Asn Gly Trp Ser Ala Leu His
                645                 650                 655

Trp Ala Ala Phe Ser Gly Arg Glu Glu Thr Val Ala Val Leu Val Ser
            660                 665                 670

Leu Gly Ala Asp Ala Gly Ala Leu Thr Asp Pro Ser Pro Glu Leu Pro
        675                 680                 685

Leu Gly Lys Thr Ala Ala Asp Leu Ala Tyr Gly Lys Glu His Arg Gly
690                 695                 700

Ile Ser Gly Xaa Leu Ala Glu Ser Ser Leu Thr Ser Tyr Leu Glu Lys
705                 710                 715                 720

Leu Thr Met Glu Ser Lys Glu Asn Ser Pro Ala Asn Ser Gly Gly Pro
                725                 730                 735

Lys Ala Val Gln Thr Val Tyr Glu Xaa Thr Ala Ala Pro Met Ser Tyr
            740                 745                 750

Gly Asp Val Pro Glu Thr Leu Ser Leu Lys Asp Ser Leu Thr Ala Val
        755                 760                 765

Arg Asn Ala Thr Gln Ala Ala Asp Arg Leu His Gln Val Phe Arg Met
770                 775                 780

Gln Ser Phe Gln Arg Lys Gln Leu Ser Gly Phe Asp Asp Asp Gly
785                 790                 795                 800

Asp Glu Ile Gly Ile Ser Asn Glu Leu Ala Val Ser Phe Ala Ala Ser
                805                 810                 815

Lys Ala Lys Asn Pro Gly Gln Ser Glu Val Phe Val His Ser Ala Val
            820                 825                 830

Thr His Ile Gln Lys Lys Tyr Arg Gly Trp Lys Lys Arg Lys Glu Phe
        835                 840                 845

Leu Leu Ile Arg Gln Arg Val Val Lys Ile Gln Ala His Val Arg Gly
850                 855                 860
```

| | | | | | | | | | | | |
|---|---|---|---|---|---|---|---|---|---|---|---|
| His | Gln | Val | Arg | Lys | Gln | Tyr | Lys | Pro | Ile | Val | Trp | Ser | Val | Gly | Leu |
| 865 | | | | 870 | | | | 875 | | | | 880 |

```
His Gln Val Arg Lys Gln Tyr Lys Pro Ile Val Trp Ser Val Gly Leu
865                 870                 875                 880

Leu Glu Lys Ile Ile Leu Arg Trp Arg Arg Lys Gly Thr Gly Leu Arg
                885                 890                 895

Gly Phe Lys Arg Asn Ala Val Pro Lys Thr Val Glu Pro Glu Pro Gln
            900                 905                 910

Cys Pro Met Ile Pro Lys Glu Gly Asp Tyr Asp Phe Leu Glu Lys Gly
        915                 920                 925

Arg Lys Gln Thr Glu Glu Arg Leu Gln Lys Ala Leu Thr Arg Val Lys
    930                 935                 940

Ser Met Val Gln Tyr Pro Glu Ala Arg Asp Gln Tyr Arg Arg Leu Leu
945                 950                 955                 960

Thr Val Val Glu Gly Phe Arg Glu Asn Glu Ala Ser Ser Ser Leu Ser
                965                 970                 975

Val Asn Asn Arg Glu Glu Pro Val Asn Cys Glu Asp Asp Leu Ile
            980                 985                 990

Asp Ile Asp Ser Leu Leu Asn Asp Asp Ile Leu Met Ser Thr Ser Pro
        995                 1000                1005

Leu Asn Asp Ser Phe Val Tyr Ser Phe Ser Phe Phe Gln Leu Ser
    1010                1015                1020

Asn Phe Leu His Leu Phe Ser Val Asn Ile Ile Ser
1025            1030                1035
```

<210> SEQ ID NO 26
<211> LENGTH: 3024
<212> TYPE: DNA
<213> ORGANISM: Arabidopsis thaliana

<400> SEQUENCE: 26

```
atggtggatc gcagatcttt tggctctata actcctcctc tccaattaga tatggaacag    60
ttgctgtcag aagcccaaca caggtggctt aggcctactg agatttgtga aattcttcag   120
aactatcaca gtttcatatt agcatcagag tctcccaccc gacccgccag tggttcactt   180
tttcttttg ataggaaggt actgagatat tttaggaaag acggacataa ctggaggaag   240
aagaaagatg gtaaaaccat aagagaagct catgagaagc tcaaggtagg aagcatagat   300
gtgctacatt gttactatgc acatggggaa gccaacgaga atttccagag acgtgctac    360
tggatgcttg aacaacattt gatgcatatc gttttgtgc actacttgca ggttaagggt   420
aaccggacca gtataggaat gaagaaaaac aattcaaatt ctgtaaatgg cacagcttca   480
gtgaatattg attcaacagc aagcccaact agcacattgt catcattatg tgaagatgct   540
gataccgggg atagtcaaca agcaagttcc gtcttacgac catctcctga acctcaaact   600
ggaaatcgct atggttggac acctgctcct ggcatgcgta atgtttcaca ggttcatggg   660
aacagagtca gagaaagtga ttcccagaga ttagttgatg tcagagcttt ggataccgtt   720
gggaattcgc tgacaagatt tcatgatcag cctattgta taatttgtt gactcagatg    780
cagccttcta atactgactc aatgctggtg gaagaaaatt cagaaaaagg tgggcggtta   840
aaggcagagc atatcagaaa tcctcttcaa actcaattta attggcagga tgacactgat   900
ctggcgttat ttgagcaaag tgcacaagat aattttgaga cattttccag tctccttggc   960
agtgaaaatc tgcaaccttt tggaattagt tatcaagctc ctccttcaaa tatggactct  1020
gaatatatgc ctgtaatgaa aatattgcga agaagcgaag atagtttgaa aaagtcgat   1080
agttttcta gtgggctat taagaactt ggggagatgg aggatttgca gatgcagtct   1140
```

```
tcacgtggag atattgcatg gaccactgtt gaatgtgaaa ctgcagcagc tgggatctcc   1200
ttgagcccett ctctctctga ggatcagcgt ttcaccatag ttgattttg gccaaaaagt   1260
gcaaagacag acgcagaagt tgaggtcatg gttattggga catttctact tagtccgcaa   1320
gaagtaacta aatataattg gtcatgcatg tttggtgaag tggaagttcc tgctgagatt   1380
ttagtagatg gtgttctttg ctgtcatgct ccaccgcata cagctggtca cgtccccttt   1440
tatgttacat gttccaacag atttgcttgc agtgaagtac gagaatttga tttccttttct  1500
ggttctaccc aaaaaatcaa tgctacagat gtttatggta cctatacaaa tgaagcatca   1560
cttcagttgc ggtttgagaa gatgcttgct cacagggatt tgttcacga acaccatata    1620
ttcgaagatg ttggggacaa acgaagacaa atcagtaaaa ttatgttgct aaaggaggag   1680
aaagagtatc tccttccagg gacatatcag agagactcaa ccaaacaaga accaaaagga   1740
cagctttta gggaactgtt tgaagaagaa ctatatatat ggctcataca taaagtgact   1800
gaagagggta aggtccaaa catattggat gaagatggac agggtatttt acactttgtt   1860
gcagcgcttg ggtatgactg ggccattaaa ccggtgttag cagcaggagt taacattaac   1920
ttccgtgatg ccaatggctg gtctgcccctt cattgggctg cgtttagtgg cagggaggaa   1980
actgtcgctg tgcttgtctc tctaggtgct gatgctgggg cattaacgga tccatctcca   2040
gagcttccat tgggtaaaac agcagctgat ttggcttacg caaatggaca caggggaatt   2100
tcgggatttc ttgcagagtc ttccttaact agttatcttg aaaagctaac agtggactca   2160
aaggaaaata gccctgccaa ctcttgtgga gaaaaagctg ttcaaacagt ctctgagcga   2220
accgctgctc ctatgaccta tggcgatgta ccagagaaac tttccttgaa ggattcactt   2280
actgctgtcc gtaatgctac gcaagcggct gatcgtctcc atcaagtatt caggatgcaa   2340
tcattccaac ggaaacagct gtgtgatatt ggcgatgatg aaaagattga tatctccgac   2400
cagttagctg tttctttttgc agcttctaaa actaagaatc caggacaggg tgatgtctct   2460
cttagttgtg ctgctacccca tatccagaag aaatatcgtg gttggaagaa gagaaaagag   2520
tttcttttaa tccgacaaag aatcgttaaa attcaggctc atgtgagagg acatcaggtc   2580
cggaaacaat accgaacagt catctggtct gtgggattac tcgagaaaat cattttgcgt   2640
tggagacgca aagtaatgg tttgagaggg tttaaacgca atgcagtcgc caaaaccgtg   2700
gaaccggaac cgcctgtatc agctatatgt cctaggatcc cacaggaaga tgagtatgat   2760
tatcttaaag agggaagaaa acaaacagag gaaaggctac agaaggctct gactcgtgtt   2820
aagtcgatgg ttcaataccc agaagcacgg gatcaatacc gtagactcct aacgttgtt    2880
gagggcttcc gtgaaaatga ggcttcatca agtgcatcta taaacaataa agaagaagaa   2940
gcagtcaact gtgaagaaga cgattttatt gacattgagt ctcttttgaa cgatgacaca   3000
ttgatgatgt ctatttctcc ttga                                         3024
```

<210> SEQ ID NO 27
<211> LENGTH: 1007
<212> TYPE: PRT
<213> ORGANISM: Arabidopsis thaliana

<400> SEQUENCE: 27

Met Val Asp Arg Arg Ser Phe Gly Ser Ile Thr Pro Pro Leu Gln Leu
1               5                   10                  15

Asp Met Glu Gln Leu Leu Ser Glu Ala Gln His Arg Trp Leu Arg Pro
            20                  25                  30

-continued

Thr Glu Ile Cys Glu Ile Leu Gln Asn Tyr His Lys Phe His Ile Ala
                35                  40                  45

Ser Glu Ser Pro Thr Arg Pro Ala Ser Gly Ser Leu Phe Leu Phe Asp
 50                  55                  60

Arg Lys Val Leu Arg Tyr Phe Arg Lys Asp Gly His Asn Trp Arg Lys
 65                  70                  75                  80

Lys Lys Asp Gly Lys Thr Ile Arg Glu Ala His Glu Lys Leu Lys Val
                85                  90                  95

Gly Ser Ile Asp Val Leu His Cys Tyr Tyr Ala His Gly Glu Ala Asn
                100                 105                 110

Glu Asn Phe Gln Arg Arg Cys Tyr Trp Met Leu Glu Gln His Leu Met
            115                 120                 125

His Ile Val Phe Val His Tyr Leu Gln Val Lys Gly Asn Arg Thr Ser
        130                 135                 140

Ile Gly Met Lys Glu Asn Asn Ser Asn Ser Val Asn Gly Thr Ala Ser
145                 150                 155                 160

Val Asn Ile Asp Ser Thr Ala Ser Pro Thr Ser Thr Leu Ser Ser Leu
                165                 170                 175

Cys Glu Asp Ala Asp Thr Gly Asp Ser Gln Gln Ala Ser Ser Val Leu
            180                 185                 190

Arg Pro Ser Pro Glu Pro Gln Thr Gly Asn Arg Tyr Gly Trp Thr Pro
        195                 200                 205

Ala Pro Gly Met Arg Asn Val Ser Gln Val His Gly Asn Arg Val Arg
    210                 215                 220

Glu Ser Asp Ser Gln Arg Leu Val Asp Val Arg Ala Leu Asp Thr Val
225                 230                 235                 240

Gly Asn Ser Leu Thr Arg Phe His Asp Gln Pro Tyr Cys Asn Asn Leu
                245                 250                 255

Leu Thr Gln Met Gln Pro Ser Asn Thr Asp Ser Met Leu Val Glu Glu
            260                 265                 270

Asn Ser Glu Lys Gly Gly Arg Leu Lys Ala Glu His Ile Arg Asn Pro
        275                 280                 285

Leu Gln Thr Gln Phe Asn Trp Gln Asp Asp Thr Asp Leu Ala Leu Phe
    290                 295                 300

Glu Gln Ser Ala Gln Asp Asn Phe Glu Thr Phe Ser Ser Leu Leu Gly
305                 310                 315                 320

Ser Glu Asn Leu Gln Pro Phe Gly Ile Ser Tyr Gln Ala Pro Pro Ser
                325                 330                 335

Asn Met Asp Ser Glu Tyr Met Pro Val Met Lys Ile Leu Arg Arg Ser
            340                 345                 350

Glu Asp Ser Leu Lys Lys Val Asp Ser Phe Ser Lys Trp Ala Ile Lys
        355                 360                 365

Glu Leu Gly Glu Met Glu Asp Leu Gln Met Gln Ser Ser Arg Gly Asp
    370                 375                 380

Ile Ala Trp Thr Thr Val Glu Cys Glu Thr Ala Ala Gly Ile Ser
385                 390                 395                 400

Leu Ser Pro Ser Leu Ser Glu Asp Gln Arg Phe Thr Ile Val Asp Phe
                405                 410                 415

Trp Pro Lys Ser Ala Lys Thr Asp Ala Glu Val Glu Val Met Val Ile
            420                 425                 430

Gly Thr Phe Leu Leu Ser Pro Gln Glu Val Thr Lys Tyr Asn Trp Ser
        435                 440                 445

Cys Met Phe Gly Glu Val Glu Val Pro Ala Glu Ile Leu Val Asp Gly

```
            450                 455                 460
Val Leu Cys Cys His Ala Pro Pro His Thr Ala Gly His Val Pro Phe
465                 470                 475                 480

Tyr Val Thr Cys Ser Asn Arg Phe Ala Cys Ser Glu Val Arg Glu Phe
                    485                 490                 495

Asp Phe Leu Ser Gly Ser Thr Gln Lys Ile Asn Ala Thr Asp Val Tyr
                500                 505                 510

Gly Thr Tyr Thr Asn Glu Ala Ser Leu Gln Leu Arg Phe Glu Lys Met
            515                 520                 525

Leu Ala His Arg Asp Phe Val His Glu His His Ile Phe Glu Asp Val
        530                 535                 540

Gly Asp Lys Arg Arg Gln Ile Ser Lys Ile Met Leu Leu Lys Glu Glu
545                 550                 555                 560

Lys Glu Tyr Leu Leu Pro Gly Thr Tyr Gln Arg Asp Ser Thr Lys Gln
                    565                 570                 575

Glu Pro Lys Gly Gln Leu Phe Arg Glu Leu Phe Glu Glu Leu Tyr
                580                 585                 590

Ile Trp Leu Ile His Lys Val Thr Glu Glu Lys Gly Pro Asn Ile
            595                 600                 605

Leu Asp Glu Asp Gly Gln Gly Ile Leu His Phe Val Ala Ala Leu Gly
        610                 615                 620

Tyr Asp Trp Ala Ile Lys Pro Val Leu Ala Ala Gly Val Asn Ile Asn
625                 630                 635                 640

Phe Arg Asp Ala Asn Gly Trp Ser Ala Leu His Trp Ala Ala Phe Ser
                    645                 650                 655

Gly Arg Glu Glu Thr Val Ala Val Leu Val Ser Leu Gly Ala Asp Ala
                660                 665                 670

Gly Ala Leu Thr Asp Pro Ser Pro Glu Leu Pro Leu Gly Lys Thr Ala
            675                 680                 685

Ala Asp Leu Ala Tyr Ala Asn Gly His Arg Gly Ile Ser Gly Phe Leu
        690                 695                 700

Ala Glu Ser Ser Leu Thr Ser Tyr Leu Glu Lys Leu Thr Val Asp Ser
705                 710                 715                 720

Lys Glu Asn Ser Pro Ala Asn Ser Cys Gly Glu Lys Ala Val Gln Thr
                    725                 730                 735

Val Ser Glu Arg Thr Ala Ala Pro Met Thr Tyr Gly Asp Val Pro Glu
                740                 745                 750

Lys Leu Ser Leu Lys Asp Ser Leu Thr Ala Val Arg Asn Ala Thr Gln
            755                 760                 765

Ala Ala Asp Arg Leu His Gln Val Phe Arg Met Gln Ser Phe Gln Arg
        770                 775                 780

Lys Gln Leu Cys Asp Ile Gly Asp Asp Glu Lys Ile Asp Ile Ser Asp
785                 790                 795                 800

Gln Leu Ala Val Ser Phe Ala Ala Ser Lys Thr Lys Asn Pro Gly Gln
                    805                 810                 815

Gly Asp Val Ser Leu Ser Cys Ala Ala Thr His Ile Gln Lys Lys Tyr
                820                 825                 830

Arg Gly Trp Lys Lys Arg Lys Glu Phe Leu Leu Ile Arg Gln Arg Ile
            835                 840                 845

Val Lys Ile Gln Ala His Val Arg Gly His Gln Val Arg Lys Gln Tyr
        850                 855                 860

Arg Thr Val Ile Trp Ser Val Gly Leu Leu Glu Lys Ile Ile Leu Arg
865                 870                 875                 880
```

Trp Arg Arg Lys Gly Asn Gly Leu Arg Gly Phe Lys Arg Asn Ala Val
            885                 890                 895

Ala Lys Thr Val Glu Pro Glu Pro Val Ser Ala Ile Cys Pro Arg
        900                 905                 910

Ile Pro Gln Glu Asp Glu Tyr Asp Tyr Leu Lys Glu Gly Arg Lys Gln
        915                 920                 925

Thr Glu Glu Arg Leu Gln Lys Ala Leu Thr Arg Val Lys Ser Met Val
        930                 935                 940

Gln Tyr Pro Glu Ala Arg Asp Gln Tyr Arg Arg Leu Leu Thr Val Val
945                 950                 955                 960

Glu Gly Phe Arg Glu Asn Glu Ala Ser Ser Ser Ala Ser Ile Asn Asn
                965                 970                 975

Lys Glu Glu Glu Ala Val Asn Cys Glu Glu Asp Asp Phe Ile Asp Ile
            980                 985                 990

Glu Ser Leu Leu Asn Asp Asp Thr Leu Met Met Ser Ile Ser Pro
            995                 1000                1005

<210> SEQ ID NO 28
<211> LENGTH: 2559
<212> TYPE: DNA
<213> ORGANISM: Arabidopsis thaliana

<400> SEQUENCE: 28

| | | | | | |
|---|---|---|---|---|---|
| atggacggcg | acggtttagg | cagactaatc | ggctcggaga | ttcatggatt | ccatacctta | 60 |
| caagatcttg | atgtacagac | aatgttggag | gaagcaaaaa | gcaggtggct | acggccaaac | 120 |
| gagatccatg | caatcctcta | taacccgaaa | tacttcacta | tcaatgtcaa | gccagtgaac | 180 |
| ttacccaata | gtggcagaat | tatattattc | gaccgtaaga | tgttgaggaa | cttcagaaag | 240 |
| gatggtcata | actggaaaaa | gaaaaaggat | ggaaggacag | tcaaagaggc | tcatgaacac | 300 |
| ctgaaagttg | gtaacgagga | aaggattcat | gtatactatg | cgcatggtga | agataacact | 360 |
| acctttgttc | gaagatgtta | ttggttactg | gataaggctc | gagagaacat | cgtccttgta | 420 |
| cattaccgtg | atacacagga | ggcagctaca | acatcggggg | actcaatctc | tagtccaatc | 480 |
| tccgtctcgg | aacaaacatt | ccctaatcgc | gtggcagctg | aagatattga | tacagttgtt | 540 |
| agaaatcatg | atattagcct | tcatgatatc | aatacgcttg | attgggatga | gctgctagta | 600 |
| ccaaccgatc | ttaataacca | atctgcacca | accgtagata | atctttcata | tttcacagaa | 660 |
| ccgctccaaa | tgctgcaaa | tggcactgca | gagcatggga | atgcgacagt | ggctgatgga | 720 |
| tctcttgatg | ctttgcttaa | cgatggtcca | caaagtcgag | agagttttgg | aaggtggatg | 780 |
| aattcattta | tcagcgaatc | taatggctca | ctggaggatc | cttcctttga | acccatggtt | 840 |
| atgcctaggc | aggatccatt | agctcctcaa | gctgtatttc | attctcactc | taacatacct | 900 |
| gagcaagtgt | ttaacataac | cgatgtttca | cctgcttggg | cctattcttc | cgagaaaact | 960 |
| aagattctgg | taactgggtt | cttgcatgac | agttatcaac | atctcgaaag | atcaaacctt | 1020 |
| tattgcgttt | gcggtgactt | ttgtgtccct | gcggaatatc | tccaggctgg | agtctaccgt | 1080 |
| tgcatcatac | ctccacactc | gcctggtatg | gtaaacctct | atcttagtgc | agatggacac | 1140 |
| aaaccaatca | gccaatgttt | cagattcgaa | caccgtgcag | tcccagttct | tgataagacc | 1200 |
| gtccctgaag | acaatcaaga | ttccaaatgg | aagagtttga | gttccaagt | cgactttct | 1260 |
| catcttctgt | ttacgtcttc | caacaaactc | aacgttctct | ccagcaaaat | ctcacctcat | 1320 |
| aacctgcgag | atgctaaaaa | actcgctagc | aaaacaaatc | atctcttaaa | cagttgggct | 1380 |

-continued

```
tatctagtca agtccatcca ggggaataag gtatcgtttg atcaagcgaa agatcatctc      1440
ttcgagcttt ctctgaagaa caggcttaag gaatggctta tggagaaagt gcttgaaggt      1500
cgcaacacat tggattatga ttctaaaggc ctcggcgtga tccacctctg tgccagtctt      1560
ggatacactt ggtcagtcca gctgttctca ttgtcaggct tatcgttgaa tttccgtgat      1620
aaacaagggt ggactgctct tcattgggca gcatactacg aagggagaa atggtggct       1680 gctcttctct ctgctggggc aagaccgaac ctggtgacag actcgacgaa ggataatctt      1740
ggtggatgca tggcagctga tttggcacag caaaacggat atgacggttt agctgcttat      1800
cttgctgaga atgtttggt tgctcagttt agagacatga aaattgctgg aaacatcact       1860
ggcgatctgg aggcttgcaa ggcagagatg ttgaaccaag cactctacc ggaagatgag       1920 cagagtctca aggatgctct tgcagcatac agaacagctg cagaagcagc ggctcggatt      1980
caaggtgcgt ttagggaaaa agcgctaaag gcagcacggt caagcgtgat tcagtttgct      2040
aacaaagaag aagaggccaa gagcataatc gcggcgatga agattcagaa tgcgttccgg      2100
aaatatgata cacgtaggaa gatagaagcc gcttaccgga ttcaatgcag gttccaaact      2160
tggaaaatac gaagagagta tctgaacatg cggcgccaag caattaggat ccaggctgct      2220 ttcagggat tacaagcaag gaggcagtac aagaagatat tgtggtcggt aggagtattg       2280
gagaaggcag ttttgaggtg gagacaaaag agaaaagggt ttagaggact ccaggttgca      2340
gcagaggagg attctcctgg tgaggcacag gaagatttct acaagacaag ccagagacaa      2400
gcagaggaga ggctcgagag atctgtagtg cgagtacaag ccatgttcag gtctaagaag      2460
gctcaacagg attacagaag gatgaaactc actcatgaag aagctcagtc ttgttatggt      2520
gtgacacagt tggagtacgg ttgcctggaa gatatttga                             2559
```

<210> SEQ ID NO 29
<211> LENGTH: 852
<212> TYPE: PRT
<213> ORGANISM: Arabidopsis thaliana

<400> SEQUENCE: 29

```
Met Asp Gly Asp Gly Leu Gly Arg Leu Ile Gly Ser Glu Ile His Gly
 1               5                   10                  15

Phe His Thr Leu Gln Asp Leu Asp Val Gln Thr Met Leu Glu Glu Ala
                20                  25                  30

Lys Ser Arg Trp Leu Arg Pro Asn Glu Ile His Ala Ile Leu Tyr Asn
            35                  40                  45

Pro Lys Tyr Phe Thr Ile Asn Val Lys Pro Val Asn Leu Pro Asn Ser
        50                  55                  60

Gly Arg Ile Ile Leu Phe Asp Arg Lys Met Leu Arg Asn Phe Arg Lys
 65                  70                  75                  80

Asp Gly His Asn Trp Lys Lys Lys Asp Gly Arg Thr Val Lys Glu
                85                  90                  95

Ala His Glu His Leu Lys Val Gly Asn Glu Arg Ile His Val Tyr
            100                 105                 110

Tyr Ala His Gly Glu Asp Asn Thr Thr Phe Val Arg Arg Cys Tyr Trp
        115                 120                 125

Leu Leu Asp Lys Ala Arg Glu Asn Ile Val Leu Val His Tyr Arg Asp
    130                 135                 140

Thr Gln Glu Ala Ala Thr Thr Ser Gly Asp Ser Ile Ser Ser Pro Ile
145                 150                 155                 160

Ser Val Ser Glu Gln Thr Phe Pro Asn Arg Val Ala Ala Glu Asp Ile
```

```
                165                 170                 175
Asp Thr Val Val Arg Asn His Asp Ile Ser Leu His Asp Ile Asn Thr
                    180                 185                 190

Leu Asp Trp Asp Glu Leu Leu Val Pro Thr Asp Leu Asn Asn Gln Ser
                195                 200                 205

Ala Pro Thr Val Asp Asn Leu Ser Tyr Phe Thr Glu Pro Leu Gln Asn
            210                 215                 220

Ala Ala Asn Gly Thr Ala Glu His Gly Asn Ala Thr Val Ala Asp Gly
225                 230                 235                 240

Ser Leu Asp Ala Leu Leu Asn Asp Gly Pro Gln Ser Arg Glu Ser Phe
                245                 250                 255

Gly Arg Trp Met Asn Ser Phe Ile Ser Glu Ser Asn Gly Ser Leu Glu
                260                 265                 270

Asp Pro Ser Phe Glu Pro Met Val Met Pro Arg Gln Asp Pro Leu Ala
                275                 280                 285

Pro Gln Ala Val Phe His Ser His Ser Asn Ile Pro Glu Gln Val Phe
            290                 295                 300

Asn Ile Thr Asp Val Ser Pro Ala Trp Ala Tyr Ser Ser Glu Lys Thr
305                 310                 315                 320

Lys Ile Leu Val Thr Gly Phe Leu His Asp Ser Tyr Gln His Leu Glu
                325                 330                 335

Arg Ser Asn Leu Tyr Cys Val Cys Gly Asp Phe Cys Val Pro Ala Glu
                340                 345                 350

Tyr Leu Gln Ala Gly Val Tyr Arg Cys Ile Ile Pro Pro His Ser Pro
            355                 360                 365

Gly Met Val Asn Leu Tyr Leu Ser Ala Asp Gly His Lys Pro Ile Ser
            370                 375                 380

Gln Cys Phe Arg Phe Glu His Arg Ala Val Pro Val Leu Asp Lys Thr
385                 390                 395                 400

Val Pro Glu Asp Asn Gln Asp Ser Lys Trp Glu Glu Phe Glu Phe Gln
                405                 410                 415

Val Arg Leu Ser His Leu Leu Phe Thr Ser Ser Asn Lys Leu Asn Val
                420                 425                 430

Leu Ser Ser Lys Ile Ser Pro His Asn Leu Arg Asp Ala Lys Lys Leu
                435                 440                 445

Ala Ser Lys Thr Asn His Leu Leu Asn Ser Trp Ala Tyr Leu Val Lys
            450                 455                 460

Ser Ile Gln Gly Asn Lys Val Ser Phe Asp Gln Ala Lys Asp His Leu
465                 470                 475                 480

Phe Glu Leu Ser Leu Lys Asn Arg Leu Lys Glu Trp Leu Met Glu Lys
                485                 490                 495

Val Leu Glu Gly Arg Asn Thr Leu Asp Tyr Asp Ser Lys Gly Leu Gly
                500                 505                 510

Val Ile His Leu Cys Ala Ser Leu Gly Tyr Thr Trp Ser Val Gln Leu
            515                 520                 525

Phe Ser Leu Ser Gly Leu Ser Leu Asn Phe Arg Asp Lys Gln Gly Trp
            530                 535                 540

Thr Ala Leu His Trp Ala Ala Tyr Tyr Gly Arg Glu Lys Met Val Ala
545                 550                 555                 560

Ala Leu Leu Ser Ala Gly Ala Arg Pro Asn Leu Val Thr Asp Ser Thr
                565                 570                 575

Lys Asp Asn Leu Gly Gly Cys Met Ala Ala Asp Leu Ala Gln Gln Asn
                580                 585                 590
```

```
Gly Tyr Asp Gly Leu Ala Ala Tyr Leu Ala Glu Lys Cys Leu Val Ala
        595                 600                 605
Gln Phe Arg Asp Met Lys Ile Ala Gly Asn Ile Thr Gly Asp Leu Glu
    610                 615                 620
Ala Cys Lys Ala Glu Met Leu Asn Gln Gly Thr Leu Pro Glu Asp Glu
625                 630                 635                 640
Gln Ser Leu Lys Asp Ala Leu Ala Ala Tyr Arg Thr Ala Ala Glu Ala
                645                 650                 655
Ala Ala Arg Ile Gln Gly Ala Phe Arg Glu Lys Ala Leu Lys Ala Ala
            660                 665                 670
Arg Ser Ser Val Ile Gln Phe Ala Asn Lys Glu Glu Ala Lys Ser
        675                 680                 685
Ile Ile Ala Ala Met Lys Ile Gln Asn Ala Phe Arg Lys Tyr Asp Thr
    690                 695                 700
Arg Arg Lys Ile Glu Ala Ala Tyr Arg Ile Gln Cys Arg Phe Gln Thr
705                 710                 715                 720
Trp Lys Ile Arg Arg Glu Tyr Leu Asn Met Arg Gln Ala Ile Arg
                725                 730                 735
Ile Gln Ala Ala Phe Arg Gly Leu Gln Ala Arg Gln Tyr Lys Lys
            740                 745                 750
Ile Leu Trp Ser Val Gly Val Leu Glu Lys Ala Val Leu Arg Trp Arg
        755                 760                 765
Gln Lys Arg Lys Gly Phe Arg Gly Leu Gln Val Ala Ala Glu Glu Asp
    770                 775                 780
Ser Pro Gly Glu Ala Gln Glu Asp Phe Tyr Lys Thr Ser Gln Arg Gln
785                 790                 795                 800
Ala Glu Glu Arg Leu Glu Arg Ser Val Val Arg Val Gln Ala Met Phe
                805                 810                 815
Arg Ser Lys Lys Ala Gln Gln Asp Tyr Arg Arg Met Lys Leu Thr His
            820                 825                 830
Glu Glu Ala Gln Ser Cys Tyr Gly Val Thr Gln Leu Glu Tyr Gly Cys
        835                 840                 845
Leu Glu Asp Ile
    850

<210> SEQ ID NO 30
<211> LENGTH: 3153
<212> TYPE: DNA
<213> ORGANISM: Arabidopsis thaliana

<400> SEQUENCE: 30
atggcggatc gcggatctttt cggatttgct cctcgattag atatcaagca attgctgtca    60
gaagcacaac acaggtggct gagacctgct gagatttgtg aaattcttcg gaatcatcag   120
aagtttcata ttgcgtcaga gcctcccaac cgaccaccca gtggttcact ctttctcttc   180
gataggaagg tgctcagata tttccgaaaa gacgggcaca attggaggaa gaagaaagat   240
gggaaaacag tgaaagaggc tcacgaaaag ctgaaggtag aagcattga tgtgttacat   300 tgttactatg cacatggaga agataatgag aacttccaga gcgcgtgcta ctggatgctt   360
gaacaggatc tgatgcacat tgttttcgtt cactacttgg aggttaaggg taaccgaatg   420
agtaccagtg gaactaaaga aaaccattca aattctctga gtggcacggg ttctgtaaat   480
gttgattcca cagcaacccg atccagcata ttgtcaccat tatgtgaaga tgctgattct   540
ggggatagtc gtcaagcaag ttccagtttg caacaaaatc ctgaacctca aactgttgtt   600
```

```
cctcagatta tgcatcatca gaatgctagc acaatcaatt cttacaatac aacctctgtt    660
ttgggaaatc gagatggttg gacgtcagct catgggaaca gggtcaaagg aagtaactcc    720
caaagatcag gtgatgtccc agcatgggat gcttcctttg agaattcatt ggcaagatac    780
cagaatctac cttataatgc tccgttgact cagacacagc cttctacttt tggtttgatc    840
cccatggaag ggaaaacaga gaaaggttcc ctgttaacgt cagagcatct tagaaatcct    900
cttcaaagtc aagtaaattg gcagactcct gttcaggaaa gcgtgccatt gcaaaaatgg    960
cccatggatt cgcattctgg aatgactgat gctactgatc ttgccttatt tgggcaagga   1020
gcacatgaaa attttgggac attttccagt cttcttggta gtcaagatca acagtctagt   1080
agtttccaag ctcctttcac aaataatgaa gcagcatata acctaaattt aggccccgag   1140
gatcttatat atgaagcaag tgcaaatcaa acactacctc ttagaaaagc attgttaaaa   1200
aaagaggata gtttgaaaaa ggttgacagt ttctctcggt gggttagtaa agaacttggg   1260
gagatggaag acttgcagat gcaatcttca tctggaggta ttgcatggac ttctgttgaa   1320
tgtgaaaacg cagcagctgg gtcttcctta agtccttctc tgtccgagga tcagcgcttc   1380
actatgatcg acttttggcc caaatggact cagacagact cagaagttga ggtaatggtt   1440
atcgggacat ttctgttgag tcctcaggaa gtaactagct atagctggtc atgcatgttt   1500
ggagaagtgg aggttccggc tgatatttta gtagatggtg ttctttgttg tcatgctccg   1560
ccacatgaag tcggtcgagt cccgttctat ataacatgtt ctgacagatt ttcttgcagt   1620
gaagtacgag aattcgattt ccttcctggg tctaccagaa agttaaatgc tactgacatt   1680
tatggtgcca atacaattga acatcactc catttgcggt ttgaaaactt gctggctctc   1740
agatgttctg ttcaggaaca ccatatattt gaaaatgttg gggagaaacg aagaaaaatc   1800
agcaaaatca tgttgctaaa ggatgaaaaa gagcctcctc tccccggaac aattgagaaa   1860
gatctaacag agctggaagc aaaagagcga ttgattaggg aagagtttga agataaaatta   1920 tatctgtggc tcatccataa ggtgactgaa gagggcaagg gtccaaatat attagatgaa   1980
gatggacagg gtgttctaca cctagccgca gcgctggggt atgattgggc gataaagcca   2040
atcttagcag caggagttag catcaacttc cgcgatgcaa atgggtggtc tgctcttcac   2100
tgggctgcat tcagtggcag ggaggatact gtcgctgtac ttgtctcact gggtgctgat   2160
gctggagcat tggcggaccc atctccagaa catcctttgg ggaaaacagc tgctgacttg   2220
gcttatggaa acggacacag gggaatatcg ggtttccttg cagagtcatc cctcactagc   2280
taccttgaaa aactaacagt ggacgctaag gaaaacagct ccgctgactc ctctggagca   2340
aaagctgttc tgacagtagc tgagcgaaca gctactccta tgagttatgg tgatgtacca   2400
gaaacacttt cgatgaagga ttcacttact gctgtcttaa atgctacaca agcagctgat   2460
cgtcttcatc aagtgttcag aatgcagtcg ttccagcgga acagctctc tgaacttggt   2520 ggcgacaaca aattcgatat atccgatgag ttagctgtgt cttttgcggc tgcaaagact   2580
aagaagtcag gacacagtag tggtgctgtt catgctgctg cggttcaaat ccagaaaaaa   2640
taccgtggtt ggaagaagag aaaggagttc cttctgatcc gacaaagaat cgtcaagatt   2700
caggctcatg tgagaggaca tcaagtccga aaacaatacc gagccattat ttggtccgta   2760
ggattgcttg agaaaatcat cttgcgatgg aggcgtaaag gtagtggctt acgcggtttc   2820
aaacgtgata caatcagcaa gccaacagaa cctgtatgtc ctgccccaca agaagatgat   2880
tatgattttc tcaaggaagg aaggaaacaa acagaggaaa ggcttcaaaa ggctctaacc   2940
```

-continued

```
cgagtgaagt ctatggctca atatccagag gcacgggctc aataccgtag actattgact      3000
gtcgttgaag gcttccgtga gaacgaggct tcttctagct cggcattgaa aaacaacaca      3060
gaggaagctg caaattacaa cgaagaagac gatttaattg acattgattc tcttttggat      3120
gacgacactt tcatgtctct tgcatttgaa tga                                    3153

<210> SEQ ID NO 31
<211> LENGTH: 1050
<212> TYPE: PRT
<213> ORGANISM: Arabidopsis thaliana

<400> SEQUENCE: 31

Met Ala Asp Arg Gly Ser Phe Gly Phe Ala Pro Arg Leu Asp Ile Lys
1               5                   10                  15

Gln Leu Leu Ser Glu Ala Gln His Arg Trp Leu Arg Pro Ala Glu Ile
            20                  25                  30

Cys Glu Ile Leu Arg Asn His Gln Lys Phe His Ile Ala Ser Glu Pro
        35                  40                  45

Pro Asn Arg Pro Pro Ser Gly Ser Leu Phe Leu Phe Asp Arg Lys Val
    50                  55                  60

Leu Arg Tyr Phe Arg Lys Asp Gly His Asn Trp Arg Lys Lys Lys Asp
65                  70                  75                  80

Gly Lys Thr Val Lys Glu Ala His Glu Lys Leu Lys Val Gly Ser Ile
                85                  90                  95

Asp Val Leu His Cys Tyr Tyr Ala His Gly Glu Asp Asn Glu Asn Phe
            100                 105                 110

Gln Arg Arg Cys Tyr Trp Met Leu Glu Gln Asp Leu Met His Ile Val
        115                 120                 125

Phe Val His Tyr Leu Glu Val Lys Gly Asn Arg Met Ser Thr Ser Gly
    130                 135                 140

Thr Lys Glu Asn His Ser Asn Ser Leu Ser Gly Thr Gly Ser Val Asn
145                 150                 155                 160

Val Asp Ser Thr Ala Thr Arg Ser Ser Ile Leu Ser Pro Leu Cys Glu
                165                 170                 175

Asp Ala Asp Ser Gly Asp Ser Arg Gln Ala Ser Ser Ser Leu Gln Gln
            180                 185                 190

Asn Pro Glu Pro Gln Thr Val Val Pro Gln Ile Met His His Gln Asn
        195                 200                 205

Ala Ser Thr Ile Asn Ser Tyr Asn Thr Thr Ser Val Leu Gly Asn Arg
    210                 215                 220

Asp Gly Trp Thr Ser Ala His Gly Asn Arg Val Lys Gly Ser Asn Ser
225                 230                 235                 240

Gln Arg Ser Gly Asp Val Pro Ala Trp Asp Ala Ser Phe Glu Asn Ser
                245                 250                 255

Leu Ala Arg Tyr Gln Asn Leu Pro Tyr Asn Ala Pro Leu Thr Gln Thr
            260                 265                 270

Gln Pro Ser Thr Phe Gly Leu Ile Pro Met Glu Gly Lys Thr Glu Lys
        275                 280                 285

Gly Ser Leu Leu Thr Ser Glu His Leu Arg Asn Pro Leu Gln Ser Gln
    290                 295                 300

Val Asn Trp Gln Thr Pro Val Gln Glu Ser Val Pro Leu Gln Lys Trp
305                 310                 315                 320

Pro Met Asp Ser His Ser Gly Met Thr Asp Ala Thr Asp Leu Ala Leu
                325                 330                 335
```

```
Phe Gly Gln Gly Ala His Glu Asn Phe Gly Thr Phe Ser Ser Leu Leu
            340                 345                 350

Gly Ser Gln Asp Gln Gln Ser Ser Phe Gln Ala Pro Phe Thr Asn
355                 360                 365

Asn Glu Ala Ala Tyr Ile Pro Lys Leu Gly Pro Glu Asp Leu Ile Tyr
    370                 375                 380

Glu Ala Ser Ala Asn Gln Thr Leu Pro Leu Arg Lys Ala Leu Leu Lys
385                 390                 395                 400

Lys Glu Asp Ser Leu Lys Lys Val Asp Ser Phe Ser Arg Trp Val Ser
                405                 410                 415

Lys Glu Leu Gly Glu Met Glu Asp Leu Gln Met Gln Ser Ser Ser Gly
            420                 425                 430

Gly Ile Ala Trp Thr Ser Val Glu Cys Glu Asn Ala Ala Ala Gly Ser
            435                 440                 445

Ser Leu Ser Pro Ser Leu Ser Glu Asp Gln Arg Phe Thr Met Ile Asp
    450                 455                 460

Phe Trp Pro Lys Trp Thr Gln Thr Asp Ser Glu Val Glu Val Met Val
465                 470                 475                 480

Ile Gly Thr Phe Leu Leu Ser Pro Gln Glu Val Thr Ser Tyr Ser Trp
                485                 490                 495

Ser Cys Met Phe Gly Glu Val Glu Val Pro Ala Asp Ile Leu Val Asp
            500                 505                 510

Gly Val Leu Cys Cys His Ala Pro His Glu Val Gly Arg Val Pro
            515                 520                 525

Phe Tyr Ile Thr Cys Ser Asp Arg Phe Ser Cys Ser Glu Val Arg Glu
    530                 535                 540

Phe Asp Phe Leu Pro Gly Ser Thr Arg Lys Leu Asn Ala Thr Asp Ile
545                 550                 555                 560

Tyr Gly Ala Asn Thr Ile Glu Thr Ser Leu His Leu Arg Phe Glu Asn
                565                 570                 575

Leu Leu Ala Leu Arg Cys Ser Val Gln Glu His Ile Phe Glu Asn
            580                 585                 590

Val Gly Glu Lys Arg Arg Lys Ile Ser Lys Ile Met Leu Leu Lys Asp
            595                 600                 605

Glu Lys Glu Pro Pro Leu Pro Gly Thr Ile Glu Lys Asp Leu Thr Glu
    610                 615                 620

Leu Glu Ala Lys Glu Arg Leu Ile Arg Glu Glu Phe Glu Asp Lys Leu
625                 630                 635                 640

Tyr Leu Trp Leu Ile His Lys Val Thr Glu Glu Gly Lys Gly Pro Asn
                645                 650                 655

Ile Leu Asp Glu Asp Gly Gln Gly Val Leu His Leu Ala Ala Leu
            660                 665                 670

Gly Tyr Asp Trp Ala Ile Lys Pro Ile Leu Ala Ala Gly Val Ser Ile
    675                 680                 685

Asn Phe Arg Asp Ala Asn Gly Trp Ser Ala Leu His Trp Ala Ala Phe
690                 695                 700

Ser Gly Arg Glu Asp Thr Val Ala Val Leu Val Ser Leu Gly Ala Asp
705                 710                 715                 720

Ala Gly Ala Leu Ala Asp Pro Ser Pro Glu His Pro Leu Gly Lys Thr
                725                 730                 735

Ala Ala Asp Leu Ala Tyr Gly Asn Gly His Arg Gly Ile Ser Gly Phe
            740                 745                 750

Leu Ala Glu Ser Ser Leu Thr Ser Tyr Leu Glu Lys Leu Thr Val Asp
```

```
                755                 760                 765
Ala Lys Glu Asn Ser Ser Ala Asp Ser Ser Gly Ala Lys Ala Val Leu
            770                 775                 780

Thr Val Ala Glu Arg Thr Ala Thr Pro Met Ser Tyr Gly Asp Val Pro
785                 790                 795                 800

Glu Thr Leu Ser Met Lys Asp Ser Leu Thr Ala Val Leu Asn Ala Thr
                805                 810                 815

Gln Ala Ala Asp Arg Leu His Gln Val Phe Arg Met Gln Ser Phe Gln
            820                 825                 830

Arg Lys Gln Leu Ser Glu Leu Gly Gly Asp Asn Lys Phe Asp Ile Ser
        835                 840                 845

Asp Glu Leu Ala Val Ser Phe Ala Ala Lys Thr Lys Lys Ser Gly
850                 855                 860

His Ser Ser Gly Ala Val His Ala Ala Val Gln Ile Gln Lys Lys
865                 870                 875                 880

Tyr Arg Gly Trp Lys Lys Arg Lys Glu Phe Leu Leu Ile Arg Gln Arg
                885                 890                 895

Ile Val Lys Ile Gln Ala His Val Arg Gly His Gln Val Arg Lys Gln
            900                 905                 910

Tyr Arg Ala Ile Ile Trp Ser Val Gly Leu Leu Glu Lys Ile Ile Leu
        915                 920                 925

Arg Trp Arg Arg Lys Gly Ser Gly Leu Arg Gly Phe Lys Arg Asp Thr
930                 935                 940

Ile Ser Lys Pro Thr Glu Pro Val Cys Pro Ala Pro Gln Glu Asp Asp
945                 950                 955                 960

Tyr Asp Phe Leu Lys Glu Gly Arg Lys Gln Thr Glu Arg Leu Gln
                965                 970                 975

Lys Ala Leu Thr Arg Val Lys Ser Met Ala Gln Tyr Pro Glu Ala Arg
            980                 985                 990

Ala Gln Tyr Arg Arg Leu Leu Thr  Val Val Glu Gly Phe  Arg Glu Asn
        995                 1000                1005

Glu Ala  Ser Ser Ser Ser Ala  Leu Lys Asn Asn Thr  Glu Glu Ala
1010                1015                1020

Ala Asn  Tyr Asn Glu Glu Asp  Asp Leu Ile Asp Ile  Asp Ser Leu
1025                1030                1035

Leu Asp Asp Asp Thr Phe Met  Ser Leu Ala Phe Glu
1040                1045                1050

<210> SEQ ID NO 32
<211> LENGTH: 3108
<212> TYPE: DNA
<213> ORGANISM: Arabidopsis thaliana

<400> SEQUENCE: 32
atgagtagcg tcgcagagga taattccttt acctgtgaca tagcaaccat cttcgtggct    60
atctgtcgga accctcctgc taatccttca gattctttat ttcgtcagtc cataattgac   120
ttactctact tcaattcgtc accagtcgtt atgcaatctg aatatgaaat tagtactctg   180
tatcaagaag ctcatagccg ttggttgaaa cctcctgagg tactcttcat attgcagaat   240
catgaaagct tgacgcttac taatacagct cctcaaagac ctacaagtgg gtctttgttg   300
cttttcaata aagggttctc taaattcttt cgtaaagatg gtcatcaatg gcggagaaaa   360
agagatggta gagctattgc tgaagcacat gaacgactta aggtgggtaa cgctgaggca   420
ttgaattgtt attatgctca tggagagcaa gaccctactt tcggaggcg tatctactgg   480
```

```
atgttagatc cggaatacga gcatattgtc cttgttcatt acagggatgt aagcgaacga    540
gaagagggac aacaaactgg tggacaagtt tatcagtttg caccaattct ttccactcaa    600
aatgtaagct acaatcagta cattggtgat tcttcggaca tatatcagca gtcttctact    660
tcgccgggcg ttgcagaggt taactctaac ttggaaggca gtgcaagttc ttctgagttt    720
ggacaggctt taaagatgct taaggaacaa ctgagtatcg gagatgaaca tgttaattct    780
gttgatccac actacattca accagaaagt cttgatagtc tccagttttt agagtacagt    840
gacatagatc accttgctca accaacaact gtatatcaga gaccagagaa taacaaacta    900
gagagatgtt atggaggcaa ttttggagcc caatacagtg ccaagaatga ttctaacaaa    960
ctagagagat gctatggagg gtatgttggt ggagccgaat accattctag caatctcatg   1020
ctcgtaaaga atggttcagg accttcaggt ggtacaggag ggagtggaga tcaagggtct   1080
gaatcttgga agatgtgtt ggaggcatgt gaggcttcta tacctcttaa ctctgaggga   1140
agcacaccaa gttctgcaaa aggattgcta gctggattgc aggaagactc aaattggagt   1200
tacagcaatc aggttgacca atctacattt ttgttgcctc aagatcttgg ttcttttccaa   1260 cttcctgctt cttattctgc actggtagct cctgagaata tggtgaata ctgtggaatg    1320 atggaggacg gaatgaaaat cggtctgcct ttcgagcaag aaatgagagt tacaggtgct   1380
cataatcaaa agtttactat ccaggacata tcaccagact ggggttacgc gaatgaaact   1440
acaaaggtga taatcattgg atcatttctc tgtgatccaa cagaatctac atggtcttgc   1500
atgtttggga tgctcaagt tccttttgag atcattaaag aaggtgttat acggtgtgaa   1560 gccctcaat gtggtcctgg aaaagtcaat ttatgcatta cttctggaga tggactcttg   1620
tgtagtgaaa taagggaatt tgagtatcgt gagaagcctg acacatgttg ccctaaatgc   1680
agtgagccac agacctctga tatgtccaca agtccaaatg agcttatatt acttgtaagg   1740
tttgtgcaaa cacttctatc agaccgatcg tcggaaagaa aaagtaactt agagtctggc   1800
aatgataagc tgttgacgaa actgaaagct gatgatgatc aatggagaca tgtcatagga   1860
acgatcatag atggcagtgc atcatcaaca agtacagttg attggcttct acaggaactg   1920
cttaaagaca agctggatac atggctgtct tcaagatcat gtgatgaaga ttacataacg   1980
tgttctttgt caaagcagga acaaggtatt atccatatgg ttgcaggcct tggcttcgag   2040
tgggcatttt atccaatcct tgctcatgga gtcaatgtag attttcgtga tattaaggga   2100
tggagcgctc ttcattgggc tgcacaattt ggaagtgaaa aaatggtggc tgcccttata   2160
gcttcagggg catcggctgg agcagtgact gatccaagtc ggcaagatcc aaatggcaaa   2220
actgcagctt caatagctgc ctctaatggc cacaagggtc ttgcaggtta tctgtcagag   2280
gtggcgttaa caaccatct ctcatcgctc acacttgaag aaaccgagaa ttcaaaagac   2340
actgctcaag tgcaaactga gaaaactttg aattccatct cagaacaaag tccttccggt   2400
aacgaggatc aagtgtcatt gaaagacaca ctggctgcag tacgaaatgc agctcaagca   2460
gctgcaagaa tccaagcagc ttttcgcgca cattcattca gaaagcgaaa acaaagagaa   2520
gcagctttgg ttgcttgctt acaagagtat gggatgtatt gtgaagatat agaagggatc   2580
tcggccatgt caaagctaac gtttggaaag ggcaggaact acaattcagc agctttatct   2640
attcagaaga attttcgtgg ctataaagat cgtaaatgtt ttctagagct tcgccagaaa   2700
gttgtaaaga ttcaggctca gtgcgaggt accaaataa ggaaaaatta caaagtaatc   2760
tgttgggcag taagaatttt agataaggtt gtactcaggt ggagaagaaa aggagttgga   2820
```

```
ctaagagggt tcagacaaga cgtagagagt acagaggaca gtgaagacga agacattctc    2880
aaggtgttcc gcaaacagaa agtagatgtt gcagtgaacg aggctttctc tcgtgttcta    2940
tcgatgtcta actctccaga ggctcgccag caataccacc gagtgctcaa gagatattgt    3000
cagacaaagg ctgagcttgg aaaaacagag acattagttg gagaggacga tgatgggttg    3060
ttcgacatag ctgatatgga atatgacact ttgttttcat tgccttga                3108
```

<210> SEQ ID NO 33
<211> LENGTH: 1035
<212> TYPE: PRT
<213> ORGANISM: Arabidopsis thaliana

<400> SEQUENCE: 33

```
Met Ser Ser Val Ala Glu Asp Asn Ser Phe Thr Cys Asp Ile Ala Thr
1               5                   10                  15

Ile Phe Val Ala Ile Cys Arg Asn Pro Pro Ala Asn Pro Ser Asp Ser
            20                  25                  30

Leu Phe Arg Gln Ser Ile Ile Asp Leu Leu Tyr Phe Asn Ser Ser Pro
        35                  40                  45

Val Val Met Gln Ser Glu Tyr Glu Ile Ser Thr Leu Tyr Gln Glu Ala
    50                  55                  60

His Ser Arg Trp Leu Lys Pro Pro Glu Val Leu Phe Ile Leu Gln Asn
65                  70                  75                  80

His Glu Ser Leu Thr Leu Thr Asn Thr Ala Pro Gln Arg Pro Thr Ser
                85                  90                  95

Gly Ser Leu Leu Leu Phe Asn Lys Arg Val Leu Lys Phe Phe Arg Lys
            100                 105                 110

Asp Gly His Gln Trp Arg Arg Lys Arg Asp Gly Arg Ala Ile Ala Glu
        115                 120                 125

Ala His Glu Arg Leu Lys Val Gly Asn Ala Glu Ala Leu Asn Cys Tyr
    130                 135                 140

Tyr Ala His Gly Glu Gln Asp Pro Thr Phe Arg Arg Ile Tyr Trp
145                 150                 155                 160

Met Leu Asp Pro Glu Tyr Glu His Ile Val Leu Val His Tyr Arg Asp
                165                 170                 175

Val Ser Glu Arg Glu Glu Gly Gln Gln Thr Gly Gly Gln Val Tyr Gln
            180                 185                 190

Phe Ala Pro Ile Leu Ser Thr Gln Asn Val Ser Tyr Asn Gln Tyr Ile
        195                 200                 205

Gly Asp Ser Ser Asp Ile Tyr Gln Gln Ser Ser Thr Ser Pro Gly Val
    210                 215                 220

Ala Glu Val Asn Ser Asn Leu Glu Gly Ser Ala Ser Ser Ser Glu Phe
225                 230                 235                 240

Gly Gln Ala Leu Lys Met Leu Lys Glu Gln Leu Ser Ile Gly Asp Glu
                245                 250                 255

His Val Asn Ser Val Asp Pro His Tyr Ile Gln Pro Glu Ser Leu Asp
            260                 265                 270

Ser Leu Gln Phe Leu Glu Tyr Ser Asp Ile Asp His Leu Ala Gln Pro
        275                 280                 285

Thr Thr Val Tyr Gln Arg Pro Glu Asn Asn Lys Leu Glu Arg Cys Tyr
    290                 295                 300

Gly Gly Asn Phe Gly Ala Gln Tyr Ser Ala Lys Asn Asp Ser Asn Lys
305                 310                 315                 320

Leu Glu Arg Cys Tyr Gly Gly Tyr Val Gly Gly Ala Glu Tyr His Ser
```

```
              325                 330                 335
Ser Asn Leu Met Leu Val Lys Asn Gly Ser Gly Pro Ser Gly Gly Thr
            340                 345                 350
Gly Gly Ser Gly Asp Gln Gly Ser Glu Ser Trp Lys Asp Val Leu Glu
            355                 360                 365
Ala Cys Glu Ala Ser Ile Pro Leu Asn Ser Glu Gly Ser Thr Pro Ser
            370                 375                 380
Ser Ala Lys Gly Leu Leu Ala Gly Leu Gln Glu Asp Ser Asn Trp Ser
385                 390                 395                 400
Tyr Ser Asn Gln Val Asp Gln Ser Thr Phe Leu Leu Pro Gln Asp Leu
                405                 410                 415
Gly Ser Phe Gln Leu Pro Ala Ser Tyr Ser Ala Leu Val Ala Pro Glu
            420                 425                 430
Asn Asn Gly Glu Tyr Cys Gly Met Met Glu Asp Gly Met Lys Ile Gly
            435                 440                 445
Leu Pro Phe Glu Gln Glu Met Arg Val Thr Gly Ala His Asn Gln Lys
        450                 455                 460
Phe Thr Ile Gln Asp Ile Ser Pro Asp Trp Gly Tyr Ala Asn Glu Thr
465                 470                 475                 480
Thr Lys Val Ile Ile Gly Ser Phe Leu Cys Asp Pro Thr Glu Ser
                485                 490                 495
Thr Trp Ser Cys Met Phe Gly Asn Ala Gln Val Pro Phe Glu Ile Ile
            500                 505                 510
Lys Glu Gly Val Ile Arg Cys Glu Ala Pro Gln Cys Gly Pro Gly Lys
            515                 520                 525
Val Asn Leu Cys Ile Thr Ser Gly Asp Gly Leu Leu Cys Ser Glu Ile
            530                 535                 540
Arg Glu Phe Glu Tyr Arg Glu Lys Pro Asp Thr Cys Cys Pro Lys Cys
545                 550                 555                 560
Ser Glu Pro Gln Thr Ser Asp Met Ser Thr Ser Pro Asn Glu Leu Ile
                565                 570                 575
Leu Leu Val Arg Phe Val Gln Thr Leu Leu Ser Asp Arg Ser Ser Glu
            580                 585                 590
Arg Lys Ser Asn Leu Glu Ser Gly Asn Asp Lys Leu Leu Thr Lys Leu
            595                 600                 605
Lys Ala Asp Asp Gln Trp Arg His Val Ile Gly Thr Ile Ile Asp
        610                 615                 620
Gly Ser Ala Ser Ser Thr Ser Thr Val Asp Trp Leu Leu Gln Glu Leu
625                 630                 635                 640
Leu Lys Asp Lys Leu Asp Thr Trp Leu Ser Ser Arg Ser Cys Asp Glu
                645                 650                 655
Asp Tyr Ile Thr Cys Ser Leu Ser Lys Gln Glu Gln Gly Ile Ile His
                660                 665                 670
Met Val Ala Gly Leu Gly Phe Glu Trp Ala Phe Tyr Pro Ile Leu Ala
            675                 680                 685
His Gly Val Asn Val Asp Phe Arg Asp Ile Lys Gly Trp Ser Ala Leu
            690                 695                 700
His Trp Ala Ala Gln Phe Gly Ser Glu Lys Met Val Ala Ala Leu Ile
705                 710                 715                 720
Ala Ser Gly Ala Ser Ala Gly Ala Val Thr Asp Pro Ser Arg Gln Asp
                725                 730                 735
Pro Asn Gly Lys Thr Ala Ala Ser Ile Ala Ala Ser Asn Gly His Lys
            740                 745                 750
```

```
Gly Leu Ala Gly Tyr Leu Ser Glu Val Ala Leu Thr Asn His Leu Ser
        755                 760                 765

Ser Leu Thr Leu Glu Glu Thr Glu Asn Ser Lys Asp Thr Ala Gln Val
    770                 775                 780

Gln Thr Glu Lys Thr Leu Asn Ser Ile Ser Gln Ser Pro Ser Gly
785                 790                 795                 800

Asn Glu Asp Gln Val Ser Leu Lys Asp Thr Leu Ala Ala Val Arg Asn
                805                 810                 815

Ala Ala Gln Ala Ala Ala Arg Ile Gln Ala Ala Phe Arg Ala His Ser
                820                 825                 830

Phe Arg Lys Arg Lys Gln Arg Glu Ala Ala Leu Val Ala Cys Leu Gln
            835                 840                 845

Glu Tyr Gly Met Tyr Cys Glu Asp Ile Glu Gly Ile Ser Ala Met Ser
        850                 855                 860

Lys Leu Thr Phe Gly Lys Gly Arg Asn Tyr Asn Ser Ala Ala Leu Ser
865                 870                 875                 880

Ile Gln Lys Asn Phe Arg Gly Tyr Lys Asp Arg Lys Cys Phe Leu Glu
                885                 890                 895

Leu Arg Gln Lys Val Val Lys Ile Gln Ala His Val Arg Gly Tyr Gln
            900                 905                 910

Ile Arg Lys Asn Tyr Lys Val Ile Cys Trp Ala Val Arg Ile Leu Asp
            915                 920                 925

Lys Val Leu Arg Trp Arg Arg Lys Gly Val Gly Leu Arg Gly Phe
        930                 935                 940

Arg Gln Asp Val Glu Ser Thr Glu Asp Ser Glu Asp Glu Asp Ile Leu
945                 950                 955                 960

Lys Val Phe Arg Lys Gln Lys Val Asp Val Ala Val Asn Glu Ala Phe
                965                 970                 975

Ser Arg Val Leu Ser Met Ser Asn Ser Pro Glu Ala Arg Gln Gln Tyr
            980                 985                 990

His Arg Val Leu Lys Arg Tyr Cys Gln Thr Lys Ala Glu Leu Gly Lys
        995                 1000                1005

Thr Glu  Thr Leu Val Gly Glu  Asp Asp Asp Gly Leu  Phe Asp Ile
    1010                1015                1020

Ala Asp  Met Glu Tyr Asp Thr  Leu Phe Ser Leu Pro
    1025                1030                1035

<210> SEQ ID NO 34
<211> LENGTH: 2721
<212> TYPE: DNA
<213> ORGANISM: Arabidopsis thaliana

<400> SEQUENCE: 34
atggccggcg ttgattccgg caagcttatc ggctctgaga ttcatggatt ccatacttta      60
caagatctag atatacaaac aatgttagat gaagcataca gtaggtggct ccgtcctaat     120
gagatccatg ctcttctctg taaccataaa ttcttcacca tcaacgtcaa gccctgtggt     180
acgattgtgt gtgtttgatcg taagatgttg aggaacttta gaaggatgg tcataactgg     240 aaaagaaaa aggatggaaa gacaattaag gaagctcatg aacatctaaa agttggtaat     300
gaggaaagga ttcatgttta ttatgcccac ggtgaggata cccctacatt tgtgcgaagg     360
tgttactggt tattggataa gtctcaggag cacatagttc ttgtcccacta tcgcgagaca     420 catgaggttc atgcagctcc agcaacacct gggaactcgt actcaagttc gatcactgac     480
```

```
cacttatctc ctaaaattgt agctgaagat accagttctg gtgtccataa tacttgtaat    540
acagtgcgga gcaacagtct gggttctaga aatcatgaga ttaggcttca tgagatcaac    600
acacttgatt gggatgagct tctagtacct gcagatatta gcaaccaatc tcatccaacc    660
gaagaagata tgctatactt cacagaacag ctccaaactg cacccagggg atctgtaaag    720
caaggaaatc accttgcagg ctacaacgga tcagtagata taccatcatt cccgggtctt    780
gaagatcctg tatatcaaaa taataactca tgtggtgcag gagaattttc tagtcagcat    840
tcgcactgtg gagtagatcc aaatctacag agaagggatt tcagtgcaac agttactgat    900
caaccaggtg atgctttgct taataacggt tatggaagtc aggatagttt tggaaggtgg    960
gtgaacaact tcattagtga ctctcctggt tccgtcgatg atccttccct tgaagctgta   1020
tatacacctg gcaggattc atctactcct cctactgtat ttcattccca ctctgacata   1080
ccggagcaag tattcaacat aactgatgtt tcacctgcct ggggcgtatt cgacagagaa   1140
aacaaaggtc ttatgcatct cttatggcta agtgtgagta ctgagtactt ccaacatttg   1200
ggaagatcaa acctcatctg catatgtgga gagttgcgtg tccccgccga atttctccag   1260
atgggggttt atcgttgctt ccttcctcct caatctcctg gggtggtgaa cctttatctt   1320
agtgtcgatg gaaacaaacc gatcagccaa ttgttcagct tcgaacaccg ctcagttcag   1380
tttatcgaaa aagccatccc tcaagacgac cagctataca agtgggaaga atttgagttc   1440
caagtcgagac ttgctcatct tctgttcact tcttcgaaca aaatcagcgt tttaactagt   1500
aaaatatcac ctgaaaacct tcttgaggct aagaaactcg ccagcaggac ttcgcatctc   1560
ttaaatagtt gggcttattt aatgaagtca attcaggcaa atgaggtacc gtttgatcaa   1620
gcgagggacc atctctttga gcttactctg aaaaataggc tgaaagagtg gcttttggag   1680
aaggtcatcg aaaaccgcaa cactaaggaa tatgactcta aagggcttgg agtgatccac   1740
ctctgtgccg tcctaggata cacttggtca atccttctct tctcctgggc aaatatatcg   1800
ttggatttcc gtgataagca gggttggact gctcttcatt gggcagcata ctatggaagg   1860
ccaaacctgg tgacagaccc tactaaggaa ttcctcggcg gctgcacggc agctgatctg   1920
gcacaacaga aaggttatga cggtttagca gcttttcttg ctgagaaatg tcttgtagca   1980
cagttcaagg acatgcaaac ggctggaaac attagtggca accttgaaac catcaaggca   2040
gagaagtcgt caaatccagg gaatgcaaat gaagaggagc aaagcctgaa ggacactcta   2100
gcggcataca gaactgctgc agaggcagcg cgcggattc agggagcgtt cagggagcac   2160
gagctgaaag ttaggtcaag cgcagttagg tttgctagca aggaagaaga agccaaaaac   2220
ataatagccg cgatgaagat tcagcacgcg tttcgcaatt tcgaggttcg taggaagatt   2280
gcagccgctg ctcggattca gtataggttc caaacatgga aaatgaggcg ggaatttctg   2340
aacatgcgaa agaaggcaat taggatccag gctgcgttta gaggtttcca agtaagaaga   2400
cagtaccaga aaataacatg gtcagtggga gttcttgaga aggcaattct gagatggaga   2460
ctgaagagaa aaggattcag aggccttcag gtaagtcaac ctgacgagaa ggaagggagt   2520
gaggcggtgg aggatttcta caagacaagc cagaaacaag cggaggaacg gcttgagagg   2580
tcagtggtta aagtccaggc catgttccgg tccaagaagg ctcagcaaga ttacagaagg   2640
atgaaactgg ctcatgaaga agctcagctg gagtatgatg ggatgcaaga acttgatcaa   2700
atggctacgg aggagagctg a                                             2721
```

<210> SEQ ID NO 35
<211> LENGTH: 906

<212> TYPE: PRT
<213> ORGANISM: Arabidopsis thaliana

<400> SEQUENCE: 35

```
Met Ala Gly Val Asp Ser Gly Lys Leu Ile Gly Ser Glu Ile His Gly
1               5                   10                  15

Phe His Thr Leu Gln Asp Leu Asp Ile Gln Thr Met Leu Asp Glu Ala
            20                  25                  30

Tyr Ser Arg Trp Leu Arg Pro Asn Glu Ile His Ala Leu Leu Cys Asn
        35                  40                  45

His Lys Phe Phe Thr Ile Asn Val Lys Pro Cys Gly Thr Ile Val Leu
    50                  55                  60

Phe Asp Arg Lys Met Leu Arg Asn Phe Arg Lys Asp Gly His Asn Trp
65                  70                  75                  80

Lys Lys Lys Lys Asp Gly Lys Thr Ile Lys Glu Ala His Glu His Leu
                85                  90                  95

Lys Val Gly Asn Glu Glu Arg Ile His Val Tyr Tyr Ala His Gly Glu
            100                 105                 110

Asp Thr Pro Thr Phe Val Arg Arg Cys Tyr Trp Leu Leu Asp Lys Ser
        115                 120                 125

Gln Glu His Ile Val Leu Val His Tyr Arg Glu Thr His Glu Val His
130                 135                 140

Ala Ala Pro Ala Thr Pro Gly Asn Ser Tyr Ser Ser Ser Ile Thr Asp
145                 150                 155                 160

His Leu Ser Pro Lys Ile Val Ala Glu Asp Thr Ser Ser Gly Val His
                165                 170                 175

Asn Thr Cys Asn Thr Val Arg Ser Asn Ser Leu Gly Ser Arg Asn His
            180                 185                 190

Glu Ile Arg Leu His Glu Ile Asn Thr Leu Asp Trp Asp Glu Leu Leu
        195                 200                 205

Val Pro Ala Asp Ile Ser Asn Gln Ser His Pro Thr Glu Glu Asp Met
210                 215                 220

Leu Tyr Phe Thr Glu Gln Leu Gln Thr Ala Pro Arg Gly Ser Val Lys
225                 230                 235                 240

Gln Gly Asn His Leu Ala Gly Tyr Asn Gly Ser Val Asp Ile Pro Ser
                245                 250                 255

Phe Pro Gly Leu Glu Asp Pro Val Tyr Gln Asn Asn Asn Ser Cys Gly
            260                 265                 270

Ala Gly Glu Phe Ser Ser Gln His Ser His Cys Gly Val Asp Pro Asn
        275                 280                 285

Leu Gln Arg Arg Asp Phe Ser Ala Thr Val Thr Asp Gln Pro Gly Asp
290                 295                 300

Ala Leu Leu Asn Asn Gly Tyr Gly Ser Gln Asp Ser Phe Gly Arg Trp
305                 310                 315                 320

Val Asn Asn Phe Ile Ser Asp Ser Pro Gly Ser Val Asp Asp Pro Ser
                325                 330                 335

Leu Glu Ala Val Tyr Thr Pro Gly Gln Asp Ser Ser Thr Pro Pro Thr
            340                 345                 350

Val Phe His Ser His Ser Asp Ile Pro Glu Gln Val Phe Asn Ile Thr
        355                 360                 365

Asp Val Ser Pro Ala Trp Gly Val Phe Asp Arg Glu Asn Lys Gly Leu
370                 375                 380

Met His Leu Leu Trp Leu Ser Val Ser Thr Glu Tyr Phe Gln His Leu
385                 390                 395                 400
```

```
Gly Arg Ser Asn Leu Ile Cys Ile Cys Gly Glu Leu Arg Val Pro Ala
                405                 410                 415
Glu Phe Leu Gln Met Gly Val Tyr Arg Cys Phe Leu Pro Pro Gln Ser
            420                 425                 430
Pro Gly Val Val Asn Leu Tyr Leu Ser Val Asp Gly Asn Lys Pro Ile
        435                 440                 445
Ser Gln Leu Phe Ser Phe Glu His Arg Ser Val Gln Phe Ile Glu Lys
    450                 455                 460
Ala Ile Pro Gln Asp Asp Gln Leu Tyr Lys Trp Glu Phe Glu Phe
465                 470                 475                 480
Gln Val Arg Leu Ala His Leu Leu Phe Thr Ser Ser Asn Lys Ile Ser
                485                 490                 495
Val Leu Thr Ser Lys Ile Ser Pro Glu Asn Leu Leu Glu Ala Lys Lys
            500                 505                 510
Leu Ala Ser Arg Thr Ser His Leu Leu Asn Ser Trp Ala Tyr Leu Met
        515                 520                 525
Lys Ser Ile Gln Ala Asn Glu Val Pro Phe Asp Gln Ala Arg Asp His
    530                 535                 540
Leu Phe Glu Leu Thr Leu Lys Asn Arg Leu Lys Glu Trp Leu Leu Glu
545                 550                 555                 560
Lys Val Ile Glu Asn Arg Asn Thr Lys Glu Tyr Asp Ser Lys Gly Leu
                565                 570                 575
Gly Val Ile His Leu Cys Ala Val Leu Gly Tyr Thr Trp Ser Ile Leu
            580                 585                 590
Leu Phe Ser Trp Ala Asn Ile Ser Leu Asp Phe Arg Asp Lys Gln Gly
        595                 600                 605
Trp Thr Ala Leu His Trp Ala Ala Tyr Tyr Gly Arg Pro Asn Leu Val
    610                 615                 620
Thr Asp Pro Thr Lys Glu Phe Leu Gly Gly Cys Thr Ala Ala Asp Leu
625                 630                 635                 640
Ala Gln Gln Lys Gly Tyr Asp Gly Leu Ala Ala Phe Leu Ala Glu Lys
                645                 650                 655
Cys Leu Val Ala Gln Phe Lys Asp Met Gln Thr Ala Gly Asn Ile Ser
            660                 665                 670
Gly Asn Leu Glu Thr Ile Lys Ala Glu Lys Ser Ser Asn Pro Gly Asn
        675                 680                 685
Ala Asn Glu Glu Glu Gln Ser Leu Lys Asp Thr Leu Ala Ala Tyr Arg
    690                 695                 700
Thr Ala Ala Glu Ala Ala Arg Ile Gln Gly Ala Phe Arg Glu His
705                 710                 715                 720
Glu Leu Lys Val Arg Ser Ser Ala Val Arg Phe Ala Ser Lys Glu Glu
                725                 730                 735
Glu Ala Lys Asn Ile Ile Ala Met Lys Ile Gln His Ala Phe Arg
            740                 745                 750
Asn Phe Glu Val Arg Arg Lys Ile Ala Ala Ala Arg Ile Gln Tyr
        755                 760                 765
Arg Phe Gln Thr Trp Lys Met Arg Arg Glu Phe Leu Asn Met Arg Lys
    770                 775                 780
Lys Ala Ile Arg Ile Gln Ala Ala Phe Arg Gly Phe Gln Val Arg Arg
785                 790                 795                 800
Gln Tyr Gln Lys Ile Thr Trp Ser Val Gly Val Leu Glu Lys Ala Ile
                805                 810                 815
```

```
Leu Arg Trp Arg Leu Lys Arg Lys Gly Phe Arg Gly Leu Gln Val Ser
            820                 825                 830

Gln Pro Asp Glu Lys Glu Gly Ser Glu Ala Val Glu Asp Phe Tyr Lys
        835                 840                 845

Thr Ser Gln Lys Gln Ala Glu Glu Arg Leu Glu Arg Ser Val Val Lys
    850                 855                 860

Val Gln Ala Met Phe Arg Ser Lys Lys Ala Gln Asp Tyr Arg Arg
865                 870                 875                 880

Met Lys Leu Ala His Glu Glu Ala Gln Leu Glu Tyr Asp Gly Met Gln
                885                 890                 895

Glu Leu Asp Gln Met Ala Thr Glu Glu Ser
            900                 905

<210> SEQ ID NO 36
<211> LENGTH: 427
<212> TYPE: DNA
<213> ORGANISM: Oryza sativa

<400> SEQUENCE: 36
ggatggcgga ggttcgcaag tacgggctgc ccaatcagcc gccagatatt ccccagatac      60
tgctggaagc tcagaatcga tggctacgtc tactgaaat ctgccatata ctgtcgaact     120
acaagaaatt ctccattgcg cccgagccac cgaacagacc tgcaagtggc tcgcttttc    180 tgttcgatcg gaaatattg agatacttca gaaaggatgg acataactgg aggaagaaaa    240
aggatggaaa gacagtcaaa gaagctcatg agaagctgaa agttggtagt gttgatgtac    300
ttcattgcta ctatgcccat ggggaggaga atgagaactt ccagagacgt acctattggt    360
tgttagaaga gggtttcatg aatattgttc ttgtgcacta ccttgaagtt aagcttctgc    420
ttccatg                                                               427

<210> SEQ ID NO 37
<211> LENGTH: 41
<212> TYPE: DNA
<213> ORGANISM: Artificial Sequence
<220> FEATURE:
<223> OTHER INFORMATION: EDS1P-F; forward primer to amplify EDS1
      promoter region

<400> SEQUENCE: 37
gcaagcttag agcttttaag aatattatgc acaagagaga g                         41

<210> SEQ ID NO 38
<211> LENGTH: 47
<212> TYPE: DNA
<213> ORGANISM: Artificial Sequence
<220> FEATURE:
<223> OTHER INFORMATION: EDS1P-R; reverse primer to amplify EDS1
      promoter region

<400> SEQUENCE: 38
gcggatcctg atctatatct attctctttt ctttagtgga ctttctt                   47

<210> SEQ ID NO 39
<211> LENGTH: 37
<212> TYPE: DNA
<213> ORGANISM: Artificial Sequence
<220> FEATURE:
<223> OTHER INFORMATION: Luc-F; forward primer to amplify luciferase
      gene

<400> SEQUENCE: 39
```

```
gcggatccat ggaagacgcc aaaaacataa agaaagg                              37

<210> SEQ ID NO 40
<211> LENGTH: 37
<212> TYPE: DNA
<213> ORGANISM: Artificial Sequence
<220> FEATURE:
<223> OTHER INFORMATION: LucR; reverse primer to amplify luciferase gene

<400> SEQUENCE: 40
gcgtcgactt acaatttgga ctttccgccc ttcttgg                              37

<210> SEQ ID NO 41
<211> LENGTH: 32
<212> TYPE: DNA
<213> ORGANISM: Artificial Sequence
<220> FEATURE:
<223> OTHER INFORMATION: AtSR1f; forward primer to characterize AtSR1
      mutants

<400> SEQUENCE: 41
gaactactga acattttcta gaagttactc ac                                   32

<210> SEQ ID NO 42
<211> LENGTH: 21
<212> TYPE: DNA
<213> ORGANISM: Artificial Sequence
<220> FEATURE:
<223> OTHER INFORMATION: AtSR1r; reverse primer to characterize AtSR1
      mutants

<400> SEQUENCE: 42
tgtttgggca aacagaagtt c                                               21

<210> SEQ ID NO 43
<211> LENGTH: 22
<212> TYPE: DNA
<213> ORGANISM: Artificial Sequence
<220> FEATURE:
<223> OTHER INFORMATION: AtSR1f2; forward primer to characterize AtSR1
      mutants

<400> SEQUENCE: 43
ttcagcccag ttcatgaatt ag                                              22

<210> SEQ ID NO 44
<211> LENGTH: 20
<212> TYPE: DNA
<213> ORGANISM: Artificial Sequence
<220> FEATURE:
<223> OTHER INFORMATION: AtSR1r2; reverse primer to characterize AtSR1
      mutants

<400> SEQUENCE: 44
ccatccatgt ccctcctaga                                                 20

<210> SEQ ID NO 45
<211> LENGTH: 21
<212> TYPE: DNA
<213> ORGANISM: Artificial Sequence
<220> FEATURE:
<223> OTHER INFORMATION: PAD4f; forward primer to characterize AtSR1
      mutants

<400> SEQUENCE: 45
tcattccgcg tcttttgtat c                                               21
```

<210> SEQ ID NO 46
<211> LENGTH: 21
<212> TYPE: DNA
<213> ORGANISM: Artificial Sequence
<220> FEATURE:
<223> OTHER INFORMATION: PAD4r; reverse primer to characterize AtSR1 mutants

<400> SEQUENCE: 46
caaagatctc ctctggggat c                                           21

<210> SEQ ID NO 47
<211> LENGTH: 21
<212> TYPE: DNA
<213> ORGANISM: Artificial Sequence
<220> FEATURE:
<223> OTHER INFORMATION: EDS5f; forward primer to characterize AtSR1 mutants

<400> SEQUENCE: 47
atgggaactc acgttttagc c                                           21

<210> SEQ ID NO 48
<211> LENGTH: 20
<212> TYPE: DNA
<213> ORGANISM: Artificial Sequence
<220> FEATURE:
<223> OTHER INFORMATION: AtSR1r; reverse primer to characterize AtSR1 mutants

<400> SEQUENCE: 48
tctccaccgt gtatggactc                                             20

<210> SEQ ID NO 49
<211> LENGTH: 23
<212> TYPE: DNA
<213> ORGANISM: Artificial Sequence
<220> FEATURE:
<223> OTHER INFORMATION: ICS1f; forward primer to characterize AtSR1 mutants

<400> SEQUENCE: 49
acttattttc tggcccacaa aac                                         23

<210> SEQ ID NO 50
<211> LENGTH: 23
<212> TYPE: DNA
<213> ORGANISM: Artificial Sequence
<220> FEATURE:
<223> OTHER INFORMATION: ICS1r; reverse primer to characterize AtSR1 mutants

<400> SEQUENCE: 50
cactttacga atttctgcaa tgg                                         23

<210> SEQ ID NO 51
<211> LENGTH: 22
<212> TYPE: DNA
<213> ORGANISM: Artificial Sequence
<220> FEATURE:
<223> OTHER INFORMATION: EDSUE-F; forward primer to amplify edsue

<400> SEQUENCE: 51
tggcttttcg tagaaatttc cc                                          22

<210> SEQ ID NO 52

```
<211> LENGTH: 21
<212> TYPE: DNA
<213> ORGANISM: Artificial Sequence
<220> FEATURE:
<223> OTHER INFORMATION: EDSUE-R; reverse primer to amplify edsue

<400> SEQUENCE: 52
ggaaccggtt cgatttctct c                                              21

<210> SEQ ID NO 53
<211> LENGTH: 32
<212> TYPE: DNA
<213> ORGANISM: Artificial Sequence
<220> FEATURE:
<223> OTHER INFORMATION: AtSR1-L; left primer for RT-PCR

<400> SEQUENCE: 53
gaactactga acattttcta gaagttactc ac                                  32

<210> SEQ ID NO 54
<211> LENGTH: 21
<212> TYPE: DNA
<213> ORGANISM: Artificial Sequence
<220> FEATURE:
<223> OTHER INFORMATION: AtSR1-R; right primer for RT-PCR

<400> SEQUENCE: 54
tgtttgggca aacagaagtt c                                              21

<210> SEQ ID NO 55
<211> LENGTH: 20
<212> TYPE: DNA
<213> ORGANISM: Artificial Sequence
<220> FEATURE:
<223> OTHER INFORMATION: P1; primer 1

<400> SEQUENCE: 55
ccatccatgt ccctcctaga                                                20

<210> SEQ ID NO 56
<211> LENGTH: 20
<212> TYPE: DNA
<213> ORGANISM: Artificial Sequence
<220> FEATURE:
<223> OTHER INFORMATION: P2; primer 2

<400> SEQUENCE: 56
tccattgatt cccaaacctg                                                20

<210> SEQ ID NO 57
<211> LENGTH: 22
<212> TYPE: DNA
<213> ORGANISM: Artificial Sequence
<220> FEATURE:
<223> OTHER INFORMATION: P3; primer 3

<400> SEQUENCE: 57
ttcagcccag ttcatgaatt ag                                             22

<210> SEQ ID NO 58
<211> LENGTH: 32
<212> TYPE: DNA
<213> ORGANISM: Artificial Sequence
<220> FEATURE:
<223> OTHER INFORMATION: EDS1 promoter fragment

<400> SEQUENCE: 58
```

```
gtaaaagtcg aatgtgacgc gtcttgccga ac                                32
```

<210> SEQ ID NO 59
<211> LENGTH: 120
<212> TYPE: PRT
<213> ORGANISM: Arabidopsis thaliana

<400> SEQUENCE: 59

| Lys | His | Glu | Ser | Lys | Glu | Ala | Glu | Asp | Trp | Lys | Glu | Ala | Asp | Gly | Glu |
|---|---|---|---|---|---|---|---|---|---|---|---|---|---|---|---|
| 1 | | | | 5 | | | | | 10 | | | | | 15 | |

| Lys | Val | Lys | Glu | Arg | Ile | Lys | Leu | Val | Leu | Lys | Thr | Glu | Glu | Ala | Leu |
|---|---|---|---|---|---|---|---|---|---|---|---|---|---|---|---|
| | | | 20 | | | | | 25 | | | | | 30 | | |

| Leu | Ser | Leu | Ala | Gln | Lys | Pro | Cys | Asn | Arg | Glu | Glu | Cys | Ile | Glu | Asp |
|---|---|---|---|---|---|---|---|---|---|---|---|---|---|---|---|
| | | | 35 | | | | | 40 | | | | | 45 | | |

| Cys | Arg | Arg | Leu | Asn | Pro | Arg | Glu | Pro | Asn | Tyr | Ile | Gln | Thr | Thr | Val |
|---|---|---|---|---|---|---|---|---|---|---|---|---|---|---|---|
| | 50 | | | | | 55 | | | | | 60 | | | | |

| Glu | Pro | Ser | Asn | Glu | Thr | Val | Asp | Leu | Arg | His | Gln | Asp | Met | Asp | Glu |
|---|---|---|---|---|---|---|---|---|---|---|---|---|---|---|---|
| 65 | | | | | 70 | | | | | 75 | | | | | 80 |

| Arg | Lys | Lys | Ala | Glu | Glu | Trp | Met | Ile | Asp | Tyr | Ala | Leu | Gln | His | Thr |
|---|---|---|---|---|---|---|---|---|---|---|---|---|---|---|---|
| | | | | 85 | | | | | 90 | | | | | 95 | |

| Val | Ser | Lys | Leu | Val | Val | Glu | Arg | Lys | Lys | Asp | Val | Ala | Leu | Leu | Val |
|---|---|---|---|---|---|---|---|---|---|---|---|---|---|---|---|
| | | | 100 | | | | | 105 | | | | | 110 | | |

| Glu | Ala | Phe | Glu | Thr | Thr | Val | Pro |
|---|---|---|---|---|---|---|---|
| | | | 115 | | | | 120 |

<210> SEQ ID NO 60
<211> LENGTH: 108
<212> TYPE: PRT
<213> ORGANISM: Arabidopsis thaliana

<400> SEQUENCE: 60

| Thr | His | Leu | Ser | Val | Ile | Ala | Ser | Thr | Phe | His | Met | Arg | Asp | Glu | Phe |
|---|---|---|---|---|---|---|---|---|---|---|---|---|---|---|---|
| 1 | | | | 5 | | | | | 10 | | | | | 15 | |

| Gly | His | Gln | Arg | Gly | Pro | Lys | Lys | Trp | Ser | Tyr | Leu | Lys | Arg | Val | Ile |
|---|---|---|---|---|---|---|---|---|---|---|---|---|---|---|---|
| | | | 20 | | | | | 25 | | | | | 30 | | |

| Leu | Leu | Lys | Arg | Phe | Leu | Lys | Ser | Leu | Asp | Arg | Lys | Glu | Arg | Arg | Lys |
|---|---|---|---|---|---|---|---|---|---|---|---|---|---|---|---|
| | | | 35 | | | | | 40 | | | | | 45 | | |

| Leu | Ser | Asp | Gly | Lys | Glu | Ser | Glu | Thr | Ile | Met | Arg | Leu | Arg | Arg | Glu |
|---|---|---|---|---|---|---|---|---|---|---|---|---|---|---|---|
| | 50 | | | | | 55 | | | | | 60 | | | | |

| Leu | Val | Gly | Glu | Arg | Lys | Asn | Ala | Glu | Glu | Trp | Met | Leu | Asp | His | Ala |
|---|---|---|---|---|---|---|---|---|---|---|---|---|---|---|---|
| 65 | | | | | 70 | | | | | 75 | | | | | 80 |

| Leu | Arg | Gln | Val | Ile | Ser | Thr | Leu | Ala | Pro | Ser | Gln | Lys | Lys | Lys | Val |
|---|---|---|---|---|---|---|---|---|---|---|---|---|---|---|---|
| | | | | 85 | | | | | 90 | | | | | 95 | |

| Lys | His | Leu | Val | Lys | Ala | Phe | Glu | Ser | Leu | Ile | Pro |
|---|---|---|---|---|---|---|---|---|---|---|---|
| | | | 100 | | | | | 105 | | | |

<210> SEQ ID NO 61
<211> LENGTH: 115
<212> TYPE: PRT
<213> ORGANISM: Arabidopsis thaliana

<400> SEQUENCE: 61

| Val | Ser | Glu | Glu | Lys | Ser | Glu | Val | Ser | Ser | Ala | Thr | Phe | Lys | Pro | Lys |
|---|---|---|---|---|---|---|---|---|---|---|---|---|---|---|---|
| 1 | | | | 5 | | | | | 10 | | | | | 15 | |

| Phe | Thr | Glu | Lys | Arg | Val | Lys | Gly | Trp | Asn | Asn | Val | Lys | Lys | Val | Ile |
|---|---|---|---|---|---|---|---|---|---|---|---|---|---|---|---|
| | | | 20 | | | | | 25 | | | | | 30 | | |

| Leu | Leu | Lys | Arg | Phe | Val | Ser | Asp | Leu | Gly | Ser | Leu | Thr | Arg | Leu | Ser |
|---|---|---|---|---|---|---|---|---|---|---|---|---|---|---|---|

```
                35                  40                  45
Pro Lys Thr Pro Arg Val Leu Pro Trp Glu Pro Asp Pro Glu Thr Glu
    50                  55                  60
Lys Ile Arg Leu Arg His Gln Glu Ile Gly Gly Lys Arg Asn Ser Glu
 65                  70                  75                  80
Glu Trp Met Leu Asp Tyr Ala Leu Arg Gln Ala Ile Ser Thr Leu Ala
                85                  90                  95
Pro Ser Gln Lys Arg Lys Val Ser Leu Leu Ala Gln Ala Phe Asp Thr
            100                 105                 110
Ile Ser Leu
        115

<210> SEQ ID NO 62
<211> LENGTH: 115
<212> TYPE: PRT
<213> ORGANISM: Arabidopsis thaliana

<400> SEQUENCE: 62

Val Gly Gly Ser Lys Lys Glu Ile Thr Pro Lys Glu Val Lys Asn Lys
 1               5                  10                  15
Ser Glu Lys Arg Ala Pro Lys His Trp Ser Asn Leu Lys Lys Trp Ile
                20                  25                  30
Leu Leu Gln Arg Phe Val Lys Glu Leu Glu Lys Val Arg Lys Ile Asn
            35                  40                  45
Pro Arg Lys Pro Gln Phe Leu Gln Leu Asn Pro Asp Pro Glu Ala Glu
    50                  55                  60
Lys Val Asn Leu Arg Thr Gln Thr Ala Asp Glu Arg Lys Arg Gly Glu
 65                  70                  75                  80
Glu Trp Met Leu Asp Tyr Ala Leu Gln Gln Ala Ile Ser Gln Leu Ala
                85                  90                  95
Pro Thr Gln Gln Arg Lys Val Glu Leu Leu Ile Lys Ala Phe Glu Thr
            100                 105                 110
Val Val Pro
        115

<210> SEQ ID NO 63
<211> LENGTH: 115
<212> TYPE: PRT
<213> ORGANISM: Arabidopsis thaliana

<400> SEQUENCE: 63

Gln Asn Leu Asn Asn Glu Glu Thr Arg Gln Lys Ser Glu Thr Leu Gln
 1               5                  10                  15
Val Ser Lys Val Arg Ile Asp Arg Trp Ser Asn Leu Lys Arg Ala Ile
                20                  25                  30
Leu Leu Arg Arg Phe Val Lys Ala Leu Glu Asn Val Arg Lys Phe Asn
            35                  40                  45
Pro Arg Glu Pro Arg Phe Leu Pro Pro Asn Pro Glu Val Glu Ala Glu
    50                  55                  60
Lys Val Asn Leu Arg His Gln Glu Thr Gln Asn Lys Lys Asn Gly Asp
 65                  70                  75                  80
Glu Trp Met Val Asp Asn Ala Leu Gln Gly Val Val Ser Lys Leu Thr
                85                  90                  95
Pro Ala Arg Lys Leu Lys Val Gln Leu Leu Val Gln Ala Phe Glu Ser
            100                 105                 110
Leu Ser Ala
```

<210> SEQ ID NO 64
<211> LENGTH: 115
<212> TYPE: PRT
<213> ORGANISM: Arabidopsis thaliana

<400> SEQUENCE: 64

```
Ile Thr Gln Glu Gln Glu Glu Ser Ala Pro Lys Glu Gln Asn Lys
1               5                   10                  15

Thr Asn Gln Pro Leu Ser Arg Ser Trp Ser Asn Leu Lys Lys Val Ile
                20                  25                  30

Leu Leu Arg Arg Phe Ile Lys Ser Leu Glu Lys Val Arg Lys Phe Asn
                35                  40                  45

Pro Arg Gly Pro Arg His Leu Pro Leu Glu Ala Asp Ser Glu Ala Glu
            50                  55                  60

Lys Val Asn Leu Arg His Gln Asp Met Glu Glu Arg Lys Gly Thr Glu
65                  70                  75                  80

Glu Trp Met Leu Asp Tyr Ala Leu Arg Gln Val Val Ser Lys Leu Thr
                85                  90                  95

Pro Ala Arg Lys Arg Lys Val Gly Leu Leu Val Glu Ala Phe Glu Thr
            100                 105                 110

Val Met Pro
        115
```

<210> SEQ ID NO 65
<211> LENGTH: 116
<212> TYPE: PRT
<213> ORGANISM: Arabidopsis thaliana

<400> SEQUENCE: 65

```
Thr Lys Gln Gln Met Asn Phe Lys Lys Gly Lys Val Leu Glu Pro Lys
1               5                   10                  15

Pro Glu Asp Ser Thr Thr Thr Ser Ile Lys Phe Lys Lys Ile Val Val
                20                  25                  30

Gln Glu Pro Lys Leu Arg Thr Ser Asp Val Asn Lys Lys Lys Lys Ser
            35                  40                  45

Leu Lys Asp Lys Arg Glu Gly Val Gly Lys Ile Asn Gly Glu Gly Lys
    50                  55                  60

Arg Glu Lys Val Val Leu Arg His Arg Lys Val Glu Val Lys Lys Lys
65                  70                  75                  80

Leu Gln Thr Leu Phe Asn Asn Val Ile Glu Glu Thr Val Asn Lys Leu
                85                  90                  95

Glu Glu Val Arg Lys Ser Lys Val Lys Ala Leu Val Gly Ala Phe Glu
            100                 105                 110

Thr Val Ile Ser
        115
```

<210> SEQ ID NO 66
<211> LENGTH: 116
<212> TYPE: PRT
<213> ORGANISM: Arabidopsis thaliana

<400> SEQUENCE: 66

```
Asn Ala Met Lys Leu Arg Ile Arg Gly Lys Ile Ile Asp Phe Gly
1               5                   10                  15

Ser Glu Gly Asn Ser Pro Arg Lys Leu Lys Phe Lys Arg Gly Lys Ile
                20                  25                  30
```

```
Ile Ser Gly Ala Asp Thr Thr Ser Lys Ser Gly Gly Arg Arg Leu
        35                  40                  45

Lys Thr Lys Gly Thr Asn Leu Ser Asn Asp Lys Glu Gln Gln Arg Lys
 50                  55                  60

Pro Arg Val Val Leu Lys His Gln Asp Thr Glu Lys Lys Arg Glu Ser
 65                  70                  75                  80

Arg Val Leu Leu Phe Asn Lys Val Ile Lys Glu Thr Ala Asn Lys Leu
                 85                  90                  95

Val Gln Thr Arg Lys Ser Lys Val Lys Ala Leu Val Gly Ala Phe Glu
            100                 105                 110

Ser Val Ile Ser
        115

<210> SEQ ID NO 67
<211> LENGTH: 112
<212> TYPE: PRT
<213> ORGANISM: Arabidopsis thaliana

<400> SEQUENCE: 67

His His Ser Lys Ser Phe Ser His Arg Ser Phe Thr Ser Thr Leu Phe
 1               5                  10                  15

Asn His His Gln Lys Pro Lys Ser Thr Ser Leu Phe Ala Leu Pro Gln
             20                  25                  30

Ser Lys Lys Thr Ser Ser Thr Glu Gly Asn Leu Lys Gln Lys Lys Val
         35                  40                  45

Pro Lys Ser Leu Phe Arg Ser Arg Ser Glu Pro Gly Arg Lys Gly Ile
 50                  55                  60

Arg His Val Arg Glu Pro Gly Ser Pro Lys Val Ser Cys Ile Gly Arg
 65                  70                  75                  80

Val Asp Tyr Ala Leu Gln Lys Ala Ile Ser Gln Leu Ala Pro Thr Gln
                 85                  90                  95

Gln Arg Lys Val Glu Leu Leu Ile Lys Ala Phe Glu Thr Val Val Pro
            100                 105                 110

<210> SEQ ID NO 68
<211> LENGTH: 117
<212> TYPE: PRT
<213> ORGANISM: Arabidopsis thaliana

<400> SEQUENCE: 68

Glu Glu Ser Val Ser Glu Ser Ser Asn Ser Leu Lys Glu Gly Lys Glu
 1               5                  10                  15

His Gln Gly Glu Thr Lys Arg Ser Trp Asn Ser Leu Arg Lys Val Ile
             20                  25                  30

Leu Leu Lys Arg Phe Val Lys Ser Leu Glu Lys Val Gln Val Pro Asn
         35                  40                  45

Pro Arg Lys Met Arg Asn Leu Pro Val Glu Ser Ala Phe Glu Ala Glu
 50                  55                  60

Asn Val Phe Leu Arg His Arg Ser Ile Met Glu Gly Thr Arg Thr Glu
 65                  70                  75                  80

Gly Glu Glu Met Met Leu Asp Tyr Ala Leu Arg Gln Ala Ile Ser Arg
                 85                  90                  95

Leu Ala Pro Ile Gln Arg Lys Lys Val Asp Leu Leu Val Gln Ala Phe
            100                 105                 110

Asp Ile Val Leu Asp
        115
```

-continued

```
<210> SEQ ID NO 69
<211> LENGTH: 75
<212> TYPE: DNA
<213> ORGANISM: Arabidopsis thaliana
<220> FEATURE:
<221> NAME/KEY: CDS
<222> LOCATION: (1)..(75)

<400> SEQUENCE: 69 att tgg tca gtg ggg gta tta gag aag gtg ata tta cgt tgg aga cgg      48
Ile Trp Ser Val Gly Val Leu Glu Lys Val Ile Leu Arg Trp Arg Arg
1               5                   10                  15 aaa gga gct ggt ttg cgc ggg ttt aag                                  75
Lys Gly Ala Gly Leu Arg Gly Phe Lys
            20                  25

<210> SEQ ID NO 70
<211> LENGTH: 25
<212> TYPE: PRT
<213> ORGANISM: Arabidopsis thaliana

<400> SEQUENCE: 70

Ile Trp Ser Val Gly Val Leu Glu Lys Val Ile Leu Arg Trp Arg Arg
1               5                   10                  15

Lys Gly Ala Gly Leu Arg Gly Phe Lys
            20                  25

<210> SEQ ID NO 71
<211> LENGTH: 75
<212> TYPE: DNA
<213> ORGANISM: Arabidopsis thaliana
<220> FEATURE:
<221> NAME/KEY: CDS
<222> LOCATION: (1)..(75)

<400> SEQUENCE: 71 att tgg tca gtg ggg gta tta gag aag gtg gta tta cgt tgg aga cgg      48
Ile Trp Ser Val Gly Val Leu Glu Lys Val Val Leu Arg Trp Arg Arg
1               5                   10                  15 aaa gga gct ggt ttg cgc ggg ttt aag                                  75
Lys Gly Ala Gly Leu Arg Gly Phe Lys
            20                  25

<210> SEQ ID NO 72
<211> LENGTH: 25
<212> TYPE: PRT
<213> ORGANISM: Arabidopsis thaliana

<400> SEQUENCE: 72

Ile Trp Ser Val Gly Val Leu Glu Lys Val Val Leu Arg Trp Arg Arg
1               5                   10                  15

Lys Gly Ala Gly Leu Arg Gly Phe Lys
            20                  25

<210> SEQ ID NO 73
<211> LENGTH: 75
<212> TYPE: DNA
<213> ORGANISM: Arabidopsis thaliana
<220> FEATURE:
<221> NAME/KEY: CDS
<222> LOCATION: (1)..(75)

<400> SEQUENCE: 73 att tgg tca gtg ggg gta tta gag gag gtg ata tta cgt tgg aga cgg      48
```

-continued

```
Ile Trp Ser Val Gly Val Leu Glu Glu Val Ile Leu Arg Trp Arg Arg
1               5                   10                  15 aaa gga gct ggt ttg cgc ggg ttt aag                              75
Lys Gly Ala Gly Leu Arg Gly Phe Lys
            20              25

<210> SEQ ID NO 74
<211> LENGTH: 25
<212> TYPE: PRT
<213> ORGANISM: Arabidopsis thaliana

<400> SEQUENCE: 74

Ile Trp Ser Val Gly Val Leu Glu Glu Val Ile Leu Arg Trp Arg Arg
1               5                   10                  15

Lys Gly Ala Gly Leu Arg Gly Phe Lys
            20              25
```